Figure 1:
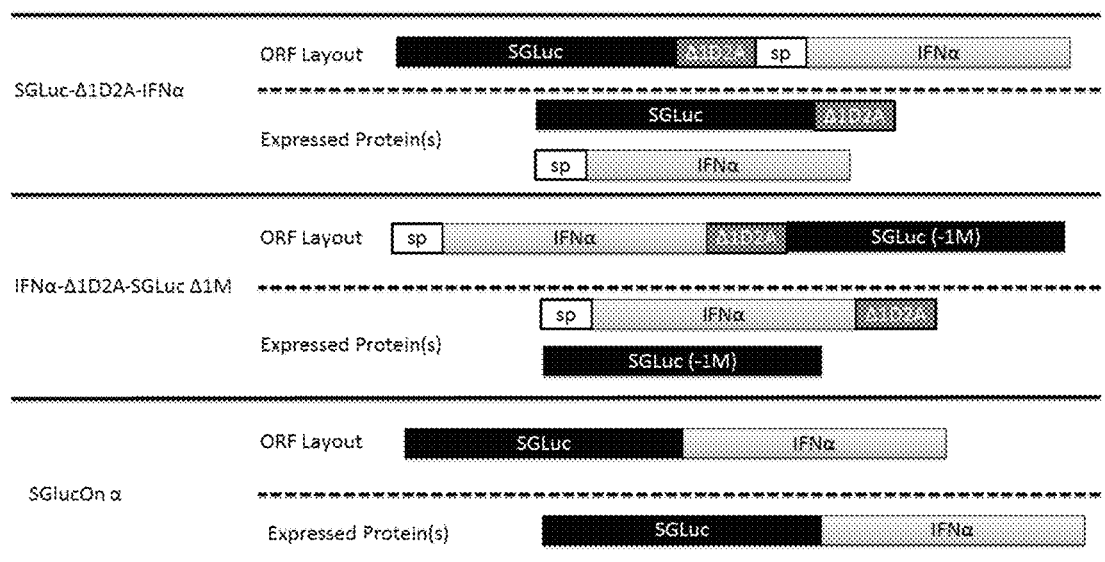

US010435695B2

(12) United States Patent
Puckette et al.

(10) Patent No.: US 10,435,695 B2
(45) Date of Patent: Oct. 8, 2019

(54) FUSION PROTEIN COMPRISING *GAUSSIA LUCIFERASE*, TRANSLATION INTERRUPTER SEQUENCE, AND INTERFERON AMINO ACID SEQUENCES

(71) Applicant: The United States of America, as represented by the Secretary of Homeland Security, Washington, DC (US)

(72) Inventors: Michael Puckette, Waterford, CT (US); Max V. Rasmussen, Guilford, CT (US)

(73) Assignee: The Government of the United States of America, as represented by the Secretary of Homeland Security, Washington, DC (US)

( * ) Notice: Subject to any disclaimer, the term of this patent is extended or adjusted under 35 U.S.C. 154(b) by 0 days.

(21) Appl. No.: 15/583,459

(22) Filed: May 1, 2017

(65) Prior Publication Data

US 2018/0066267 A1 Mar. 8, 2018

Related U.S. Application Data

(63) Continuation-in-part of application No. 15/259,409, filed on Sep. 8, 2016.

(51) Int. Cl.
| | |
|---|---|
| *C12N 15/63* | (2006.01) |
| *A61K 39/21* | (2006.01) |
| *C07K 14/005* | (2006.01) |
| *C12Q 1/66* | (2006.01) |
| *A61K 38/21* | (2006.01) |
| *C07K 14/705* | (2006.01) |
| *C07K 14/56* | (2006.01) |
| *C12N 9/02* | (2006.01) |
| *C07K 14/00* | (2006.01) |
| *C12N 15/00* | (2006.01) |
| *A61K 38/00* | (2006.01) |

(52) U.S. Cl.
CPC .............. *C12N 15/63* (2013.01); *A61K 38/21* (2013.01); *C07K 14/56* (2013.01); *C07K 14/705* (2013.01); *C12N 9/0069* (2013.01); *C12Q 1/66* (2013.01); *A61K 38/00* (2013.01); *C07K 14/00* (2013.01); *C07K 2319/00* (2013.01); *C12N 15/00* (2013.01)

(58) Field of Classification Search
None
See application file for complete search history.

(56) References Cited

U.S. PATENT DOCUMENTS 6,232,107 B1 * 5/2001 Bryan ................ A61K 49/0013 435/183
8,236,548 B2 8/2012 Chen
2011/0143362 A1 * 6/2011 Oyler ................ C12N 15/1034 435/6.18
2011/0236416 A1 9/2011 Audonnet et al.
2012/0122182 A1 5/2012 Tannous et al.
2012/0258133 A1 10/2012 Charleston
2012/0315295 A1 12/2012 Rieder et al.
2013/0243809 A1 9/2013 Liao et al.
2014/0186959 A1 7/2014 Slater et al.
2018/0066235 A1 3/2018 Puckette et al.
2018/0066267 A1 * 3/2018 Puckette ................ C07K 14/56

OTHER PUBLICATIONS

Wu et al. (Biochemica et Biophysica Acta. 2015; 1854: 1392-1399).*

Alignment of SEQ ID 24 with Genseq access No. ABB81097 Jun. 2007 Zuckermann in WO200260921.*

Cheng et al. (Gene. 2006; 382: 28-38).*

Alignment of SEQ ID 4 with Genseq db access AYL17606 Dec. 2010 Sungbae et al in WO2010119721.*

Luker et al. (Nature Medicine. Jan. 2012; 18 (1): 172-177).*

G. R. Stark, I. M. Kerr, B. R. Williams, R. H. Silverman, R. D. Schreiber, How cells respond to interferons. Annual review of biochemistry 67, 227-264 (1998).

K. Schroder, P. J. Hertzog, T. Ravasi, D. A. Hume, Interferon-gamma: an overview of signals, mechanisms and functions. Journal of leukocyte biology 75, 163-189 (2004).

H. M. Lazear, T. J. Nice, M. S. Diamond, Interferon-lambda: Immune Functions at Barrier Surfaces and Beyond. Immunity 43, 15-28 (2015).

J. Chinsangaram, M. Koster, M. J. Grubman, Inhibition of L-deleted foot-and-mouth disease virus replication by alpha/beta interferon involves double-stranded RNA-dependent protein kinase. Journal of virology 75, 5498-5503 (2001).

J. Chinsangaram, M. P. Moraes, M. Koster, M. J. Grubman, Novel viral disease control strategy: adenovirus expressing alpha interferon rapidly protects swine from foot-and-mouth disease. Journal of virology 77, 1621-1625 (2003).

H. Yin et al., Antitumor potential of a synthetic interferon-alpha/PLGF-2 positive charge peptide hybrid molecule in pancreatic cancer cells. Scientific reports 5, 16975 (2015).

M. Nakamura et al., Expression and visualization of a human interferon-beta-enhanced green fluorescent protein chimeric molecule in cultured cells. Biological & pharmaceutical bulletin 27, 411-414 (2004).

M. Maruyama et al., Simultaneous detection of DsRed2-tagged and EGFP-tagged human beta-interferons in the same single cells. Journal of cellular biochemistry 93, 497-502 (2004).

M. M. Mizokami, P. Hu, L. A. Khawli, J. Li, A. L. Epstein, Chimeric TNT-3 antibody/murine interferon-gamma fusion protein for the immunotherapy of solid malignancies. Hybridoma and hybridomics 22, 197-207 (2003).

M. Verhaegen, T. K. Christopoulos, Recombinant Gaussia luciferase. Overexpression, purification, and analytical application of a bioluminescent reporter for DNA hybridization. Analytical chemistry 74, 4378-4385 (2002).

(Continued)

*Primary Examiner* — Shanon A. Foley

(74) *Attorney, Agent, or Firm* — Lavanya Ratnam; Kelly G. Hyndman; Joseph Hsiao

(57) ABSTRACT

Polynucleotides encoding fusion proteins comprising interferons and luciferases which have biotherapeutic, diagnostic, and quality control applications in biotechnological, medical, and veterinary fields.

33 Claims, 10 Drawing Sheets

Specification includes a Sequence Listing.

(56) References Cited

OTHER PUBLICATIONS

B. A. Tannous, D. E. Kim, J. L. Fernandez, R. Weissleder, X. O. Breakefield, Codon-optimized Gaussia luciferase cDna for mammalian gene expression in culture and in vivo. Molecular therapy : the journal of the American Society of Gene Therapy 11, 435-443 (2005).

S. B. Kim, H. Suzuki, M. Sato, H. Tao, Superluminescent variants of marine luciferases for bioassays. Analytical chemistry 83, 8732-8740 (2011).

Díaz-San Segundo F, et al. Antiviral activity of bovine type III interferon against foot-and-mouth disease virus. Virology. May 10, 2011;413(2):283-92.

Perez-Martin E, et al. Bovine type III interferon significantly delays and reduces the severity of foot-and-mouth disease in cattle. J Virol. Apr. 2012;86(8):4477-87.

Birtley JR, Curry S. Crystallization of foot-and-mouth disease virus 3C protease: surface mutagenesis and a novel crystal-optimization strategy. Acta Crystallographica Section D Biological Crystallography. 2005;61:646-650.

Birtley JR, Knox SR, Jaulent AM, Brick, P, Leatherbarrow RJ, et al. Crystal structure of foot-and-mouth disease virus 3C protease. 2005;280:11520-527.

Sweeney, TR, Roqué-Rosell N, Birtley JR, Leatherbarrow RJ, Curry S. Structural and mutagenic analysis of foot-and-mouth disease virus 3C protease reveals the role of the □-ribbon in proteolysis. J Virol. Jan. 2007;81(1):115-24. Epub Oct. 25, 2006.

Vakharia VN, Devaney MA, Moore DM, Dunn JJ, Grubman MJ. Proteolytic processing of foot-and-mouth disease virus polyproteins expressed in a cell-free system from clone-derived transcripts. Journal of virology. 1987;61:3199-207.

Mayr GA, Chinsangaram J, Grubman MJ. Development of replication-defective adenovirus serotype 5 containing the capsid and 3C protease coding regions of foot-and-mouth disease virus as a vaccine candidate. Virology. 1999;263:496-506.

Mayr GA, O'Donnell V, Chinsangaram J, Mason PW, Grubman MJ. Immune responses and protection against foot-and-mouth disease virus (FMDV) challenge in swine vaccinated with adenovirus-FMDV constructs. Vaccine. 2001;19:2152-62.

Moraes MP, Mayr GA, Mason PW, Grubman MJ. Early protection against homologous challenge after a single dose of replication-defective human adenovirus type 5 expressing capsid proteins of foot-and-mouth disease virus (FMDV) strain A24. Vaccine. 2002;20:1631-9.

Gullberg M, Muszynski B, Organtini LJ, Ashley RE, Hafenstein SL, Belsham GJ, et al. Assembly and characterization of foot-and-mouth disease virus empty capsid particles expressed within mammalian cells. The Journal of general virology. 2013;94:1769-79.

Porta C, Xu X, Loureiro S, Paramasivam S, Ren J, Ai-Khalil T, et al. Efficient production of foot-and-mouth disease virus empty capsids in insect cells following down regulation of 3C protease activity. Journal of virological methods. 2013;187:406-12.

Porta C, Kotecha A, Burman A, Jackson T, Ren J, Loureiro S, et al. Rational engineering of recombinant Picornavirus capsids to produce safe, protective vaccine antigen. PLOS Pathogens. 2013;9:e1003255.

Dus Santos MJ, Carrillo C, Ardila F, Rios RD, Franzone P, Piccone ME, et al. Development of transgenic alfalfa plants containing the foot and mouth disease virus structural polyprotein gene P1 and its utilization as an experimental immunogen. Vaccine. 2005;23:1838-43.
Grubman MJ, Zellner M, Bablanian G, Mason PW, Piccone ME. Identification of the active-site residues of the 3C proteinase of foot-and-mouth disease virus. Virology. 1995;213:581-9.
Falk MM, Grigera PR, Bergmann IE, Zibert A, Multhaup G, Beck E. Foot-and-mouth disease virus protease 3C induces specific proteolytic cleavage of host cell histone H3. Journal of virology. 1990;64:748-56.
Belsham GJ, McInerney GM, Ross-Smith N. Foot-and-mouth disease virus 3C protease induces cleavage of translation initiation factors eIF4A and eIF4G within infected cells. Journal of virology. 2000;74:272-80.
Li W, Ross-Smith N, Proud CG, Belsham GJ. Cleavage of translation initiation factor 4AI(eIF4AI) but not eIF4AII by foot-and-mouth disease virus 3C protease: identification of the eIF4AI cleavage site. FEBS letters. 2001;507:1-5.
Lawrence P, Schafer EA, Rieder E. The nuclear protein Sam68 is cleaved by the FMDV 3C protease redistributing Sam68 to the cytoplasm during FMDV infection of host cells. Virology. 2012;425:40-52.
Wang D, Fang L, Li K, Zhong H, Fan J, Ouyang C, et al. Foot-and-mouth disease virus 3C protease cleaves NEMO to impair innate immune signaling. Journal of virology. 2012;86:9311-22.
Zhou Z, Mogensen MM, Powell PP, Curry S, Wileman T. Foot-and-mouth disease virus 3C protease induces fragmentation of the Golgi compartment and blocks intra-Golgi transport. Journal of virology. 2013;87:11721-9.
Zunszain PA, Knox SR, Sweeney TR, Yang J, Roque-Rosell N, Belsham GJ, et al. Insights into cleavage specificity from the crystal structure of foot-and-mouth disease virus 3C protease complexed with a peptide substrate. Journal of molecular biology. 2010;395:375-89.
Tannous BA, Kim DE, Fernandez JL, Weissleder R, Breakefield XO. Codon-optimized Gaussia luciferase cDNA for mammalian gene expression in culture and in vivo. Mol Ther. 2005;11:435-43.
Verhaegent M, Christopoulos TK. Recombinant Gaussia luciferase. Overexpression, purification, and analytical application of a bioluminescent reporter for DNA hybridization. Anal Chem. 2002;74:4378-85.
Chung E, Yamashita H, Au P, Tannous BA, Fukumura D, Jain RK. Secreted Gaussia luciferase as a biomarker for monitoring tumor progression and treatment response of systemic metastases. PLoS One. 2009;4:e8316.
Tannous BA. Gaussia luciferase reporter assay for monitoring biological processes in culture and in vivo. Nat Protoc. 2009;4:582-91.
Wurdinger T, Badr C, Pike L, de Kleine R, Weissleder R, Breakefield XO, et al. A secreted luciferase for ex vivo monitoring of in vivo processes. Nat Methods. 2008;5:171-3.
Inoue Y, Sheng F, Kiryu S, Watanabe M, Ratanakanit H, Izawa K, et al. Gaussia luciferase for bioluminescence tumor monitoring in comparison with firefly luciferase. Mol Imaging. 2011;10:377-85.
El-Amouri SS, Cao P, Miao C, Pan D. Secreted luciferase for in vivo evaluation of systemic protein delivery in mice. Mol Biotechnol. 2012;53:63-73.
Griesenbach U, Vicente CC, Roberts MJ, Meng C, Soussi S, Xenariou S, et al. Secreted Gaussia luciferase as a sensitive reporter gene for in vivo and ex vivo studies of airway gene transfer. Biomaterials. 2011;32:2614-24.
Kim SB, Suzuki H, Sato M, Tao H. Superluminescent variants of marine luciferases for bioassays. Anal Chem. 2011;83:8732-40.
De Felipe P. Polycistronic viral vectors. Current gene therapy. 2002;2:355-78.
Ryan MD, Drew J. Foot-and-mouth disease virus 2A oligopeptide mediated cleavage of an artificial polyprotein. The EMBO journal. 1994;13:928-33.
Donnelly ML, Luke G, Mehrotra A, Li X, Hughes LE, Gani D, et al. Analysis of the aphthovirus 2A/2B polyprotein cleavage mechanism indicates not a proteolytic reaction, but a novel translational effect: a putative ribosomal 'skip'. The Journal of general virology. 2001;82:1013-25.
Minskaia E, Ryan MD. Protein coexpression using FMDV 2A: effect of "linker" residues. BioMed research international. 2013;2013:291730.
Donnelly ML, Gani D, Flint M, Monaghan S, Ryan MD. The cleavage activities of aphthovirus and cardiovirus 2A proteins. J Gen Virol. 1997;78 ( Pt 1):13-21.
Luke GA, de Felipe P, Lukashev A, Kallioinen SE, Bruno EA, Ryan MD. Occurrence, function and evolutionary origins of '2A-like' sequences in virus genomes. J Gen Virol. 2008;89:1036-42.

(56) References Cited

OTHER PUBLICATIONS

Kim JH, Lee SR, Li LH, Park HJ, Park JH, Lee KY, et al. High cleavage efficiency of a 2A peptide derived from porcine teschovirus-1 in human cell lines, zebrafish and mice. PLoS One. 2011;6:e18556.

Torres V, Barra L, Garces F, Ordenes K, Leal-Ortiz S, Garner CC, et al. A bicistronic lentiviral vector based on the 1D/2A sequence of foot-and-mouth disease virus expresses proteins stoichiometrically. Journal of biotechnology. 2010;146:138-42.

Ahier A, Jarriault S. Simultaneous expression of multiple proteins under a single promoter in Caenorhabditis elegans via a versatile 2A-based toolkit. Genetics. 2014;196:605-13.

Daniels RW, Rossano AJ, Macleod GT, Ganetzky B. Expression of multiple transgenes from a single construct using viral 2A peptides in *Drosophila*. PLoS One. 2014;9:e100637.

Unkles SE, Valiante V, Mattern DJ, Brakhage AA. Synthetic biology tools for bioprospecting of natural products in eukaryotes. Chemistry & biology. 2014;21:502-8.

Heinonen AM, Rahman M, Dogbevia G, Jakobi H, Wolfl S, Sprengel R, et al. Neuroprotection by rAAV-mediated gene transfer of bone morphogenic protein 7. BMC neuroscience. 2014;15:38.

Jung L, Tropel P, Moal Y, Teletin M, Jeandidier E, Gayon R, et al. ONSL and OSKM cocktails act synergistically in reprogramming human somatic cells into induced pluripotent stem cells. Molecular human reproduction. 2014;20:538-49.

Beekwilder J, van Rossum HM, Koopman F, Sonntag F, Buchhaupt M, Schrader J, et al. Polycistronic expression of a beta-carotene biosynthetic pathway in *Saccharomyces cerevisiae* coupled to beta-ionone production. Journal of biotechnology. 2014.

De Felipe P, Martin V, Cortes ML, Ryan M, Izquierdo M. Use of the 2A sequence from foot-and-mouth disease virus in the generation of retroviral vectors for gene therapy. Gene Ther. 1999;6:198-208.

Geu-Flores F, Olsen CE, Halkier BA. Towards engineering glucosinolates into non-cruciferous plants. Planta. 2009;229:261-70.

Carey BW, Markoulaki S, Hanna J, Saha K, Gao Q, Mitalipova M, et al. Reprogramming of murine and human somatic cells using a single polycistronic vector. Proceedings of the National Academy of Sciences of the United States of America. 2009;106:157-62.

Shao L, Feng W, Sun Y, Bai H, Liu J, Currie C, et al. Generation of iPS cells using defined factors linked via the self-cleaving 2A sequences in a single open reading frame. Cell research. 2009;19:296-306.

Mir FA, Kaufmann SH, Eddine AN. A multicistronic DNA vaccine induces significant protection against tuberculosis in mice and offers flexibility in the expressed antigen repertoire. Clinical and vaccine immunology : CVI. 2009;16:1467-75.

Rothwell DG, Crossley R, Bridgeman JS, Sheard V, Zhang Y, Sharp TV, et al. Functional expression of secreted proteins from a bicistronic retroviral cassette based on foot-and-mouth disease virus 2A can be position dependent. Human gene therapy. 2010;21:1631-7.

Breese SS, Jr., Graves JH. Electron microscopic observation of crystalline arrays of foot-and-mouth disease virus. Journal of bacteriology. 1966;92:1835-7.

Breese SS. Reactions of intracellular crystals of foot-and-mouth disease virus with ferritin-tagged antibody. J Gen Virol. 1969;4:343-6.

Kay MA, He CY, Chen ZY. A robust system for production of minicircle DNA vectors, Nature Biotechnology. 2010;28:1287-89.

Yang et al., "Crystal structure of the 3C protease from Southern African Territories type 2 foot-and-mouth disease virus", (Peer J. DOI 10.7717/peerj.1964) dated Apr. 26, 2016.

Veerapen et al., "Novel expression of immunogenic foot-and-mouth disease virus-like particles in Nicotiana benthamiana", (Virus Research, 2018; 244: 213-217).

Zunszain et al., "Insights into Cleavage Specificity from the Crystal Structure of Foot-and-Mouth Disease Virus 3C Protease Complexed with a Peptide Substrate", Journal of Molecular Biology, 395 pp. 375-389, 2010.

Sweeney et al., "Structural and Mutagenic Analysis of Foot-and-Mouth Disease Virus 3C Protease Reveals the Role of the β-Ribbon in Proteolysis", Journal of Virology, vol. 81, No. 1, pp. 115-124, Jan. 2007.

International Search Report and the Written Opinion of the International Searching Authority for PCT/US2017/048828 dated Jan. 29, 2018.

* cited by examiner

Layout of the three interferon α containing constructs created and evaluated. "sp" = secretion peptide sequence of interferon α.

Luciferase readings of constructs separated by the Δ1D2A translational interrupter and corresponding controls.

Western blots of media harvested off of cells transfected with constructs separated by the Δ1D2A translational interrupter and corresponding controls.

FIG. 3

Porcine IFN α
MAPTSAFLTALVLLSCNAICSLGCDLPQTHSLAHTRALRLLAQMRRISPFSCLDHRRDFG
SPHEAFGGNQVQKAQAMALVHEMLQQTFQLFSTEGSAAAWNESLLHQFCTGLDQQ
LRDLEACVMQEAGLEGTPLLEEDSILAVRKYFHRLTLYLQEKSYSPCAWEIVRAEVMRSF
SSSRNLQDRLRKKE Porcine IFN β
MANKCILQIALLMCFSTTALSMSYDVLRYQQRSSNLACQKLLGQLPGTPQYCLEDRMN
FEVPEEIMQPPQFQKEDAVLIIHEMLQQIFGILRRNFSSTGWNETVIKTILVELDGQMD
DLETILEEIMEEENFPRGDMTILHLKKYYLSILQYLKSKEYRSCAWTVVQVEILRNFSFLN
RLTDYLRN Bovine IFN γ
MKYTSYFLALLLCGLLGFSGSYGQGQFFREIENLKEYFNASSPDVAKGGPLFSEILKNWK
DESDKKIIQSQIVSFYFKLFENLKDNQVIQRSMDIIKQDMFQKFLNGSSEKLEDFKKLIQI
PVDDLQIQRKAINELIKVMNDLSPKSNLRKRKRSQNLFRGRRAST Bovine IFN λ
MAPGCTLVLVLMLTTVALSRTGAVPVPSAPRALPPARGCHVAQFKSLSPQELQAFKTA
RDAFEDSFLPKDWDCSTHLFPRTRDLKHLQVWERPVALEAELALTLTVLEAMANSSLG
HSLEQPLLTLQNIHSKLQACVPAQPTASSRPRGRLHHWLHRLQEARKESQDCLEASVM
FNLLRLLTRDLKCVASGDQCV Amino acid sequences for Porcine Interferon α, Porcine Interferon β, Bovine Interferon γ, and Bovine Interferon λ. Underlined letters represent the secretion domains of each interferon sequence.

FIG. 4

| | |
|---|---|
| SGlucON α | *MGVKVLFALICIAVAEAKPTENNEDFNIVAVASNFATTDLDADRGKLPGKKLPLEVLKEMEAN ARKAGCTRGCLICLSHIKCTPKMKKWLPGRCHTYEGDKESAQGGIGEAIVDIPEIPGFKDLEP MEQFIAQVDLCVDCTTGCLKGLANVQCSDLLKKWLPQRCATFASKIQGQVDKIKGAGGDGP* GCDLPQTHSLAHTRALRLLAQMRRISPFSCLDHRRDFGSPHEAFGGNQVQKAQAMALVHE MLQQTFQLFSTEGSAAAWNESLLHQFCTGLDQQLRDLEACVMQEAGLEGTPLLEEDSILAV RKYFHRLTLYLQEKSYSPCAWEIVRAEVMRSFSSSRNLQDRLRKKE |
| SGlucON β | *MGVKVLFALICIAVAEAKPTENNEDFNIVAVASNFATTDLDADRGKLPGKKLPLEVLKEMEAN ARKAGCTRGCLICLSHIKCTPKMKKWLPGRCHTYEGDKESAQGGIGEAIVDIPEIPGFKDLEP MEQFIAQVDLCVDCTTGCLKGLANVQCSDLLKKWLPQRCATFASKIQGQVDKIKGAGGDGP* MSYDVLRYQQRSSNLACQKLLGQLPGTPQYCLEDRMNFEVPEEIMQPPQFQKEDAVLIIHE MLQQIFGILRRNFSSTGWNETVIKTILVELDGQMDDLETILEEIMEEENFPRGDMTILHLKKY YLSILQYLKSKEYRSCAWTVVQVEILRNFSFLNRLTDYLRN |
| SGlucON γ | *MGVKVLFALICIAVAEAKPTENNEDFNIVAVASNFATTDLDADRGKLPGKKLPLEVLKEMEAN ARKAGCTRGCLICLSHIKCTPKMKKWLPGRCHTYEGDKESAQGGIGEAIVDIPEIPGFKDLEP MEQFIAQVDLCVDCTTGCLKGLANVQCSDLLKKWLPQRCATFASKIQGQVDKIKGAGGDGP* QGQFFREIENLKEYFNASSPDVAKGGPLFSEILKNWKDESDKKIIQSQIVSFYFKLFENLKDNQ VIQRSMDIIKQDMFQKFLNGSSEKLEDFKKLIQIPVDDLQIQRKAINELIKVMNDLSPKSNLRK RKRSQNLFRGRRAST |
| SGlucON λ | *MGVKVLFALICIAVAEAKPTENNEDFNIVAVASNFATTDLDADRGKLPGKKLPLEVLKEMEAN ARKAGCTRGCLICLSHIKCTPKMKKWLPGRCHTYEGDKESAQGGIGEAIVDIPEIPGFKDLEP MEQFIAQVDLCVDCTTGCLKGLANVQCSDLLKKWLPQRCATFASKIQGQVDKIKGAGGDGP* RTGAVPVPSAPRALPPARGCHVAQFKSLSPQELQAFKTARDAFEDSFLPKDWDCSTHLFPRT RDLKHLQVWERPVALEAELALTLTVLEAMANSSLGHSLEQPLLTLQNIHSKLQACVPAQPTAS SRPRGRLHHWLHRLQEARKESQDCLEASVMFNLLRLLTRDLKCVASGDQCV |

Amino acid sequences for SGLucON α, SGLucON β, SGLucON γ, and SGLucON λ. Italicized white letters with black background represent the *Gaussia* Luciferase amino acids.

Western blots of media harvested from transfected cells using anti-GLuc, Anti-IFN α, Anti-IFN β, and Anti-IFN λ antibodies.

Relative Luciferase Units per half second for IFN and SGLucON α, β, γ, and λ media samples.

FIG. 6

Plaque assay of IFN α, SGLuc-Δ1D2A-IFN α, IFN α-Δ1D2A-SGLuc (Δ1M), and SGLucON α activity against VSV-NJ.

FIG. 7

| Sample | Concentration of IFNα ± standard deviation (ng/ml) |
|---|---|
| IFNα | 1239 ± 86 |
| SGLuc-Δ1D2A-IFNα | 921 ± 55 |
| IFNα-Δ1D2A-SGLucΔ1M | 528 ± 72 |
| Δ1D2A-SGLucΔ1M (IFNα negative control) | <18 (limit of detection at 1:500 dilution) |
| SGLuc-Δ1D2A (IFNα negative control) | <18 (limit of detection at 1:500 dilution) |

Concentration of IFNα in harvested media from cells transfected with pTarget IFNα, pTarget SGLuc-Δ1D2A-IFNα, pTarget IFNα-Δ1D2A-SGLucΔ1M, pTarget Δ1D2A-SGLucΔ1M, and pTarget SGLuc-Δ1D2A. There were 3 replicates per each of 4 dilutions for each sample.

FIG 8.

| Sample | Concentration of IFNα in each sample (ng/ml) | | | | | |
|---|---|---|---|---|---|---|
| | 5 | 2.5 | 1.25 | 0.625 | 0.312 | 0.1525 |
| IFNα | 0 | 0 | 0 | 4.5 | 19 | 58 |
| SGLuc-Δ1D2A-IFNα | 0 | 0 | 2 | 17.5 | 53.5 | 116.5 |
| IFNα-Δ1D2A-SGLucΔ1M | 0 | 0 | 1 | 11.5 | 37 | 91.5 |
| SGLucONα | 0 | 0 | 0 | 1.5 | 9.5 | 25.5 |
| SGLuc-Δ1D2A (IFNα negative control) | 245 | 230 | 220.5 | ND | ND | ND |

Effects of IFNα on growth of Vesicular Stomatitis Virus-NJ (VSV-NJ). IFNα levels produced in growth media harvested from HEK293-T cells transfected with pTarget IFNα, pTarget SGLuc-Δ1D2A-IFNα, pTarget IFNα-Δ1D2A-SGLucΔ1M, mpTarget SGLucONα, or pTarget SGLuc-Δ1D2A (negative control) were measured and adjusted to concentrations listed before samples were exposed to MDBK cells. VSV-NJ was added to the MDBK cells and Plaque Forming Units (PFU) were counted after the growth period; average of 2 replicates are reported. ND, not determined.

FUSION PROTEIN COMPRISING *GAUSSIA* LUCIFERASE, TRANSLATION INTERRUPTER SEQUENCE, AND INTERFERON AMINO ACID SEQUENCES

CROSS-REFERENCE TO RELATED APPLICATIONS

This continuation in part (CIP) application claims priority to U.S. application Ser. No. 15/259,409, filed Sep. 8, 2016, which is incorporated by reference in its entirety.

REFERENCE TO A SEQUENCE LISTING

In accordance with 37 CFR § 1.52(e)(5), the present specification makes reference to a Sequence Listing submitted electronically as a .txt file named "500012us_ST25.txt" on May 1, 2017. The .txt file was generated on Feb. 21, 2017, and is 308 kb in size. The entire contents of the Sequence Listing are herein incorporated by reference.

BACKGROUND OF THE INVENTION

Field of the Invention

The present disclosure generally relates to fusion polynucleotides encoding fusion proteins comprising interferons and luciferases which have biotherapeutic, diagnostic, and quality control uses in both the medical and veterinary fields.

Description of the Related Art

Interferons (IFN) are a class of cytokines that interfere with viral replication. Interferons are divided into three classes, type I, type II, and type III. Type I interferons utilize the IFNAR1-IFNAR2 receptor complex and include IFN α and IFN β. Type II interferons consist of IFN γ and utilize the IFNGR1-IFNGR2 receptor complex. Type III interferons consist of IFN λ, also called interleukin-28A, interleukin-28B, and interleukin-29, the most recently discovered interferon type. Type III interferons utilize the IFNLR1-IL10Rβ receptor complex.

Type I interferons are used to treat a number of medical conditions in humans. Commercially available IFN alpha is used for the treatment of hairy cell leukemia, malignant melanoma, and AIDS-related Kaposi's sarcoma while IFN beta has been used as a treatment for relapsing-remitting and secondary-progressive forms of multiple sclerosis. In a veterinary setting IFN alpha can be used to treat Feline Herpesvirus 1, Feline infectious peritonitis, Feline Immunodeficiency Virus, Feline Leukemia Virus, and Canine papilloma virus in companion animals while in livestock both IFN α and IFN β have been found to inhibit Foot-and-Mouth Disease Virus (FMDV). Type III interferon, IFN λ, is also capable of inhibiting FMDV in cattle.

Interferons are naturally secreted, often by specialized cell types, and are comprised of a secretion peptide sequence along with an activity domain. The secretion domain is not essential for protective activity. Protective activity of interferons, and in particular IFN α, is often evaluated using Vesicular Stomatitis Virus (VSV). VSV is a member of the Rhabdoviridea family and is capable of infecting insects, cattle, horses, pigs, and under the right circumstances humans.

Hybrid peptides comprised of interferons and various molecules have been constructed and evaluated for a number of reasons. Previous work has made hybrid molecules comprised of IFN α and portions of placental growth factor-2 to enhance the anti-tumor properties of IFN α. Chimeras of interferons with different reporter molecules such as DsRed2 and GFP as well as with antibodies for immunotherapy have also been previously reported in literature.

Quantification of interferon concentrations is typically dependent upon either an activity assay or antibody based methods such as an ELISA. Measurements obtained by interferon activity assays are related to interferon concentration but not definitively related. For example, addition of placental growth factor-2 can enhance interferon activity resulting in detection of a higher interferon activity. However, this higher interferon activity is not directly related to the absolute concentration of interferon. This raises the potential that undesired and/or unknown contaminations during production can artificially influence determination of a final product concentration.

Antibody-based detection assays, such as ELISA, can be inaccurate because antibodies used to detect interferon can bind to more than one type of interferon or can exhibit different affinities for interferon under different conditions. Antibody binding affinities are dependent upon recognition of structural elements such as linear and conformational epitopes in the target substrate such as interferon. Amino acid sequence differences or conformation differences between or among interferon molecules in a sample can cause antibodies to exhibit different binding affinities. This leads to inaccuracies in determining the absolute concentration of an interferon, or a particular interferon, in a sample. As a result the usage of ELISA to determine the absolute concentrations of molecules with different amino acid sequences is not always a reliable option. Antibody-based detection assays also carry a high cost associated with the need to produce a consistent antibody amongst different production batches. The usage of antibodies also contributes to a limited shelf life.

In view of these problems, the inventors developed novel chimeric proteins that fuse a luciferase reporter with an interferon or enzyme of interest. The resulting chimeric proteins allow for easy and accurate determination of absolute concentrations for interferons and other biologically active molecules.

BRIEF SUMMARY OF THE INVENTION

The inventors disclose herein chimeric proteins fusing a *Gaussia* Luciferase (GLuc) or Super-luminescent *Gaussia* Luciferase (SGLuc) reporter to different kinds of interferons.

GLuc is a 185 amino acid naturally secreted luciferase isolated from *Gaussia princeps*. Mutations to GLuc which enhance luciferase output may include, but are not limited to, the 8990 mutant also identified as SGLuc.

GLuc and SGLuc constructs with 2A or 2A-like protein sequences such as, for example, a Δ1D2A translational interrupter, retained both luciferase activity and secretion, which make them viable biomarkers for expression in a single open reading frame.

Several types of such chimeric fusion proteins are exemplified. In one or more embodiments, three different chimeric molecules were created using IFN α sequence, as exemplified in FIG. 1. As a first example, SGLuc-Δ1D2A-IFNα is a SGLuc-Δ1D2A fused to a complete IFN α sequence on the C-terminus. This translated construct expresses two separate proteins—SGLuc-Δ1D2A and IFN α. As a second example, IFNα-Δ1D2A-SGLuc Δ1M, is a complete IFN α sequence with a Δ1D2A-SGLuc Δ1M fused on the C-terminus. This translated construct expresses two separate proteins IFNα-A1D2A and SGLuc Δ1M. As a third example, SGLucON α is a SGLuc sequence with just the activity domain of IFN α fused to the C-terminus. This translated construct expresses a single protein SGLucON α which is comprised of both SGLuc and just the activity domain of IFNα.

SGLucON α was used as a template to create three additional chimeric molecules based off of porcine IFN β, bovine IFN γ, and bovine IFN λ. For the creation of these constructs each IFN sequence was examined and the secretion domains identified, FIG. 3. Chimeric molecules were constructed by making chimeras only of SGLuc with the resulting non-secretion related amino acid sequences, FIG. 4. The resulting chimeras are identified as SGLucON β, SGLucON γ, and SGLucON λ.

Utilization of chimeric molecules of GLuc or SGLuc with interferons or a protein of interest provides a simple and fast method to substantially quantify an absolute concentration of a particular kind of interferon or protein of interest. When utilizing a construct containing the Δ1D2A translational interrupter the resulting product is two proteins and concentration is determined of the luciferase as a correlate to concentration of interferon or a protein of interest. When utilizing fused protein like SGLucON α, the concentration can be measured directly using the resulting luciferase activities of the chimeric protein.

BRIEF DESCRIPTION OF THE DRAWINGS

FIG. 1 depicts the layout of the three interferon α containing construct open reading frames.

FIG. 2A describes luciferase readings of constructs separated by the Δ1D2A translational interrupter and corresponding controls.

FIG. 2B depicts Western blots of media harvested off of cells transfected with constructs separated by the Δ1D2A translational interrupter and corresponding controls.

FIG. 3 describes amino acid sequences for Porcine Interferon α (SEQ ID NO: 24), Porcine Interferon β (SEQ ID NO: 66), Bovine Interferon γ (SEQ ID NO: 75), and Bovine Interferon λ, (SEQ ID NO: 84). Underlined residues represent the secretion domains of each interferon sequence.

FIG. 4 describes amino acid sequences for SGLucON α (SEQ ID NO: 48), SGLucON β (SEQ ID NO: 70), SGLucON γ (SEQ ID NO: 111), and SGLucON λ (SEQ ID NO: 113). Underlined residues represent the *Gaussia* Luciferase amino acids.

FIG. 5A depicts Western blots of media harvested from transfected cells using anti-GLuc, Anti-IFN α, Anti-IFN β, and Anti-IFN λ, antibodies.

FIG. 5B describes relative Luciferase Units per half second for IFN and SGLucON α, β, γ, and λ, media samples.

FIG. 6 depicts a plaque assay of IFN α, SGLuc-Δ1D2A-IFN α, IFN α-Δ1D2A-SGLuc (Δ1M), and SGLucON α activity against Vesicular Stomatitis Virus-NJ.

FIG. 7 depicts concentration of IFNα in harvested media from cells transfected with pTarget IFNα, pTarget SGLuc-Δ1D2A-IFNα, pTarget IFNα-Δ1D2A-SGLucΔ1M, pTarget Δ1D2A-SGLuc Δ1M, and pTarget SGLuc-Δ1D2A. There were 3 replicates per each of 4 dilutions for each sample.

FIG. 8 depicts effects of IFNα on growth of VSV-NJ. IFNα levels produced in growth media harvested from HEK293-T cells transfected with pTarget IFNα, pTarget SGLuc-Δ1D2A-IFNα, pTarget IFNα-Δ1D2A-SGLuc Δ1M, mpTarget SGLucONα, or pTarget SGLuc-Δ1D2A (negative control) were measured and adjusted to concentrations listed before samples were exposed to MDBK cells. VSV-NJ was added to the MDBK cells and Plaque Forming Units (PFU) were counted after the growth period; average of 2 replicates are reported. ND, not determined.

DETAILED DESCRIPTION OF THE INVENTION

Definitions

The term "fusion protein" or "chimeric protein" refers to a polypeptide containing polypeptides or segments of polypeptides from different sources, such as a segment of a luciferase from *Gaussia princeps* and a biologically active segment of an interferon. A fusion protein may be produced by joining two or more polynucleotides that originally coded for the separate proteins or protein segments into a single fusion polynucleotide. Besides the polynucleotide sequences encoding for the separate proteins, a fusion polynucleotide may comprise other polynucleotide sequences such as those encoding translation interrupter sequences or those encoding amino acid sequences which otherwise traffic or process an expressed protein. In some embodiments, the term "fusion protein" will refer to an intact fusion protein, such as a fusion between a luciferase and interferon sequence. In other embodiments, this term may refer to separate polypeptides derived from translation of a fusion polynucleotide, for example, can encompass separate polypeptides produced from a fusion construct containing a translation interrupter sequence.

Translation of the fusion polynucleotide results in a single or multiple polypeptides with functional properties derived from each of the original proteins. A single fusion protein may be expressed from a fusion polynucleotide. Such a single fusion protein may be processed into one, two or more polypeptides depending on the design of the fusion polynucleotide and the host cell expressing it. A fusion polynucleotide can express more than one polypeptide depending on its design, for example, depending on the presence of translation interrupters, stop codons, or other regulatory elements.

A polypeptide encoded by a fusion polynucleotide need not exactly correspond to all the residues of the original protein, for example, it may contain fewer or more amino acid residues than a full-length source protein, but contain an active site or functional domain of the source protein, for example, it may be a fragment of interferon that retains at least one interferon activity. A fusion polynucleotide may also be engineered to encode modified forms of a source protein, such as those having at least 70, 80, 90, 95 or 99% sequence identity or similarly with a source protein or with a functional segment thereof.

The term "fragment thereof," as applied to a polypeptide component of a fusion polypeptide described herein, refers to a polypeptide comprising any portion of the amino acid sequence of the polypeptide, wherein the fragment substantially retains at least one function of the full-length polypeptide from which it was derived. For example, a fragment of a luciferase may emit light or be processed and/or secreted in a manner similar to the full-length luciferase; a fragment of a translation interruption or interrupter sequence can retain the ability to interrupt translation, and a fragment of a biologically active molecule, such as interferon, can retain at least one physiological, pharmacodynamics, pharmacokinetic or immunological activity of the full-length molecule and/or an ability to be processed, trafficked or secreted in a way similar to the native biologically active molecule from which it was derived.

The term "derivative thereof" or "modified sequence" as applied to the polypeptide components disclosed herein, refers to a polypeptide consisting of an amino acid sequence that is at least 70, 80, 90, 95, or 99% identical or similar to the amino acid sequence of a biologically active molecule such as a luciferase, translation interruption or interrupter sequence, or interferon, wherein the polypeptide derivative substantially retains the ability to induce the secretion of a target polypeptide to which it is fused. In some embodiments, the derivative comprises an amino acid sequence that is at least 75%, 80%, 85%, 86%, 87%, 88%, 89%, 90%, 91%, 92%, 93%, 94%, 95%, 96%, 97%, 98%, or 99% identical to the amino acid sequence of a native or previously engineered sequence. The derivative may comprise additions, deletions, substitutions, post-translational modifications, chemical modifications, or a combination thereof to the amino acid sequence of a native or previously engineered molecule. A derivative may include a mutant polypeptide with 1, 2, 3, 4, 5, 6, 7, 8, 9, 10, 11-15, 16-20, 21-25, or 26-30 additions, substitutions, post-translational modifications, chemical modifications, or deletions. Additions or substitutions also include the use of non-naturally occurring amino acids or modified amino acids.

BLASTN may be used to identify a polynucleotide sequence having at least 70%, 75%, 80%, 85%, 87.5%, 90%, 92.5%, 95%, 97.5%, 98%, 99% sequence identity to a reference polynucleotide. A representative BLASTN setting optimized to find highly similar sequences uses an Expect Threshold of 10 and a Wordsize of 28, max matches in query range of 0, match/mismatch scores of 1/−2, and linear gap cost. Low complexity regions may be filtered or masked. Default settings of a Standard Nucleotide BLAST are described by and incorporated by reference to blast.ncbi.nlm.nih.gov/_Blast.cgi?PROGRAM=blastn&BLAST_PROGRAMS=megaBlast&PA GE_TYPE=BlastSearch&SHOW_DEFAULTS=on&LINK_LOC=blasthome (last accessed Feb. 4, 2016).

BLASTP can be used to identify an amino acid sequence having at least 70%, 75%, 80%, 85%, 87.5%, 90%, 92.5%, 95%, 97.5%, 98%, 99% sequence identity, or similarity to a reference amino acid using a similarity matrix such as BLOSUM45, BLOSUM62 or BLOSUM80 where BLOSUM45 can be used for closely related sequences, BLOSUM62 for midrange sequences, and BLOSUM80 for more distantly related sequences. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. A representative BLASTP setting that uses an Expect Threshold of 10, a Word Size of 3, BLOSUM 62 as a matrix, and Gap Penalty of 11 (Existence) and 1 (Extension) and a conditional compositional score matrix adjustment. Other default settings for BLASTP are described by and incorporated by reference to the disclosure available at: blast.ncbi.nlm.nih.gov/_Blast.cgi?PROGRAM= blastp&PAGE_TYPE=BlastSearch& LINK_LOC= blasthome (last accessed Jun. 29, 2016). Derivatives, analogs or modified versions of any of the polynucleotide or amino acid sequences specifically described herein or in the sequence listing having the above-mentioned ranges of sequence identity or similarly are specifically contemplated.

A "biologically active" or "active" interferon or other polypeptide of interest will exhibit at least one activity of the native molecule, such as an ability to modulate the immune system, treat an autoimmune disease, induce humoral or cellular immunity, interfere with virus replication, treat a tumor or microbial infection, contain diagnostically or immunologically useful epitopes, or any other function of the native molecule. These functions will depend on the nature of the native polypeptide of interest.

A "biotherapeutic" or a composition containing a fusion protein or cleavage product(s) of such a fusion protein, as described herein, including living cells which express or contain such a fusion protein or fusion protein fragments, may be formulated by any of the methods known in the art.

It can be typically prepared as an injectable (e.g. subcutaneous, intradermal and intramuscular injection, jet injections) or as a formulation for oral administration, intranasal administration (e.g. aerosol inhalation or instillation), topical administration to the eye, electroporation, gene gun, transfection, liposome-mediated delivery or combinations thereof, either as liquid solutions or suspensions. Solid forms suitable for solution in, or suspension in, liquid prior to injection or other administration may also be prepared. The preparation may also be emulsified or encapsulated in liposomes. Suitable excipients include but are not limited to water, saline, dextrose, glycerol, ethanol, or the like and combinations thereof. In a further embodiment, example diluents include, but are not limited to, water, physiological saline solution, human serum albumin, oils, polyethylene glycols, glycerin, propylene glycol or other synthetic solvents, antibacterial agents such as benzyl alcohol, antioxidants such as ascorbic acid or sodium bisulfite, chelating agents, such as ethylene diamine-tetra-acetic acid, buffers such as acetates, citrates or phosphates and agents for adjusting osmolarity, such as sodium chloride or dextrose. In a further embodiment, example carriers include, but are not limited to, liquid carriers (e.g., water, saline, culture medium, saline, aqueous dextrose, aqueous glycols) and solid carriers (e.g., carbohydrates such as starch, glucose, lactose, sucrose, dextrans; anti-oxidants such as ascorbic acid and glutathione, hydrolyzed proteins). In a further embodiment, pharmaceutically acceptable salts, include but are not limited to, the acid addition salts (formed with free amino groups of the peptide) which are formed with inorganic acids (e.g., hydrochloric acid or phosphoric acids) and organic acids (e.g., acetic, oxalic, tartaric, or maleic acid). Salts formed with the free carboxyl groups may also be derived from inorganic bases (e.g., sodium, potassium, ammonium, calcium, or ferric hydroxides), and organic bases (e.g., isopropylamine, trimethylamine, 2-ethylamino-ethanol, histidine, and procaine). In a further embodiment, the biotherapeutic or other compositions according to the invention may contain minor amounts of auxiliary substances such as wetting or emulsifying agents, pH buffering agents, and/or other agents, which enhance the effectiveness of the vaccine. Examples of agents which may be effective include, but are not limited to: aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetyl muramyl-L-alanyl-D-isoglutaminy 1-L-alanine-2-(1'-2'-dipalmitoyl-sn-glycero-3-hydroxyphosphoryloxy)-ethyl amine (CGP 19835A, referred to as MTP-PE); and RIBI, which contains three components extracted from bacteria: monophosphoryl lipid A, trehalose dimycolate and cell wall skeleton (MPL+ TDM+CWS) in a 2% squalene/Tween 80 emulsion.

In one or more embodiments, the biotherapeutics and compositions described herein may be administered prophylactically (e.g., to prevent or ameliorate the effects of a future infection), therapeutically (e.g., to treat or to empower the immune system of an infected subject) or both, in a manner compatible with the dosage formulation, and in such an amount and manner as will be prophylactically and/or therapeutically effective.

In an alternative embodiment, polynucleotides encoding a fusion protein according to the invention may be administered as a DNA composition which can be administered at dosages such as in the range of 0.05-3 µg/µl. Other factors that can form the basis of what dosage range to implement include but are not limited the size of the subject, the particular pathogen or disease being treated and the particular type of interferon or other biologically active molecule encoded.

A polynucleotide-based composition may be given in a single dose; two dose schedule, for example two to eight weeks apart; or a multiple dose schedule. A multiple dose schedule is one in which a primary course of administration may include 1 to 10 or more separate doses, followed by other doses administered at subsequent time intervals as required to maintain and/or reinforce the desired response on a subject's immune system.

"*Gaussia* luciferase" or "GLuc" describes luciferases produced by members of the genus *Gaussia*, amino acid sequence variants of native *Gaussia* luciferases, such as those having at least 70, 80, 90, 95, 99% sequence identity or homology to a native or previously engineered *Gaussia* luciferase or that contain 1, 2, 3, 4, 5, 6, 7, 8, 9, 10 or more amino acid deletions, substitutions or insertions to a native *Gaussia* luciferase amino acid sequence, and truncated native or variant *Gaussia* luciferases that retain luciferase activity. *Gaussia* luciferase or GLuc from *G. princeps* is commercially available (SEQ ID NO: 2). GLuc is a 185 amino acid naturally secreted luciferase isolated from *Gaussia princeps* and has a higher luminescence intensity than firefly or *Renilla* luciferases. It has been used to monitor tumor growth in vivo.

"Super-luminescent *Gaussia* luciferase" or "SGLuc" describes amino acid sequence variants of *Gaussia* luciferase containing an amino acid substitution at residues 89 and 90 of GLuc (SEQ ID NO:4) and which exhibit a higher stability than unmodified *G. princeps* luciferase in certain cell lysis buffers. This term encompasses other luciferase variants that are at least 70, 80, 90, 95, or 99% identical or similar to the GLuc or SGLuc of SEQ ID NO: 2 or 4, respectively, which exhibit substantially the same properties. The addition of 30 amino acid sequence comprising the FMDV 2A translational interrupter sequence, Δ1D2A, to the C-terminus of GLuc or the 8990 GLuc mutant (SGLuc) did not prevent either secretion or luminescence.

The luciferases described herein may be expressed in a form, or processed and expressed in a form that is capable of secretion from a host cell expressing a fusion polypeptide expressing them.

The term "interferon" includes native or previously-engineered mammalian Type I (IFN-α, IFN-β, IFN-ε, -κ, -δ, and -ζ, IFN-ω and IFN-ν), and non-mammalian interferons, such as those from birds, reptiles, amphibians, fish and other vertebrates. It also includes Type II interferon (IFN-γ) and Type III interferon (IFN-λ). Representative interferon polynucleotide or amino acids sequences are described by SEQ ID NOS: 23/24, 49/50, 53/54, 57/58, 61/62, 65/66, 71/72, 75/76, 79/80, 83/84, 87/88, or 91/92.

This term includes IFN α, β, and γ interferons, amino acid sequence variants of native interferons, such as those having at least 70, 80, 90, 95, 99% sequence identity or homology to a native or previously engineered interferon or that contain 1, 2, 3, 4, 5, 6, 7, 8, 9, 10 or more deletions, substitutions or insertions to a native or previously engineered interferon amino acid sequence, and truncated native or variant interferons that retain at least one functional activity of the native or previously-engineered interferon.

An interferon may be obtained or derived from a human or other mammal, avian, or vertebrate, including but not limited to monkeys and other primates, mice, rats, rabbits, horses, domestic dogs and other *Canidae*, domestic cats and other *Felidae*, pigs and other *Suidae*, cows and other *Bovinae*, cattle, sheep, goats, water buffalos, yaks, reindeer, deer, elk, llamas, alpacas, bison, moose, camels, chamois, giraffes, hogs, warthogs, kudus, antelopes, gazelles, and wildebeests.

The term "interferon secretion sequence" includes, but is not limited to, native amino acid sequences that facilitate secretion of interferons, such as those described by the amino acid sequences of SEQ ID NOS: 26, 28, 30, 32, 34, 36, 38, 40, 42, 44 and 46. Other interferon secretion sequences include those that are at least 70, 80, 90, 95, 99% identical or similar to a native interferon secretion sequence which facilitate secretion of interferon or other biologically active proteins. Modified interferon secretion sequences also include those with 1, 2, 3, 4, 5, 6, 7, 8, 9, 10 or more amino acid deletions, substitutions or insertions to a native sequence. Representative polynucleotides encoding these secretion sequences are described by SEQ ID NOS: 25, 27, 29, 31, 33, 35, 37, 39, 41, 43 and 45 as well as by degenerate versions of these sequences and by modified polynucleotide sequences that encode an interferon secretion sequence that is at least 70, 80, 90, 95, 99% identical or similar to a native interferon secretion sequence as described herein.

The term "biologically active" or "active" molecule includes members of the interferon family described herein, as well as other cytokines such as members of the IL-2 family (including IL-4, IL-7, IL-9, IL-15, IL-21, EPO, TPO and other molecules having a four alpha helix bundle), IL-10 family (including L-19, IL-20, IL-22, IL-24 and IL-26), IL-1 family (including IL-1 and IL-18), IL-17 family (including IL17A-IL17F) and cysteine-knot family (TNF-β1, TNF-β2, TNF-β3). It includes lymphokines, interleukins and chemokines as well as peptide hormones such as amyline, anti-mullerian hormone, adiponectin, adrenocorticotropic hormone, angiotensinogen, angiotensin, antidiuretic hormone, atrial-natriuretic peptide, brain natriuretic peptide, calcitonin, cholecystokinin, corticotropin-releasing hormone, cortistatin, enkephalin, endothelin, erythropoietin, follicle-stimulating hormone, galanin, gastric inhibitory polypeptide, gastrin, ghrelin, glucagon, glucagon-like peptide-1, gonadotropin-releasing hormone, growth hormone-releasing hormone, hepcidin, human chorionic gonadotropin, human placental lactogen, growth hormone, inhibin, insulin, insulin like growth factor, leptin, lipotropin, luteinizing hormone, melanocyte stimulating hormone, motilin, orexin, oxytocin, pancreatic polypeptide, parathyroid hormone, pituitary adenylate cyclase-activating peptide, prolactin, prolactin releasing hormone, relaxin, renin, secretin, somatostatin, thrombopoietin, thyroid-stimulating hormone, thyrotropin-releasing hormone, vasoactive intestinal peptide, guanylin, and uroguanylin. Modified versions of these native molecules are included, such as those that are at least 70, 80, 90, 95, 99% identical or similar to a native biologically active molecule and which retain at least one activity thereof as well as those having 1, 2, 3, 4, 5, 6, 7, 8, 9, 10 or more amino acid deletions, substitutions or insertions to a native sequence.

A "translation interrupter" includes 2A, Δ1D2A, or other 2A-like translational interrupters. The 2A translation interrupter is well known in the art pertaining to Foot-and-mouth Disease Virus (FMDV). Other such translational interrupters from other viruses are known. Variants of such interrupters with 1, 2, 3, 4, 5, 6, 7, 8, 9 or 10 insertions, deletions or substitutions of an amino acid residues that retain the ability to interrupt translation also may be used to process fusion proteins described herein. Non-limiting examples of translation interrupter sequences or polynucleotides encoding them are described by SEQ ID NOS: 5-14.

A "pharmaceutically acceptable carrier", "adjuvant", or "excipient" is known in the art, including, but not limited to, physiological saline, mineral oil, vegetable oils, aqueous carboxymethyl cellulose or polyvinylpyrrolidone. The skilled practitioner will recognize that such carriers should be compatible with the fusion proteins or nucleic acid constructs. Phosphate buffered saline (PBS) is one example of an acceptable carrier. The concentration and amount of the proteins or nucleic acid constructs in the final composition may vary depending upon the desired use and type of response needed, and the host animal. The fusion proteins or nucleic acid constructs should be provided in an amount effective to induce the preferred response as determined by routine testing. Appropriate adjuvants as known in the art may also be included in the formulation. Without being limited thereto, suitable adjuvants include but are not limited to mineral oil, vegetable oils, alum, Freund's incomplete adjuvant, and microparticles or nanoparticles or beads of biocompatible matrix materials such as agar or polyacrylate. Other known immunogenic agents used in conventional vaccines for a subject may also be included in the formulation as well as other therapeutic agents, such as antibacterial or antiviral drugs.

Additional non-limiting aspects and embodiments of the disclosure are described in the following enumerated paragraphs. Some embodiments are directed to compositions containing polynucleotides, these include, without limitation, the following:

1. A polynucleotide that encodes at least one fusion protein comprising at least one of *Gaussia* Luciferase (GLuc), super-luminescent *Gaussia* luciferase (SGLuc) or other luciferase which, preferably, when expressed can be secreted, and at least one interferon, cytokine, enzyme, or other polypeptide of interest. Examples of polynucleotides encoding GLuc and SGLuc include those comprising the sequences of SEQ ID NO: 1 and SEQ ID NO: 3. Representative luciferase sequences are described by SEQ ID NO: 2 and SEQ ID NO: 4, respectively. The polynucleotides encoding the luciferase may be directly adjoined to those encoding the interferon or other polypeptide of interest or may be separated from the sequences encoding the interferon or other polypeptide of interest, for example, by an intervening translation interruption or interrupter sequence. A polynucleotide sequence encoding a luciferase may replace a polynucleotide sequence encoding the N-terminal portion of an interferon or other polypeptide of interest, for example, it may replace a native secretion sequence or sequence not essential for the biological activity (or immunogenicity) of an interferon or other polypeptide of interest.

The above-mentioned polynucleotide sequence may encode fusion proteins having their various components in any order. For example, it may encode a fusion protein comprising in order from the N-terminal: a luciferase amino acid sequence (such as GLuc or SGLuc), a translation interrupter amino acid sequence (such as 2A or Δ1D2A) and a biologically active molecule amino acid sequence (such as IFN α). In this embodiment the fusion polynucleotide, upon translation, can produce two separate proteins: the first comprising the luciferase-translation interrupter and the second comprising the biologically active amino acid sequence, e.g., (SGLuc-Δ1D2A and IFN α).

This embodiment may encode a fusion protein comprising in order from the N-terminal: a biologically active molecule amino acid sequence (such as IFN α), a translation interrupter amino acid sequence (such as 2A or Δ1D2A), and a luciferase amino acid sequence (such as GLuc or SGLuc). In this embodiment, upon translation, the fusion polynucleotide can produce two separate proteins: the first comprising the luciferase and the second comprising the translation interrupter sequence and the biologically active amino acid sequence which may be expressed without an N-terminal Met residue (e.g., IFNα-Δ1D2A and SGLuc Δ1M).

This embodiment it may encode a GLucON or SGLucON sequence comprising in order from the N-terminal a luciferase amino acid sequence (such as GLuc or SGLuc) fused to an active domain of a biologically active protein, such as IFN α with its native secretion domain replaced with GLuc or SGLuc secretion sequence. No translation interrupter sequence is required for this fusion protein construct which can be transported out of a host cell intact.

2. The polynucleotide of embodiment 1, wherein the at least one fusion protein further comprises at least one promoter or other transcription regulatory element, at least one prokaryotic or eukaryotic translation initiation sequence or other translation regulatory element, at least one translational interrupter sequence, or at least one reporter gene operatively linked to, or embedded within the polynucleotide sequence encoding the at least one fusion protein.

3. The polynucleotide of embodiment 1, wherein the at least one fusion protein further comprises at least one of a 2A, Δ1D2A, or other translational interrupter sequence.

4. The polynucleotide of embodiment 1, wherein the at least one fusion protein further comprises at least one an Aphthovirus 2A, Δ1D2A, or other Aphthovirus translational interrupter sequence. Representative examples of polynucleotides encoding translation interrupter sequences include those comprising SEQ ID NOS: 5, 7, 9, 11, 13, 15, 17, 19, and 21. Representative encoded amino acid sequences are respectively described by SEQ ID NOS: 6, 8, 10, 12, 14, 16, 18, 20 and 22.

5. The polynucleotide of embodiment 1, wherein the at least one fusion protein further comprises at least one of a foot and mouth disease virus (FMDV) 2A, FMDV Δ1D2A, or other FMDV translational interrupter sequence.

6. The polynucleotide of embodiment 1, wherein the at least one fusion protein further comprises a Δ1D2A sequence engineered at the C-terminus of the at least one of *Gaussia* Luciferase (GLuc), super-luminescent *Gaussia* luciferase (SGLuc) or other luciferase.

7. The polynucleotide of embodiment 1, wherein the at least one fusion protein further comprises a Δ1D2A sequence engineered at the N-terminus of the at least one of *Gaussia* Luciferase (GLuc), super-luminescent *Gaussia* luciferase (SGLuc) or other luciferase.

8. The polynucleotide of embodiment 1, wherein the at least one fusion protein further comprises a translational interrupter sequence engineered at the C-terminus of at least one of *Gaussia* Luciferase (GLuc), super-luminescent *Gaussia* luciferase (SGLuc) or other luciferase.

9. The polynucleotide of embodiment 1, wherein the at least one fusion protein further comprises a translational interrupter sequence engineered at the N-terminus of the at least one of *Gaussia* Luciferase (GLuc), super-luminescent *Gaussia* luciferase (SGLuc) or other luciferase.

10. The polynucleotide of embodiment 1, wherein the at least one fusion protein further comprises an FMDV 2A sequence engineered at the C-terminus of at least one of *Gaussia* Luciferase (GLuc), super-luminescent *Gaussia* luciferase (SGLuc) or other luciferase.

11. The polynucleotide of embodiment 1, wherein the at least one fusion protein further comprises an FMDV 2A sequence engineered at the N-terminus of the at least one of *Gaussia* Luciferase (GLuc), super-luminescent *Gaussia* luciferase (SGLuc) or other luciferase.

12. The polynucleotide of embodiment 1, wherein the at least one of *Gaussia* Luciferase (GLuc), super-luminescent *Gaussia* luciferase (SGLuc) or other luciferase which can be secreted does not have an N-terminal methionine residue.

13. The polynucleotide of embodiment 1 that encodes at least one fusion protein comprising at least one of *Gaussia* Luciferase (GLuc), super-luminescent *Gaussia* luciferase (SGLuc) or other luciferase, and at least one interferon, cytokine, enzyme, or other polypeptide of interest. Representative, but not limited, polynucleotides may comprise one or more polynucleotide subsequences (e.g., encoding a luciferase, a secretion polypeptide, interferon or other biologically active molecule, translation terminator, translation interrupter sequence, etc.) described in the sequence listing or may comprise a fusion polynucleotide such as those described by SEQ ID NOS: 97-103 and 108-109. Modified polynucleotides, which retain the functional properties of those described herein are included, such as polynucleotides that are at least 70, 80, 90, 95, or 99% identical or similar to those of SEQ ID NOS: 97-109 and which encode functional luciferases, translational terminators, or interferons or fusions or secretable fusions thereof. The polynucleotides described herein may be incorporated into a vector, including transposons, or into a host chromosome.

Other embodiments of the invention are directed to vectors these include, without limitation, the following:

14. A vector comprising the polynucleotide of embodiment 1 which encodes at least one fusion protein comprising at least one of *Gaussia* Luciferase (GLuc), super-luminescent *Gaussia* luciferase (SGLuc) or other luciferase, preferably, in a form which can be secreted, and at least one interferon, cytokine, enzyme, or other polypeptide of interest.

15. The vector of embodiment 14, wherein the polynucleotide encoding the at least one fusion protein further comprises at least one promoter or other transcription regulatory element, at least one prokaryotic or eukaryotic translation initiation sequence or other translation regulatory element, at least one translational interrupter sequence, or at least one reporter gene operatively linked to, or embedded within, the polynucleotide sequence encoding the at least one fusion protein.

16. The vector of embodiment 14, wherein the at least one fusion protein further comprises at least one of a 2A, Δ1D2A, or other translational interrupter sequence.

17. The vector of embodiment 14, wherein the at least one fusion protein further comprises at least one an Aphthovirus 2A, Δ1D2A, or other Aphthovirus translational interrupter sequence.

18. The vector of embodiment 14, wherein the at least one fusion protein further comprises at least one of a foot and mouth disease virus (FMDV) 2A, FMDV Δ1D2A, or other FMDV translational interrupter sequence.

19. The vector of embodiment 14, wherein the at least one fusion protein further comprises a Δ1D2A sequence engineered at the C-terminus of the at least one of *Gaussia* Luciferase (GLuc), super-luminescent *Gaussia* luciferase (SGLuc) or other luciferase which can be secreted.

20. The vector of embodiment 14, wherein the at least one fusion protein further comprises a Δ1D2A sequence engineered at the N-terminus of the at least one of *Gaussia* Luciferase (GLuc), super-luminescent *Gaussia* luciferase (SGLuc) or other luciferase which can be secreted.

21. The vector of embodiment 14, wherein the at least one fusion protein further comprises a translational interrupter sequence engineered at the C-terminus of the at least one of *Gaussia* Luciferase (GLuc), super-luminescent *Gaussia* luciferase (SGLuc) or other luciferase which can be secreted.

22. The vector of embodiment 14, wherein the at least one fusion protein further comprises a translational interrupter sequence engineered at the N-terminus of the at least one of *Gaussia* Luciferase (GLuc), super-luminescent *Gaussia* luciferase (SGLuc) or other luciferase which can be secreted.

23. The vector of embodiment 14, wherein the at least one fusion protein further comprises an FMDV 2A sequence engineered at the C-terminus of at least one of *Gaussia* Luciferase (GLuc), super-luminescent *Gaussia* luciferase (SGLuc) or other luciferase which can be secreted.

24. The vector of embodiment 14, wherein the at least one fusion protein further comprises an FMDV 2A sequence engineered at the N-terminus of the at least one of *Gaussia* Luciferase (GLuc), super-luminescent *Gaussia* luciferase (SGLuc) or other luciferase which can be secreted.

25. The vector of embodiment 14, wherein the at least one of *Gaussia* Luciferase (GLuc), super-luminescent *Gaussia* luciferase (SGLuc) or other luciferase which can be secreted does not have an N-terminal methionine residue.

26. The vector of embodiment 14 that expresses the at least one engineered polypeptide of interest in a eukaryotic cell.

27. The vector of embodiment 14 that expresses the at least one engineered polypeptide of interest in a yeast cell.

28. The vector of embodiment 14 that expresses the at least one engineered polypeptide of interest in a fungus cell.

29. The vector of embodiment 14 that expresses the at least one engineered polypeptide of interest in an insect cell.

30. The vector of embodiment 14 that expresses the at least one engineered polypeptide of interest in a vertebrate cell.

31. The vector of embodiment 14 that expresses the at least one engineered polypeptide of interest in a mammalian cell.

32. The vector of embodiment 14 that expresses the at least one engineered polypeptide of interest in a prokaryotic cell.

33. The vector of embodiment 14 that expresses the at least one engineered polypeptide of interest in a gram-positive prokaryote.

34. The vector of embodiment 14 that expresses the at least one engineered polypeptide of interest in a gram-negative prokaryote.

35. The vector of embodiment 14 that is a minicircle vector, a replication deficient adenovirus vector, a vaccinia virus vector, or other viral vector that expresses the at least one fusion protein comprising at least one of *Gaussia* Luciferase (GLuc), super-luminescent *Gaussia* luciferase (SGLuc) or other luciferase which can be secreted, and at least one interferon, cytokine, enzyme or other polypeptide of interest.

36. The vector of embodiment 14, further comprising a polynucleotide described by any of embodiments 1-13. A vector includes episomes, plasmids, phage sequences, viral sequences, transposons, and other polynucleotide constructs that can transform a host cell or be expressed by a host cell.

Other embodiments of the invention are directed to host cells, these include, without limitation, the following:

37. A host cell comprising a vector of embodiment 14, wherein the host cell expresses the at least one fusion protein comprising at least one of *Gaussia* Luciferase (GLuc), super-luminescent *Gaussia* luciferase (SGLuc) or other luciferase preferably in a form which can be secreted, and at least one interferon, cytokine, enzyme or other polypeptide of interest.

38. The host cell of embodiment 37, wherein the vector comprises at least one promoter or other transcription regulatory element, at least one prokaryotic or eukaryotic translation initiation sequence or other translation regulatory element, at least one translational interrupter sequence, or at least one reporter gene operatively linked to, or embedded within, the polynucleotide sequence encoding the at least one fusion protein.

39. The host cell of embodiment 37, wherein the at least one fusion protein further comprises at least one of a 2A, Δ1D2A, or other translational interrupter sequence.

40. The host cell of embodiment 37, wherein the at least one fusion protein further comprises at least one of an Aphthovirus 2A, Δ1D2A, or other Aphthovirus translational interrupter sequence.

41. The host cell of embodiment 37 wherein the at least one fusion protein further comprises at least one of a foot and mouth disease virus (FMDV) 2A, FMDV Δ1D2A, or other FMDV translational interrupter sequence.

42. The host cell of embodiment 37, wherein the at least one fusion protein further comprises a Δ1D2A sequence engineered at the C-terminus of the at least one of *Gaussia* Luciferase (GLuc), super-luminescent *Gaussia* luciferase (SGLuc) or other luciferase which can be secreted.

43. The host cell of embodiment 37, wherein the at least one fusion protein further comprises a Δ1D2A sequence engineered at the N-terminus of the at least one of *Gaussia* Luciferase (GLuc), super-luminescent *Gaussia* luciferase (SGLuc) or other luciferase which can be secreted.

44. The host cell of embodiment 37, wherein the at least one fusion protein further comprises a translational interrupter sequence engineered at the C-terminus of the at least one of *Gaussia* Luciferase (GLuc), super-luminescent *Gaussia* luciferase (SGLuc) or other luciferase which can be secreted.

45. The host cell of embodiment 37, wherein the at least one fusion protein further comprises a translational interrupter sequence engineered at the N-terminus of the at least one of *Gaussia* Luciferase (GLuc), super-luminescent *Gaussia* luciferase (SGLuc) or other luciferase which can be secreted.

46. The host cell of embodiment 37, wherein the at least one fusion protein further comprises an FMDV 2A sequence engineered at the C-terminus of the at least one of *Gaussia* Luciferase (GLuc), super-luminescent *Gaussia* luciferase (SGLuc) or other luciferase which can be secreted.

47. The host cell of embodiment 37, wherein the at least one fusion protein further comprises an FMDV 2A sequence engineered at the N-terminus of the at least one of *Gaussia* Luciferase (GLuc), super-luminescent *Gaussia* luciferase (SGLuc) or other luciferase which can be secreted.

48. The host cell of embodiment 37, wherein the at least one of *Gaussia* Luciferase (GLuc), super-luminescent *Gaussia* luciferase (SGLuc) or other luciferase which can be secreted does not have an N-terminal methionine residue.

49. The host cell of embodiment 37 that is a eukaryotic cell.

50. The host cell of embodiment 37 that is a yeast cell.

51. The host cell of embodiment 37 that is a fungus cell.

52. The host cell of embodiment 37 that is an insect cell.

53. The host cell of embodiment 37 that is a vertebrate cell.

54. The host cell of embodiment 37 that is mammalian cell.

55. The host cell of embodiment 37 that is a prokaryotic cell.

56. The host cell of embodiment 37 that is a gram-positive prokaryote.

57. The host cell of embodiment 37 that is a gram-negative prokaryote.

58. The host cell of embodiment 37, wherein the vector is a minicircle vector, a replication deficient adenovirus vector, a vaccinia virus vector, or other viral vector that expresses the at least one fusion protein comprising at least one of *Gaussia* Luciferase (GLuc), super-luminescent *Gaussia* luciferase (SGLuc) or other luciferase which can be secreted, and at least one interferon, cytokine, enzyme or other polypeptide of interest.

59. The host cell of embodiment 37, wherein the vector further comprises a polynucleotide selected from the group of polynucleotide sequences or vectors described by embodiments 1-36.

Other embodiments of the invention are directed to polypeptides or fusion proteins these include, without limitation, the following:

60. A fusion protein comprising at least one of *Gaussia* Luciferase (GLuc), super-luminescent *Gaussia* luciferase (SGLuc) or other luciferase, preferably in a form which can be secreted, and at least one interferon, cytokine, enzyme or other polypeptide of interest. The fusion protein may be expressed intact with the luciferase and polypeptide of interest fused together, or may be expressed, for example, via translation interruption, where the fusion protein is separated into at least two polypeptide components.

61. The fusion protein of embodiment 60, which is encoded by a polynucleotide or vector further comprising at least one promoter or other transcription regulatory element, at least one prokaryotic or eukaryotic translation initiation sequence or other translation regulatory element, at least one translational interrupter sequence, or at least one reporter gene operatively linked to, or embedded within, the polynucleotide sequence encoding the fusion protein.

62. The fusion protein of embodiment 60, further comprising at least one of a 2A, Δ1D2A, or other translational interrupter sequence.

63. The fusion protein of embodiment 60, further comprising at least one of an Aphthovirus 2A, Δ1D2A, or other Aphthovirus translational interrupter sequence.

64. The fusion protein of embodiment 60, further comprising at least one of a foot and mouth disease virus (FMDV) 2A, FMDV Δ1D2A, or other FMDV translational interrupter sequence.

65. The fusion protein of embodiment 60, further comprising a Δ1D2A sequence engineered at the C-terminus of the at least one of *Gaussia* Luciferase (GLuc), super-luminescent *Gaussia* luciferase (SGLuc) or other luciferase which can be secreted.

66. The fusion protein of embodiment 60, further comprising a Δ1D2A sequence engineered at the N-terminus of the at least one of *Gaussia* Luciferase (GLuc), super-luminescent *Gaussia* luciferase (SGLuc) or other luciferase which can be secreted.

67. The fusion protein of embodiment 60, further comprising a translator interrupter sequence engineered at the N-terminus of the at least one of *Gaussia* Luciferase (GLuc), super-luminescent *Gaussia* luciferase (SGLuc) or other luciferase which can be secreted.

68. The fusion protein of embodiment 60, further comprising a translator interrupter sequence engineered at the C-terminus of the at least one of *Gaussia* Luciferase (GLuc), super-luminescent *Gaussia* luciferase (SGLuc) or other luciferase which can be secreted.

69. The fusion protein of embodiment 60, further comprising an FMDV 2A sequence engineered at the N-terminus of the at least one of *Gaussia* Luciferase (GLuc), super-luminescent *Gaussia* luciferase (SGLuc) or other luciferase which can be secreted.

70. The fusion protein of embodiment 60, further comprising an FMDV 2A sequence engineered at the C-terminus of the at least one of *Gaussia* Luciferase (GLuc), super-luminescent *Gaussia* luciferase (SGLuc) or other luciferase which can be secreted.

71. The fusion protein of embodiment 60, wherein the at least one of *Gaussia* Luciferase (GLuc), super-luminescent *Gaussia* luciferase (SGLuc) or other luciferase which can be secreted does not have an N-terminal methionine residue.

72. The fusion protein of embodiment 60 that encoded by any of the polynucleotide or vector embodiments 1-36 or which expressed by the host cells of any of embodiments 37-59.

Other embodiments of the invention are directed to vaccines, these include, without limitation, the following:

73. An antigen, immunogen, or vaccine comprising the fusion protein of embodiment 60 and a suitable carrier, excipient or adjuvant.

74. An antigen, immunogen, or vaccine comprising the fusion protein of embodiment 61 and a suitable carrier, excipient or adjuvant.

75. An antigen, immunogen, or vaccine comprising the fusion protein of embodiment 62 and a suitable carrier, excipient or adjuvant.

76. An antigen, immunogen, or vaccine comprising the fusion protein of embodiment 63 and a suitable carrier, excipient or adjuvant.

77. An antigen, immunogen, or vaccine comprising the fusion protein of embodiment 64 and a suitable carrier, excipient or adjuvant.

78. An antigen, immunogen, or vaccine comprising the fusion protein of embodiment 65 and a suitable carrier, excipient or adjuvant.

79. An antigen, immunogen, or vaccine comprising the fusion protein of embodiment 66 and a suitable carrier, excipient or adjuvant.

80. An antigen, immunogen, or vaccine comprising the fusion protein of embodiment 67 and a suitable carrier, excipient or adjuvant.

81. An antigen, immunogen, or vaccine comprising the fusion protein of embodiment 68 and a suitable carrier, excipient or adjuvant.

82. An antigen, immunogen, or vaccine comprising the fusion protein of embodiment 69 and a suitable carrier, excipient or adjuvant.

83. An antigen, immunogen, or vaccine comprising the fusion protein of embodiment 70 and a suitable carrier, excipient or adjuvant.

84. An antigen, immunogen, or vaccine comprising the fusion protein of embodiment 71 and a suitable carrier, excipient or adjuvant.

85. An antigen, immunogen, or vaccine comprising the fusion protein of embodiment 72 and a suitable carrier, excipient or adjuvant.

The antigen, immunogen or vaccine described above may comprise an intact fusion protein or may be in the form of one or more immunologically active fragments of such a fusion protein. Suitable carriers, excipients or adjuvants are known in the art and are described elsewhere herein.

Other embodiments of the invention include a method of making fusion protein and include, without limitation, the following:

86. A method for making, expressing and/or processing a fusion protein comprising at least one of *Gaussia* Luciferase (GLuc), super-luminescent *Gaussia* luciferase (SGLuc) or other luciferase, preferably in a form which can be secreted, and at least one interferon, cytokine, enzyme or other polypeptide of interest, comprising culturing the host cell according to embodiment 37 in a suitable medium and recovering the fusion protein.

87. A method for expressing and processing a fusion protein comprising at least one of *Gaussia* Luciferase (GLuc), super-luminescent *Gaussia* luciferase (SGLuc) or other luciferase, preferably in a form which can be secreted, and at least one interferon, cytokine, enzyme or other polypeptide of interest, comprising culturing the host cell according to embodiment 38 in a suitable medium and recovering the fusion protein.

88. A method for expressing and processing a fusion protein comprising at least one of *Gaussia* Luciferase (GLuc), super-luminescent *Gaussia* luciferase (SGLuc) or other luciferase preferably in a form which can be secreted, and at least one interferon, cytokine, enzyme or other polypeptide of interest, comprising culturing the host cell according to embodiment 39 in a suitable medium and recovering the fusion protein.

89. A method for expressing and processing a fusion protein comprising at least one of *Gaussia* Luciferase (GLuc), super-luminescent *Gaussia* luciferase (SGLuc) or other luciferase preferably in a form which can be secreted, and at least one interferon, cytokine, enzyme or other polypeptide of interest, comprising culturing the host cell according to embodiment 40 in a suitable medium and recovering the fusion protein.

90. A method for expressing and processing a fusion protein comprising at least one of *Gaussia* Luciferase (GLuc), super-luminescent *Gaussia* luciferase (SGLuc) or other luciferase preferably in a form which can be secreted, and at least one interferon, cytokine, enzyme or other polypeptide of interest, comprising culturing the host cell according to embodiment 41 in a suitable medium and recovering the fusion protein.

91. A method for expressing and processing a fusion protein comprising at least one of *Gaussia* Luciferase (GLuc), super-luminescent *Gaussia* luciferase (SGLuc) or other luciferase preferably in a form which can be secreted, and at least one interferon, cytokine, enzyme or other polypeptide of interest, comprising culturing the host cell according to embodiment 42 in a suitable medium and recovering the fusion protein.

92. A method for expressing and processing a fusion protein comprising at least one of *Gaussia* Luciferase (GLuc), super-luminescent *Gaussia* luciferase (SGLuc) or other luciferase preferably in a form which can be secreted, and at least one interferon, cytokine, enzyme or other polypeptide of interest, comprising culturing the host cell according to embodiment 43 in a suitable medium and recovering the fusion protein.

93. A method for expressing and processing a fusion protein comprising at least one of *Gaussia* Luciferase (GLuc), super-luminescent *Gaussia* luciferase (SGLuc) or other luciferase preferably in a form which can be secreted, and at least one interferon, cytokine, enzyme or other polypeptide of interest, comprising culturing the host cell according to embodiment 44 in a suitable medium and recovering the fusion protein.

94. A method for expressing and processing a fusion protein comprising at least one of *Gaussia* Luciferase (GLuc), super-luminescent *Gaussia* luciferase (SGLuc) or other luciferase preferably in a form which can be secreted, and at least one interferon, cytokine, enzyme or other polypeptide of interest, comprising culturing the host cell according to embodiment 45 in a suitable medium and recovering the fusion protein.

95. A method for expressing and processing a fusion protein comprising at least one of *Gaussia* Luciferase (GLuc), super-luminescent *Gaussia* luciferase (SGLuc) or other luciferase preferably in a form which can be secreted, and at least one interferon, cytokine, enzyme or other polypeptide of interest, comprising culturing the host cell according to embodiment 46 in a suitable medium and recovering the fusion protein.

96. A method for expressing and processing a fusion protein comprising at least one of *Gaussia* Luciferase (GLuc), super-luminescent *Gaussia* luciferase (SGLuc) or other luciferase preferably in a form which can be secreted, and at least one interferon, cytokine, enzyme or other polypeptide of interest, comprising culturing the host cell according to embodiment 47 in a suitable medium and recovering the fusion protein.

97. A method for expressing and processing a fusion protein comprising at least one of *Gaussia* Luciferase (GLuc), super-luminescent *Gaussia* luciferase (SGLuc) or other luciferase preferably in a form which can be secreted, and at least one interferon, cytokine, enzyme or other polypeptide of interest, comprising culturing the host cell according to any of embodiments 48-57 in a suitable medium and recovering the fusion protein.

98. A method for expressing and processing a fusion protein comprising at least one of *Gaussia* Luciferase (GLuc), super-luminescent *Gaussia* luciferase (SGLuc) or other luciferase preferably in a form which can be secreted, and at least one interferon, cytokine, enzyme or other polypeptide of interest, comprising culturing the host cell according to embodiment 58 in a suitable medium and recovering the fusion protein.

99. A method for expressing and processing a fusion protein comprising at least one of *Gaussia* Luciferase (GLuc), super-luminescent *Gaussia* luciferase (SGLuc) or other luciferase preferably in a form which can be secreted, and at least one interferon, cytokine, enzyme or other polypeptide of interest, comprising culturing the host cell according to embodiment 59 in a suitable medium and recovering the fusion protein.

In preferred embodiments of the method described above, the luciferase will be one that can be expressed and exported from the cell. Prior to export or secretion from the cell, it may be processed, for example, by action of a translation interruption sequence, to separate it from other sequences encoded by a fusion polynucleotide. Alternatively, if may be exported or secreted as part of a fusion polypeptide.

Other embodiments of the invention include a method for quantifying an amount of interferon, cytokine, enzyme or other polypeptide of interest and include, without limitation, the following:

100. A method for quantifying an amount of an interferon, cytokine, enzyme or other polypeptide of interest produced in an expression system comprising:
    providing the vector according to embodiment 14;
    transforming the vector into a host cell;
    culturing the cells in a medium;
    harvesting the medium; and
    quantifying the intensity of luminescent output in the harvested medium, thus quantifying the amount of the interferon, cytokine, enzyme or other polypeptide of interest produced in an expression system.

101. A method for quantifying an amount of an interferon, cytokine, enzyme or other polypeptide of interest produced in an expression system comprising:
    providing the vector according to embodiment 15;
    transforming the vector into a host cell;
    culturing the cells in a medium;
    harvesting the medium; and
    quantifying the intensity of luminescent output in the harvested medium, thus quantifying the amount of the interferon, cytokine, enzyme or other polypeptide of interest produced in an expression system.

102. A method for quantifying an amount of an interferon, cytokine, enzyme or other polypeptide of interest produced in an expression system comprising:
    providing the vector according to embodiment 16;
    transforming the vector into a host cell;
    culturing the cells in a medium;
    harvesting the medium; and
    quantifying the intensity of luminescent output in the harvested medium, thus quantifying the amount of the interferon, cytokine, enzyme or other polypeptide of interest produced in an expression system.

103. A method for quantifying an amount of an interferon, cytokine, enzyme or other polypeptide of interest produced in an expression system comprising:
    providing the vector according to embodiment 17;
    transforming the vector into a host cell;
    culturing the cells in a medium;
    harvesting the medium; and
    quantifying the intensity of luminescent output in the harvested medium, thus quantifying the amount of the interferon, cytokine, enzyme or other polypeptide of interest produced in an expression system.

104. A method for quantifying an amount of an interferon, cytokine, enzyme or other polypeptide of interest produced in an expression system comprising:
    providing the vector according to embodiment 18;
    transforming the vector into a host cell;
    culturing the cells in a medium;
    harvesting the medium; and
    quantifying the intensity of luminescent output in the harvested medium, thus quantifying the amount of the interferon, cytokine, enzyme or other polypeptide of interest produced in an expression system.

105. A method for quantifying an amount of an interferon, cytokine, enzyme or other polypeptide of interest produced in an expression system comprising:
    providing the vector according to embodiment 19;
    transforming the vector into a host cell;
    culturing the cells in a medium;
    harvesting the medium; and
    quantifying the intensity of luminescent output in the harvested medium, thus quantifying the amount of the interferon, cytokine, enzyme or other polypeptide of interest produced in an expression system.

106. A method for quantifying an amount of an interferon, cytokine, enzyme or other polypeptide of interest produced in an expression system comprising:
    providing the vector according to embodiment 20;
    transforming the vector into a host cell;
    culturing the cells in a medium;
    harvesting the medium; and
    quantifying the intensity of luminescent output in the harvested medium, thus quantifying the amount of the interferon, cytokine, enzyme or other polypeptide of interest produced in an expression system.

107. A method for quantifying an amount of an interferon, cytokine, enzyme or other polypeptide of interest produced in an expression system comprising:
    providing the vector according to embodiment 21;
    transforming the vector into a host cell;
    culturing the cells in a medium;
    harvesting the medium; and
    quantifying the intensity of luminescent output in the harvested medium, thus quantifying the amount of the interferon, cytokine, enzyme or other polypeptide of interest produced in an expression system.

108. A method for quantifying an amount of an interferon, cytokine, enzyme or other polypeptide of interest produced in an expression system comprising:
    providing the vector according to embodiment 22;
    transforming the vector into a host cell;
    culturing the cells in a medium;
    harvesting the medium; and
    quantifying the intensity of luminescent output.

109. A method for quantifying an amount of an interferon, cytokine, enzyme or other polypeptide of interest produced in an expression system comprising:
    providing the vector according to embodiment 23;
    transforming the vector into a host cell;
    culturing the cells in a medium;
    harvesting the medium; and
    quantifying the intensity of luminescent output in the harvested medium, thus quantifying the amount of the interferon, cytokine, enzyme or other polypeptide of interest produced in an expression system.

110. A method for quantifying an amount of an interferon, cytokine, enzyme or other polypeptide of interest produced in an expression system comprising:
    providing the vector according to embodiment 24;
    transforming the vector into a host cell;
    culturing the cells in a medium;
    harvesting the medium; and
    quantifying the intensity of luminescent output in the harvested medium, thus quantifying the amount of the interferon, cytokine, enzyme or other polypeptide of interest produced in an expression system.

111. A method for quantifying an amount of an interferon, cytokine, enzyme or other polypeptide of interest produced in an expression system comprising:
    providing the vector according to embodiment 25;
    transforming the vector into a host cell;
    culturing the cells in a medium;
    harvesting the medium; and
    quantifying the intensity of luminescent output in the harvested medium, thus quantifying the amount of the interferon, cytokine, enzyme or other polypeptide of interest produced in an expression system.

112. A method for quantifying an amount of an interferon, cytokine, enzyme or other polypeptide of interest produced in an expression system comprising:
    providing the vector according to embodiment 35;
    transforming the vector into a host cell;
    culturing the cells in a medium;
    harvesting the medium; and
    quantifying the intensity of luminescent output in the harvested medium, thus quantifying the amount of the interferon, cytokine, enzyme or other polypeptide of interest produced in an expression system.

113. A method for quantifying an amount of an interferon, cytokine, enzyme or other polypeptide of interest produced in an expression system comprising:
    providing the vector according to embodiment 36;
    transforming the vector into a host cell;
    culturing the cells in a medium;
    harvesting the medium; and
    quantifying the intensity of luminescent output in the harvested medium, thus quantifying the amount of the interferon, cytokine, enzyme or other polypeptide of interest produced in an expression system.

In the methods described above the intensity of the luminescent output in the harvested medium is usually measured. This luminescent output may be correlated to the amount of luciferase or fusion protein containing luciferase in the medium and used to quantify expression or activity of a biological molecule. However, in some embodiments, the luminescent intensity of cells separated from the harvested medium may be measured, or measurements may be taken for a combination of both cells and medium or for each separately. In other embodiments, the harvested medium or cells may be further processed, diluted, or purified prior to detection of luminescence. This method may be practiced in conjunction with conventional methods for determining the presence, activity or quantity of a biologically active molecule, such as antibody-based methods, as described herein. Luminescence may be detected or quantified by equipment or methods known in the art, for example, spectrophotometrically.

Other embodiments of the invention include a method for quantifying a concentration of interferon, cytokine, enzyme or other polypeptide of interest and include, without limitation, the following:

114. A method for quantifying a concentration of an interferon, cytokine, enzyme or other polypeptide of interest produced in an expression system comprising:
    providing the vector according to embodiment 14;
    transforming the vector into a host cell;
    culturing the cells in a medium;
    harvesting the medium; and
    quantifying the intensity of luminescent output in the harvested medium, thus quantifying the concentration of the interferon, cytokine, enzyme or other polypeptide of interest produced in an expression system.

115. A method for quantifying a concentration of an interferon, cytokine, enzyme or other polypeptide of interest produced in an expression system comprising:
    providing the vector according to embodiment 15,
    transforming the vector into a host cell;

culturing the cells in a medium;
harvesting the medium; and
quantifying the intensity of luminescent output in the harvested medium, thus quantifying the concentration of the interferon, cytokine, enzyme or other polypeptide of interest produced in an expression system.

116. A method for quantifying a concentration of an interferon, cytokine, enzyme produced in an expression system comprising:
providing the vector according to embodiment 16,
transforming the vector into a host cell;
culturing the cells in a medium;
harvesting the medium; and
quantifying the intensity of luminescent output in the harvested medium, thus quantifying the concentration of the interferon, cytokine, enzyme or other polypeptide of interest produced in an expression system.

117. A method for quantifying a concentration of an interferon, cytokine, enzyme or other polypeptide of interest produced in an expression system comprising:
providing the vector according to any one embodiments 17-36,
transforming the vector into a host cell;
culturing the cells in a medium;
harvesting the medium; and
quantifying the intensity of luminescent output.

In the methods described above the intensity of the luminescent output in the harvested medium is usually measured. This luminescent output may be correlated to the concentration of luciferase or fusion protein containing luciferase in the medium and used to quantify expression or activity of a biological molecule. However, in some embodiments, the luminescent intensity of cells separated from the harvested medium may be measured, or measurements may be taken for a combination of both cells and medium or for each separately. In other embodiments, the harvested medium or cells may be further processed, diluted, or purified prior to detection of luminescence. This method may be practiced in conjunction with conventional methods for determining the presence, activity or quantity of a biologically active molecule, such as antibody-based methods, as described herein. Luminescence may be detected or quantified by equipment or methods known in the art, for example, spectrophotometrically.

Other embodiments of the invention include a method for facilitating secretion of a fusion protein and include, without limitation, the following:

118. A method for facilitating secretion of a fusion protein from a host cell comprising:
providing the vector according to embodiment 14;
transforming the vector into a host cell;
culturing the cells in a medium; and
recovering the secretable fusion protein from the medium.

119. A method for facilitating secretion of a fusion protein from a host cell comprising:
providing the vector according to embodiment 15;
transforming the vector into a host cell;
culturing the cells in a medium; and
recovering the secretable fusion protein from the medium.

120. A method for facilitating secretion of a fusion protein from a host cell comprising:
providing the vector according to embodiment 16;
transforming the vector into a host cell;
culturing the cells in a medium; and
recovering the secretable fusion protein from the medium.

121. A method for facilitating secretion of a fusion protein from a host cell comprising:
providing the vector according to embodiment 17;
transforming the vector into a host cell;
culturing the cells in a medium; and
recovering the secretable fusion protein from the medium.

122. A method for facilitating secretion of a fusion protein from a host cell comprising:
providing the vector according to embodiment 18;
transforming the vector into a host cell;
culturing the cells in a medium; and
recovering the secretable fusion protein from the medium.

123. A method for facilitating secretion of a fusion protein from a host cell comprising:
providing the vector according to embodiment 19;
transforming the vector into a host cell;
culturing the cells in a medium; and
recovering the secretable fusion protein from the medium.

124. A method for facilitating secretion of a fusion protein from a host cell comprising:
providing the vector according to embodiment 20;
transforming the vector into a host cell;
culturing the cells in a medium; and
recovering the secretable fusion protein from the medium.

125. A method for facilitating secretion of a fusion protein from a host cell comprising:
providing the vector according to embodiment 21;
transforming the vector into a host cell;
culturing the cells in a medium; and
recovering the secretable fusion protein from the medium.

126. A method for facilitating secretion of a fusion protein from a host cell comprising:
providing the vector according to embodiment 22;
transforming the vector into a host cell;
culturing the cells in a medium; and
recovering the secretable fusion protein from the medium.

127. A method for facilitating secretion of a fusion protein from a host cell comprising:
providing the vector according to embodiment 23;
transforming the vector into a host cell;
culturing the cells in a medium; and
recovering the secretable fusion protein from the medium.

128. A method for facilitating secretion of a fusion protein from a host cell comprising:
providing the vector according to embodiment 24;
transforming the vector into a host cell;
culturing the cells in a medium; and
recovering the secretable fusion protein from the medium.

129. A method for facilitating secretion of a fusion protein from a host cell comprising:
providing the vector according to any one of embodiments 25-34;
transforming the vector into a host cell;
culturing the cells in a medium; and
recovering the secretable fusion protein from the medium.

130. A method for facilitating secretion of a fusion protein from a host cell comprising:
providing the vector according to embodiment 35;
transforming the vector into a host cell;
culturing the cells in a medium; and
recovering the secretable fusion protein from the medium.

131. A method for facilitating secretion of a fusion protein from a host cell comprising:
providing the vector according to embodiment 36;
transforming the vector into a host cell;
culturing the cells in a medium; and
recovering the secretable fusion protein from the medium.

Recovery of a fusion protein includes concentration, purification, and/or isolation from other polypeptide components or nonpolypeptide components of a medium, cells or cell lysate. Examples of recovery methods include chromatographic isolation or separation of a fusion protein, affinity purification using antibodies or ligands that bind to epitopes of tags in a target fusion protein, PAGE, isoelectric focusing, or dialysis and concentration. A recovered fusion protein may be purified to homogeneity or to represent 10, 20, 30, 40, 50, 60, 70, 80, 90, 95, 99% by mass of the protein content (or the solid, nonaqueous content) in a recovered fusion protein composition.

Other embodiments of the invention include a method for measuring an amount of a biotherapeutic peptide in a subject and include, without limitation, the following:

132. A method for measuring an amount of a biotherapeutic peptide (or biotherapeutic polypeptide) in a subject in need thereof comprising:
 providing the vector according to embodiment 14;
 transforming the vector into the subject;
 recovering from the subject a sample of biological material, such as blood, serum, plasma, CSF, or urine, containing a fusion protein comprising a biotherapeutic peptide and a luciferase, or a luciferase expressed by the vector; and
 detecting or quantifying the intensity of luminescent output in the sample thereby determining an amount of a biotherapeutic peptide in the subject.

133. A method for measuring an amount of a biotherapeutic peptide in a subject in need thereof comprising:
 providing the vector according to embodiment 15;
 transforming the vector into the subject;
 recovering from the subject a sample of biological material, such as blood, serum, plasma, CSF, or urine, containing a fusion protein comprising a biotherapeutic peptide and a luciferase, or a luciferase expressed by the vector; and
 detecting or quantifying the intensity of luminescent output in the sample thereby determining an amount of a biotherapeutic peptide in the subject.

134. A method for measuring an amount of a biotherapeutic peptide in a subject in need thereof comprising:
 providing the vector according to embodiment 16;
 transforming the vector into the subject;
 recovering from the subject a sample of biological material, such as blood, serum, plasma, CSF, or urine, containing a fusion protein comprising a biotherapeutic peptide and a luciferase, or a luciferase expressed by the vector; and
 detecting or quantifying the intensity of luminescent output in the sample thereby determining an amount of a biotherapeutic peptide in the subject.

135. A method for measuring an amount of a biotherapeutic peptide in a subject in need thereof comprising:
 providing the vector according to embodiment 17;
 transforming the vector into the subject;
 recovering from the subject a sample of biological material, such as blood, serum, plasma, CSF, or urine, containing a fusion protein comprising a biotherapeutic peptide and a luciferase, or a luciferase expressed by the vector; and
 detecting or quantifying the intensity of luminescent output in the sample thereby determining an amount of a biotherapeutic peptide in the subject.

136. A method for measuring an amount of a biotherapeutic peptide in a subject in need thereof comprising:
 providing the vector according to embodiment 18;
 transforming the vector into the subject;
 recovering from the subject a sample of biological material, such as blood, serum, plasma, CSF, or urine, containing a fusion protein comprising a biotherapeutic peptide and a luciferase, or a luciferase expressed by the vector; and
 detecting or quantifying the intensity of luminescent output in the sample thereby determining an amount of a biotherapeutic peptide in the subject.

137. A method for measuring an amount of a biotherapeutic peptide in a subject in need thereof comprising:
 providing the vector according to embodiment 19;
 transforming the vector into the subject;
 recovering from the subject a sample of biological material, such as blood, serum, plasma, CSF, or urine, containing a fusion protein comprising a biotherapeutic peptide and a luciferase, or a luciferase expressed by the vector; and
 detecting or quantifying the intensity of luminescent output in the sample thereby determining an amount of a biotherapeutic peptide in the subject.

138. A method for measuring an amount of a biotherapeutic peptide in a subject in need thereof comprising:
 providing the vector according to embodiment 20;
 transforming the vector into the subject;
 recovering from the subject a sample of biological material, such as blood, serum, plasma, CSF, or urine, containing a fusion protein comprising a biotherapeutic peptide and a luciferase, or a luciferase expressed by the vector; and
 detecting or quantifying the intensity of luminescent output in the sample thereby determining an amount of a biotherapeutic peptide in the subject.

139. A method for measuring an amount of a biotherapeutic peptide in a subject in need thereof comprising:
 providing the vector according to embodiment 21;
 transforming the vector into the subject;
 recovering from the subject a sample of biological material, such as blood, serum, plasma, CSF, or urine, containing a fusion protein comprising a biotherapeutic peptide and a luciferase, or a luciferase expressed by the vector; and
 detecting or quantifying the intensity of luminescent output in the sample thereby determining an amount of a biotherapeutic peptide in the subject.

140. A method for measuring an amount of a biotherapeutic peptide in a subject in need thereof comprising:
 providing the vector according to embodiment 22;
 transforming the vector into the subject;
 recovering from the subject a sample of biological material, such as blood, serum, plasma, CSF, or urine, containing a fusion protein comprising a biotherapeutic peptide and a luciferase, or a luciferase expressed by the vector; and
 detecting or quantifying the intensity of luminescent output in the sample thereby determining an amount of a biotherapeutic peptide in the subject.

141. A method for measuring an amount of a biotherapeutic peptide in a subject in need thereof comprising:
 providing the vector according to embodiment 23;
 transforming the vector into the subject;
 recovering from the subject a sample of biological material, such as blood, serum, plasma, CSF, or urine, containing a fusion protein comprising a biotherapeutic peptide and a luciferase, or a luciferase expressed by the vector; and
 detecting or quantifying the intensity of luminescent output in the sample thereby determining an amount of a biotherapeutic peptide in the subject.

142. A method for measuring an amount of a biotherapeutic peptide in a subject in need thereof comprising:
 providing the vector according to embodiment 24;
 transforming the vector into the subject;
 recovering from the subject a sample of biological material, such as blood, serum, plasma, CSF, or urine, containing a fusion protein comprising a biotherapeutic peptide and a luciferase, or a luciferase expressed by the vector; and detecting or quantifying the intensity of luminescent output in the sample thereby determining an amount of a biotherapeutic peptide in the subject.

143. A method for measuring an amount of a biotherapeutic peptide in a subject in need thereof comprising:
providing the vector according to any of embodiments 25-34;
transforming the vector into the subject;
recovering from the subject a sample of biological material, such as blood, serum, plasma, CSF, or urine, containing a fusion protein comprising a biotherapeutic peptide and a luciferase, or a luciferase expressed by the vector; and
detecting or quantifying the intensity of luminescent output in the sample thereby determining an amount of a biotherapeutic peptide in the subject.

144. A method for measuring an amount of a biotherapeutic peptide in a subject in need thereof comprising:
providing the vector according to embodiment 35;
transforming the vector into the subject;
recovering from the subject a sample of biological material, such as blood, serum, plasma, CSF, or urine, containing a fusion protein comprising a biotherapeutic peptide and a luciferase, or a luciferase expressed by the vector; and
detecting or quantifying the intensity of luminescent output in the sample thereby determining an amount of a biotherapeutic peptide in the subject.

145. A method for measuring an amount of a biotherapeutic peptide in a subject in need thereof comprising:
providing the vector according to embodiment 36;
transforming the vector into the subject;
recovering from the subject a sample of biological material, such as blood, serum, plasma, CSF, or urine, containing a fusion protein comprising a biotherapeutic peptide and a luciferase, or a luciferase expressed by the vector; and
detecting or quantifying the intensity of luminescent output in the sample thereby determining an amount of a biotherapeutic peptide in the subject.

Recovery of a fusion protein comprising a biotherapeutic peptide or polypeptide includes concentration, dilution, purification, and/or isolation from other polypeptide components or nonpolypeptide components of a medium, cells or cell lysate. Examples of recovery methods include chromatographic isolation or separation of a fusion protein, affinity purification using antibodies or ligands that bind to epitopes of tags in a target fusion protein, PAGE, isoelectric focusing, or dialysis and concentration. In some embodiments luminescence may be determined directly from a biological sample or a diluted biological sample. A recovered biotherapeutic peptide or polypeptide may be purified to homogeneity or to represent 10, 20, 30, 40, 50, 60, 70, 80, 90, 95, 99% by mass of the protein content (or the solid, nonaqueous content) in a recovered fusion protein composition.

Other embodiments of the invention include a method for certifying expression of a polypeptide vaccine in a subject and include, without limitation, the following:

146. A method for certifying vaccine expression in vivo comprising:
providing the vector according to embodiment 14;
transforming the vector into a host organism;
recovering from the host organism a sample of biological material, such as blood, serum, plasma, CSF, or urine, containing a fusion protein comprising a vaccine peptide (or polypeptide) and a luciferase, or a luciferase expressed by the vector; and
detecting or quantifying the intensity of luminescent output in the sample thereby certifying expression of the vaccine peptide or polypeptide in the host organism.

147. A method for certifying vaccine expression in vivo comprising:
providing the vector according to embodiment 15;
transforming the vector into a host organism;
recovering from the host organism a sample of biological material, such as blood, serum, plasma, CSF, or urine, containing a fusion protein comprising a vaccine peptide (or polypeptide) and a luciferase, or a luciferase expressed by the vector; and
detecting or quantifying the intensity of luminescent output in the sample thereby certifying expression of the vaccine peptide or polypeptide in the host organism.

148. A method for certifying vaccine expression in vivo comprising:
providing the vector according to embodiment 16;
transforming the vector into a host organism;
recovering from the host organism a sample of biological material, such as blood, serum, plasma, CSF, or urine, containing a fusion protein comprising a vaccine peptide (or polypeptide) and a luciferase, or a luciferase expressed by the vector; and
detecting or quantifying the intensity of luminescent output in the sample thereby certifying expression of the vaccine peptide or polypeptide in the host organism.

149. A method for certifying vaccine expression in vivo comprising:
providing the vector according to embodiment 17;
transforming the vector into a host organism;
recovering from the host organism a sample of biological material, such as blood, serum, plasma, CSF, or urine, containing a fusion protein comprising a vaccine peptide (or polypeptide) and a luciferase, or a luciferase expressed by the vector; and
detecting or quantifying the intensity of luminescent output in the sample thereby certifying expression of the vaccine peptide or polypeptide in the host organism.

150. A method for certifying vaccine expression in vivo comprising:
providing the vector according to embodiment 18;
transforming the vector into a host organism;
recovering from the host organism a sample of biological material, such as blood, serum, plasma, CSF, or urine, containing a fusion protein comprising a vaccine peptide (or polypeptide) and a luciferase, or a luciferase expressed by the vector; and
detecting or quantifying the intensity of luminescent output in the sample thereby certifying expression of the vaccine peptide or polypeptide in the host organism.

151. A method for certifying vaccine expression in vivo comprising:
providing the vector according to embodiment 19;
transforming the vector into a host organism;
recovering from the host organism a sample of biological material, such as blood, serum, plasma, CSF, or urine, containing a fusion protein comprising a vaccine peptide (or polypeptide) and a luciferase, or a luciferase expressed by the vector; and
detecting or quantifying the intensity of luminescent output in the sample thereby certifying expression of the vaccine peptide or polypeptide in the host organism.

152. A method for certifying vaccine expression in vivo comprising:
providing the vector according to embodiment 20;
transforming the vector into a host organism;

recovering from the host organism a sample of biological material, such as blood, serum, plasma, CSF, or urine, containing a fusion protein comprising a vaccine peptide (or polypeptide) and a luciferase, or a luciferase expressed by the vector; and detecting or quantifying the intensity of luminescent output in the sample thereby certifying expression of the vaccine peptide or polypeptide in the host organism.

153. A method for certifying vaccine expression in vivo comprising:

providing the vector according to embodiment 21;
transforming the vector into a host organism;
recovering from the host organism a sample of biological material, such as blood, serum, plasma, CSF, or urine, containing a fusion protein comprising a vaccine peptide (or polypeptide) and a luciferase, or a luciferase expressed by the vector; and detecting or quantifying the intensity of luminescent output in the sample thereby certifying expression of the vaccine peptide or polypeptide in the host organism.

154. A method for certifying vaccine expression in vivo comprising:

providing the vector according to embodiment 22;
transforming the vector into a host organism;
recovering from the host organism a sample of biological material, such as blood, serum, plasma, CSF, or urine, containing a fusion protein comprising a vaccine peptide (or polypeptide) and a luciferase, or a luciferase expressed by the vector; and detecting or quantifying the intensity of luminescent output in the sample thereby certifying expression of the vaccine peptide or polypeptide in the host organism.

155. A method for certifying vaccine expression in vivo comprising:

providing the vector according to embodiment 23;
transforming the vector into a host organism;
recovering from the host organism a sample of biological material, such as blood, serum, plasma, CSF, or urine, containing a fusion protein comprising a vaccine peptide (or polypeptide) and a luciferase, or a luciferase expressed by the vector; and detecting or quantifying the intensity of luminescent output in the sample thereby certifying expression of the vaccine peptide or polypeptide in the host organism.

156. A method for certifying vaccine expression in vivo comprising:

providing the vector according to embodiment 24;
transforming the vector into a host organism;
recovering from the host organism a sample of biological material, such as blood, serum, plasma, CSF, or urine, containing a fusion protein comprising a vaccine peptide (or polypeptide) and a luciferase, or a luciferase expressed by the vector; and detecting or quantifying the intensity of luminescent output in the sample thereby certifying expression of the vaccine peptide or polypeptide in the host organism.

157. A method for certifying vaccine expression in vivo comprising:

providing the vector according to embodiment 25-34;
transforming the vector into a host organism;
recovering from the host organism a sample of biological material, such as blood, serum, plasma, CSF, or urine, containing a fusion protein comprising a vaccine peptide (or polypeptide) and a luciferase, or a luciferase expressed by the vector; and detecting or quantifying the intensity of luminescent output in the sample thereby certifying expression of the vaccine peptide or polypeptide in the host organism.

158. A method for certifying vaccine expression in vivo comprising:

providing the vector according to embodiment 35;
transforming the vector into a host organism;
recovering from the host organism a sample of biological material, such as blood, serum, plasma, CSF, or urine, containing a fusion protein comprising a vaccine peptide (or polypeptide) and a luciferase, or a luciferase expressed by the vector; and detecting or quantifying the intensity of luminescent output in the sample thereby certifying expression of the vaccine peptide or polypeptide in the host organism.

159. A method for certifying vaccine expression in vivo comprising:

providing the vector according to embodiment 36;
transforming the vector into a host organism;
recovering from the host organism a sample of biological material, such as blood, serum, plasma, CSF, or urine, containing a fusion protein comprising a vaccine peptide (or polypeptide) and a luciferase, or a luciferase expressed by the vector; and detecting or quantifying the intensity of luminescent output in the sample thereby certifying expression of the vaccine peptide or polypeptide in the host organism.

Recovery of a fusion protein comprising a vaccine peptide or polypeptide includes concentration, dilution, purification, and/or isolation from other polypeptide components or non-polypeptide components of a medium, cells or cell lysate. Examples of recovery methods include chromatographic isolation or separation of a fusion protein, affinity purification using antibodies or ligands that bind to epitopes of tags in a target fusion protein, PAGE, isoelectric focusing, or dialysis and concentration. In some embodiments luminescence may be determined directly from a biological sample or a diluted biological sample. In the methods above, vaccine expression may be formally certified such as by a formal medical or scientific statement, attestation, logs or other records or less formally detected, determined, or recorded, for example in a laboratory notebook or workbook, photo, audio/visual recording, or other record.

Other embodiments of the invention include a pharmaceutical composition containing a fusion protein and include, without limitation, the following:

160. A pharmaceutical composition comprising the fusion protein of embodiment 60 and at least one pharmaceutically acceptable carrier, adjuvant, or excipient.

161. A pharmaceutical composition comprising the fusion protein of embodiment 61 and at least one pharmaceutically acceptable carrier, adjuvant, or excipient.

162. A pharmaceutical composition comprising the fusion protein of embodiment 62 and at least one pharmaceutically acceptable carrier, adjuvant, or excipient.

163. A pharmaceutical composition comprising the fusion protein of embodiment 63 and at least one pharmaceutically acceptable carrier, adjuvant, or excipient.

164. A pharmaceutical composition comprising the fusion protein of embodiment 64 and at least one pharmaceutically acceptable carrier, adjuvant, or excipient.

165. A pharmaceutical composition comprising the fusion protein of embodiment 65 and at least one pharmaceutically acceptable carrier, adjuvant, or excipient.

166. A pharmaceutical composition comprising the fusion protein of embodiment 66 and at least one pharmaceutically acceptable carrier, adjuvant, or excipient.

167. A pharmaceutical composition comprising the fusion protein of embodiment 67 and at least one pharmaceutically acceptable carrier, adjuvant, or excipient.

168. A pharmaceutical composition comprising the fusion protein of embodiment 68 and at least one pharmaceutically acceptable carrier, adjuvant, or excipient.

169. A pharmaceutical composition comprising the fusion protein of embodiment 69 and at least one pharmaceutically acceptable carrier, adjuvant, or excipient.

170. A pharmaceutical composition comprising the fusion protein of embodiment 70 and at least one pharmaceutically acceptable carrier, adjuvant, or excipient.

171. A pharmaceutical composition comprising the fusion protein of embodiment 71 and at least one pharmaceutically acceptable carrier, adjuvant, or excipient.

172. A pharmaceutical composition comprising the fusion protein of embodiment 72 and at least one pharmaceutically acceptable carrier, adjuvant, or excipient Other embodiments of the invention include a biotherapeutic comprising a fusion protein and include, without limitation, the following:

173. A biotherapeutic comprising the fusion protein of embodiment 60 and a suitable carrier, excipient or adjuvant.

174. A biotherapeutic comprising the fusion protein of embodiment 61 and a suitable carrier, excipient or adjuvant.

175. A biotherapeutic comprising the fusion protein of embodiment 62 and a suitable carrier, excipient or adjuvant.

176. A biotherapeutic comprising the fusion protein of embodiment 63 and a suitable carrier, excipient or adjuvant.

177. A biotherapeutic comprising the fusion protein of embodiment 64 and a suitable carrier, excipient or adjuvant.

178. A biotherapeutic comprising the fusion protein of embodiment 65 and a suitable carrier, excipient or adjuvant.

179. A biotherapeutic comprising the fusion protein of embodiment 66 and a suitable carrier, excipient or adjuvant.

180. A biotherapeutic comprising the fusion protein of embodiment 67 and a suitable carrier, excipient or adjuvant.

181. A biotherapeutic comprising the fusion protein of embodiment 68 and a suitable carrier, excipient or adjuvant.

182. A biotherapeutic comprising the fusion protein of embodiment 69 and a suitable carrier, excipient or adjuvant.

183. A biotherapeutic comprising the fusion protein of embodiment 70 and a suitable carrier, excipient or adjuvant.

184. A biotherapeutic comprising the fusion protein of embodiment 71 and a suitable carrier, excipient or adjuvant.

185. A biotherapeutic comprising the fusion protein of embodiment 72 and a suitable carrier, excipient or adjuvant.

In the biotherapeutics described above, the fusion protein preferably comprises a biologically active polypeptide, such as an interferon (e.g., interferon-alpha or interferon-beta or modified versions thereof) or an immunogenic polypeptide. These biotherapeutics may constitute a fusion protein according to the invention or a polynucleotide encoding such a fusion protein. The fusion protein may be intact or processed, for example, into separate fusion protein fragments by action of a translation interruption sequence. The fusion protein may be in a purified form isolated from other cellular components of a host cell expressing it, or may be contained within a host cell or transformed cell, such as a cell obtained from a subject being treated for a particular disease, disorder or condition. A biotherapeutic may comprise a living cell, such as a leukocyte, bone marrow, muscle, endothelial, or stem cell, that expresses interferon or other polypeptide of interest that produced by transformation of a subject's or patient's cells with a vector as described herein. It may be homologous to the subject or patient or obtained from a suitable donor.

Other embodiments of the invention include a method of treating a subject and include, without limitation, the following:

186. A method for treating Foot-and-Mouth Disease comprising administering the composition according to embodiment 160 to a subject in need thereof.

187. A method for treating Foot-and-Mouth Disease comprising administering the composition according to embodiment 161 to a subject in need thereof.

188. A method for treating Foot-and-Mouth Disease comprising administering the composition according to embodiment 162 to a subject in need thereof.

189. A method for treating Foot-and-Mouth Disease comprising administering the composition according to embodiment 163 to a subject in need thereof.

190. A method for treating Foot-and-Mouth Disease comprising administering the composition according to embodiment 164 to a subject in need thereof.

191. A method for treating Foot-and-Mouth Disease comprising administering the composition according to embodiment 165 to a subject in need thereof.

192. A method for treating Foot-and-Mouth Disease comprising administering the composition according to embodiment 166 to a subject in need thereof.

193. A method for treating Foot-and-Mouth Disease comprising administering the composition according to embodiment 167 to a subject in need thereof.

194. A method for treating Foot-and-Mouth Disease comprising administering the composition according to embodiment 168 to a subject in need thereof.

195. A method for treating Foot-and-Mouth Disease comprising administering the composition according to embodiment 169 to a subject in need thereof.

196. A method for treating Foot-and-Mouth Disease comprising administering the composition according to embodiment 170 to a subject in need thereof.

197. A method for treating Foot-and-Mouth Disease comprising administering the composition according to embodiment 171 to a subject in need thereof.

198. A method for treating Foot-and-Mouth Disease comprising administering the composition according to embodiment 172 to a subject in need thereof.

199. A method for treating malignant melanoma comprising administering the composition according to embodiment 160 to a subject in need thereof.

200. A method for treating malignant melanoma comprising administering the composition according to embodiment 161 to a subject in need thereof.

201. A method for treating malignant melanoma comprising administering the composition according to embodiment 162 to a subject in need thereof.

202. A method for treating malignant melanoma comprising administering the composition according to embodiment 163 to a subject in need thereof.

203. A method for treating malignant melanoma comprising administering the composition according to embodiment 164 to a subject in need thereof.

204. A method for treating malignant melanoma comprising administering the composition according to embodiment 165 to a subject in need thereof.

205. A method for treating malignant melanoma comprising administering the composition according to embodiment 166 to a subject in need thereof.

206. A method for treating malignant melanoma comprising administering the composition according to embodiment 167 to a subject in need thereof.

207. A method for treating malignant melanoma comprising administering the composition according to embodiment 168 to a subject in need thereof.

208. A method for treating malignant melanoma comprising administering the composition according to embodiment 169 to a subject in need thereof.

209. A method for treating malignant melanoma comprising administering the composition according to embodiment 170 to a subject in need thereof.

210. A method for treating malignant melanoma comprising administering the composition according to embodiment 171 to a subject in need thereof.

211. A method for treating malignant melanoma comprising administering the composition according to embodiment 172 to a subject in need thereof.

212. A method for treating hepatitis B, hepatitis C, or other viral infection comprising administering the composition according to embodiment 160 to a subject in need thereof.

213. A method for treating hepatitis B, hepatitis C or other viral infection comprising administering the composition according to embodiment 161 to a subject in need thereof.

214. A method for treating hepatitis B, hepatitis C, or other viral infection comprising administering the composition according to embodiment 162 to a subject in need thereof.

215. A method for treating hepatitis B, hepatitis C, or other viral infection comprising administering the composition according to embodiment 163 to a subject in need thereof.

216. A method for treating hepatitis B, hepatitis C, or other viral infection comprising administering the composition according to embodiment 164 to a subject in need thereof.

217. A method for treating hepatitis B, hepatitis C, or other viral infection comprising administering the composition according to embodiment 165 to a subject in need thereof.

218. A method for treating hepatitis B, hepatitis C, or other viral infection comprising administering the composition according to embodiment 166 to a subject in need thereof.

219. A method for treating hepatitis B, hepatitis C, or other viral infection comprising administering the composition according to embodiment 167 to a subject in need thereof.

220. A method for treating hepatitis B, hepatitis C, or other viral infection comprising administering the composition according to embodiment 168 to a subject in need thereof.

221. A method for treating hepatitis B, hepatitis C, or other viral infection comprising administering the composition according to embodiment 169 to a subject in need thereof.

222. A method for treating hepatitis B, hepatitis C, or other viral infection comprising administering the composition according to embodiment 170 to a subject in need thereof.

223. A method for treating hepatitis B, hepatitis C, or other viral infection comprising administering the composition according to embodiment 171 to a subject in need thereof.

224. A method for treating hepatitis B, hepatitis C, or other viral infection comprising administering the composition according to embodiment 172 to a subject in need thereof.

In the methods described above, the fusion protein preferably comprises a biologically active polypeptide that induces a protective effect against the particular pathological condition or pathogens mentioned, such as an interferon (e.g., interferon-alpha or interferon-beta or modified versions thereof) that enhances immune responses to FMDV, melanoma or other tumors or cancers, or hepatitis B or C infection, or such as an immunogen that induces cellular or humoral immunity against tumors or viral pathogens. This method may be performed by administering a fusion protein according to the invention or a polynucleotide encoding such a fusion protein, for example, by transformation of a cell with a vector encoding a fusion protein, and administration of the transformed cells to a subject or patient in need treatment for a particular disease, disorder or condition.

Other embodiments of the invention include a method of treating a subject and include, without limitation, the following:

225. A method for cytokine therapy comprising administering the composition according to embodiment 160 to a subject in need thereof.

226. A method for cytokine therapy comprising administering the composition according to embodiment 161 to a subject in need thereof.

227. A method for cytokine therapy comprising administering the composition according to embodiment 162 to a subject in need thereof.

228. A method for cytokine therapy comprising administering the composition according to embodiment 163 to a subject in need thereof.

229. A method for cytokine therapy comprising administering the composition according to embodiment 164 to a subject in need thereof.

230. A method for cytokine therapy comprising administering the composition according to embodiment 165 to a subject in need thereof.

231. A method for cytokine therapy comprising administering the composition according to embodiment 166 to a subject in need thereof.

232. A method for cytokine therapy comprising administering the composition according to embodiment 167 to a subject in need thereof.

233. A method for cytokine therapy comprising administering the composition according to embodiment 168 to a subject in need thereof.

234. A method for cytokine therapy comprising administering the composition according to embodiment 169 to a subject in need thereof.

235. A method for cytokine therapy comprising administering the composition according to embodiment 170 to a subject in need thereof.

236. A method for cytokine therapy comprising administering the composition according to embodiment 171 to a subject in need thereof.

237. A method for cytokine therapy comprising administering the composition according to embodiment 172 to a subject in need thereof.

In the method described above, the fusion protein preferably comprises a biologically active cytokine that modulates or enhances a subject's immune system. This method may be performed by administering a fusion protein according to the invention or a polynucleotide encoding such a fusion protein. It may be practiced with cells transformed to express a fusion protein or fusion protein fragments having cytokine activity, for example, by transformation of a cell with a vector encoding a fusion protein, and administration of the transformed cells to a subject or patient in need of cytokine activity.

Other embodiments of the invention include a method of treating a subject and include, without limitation, the following:

238. A method for treating Feline Herpesvirus 1, Feline infectious peritonitis, Feline Immunodeficiency Virus, Feline Leukemia Virus, Canine papilloma virus or other viral infection in domestic or wild animals comprising administering the composition according to embodiment 160 to the animal in need thereof.

239. A method for treating Feline Herpesvirus 1, Feline infectious peritonitis, Feline Immunodeficiency Virus, Feline Leukemia Virus, Canine papilloma virus or other viral infection in domestic or wild animals comprising administering the composition according to embodiment 161 to the animal in need thereof.

240. A method for treating Feline Herpesvirus 1, Feline infectious peritonitis, Feline Immunodeficiency Virus, Feline Leukemia Virus, Canine papilloma virus or other viral infection in domestic or wild animals comprising administering the composition according to embodiment 162 to the animal in need thereof.

241. A method for treating Feline Herpesvirus 1, Feline infectious peritonitis, Feline Immunodeficiency Virus, Feline Leukemia Virus, Canine papilloma virus or other viral infection in domestic or wild animals comprising administering the composition according to embodiment 163 to the animal in need thereof.

242. A method for treating Feline Herpesvirus 1, Feline infectious peritonitis, Feline Immunodeficiency Virus, Feline Leukemia Virus, Canine papilloma virus or other viral infection in domestic or wild animals comprising administering the composition according to embodiment 164 to the animal in need thereof.

243. A method for treating Feline Herpesvirus 1, Feline infectious peritonitis, Feline Immunodeficiency Virus, Feline Leukemia Virus, Canine papilloma virus or other viral infection in domestic or wild animals comprising administering the composition according to embodiment 165 to the animal in need thereof.

244. A method for treating Feline Herpesvirus 1, Feline infectious peritonitis, Feline Immunodeficiency Virus, Feline Leukemia Virus, Canine papilloma virus or other viral infection in domestic or wild animals comprising administering the composition according to embodiment 166 to the animal in need thereof.

245. A method for treating Feline Herpesvirus 1, Feline infectious peritonitis, Feline Immunodeficiency Virus, Feline Leukemia Virus, Canine papilloma virus or other viral infection in domestic or wild animals comprising administering the composition according to embodiment 167 to the animal in need thereof.

246. A method for treating Feline Herpesvirus 1, Feline infectious peritonitis, Feline Immunodeficiency Virus, Feline Leukemia Virus, Canine papilloma virus or other viral infection in domestic or wild animals comprising administering the composition according to embodiment 168 to the animal in need thereof.

247. A method for treating Feline Herpesvirus 1, Feline infectious peritonitis, Feline Immunodeficiency Virus, Feline Leukemia Virus, Canine papilloma virus or other viral infection in domestic or wild animals comprising administering the composition according to embodiment 169 to the animal in need thereof.

248. A method for treating Feline Herpesvirus 1, Feline infectious peritonitis, Feline Immunodeficiency Virus, Feline Leukemia Virus, Canine papilloma virus or other viral infection in domestic or wild animals comprising administering the composition according to embodiment 170 to the animal in need thereof.

249. A method for treating Feline Herpesvirus 1, Feline infectious peritonitis, Feline Immunodeficiency Virus, Feline Leukemia Virus, Canine papilloma virus or other viral infection in domestic or wild animals comprising administering the composition according to embodiment 171 to the animal in need thereof.

250. A method for treating Feline Herpesvirus 1, Feline infectious peritonitis, Feline Immunodeficiency Virus, Feline Leukemia Virus, Canine papilloma virus or other viral infection in domestic or wild animals comprising administering the composition according to embodiment 172 to the animal in need thereof.

In the methods described above, the fusion protein preferably comprises a biologically active cytokine that modulates or enhances a subject's immune system response to the above-mentioned viruses or that comprises protective antigens or epitopes of said viruses. This method may be performed by administering a fusion protein according to the invention or a polynucleotide encoding such a fusion protein.

The methods described above for treating feline diseases or disorders may be practiced with *Felis catus* α, β and/or γ interferon(s) such as those encoded by Accession numbers: NM_001031830.1 or GI:73611927 (a interferon); NM_001009297.1 or GI:57163828 ((β interferon); or NM_001009873.1 or GI:57619124 (γ interferon); or analogs, derivatives or modified forms thereof as described herein. These accession numbers are incorporated by reference.

The methods described above for treating canine diseases or disorders may be practiced with *Canis lupus familiaris* α, β and/or γ interferon(s) such as those encoded by Accession numbers: M28624.1 or GI:163973 (α), GenBank: E11229.1 ((β) and EF095772.1 or GI: 118505119 (γ); or analogs, derivatives or modified forms thereof as described herein. These accession numbers are incorporated by reference.

Example 1

Δ1D2A Constructs Retain Luciferase and Interferon Secretion

Figure 2A:
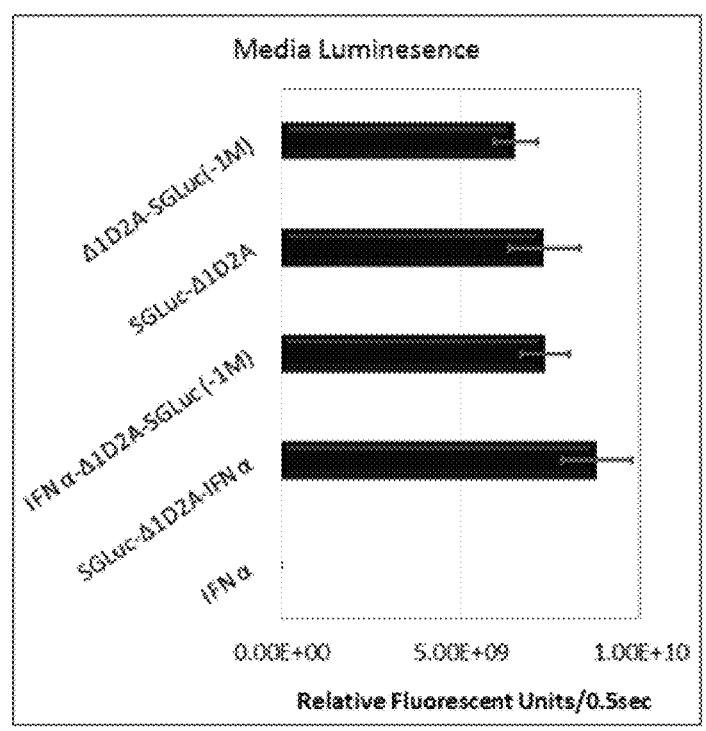
Figure 2B:
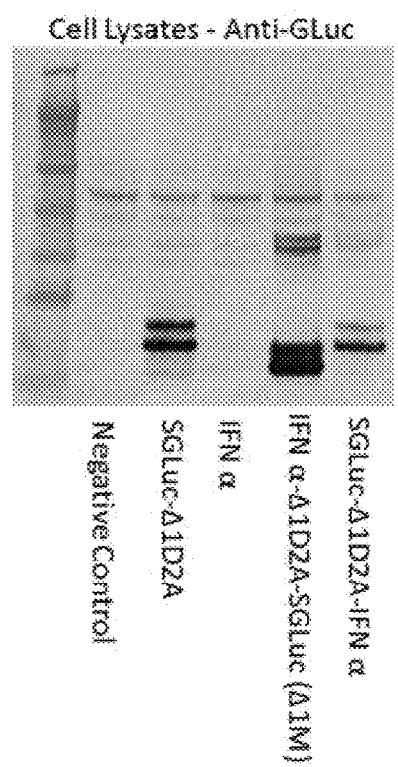

Two constructs comprising interferon and luciferase sequences were made utilizing the translation interrupter Δ1D2A to separate SGLuc and IFN α, see FIG. 1.

These constructs expressed two polypeptides which differed as to which polypeptide retained the Δ1D2A sequence, see FIG. 1. The addition of the Δ1D2A sequence to either the N-terminus or C-terminus of SGLuc was found to not inhibit either secretion or luminescence of the SGLuc and as shown by FIG. 2A top two bars (media luminescence) and FIG. 2B (Western blot of harvested media). To confirm that the addition of an IFN α sequence to either the N-terminus, in the case of IFNα-Δ1D2A-SGLuc Δ1M, or to the C-terminus, in the case of SGLuc-Δ1D2A-IFNα, did not alter critical luminescence properties, media from HEK293-T cells transfected with constructs pTarget IFNα-Δ1D2A-SGLuc Δ1M and pTarget SGLuc-Δ1D2A-IFNα was evaluated for luciferase activity, see FIG. 2A. HEK293-T cells transfected with constructs pTarget SGLuc-Δ1D2A and pTarget Δ1D2A-SGLuc Δ1M were used as controls, see FIG. 2A.

Confirmation of the presence of GLuc in the media and of separation of the fusion protein by Δ1D2A was performed by western blotting using a polyclonal anti-GLuc antibody, see FIG. 2B, which shows efficient separation of GLuc from fusion polypeptides. Only a small amount of unseparated fused peptide was present in the media, FIG. 2B.

To confirm that the addition of an IFN α sequence to either the N-terminus, in the case of IFNα-Δ1D2A-SGLuc Δ1M, or to the C-terminus, in the case of SGLuc-Δ1D2A-IFNα, did not alter critical secretion properties the presence of IFNα and IFNα-Δ1D2A in cell culture media was determined using a commercially available ELISA assay. A standard curve of IFN α concentration was determined using nine different concentrations of an IFN α standard Four different dilutions of media from cells transfected with pTarget IFN α, pTarget IFNα-Δ1D2A-SGLuc Δ1M, pTarget SGLuc-Δ1D2A-IFNα, pTarget SGLuc-Δ1D2A, and pTarget Δ1D2A-SGLuc Δ1M were assayed using the same ELISA assay, see FIG. 7. The ELISA results of media show in FIG. 7 demonstrate that IFNα is present in the media of cells transfected with plasmids pTarget IFN α, pTarget IFNα-Δ1D2A-SGLuc Δ1M, and pTarget SGLuc-Δ1D2A-IFNα but not in cells transfected with the control plasmids pTarget SGLuc-Δ1D2A, and pTarget Δ1D2A-SGLuc Δ1M. This confirms that the addition of the Δ1D2A peptide to either the N- or C-terminus of IFNα does not prevent secretion.

This example demonstrates that the Δ1D2A sequence can be successfully used to separate SGLuc and IFN α components of a fusion polypeptide and that both the SGLuc and IFN α components retain the ability to be secreted.

These results provide a new way to design a luciferase assay that can be used to quantify the amount of IFN produced in an expression system without the drawbacks of an antibody-based system. Such an assay provides a fast and reliable way to substantially determine the absolute concentration of a molecule in an expression system. The amount of GLuc or SGLuc moieties secreted into culture medium measured by luminescence, after these are released from a longer precursor fusion polypeptide by translational interruption, provides a proportionate way to substantially determine the absolute amount of interferon expressed. The amount of interferon expressed by the expression system will directly correlate with the amount of luminescence appearing in the culture medium. No interferon-binding antibodies are necessary.

This new method provides a more reliable way to standardize samples and avoid the unpredictability and problems associated with antibody-based systems like ELISA. As described above, many of these problems are attributable to the variation of antibody binding affinities for different interferon mutants, different kinds of interferons, or interferons in different kinds of samples.

While constructs using the Δ1D2A sequence can be conveniently used to monitor interferon expression, they do not directly quantify interferon concentrations. That is because they detect extracellular luminescence produced by the luciferase, not a direct and dependent property of interferon. Indirect methods using Δ1D2A may be biased by differential expression, degradation or trafficking of soluble GLuc moieties into the extracellular medium. For example, differential rates of GLuc or SGLuc moiety degradation for a mutant compared to a non-mutant IFN might bias results. To address these problems the inventors tested interferon-luciferase constructs that did not contain the Δ1D2A translation interruption sequence, see FIG. 4. The luminescent moieties in such constructs are directly attached to interferon and thus luminescence detected extracellularly indicates the amount of interferon present.

Example 2

Comparison of Secretion of Interferon to GLucON Constructs

Native interferons contain an N-terminal secretion domain to facilitate their secretion into the extracellular medium. Examples of the secretion domains for interferons are described by SEQ ID NOS: 25-46. This secretion sequence is not necessary to elicit a desired immune stimulatory response. To this end the inventors constructed fusion peptides that contain the SGLuc luciferase and the non-secretion domain of four different interferons, α, β, γ, and λ, collectively identified as SGLucONs and depicted by FIG. 4.

The secretion of two types of porcine interferons, α and β, and two types of bovine interferons, γ and λ, were compared to SGLucON constructs containing the same interferon types. The SGLucON constructs take advantage of the naturally secretable properties of SGLuc to facilitate the secretion of the fusion peptide.

Figure 5A:
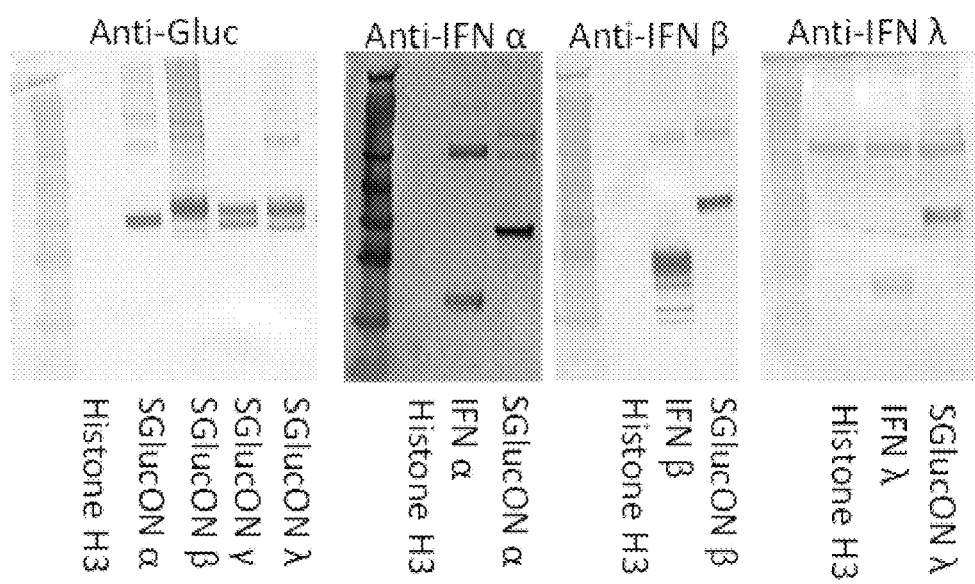
Figure 5B:
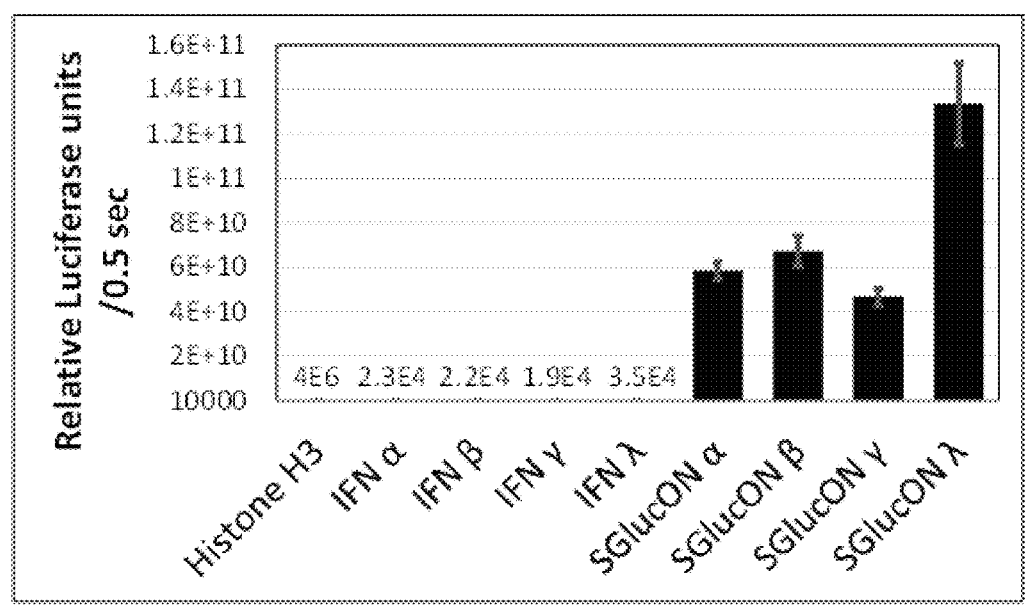

All four interferons and all four SGLucON constructs were demonstrated to be secreted into the extracellular medium as shown in FIGS. 5A and 5B. This confirms that the creation of these fusion peptides does not prevent the secretion of the peptide from the cell. Since all SGLucONs (α, β, γ, λ) showed retention of secretion, FIG. 5A, we tested media samples harvested from transfected HEK293-T cells for luciferase activity, FIG. 5B. Media harvested from cells expressing Interferon (α, β, γ, λ) samples was also tested for luciferase activity to ensure that any luciferase activity observed was the result of the presence of the SGLuc component. All four SGLucON samples (α, β, γ, λ) and only the SGLucON samples showed luciferase activity, FIG. 5B. This confirms that the addition of the interferon sequence to SGLuc does not prevent luminescence.

The SGLucON λ sample showed a more than two-fold higher luciferase readings than the other three other SGLucON samples, FIG. 5B, but did not appear to have a proportionally greater concentration when examined by western blotting with the anti-GLuc antibody, FIG. 5A. This result suggests that in the case of SGLucON λ the addition of the IFN λ sequence may either enhance luminescence or hinder luminescence less than the other IFN sequences, α, β, γ, when comparing amongst the SGLucON constructs.

Control constructs of IFN α, β, and γ were also shown to be secreted by usage of antibodies specific to each one. There was no reliable available antibody to bovine IFN γ limiting the ability to confirm its presence. Western blots using anti-GLuc, anti-IFN α, anti-IFN β, and anti-IFN λ show that the SGLucON chimeras retain both luciferase and interferon components fused together and are not post-translationally processed, FIG. 5A. In the case of Interferon β there was a notable difference in post-translational modifications between IFN β and SGLucON β, FIG. 5A. IFN β shows substantial post-translational modifications, possibly through glycosylation or differential processing, resulting in multiple bands being present in the anti-IFN β western blot FIG. 5A. SGLucON β is predominantly in a single band as shown by FIG. 5A, suggesting that SGLucON β is not subject to the same degree of post-translational modifications as IFN β.

These results demonstrate that direct fusion of SGLuc to an interferon can be successfully secreted by a cell and then detected by luminescence. These constructs do not rely on separation of SGLuc from the interferon and thus are not subject to the same risks associated with the utilization of a Δ1D2A translation interruption sequence to produce two separate molecules.

Quantifying luciferase activity with SGLucON samples is a direct quantification of the concentration in the sample rather than an indirect quantification as is the case when utilizing the Δ1D2A sequence. This removes variables that may alter concentrations of either SGLuc or IFN after translation such as differential secretion rates and the potential for preferential protein degradation.

Example 3

Δ1D2A IFN Constructs Retain Biological Activity

An IFN α ELISA assay was performed to quantify the concentrations of IFN α in the cell culture media of HEK293-T cells transfected with plasmids pTarget IFN α, pTarget SGLuc-Δ1D2A-IFNα, pTarget IFNα-Δ1D2A-SGLuc Δ1M, and pTarget SGLuc-Δ1D2A. These concentrations were used to set up a dilution series to test for retention of antiviral activity against VSV and to compare this activity to an established commercially available porcine IFNα, FIG. 6 and FIG. 8.

The results show that IFN α produced from constructs pTarget SGLuc-Δ1D2A-IFNα and pTarget IFNα-Δ1D2A-SGLuc Δ1M retains anti-viral activity, FIG. 6 and FIG. 8. This was particularly novel as the IFN α produced from these constructs contains additional amino acids compared to a native IFN α sequence. The IFN α produced from the pTarget SGLuc-Δ1D2A-IFNα construct contains an addition N-terminal proline while the IFN α produced from the pTarget IFNα-Δ1D2A-SGLuc Δ1M construct contains an additional 40 amino acids, containing the Δ1D2A sequence, on the C-terminus, FIG. 1. For the pTarget IFNα-Δ1D2A-SGLuc Δ1M construct the 40 additional amino acids represent a 20% increase in length for the resulting molecule. The substantial increase in the size of the molecule makes the result that it retained anti-viral activity all the more unexpected.

IFN α produced from the pTarget IFN α serves as a control to compare effectiveness to an unmodified protein produced in a similar manner. The IFN α samples only showed plaques at 0.625 ng/mL suggesting that a protective concentration was 1.25 ng/mL or less. Both the IFN α produced from the pTarget SGLuc-Δ1D2A-IFNα construct and that from the pTarget IFNα-Δ1D2A-SGLuc Δ1M construct provided complete protection at 2.5 ng/mL with plaques present at 1.25 ng/mL, FIG. 6. Even at the lowest doses tested, 0.1265 ng/mL, the plaques present in samples were noticeably smaller than those present in the SGLuc-Δ1D2A negative control.

Example 4

GLucON a Construct Retains Biological Activity

An IFN α ELISA assay was performed to quantify the concentrations of both IFN α and SGLucON α in harvested media. Equivalent concentrations of each were determined and used in a plaque assay for interferon anti-viral activity against Vesicular Stomatitis Virus (VSV). The results are shown by FIG. 6 and FIG. 8.

The results show that SGLucON α retained anti-viral activity against VSV. A concentration of less than or equal to 1.25 ng/mL but greater than 0.625 ng/mL of SGLucON α was sufficient to completely inhibit VSV and concentrations as low as 0.1265 ng/mL were shown to partially inhibit VSV when compared to the negative control SGLuc-Δ1D2A.

IFN α produced by the same means was also able to provide complete protection at a concentration of less than or equal to 1.25 ng/mL but greater than 0.3125 ng/mL. This suggests that SGLucON α has at least equivalent anti-viral activity than IFN α, FIG. 6 and FIG. 8. Interestingly SGLucON α gives consistently lower PFUs than IFN α alone at equivalent concentrations FIG. 8. While complete protection from VSV was obtained at the same concentration for both IFN α and SGLucON α consistently lower PFU numbers at susceptible dilutions suggest that SGLucON α offers better protection than IFN α, FIG. 8.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "substantially", "about" or "approximately," even if the term does not expressly appear. The terms "substantially", "substantially no", "substantially free", "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The invention claimed is:

1. A polynucleotide that encodes a fusion protein comprising a luciferase, and at least one interferon, wherein the polynucleotide encodes the fusion protein described by SEQ ID NOS: 48, 52, 56, 60, 64, 68, 70, 74, 78, 82, 86, 90, 94, 111, or 113.

2. The polynucleotide of claim 1 that further comprises a polynucleotide encoding at least one translational interrupter sequence.

3. The polynucleotide of claim 1 that further comprises a polynucleotide encoding at least one Aphthovirus translational interrupter sequence.

4. The polynucleotide of claim 1 that further comprises a polynucleotide encoding at least one foot-and-mouth disease virus (FMDV) translational interrupter sequence.

5. The polynucleotide of claim 1 that further comprises a polynucleotide encoding a FMDV 2A or Δ1D2A sequence.

6. The polynucleotide of claim 1 that comprises a polynucleotide sequence described by SEQ ID NOS: 47, 51, 55, 59, 63, 67, 69, 73, 77, 81, 85, 89, 93, 110 or 112.

7. A vector comprising the polynucleotide of claim 1.

8. The vector of claim 7 that further comprises a polynucleotide encoding at least one promoter or other transcription regulatory element, at least one prokaryotic or eukaryotic translation initiation sequence or other translation regulatory element, at least one translational interrupter sequence, or at least one reporter polynucleotide sequence operatively linked to, or embedded within, the polynucleotide sequence encoding the fusion protein.

9. The vector of claim 7 that further comprises a polynucleotide encoding at least one FMDV translational interrupter sequence.

10. The vector of claim 7 that further comprises a polynucleotide encoding a FMDV 2A or Δ1D2A sequence.

11. The vector of claim 7 that is a mRNA, DNA plasmid, minicircle vector, a replication deficient adenovirus vector, a vaccinia virus vector, or other viral vector that expresses the fusion protein.

12. The vector of claim 7 that comprises a polynucleotide sequence described by SEQ ID NOS: 47, 51, 55, 59, 63, 67, 69, 73, 77, 81, 85, 89, 93, 110 or 112.

13. A host cell comprising the vector of claim 7, wherein the host cell expresses the fusion protein.

14. The host cell of claim 13 that is an insect cell.

15. The host cell of claim 13 that is mammalian cell.

16. The host cell of claim 13 that is a prokaryotic cell.

17. A fusion protein, that is encoded by the polynucleotide of claim 1.

18. The fusion protein of claim 17, wherein the polynucleotide further comprises a polynucleotide encoding at least one translational interrupter sequence.

19. The fusion protein of claim 17, wherein the polynucleotide further comprises a polynucleotide encoding at least one Aphthovirus translational interrupter sequence.

20. The fusion protein of claim 17, wherein the polynucleotide further comprises a polynucleotide encoding at least one FMDV translational interrupter sequence.

21. The fusion protein of claim 17, wherein the polynucleotide further comprises a polynucleotide encoding a FMDV 2A or Δ1D2A sequence.

22. A composition comprising the fusion protein of claim 17 and at least one pharmaceutically acceptable carrier, excipient or adjuvant.

23. A method for producing the fusion protein of claim 17 comprising culturing a host cell that expresses the fusion protein in a suitable medium and recovering the fusion protein.

24. A method for quantifying an amount or concentration of an interferon produced in an expression system comprising:
   a. providing the vector according to claim 7;
   b. transforming the vector into a host cell;
   c. culturing the cells in a medium;
   d. harvesting the medium; and
   e. quantifying the intensity of luminescent output.

25. A method for quantifying an amount or concentration of an interferon produced in an expression system comprising:
   a. providing the vector according to claim 9;
   b. transforming the vector into a host cell;
   c. culturing the cells in a medium;
   d. harvesting the medium; and
   e. quantifying the intensity of luminescent output.

26. A method for quantifying an amount or concentration of an interferon produced in an expression system comprising:
   a. providing the vector according to claim 10;
   b. transforming the vector into a host cell;
   c. culturing the cells in a medium;
   d. harvesting the medium; and
   e. quantifying the intensity of luminescent output, thus quantifying an amount or concentration of an interferon in the expression system.

27. A method for quantifying an amount or concentration of an interferon produced in an expression system comprising:
   a. providing the vector according to claim 11;
   b. transforming the vector into a host cell;
   c. culturing the cells in a medium;
   d. harvesting the medium; and
   e. quantifying the intensity of luminescent output, thus quantifying an amount or concentration of an interferon in the expression system.

28. A method for quantifying an amount or concentration of an interferon in an expression system comprising:
   a. providing the vector according to claim 12;
   b. transforming the vector into a host cell;
   c. culturing the cells in a medium;
   d. harvesting the medium; and
   e. quantifying the intensity of luminescent output, thus quantifying an amount or concentration of an interferon in the expression system.

29. A method for facilitating secretion of a fusion protein from a host cell comprising:
   a. providing the vector according to claim 7;
   b. transforming the vector into a host cell;
   c. culturing the cells in a medium; and
   d. recovering the secretable fusion protein from the medium.

30. A method for facilitating secretion of a fusion protein from a host cell comprising:
   a. providing the vector according to claim 12;
   b. transforming the vector into a host cell;
   c. culturing the cells in a medium; and
   d. Recovering the secretable fusion protein from the medium.

31. A method for measuring an amount of a biotherapeutic peptide in a subject in need thereof comprising:
   a. providing the vector according to claim 12;
   b. transforming the vector in the subject;
   c. recovering biological material from the subject;
   d. wherein the biological material comprises blood, serum, plasma, or urine.

32. A method for certifying vaccine expression in vivo comprising:
   a. providing the vector according to claim 12;
   b. transforming the vector into a host organism;
   c. recovering biological material from the host organism;
   d. wherein the biological material comprises blood, serum, plasma, or urine.

33. A pharmaceutical composition comprising the fusion protein of claim 17 and at least one pharmaceutically acceptable carrier, adjuvant, or excipient.

* * * * *

SEQUENCE LISTING

```
<160> NUMBER OF SEQ ID NOS: 113

<210> SEQ ID NO 1
<211> LENGTH: 558
<212> TYPE: DNA
<213> ORGANISM: Gaussia princeps
<220> FEATURE:
<221> NAME/KEY: CDS
<222> LOCATION: (1)..(558)
<220> FEATURE:
<221> NAME/KEY: misc_feature
<222> LOCATION: (1)..(558)
<223> OTHER INFORMATION: GLuc polynucleotide

<400> SEQUENCE: 1 atg gga gtc aaa gtt ctg ttt gcc ctg atc tgc atc gct gtg gcc gag      48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc      96
Ala Lys Pro Thr Glu Asn Asn Glu Asp Phe Asn Ile Val Ala Val Ala
            20                  25                  30 agc aac ttc gcg acc acg gat ctc gat gct gac cgc ggg aag ttg ccc     144
Ser Asn Phe Ala Thr Thr Asp Leu Asp Ala Asp Arg Gly Lys Leu Pro
        35                  40                  45
```

```
ggc aag aag ctg ccg ctg gag gtg ctc aaa gag atg gaa gcc aat gcc    192
Gly Lys Lys Leu Pro Leu Glu Val Leu Lys Glu Met Glu Ala Asn Ala
 50                  55                  60 cgg aaa gct ggc tgc acc agg ggc tgt ctg atc tgc ctg tcc cac atc    240
Arg Lys Ala Gly Cys Thr Arg Gly Cys Leu Ile Cys Leu Ser His Ile
 65                  70                  75                  80 aag tgc acg ccc aag atg aag aag ttc atc cca gga cgc tgc cac acc    288
Lys Cys Thr Pro Lys Met Lys Lys Phe Ile Pro Gly Arg Cys His Thr
                 85                  90                  95 tac gaa ggc gac aaa gag tcc gca cag ggc ggc ata ggc gag gcg atc    336
Tyr Glu Gly Asp Lys Glu Ser Ala Gln Gly Gly Ile Gly Glu Ala Ile
                100                 105                 110 gtc gac att cct gag att cct ggg ttc aag gac ttg gag ccc atg gag    384
Val Asp Ile Pro Glu Ile Pro Gly Phe Lys Asp Leu Glu Pro Met Glu
                115                 120                 125 cag ttc atc gca cag gtc gat ctg tgt gtg gac tgc aca act ggc tgc    432
Gln Phe Ile Ala Gln Val Asp Leu Cys Val Asp Cys Thr Thr Gly Cys
130                 135                 140 ctc aaa ggg ctt gcc aac gtg cag tgt tct gac ctg ctc aag aag tgg    480
Leu Lys Gly Leu Ala Asn Val Gln Cys Ser Asp Leu Leu Lys Lys Trp
145                 150                 155                 160 ctg ccg caa cgc tgt gcg acc ttt gcc agc aag atc cag ggc cag gtg    528
Leu Pro Gln Arg Cys Ala Thr Phe Ala Ser Lys Ile Gln Gly Gln Val
                165                 170                 175 gac aag atc aag ggg gcc ggt ggt gac taa                             558
Asp Lys Ile Lys Gly Ala Gly Gly Asp
                180                 185

<210> SEQ ID NO 2
<211> LENGTH: 185
<212> TYPE: PRT
<213> ORGANISM: Gaussia princeps

<400> SEQUENCE: 2

Met Gly Val Lys Val Leu Phe Ala Leu Ile Cys Ile Ala Val Ala Glu
 1               5                  10                  15

Ala Lys Pro Thr Glu Asn Asn Glu Asp Phe Asn Ile Val Ala Val Ala
                20                  25                  30

Ser Asn Phe Ala Thr Thr Asp Leu Asp Ala Asp Arg Gly Lys Leu Pro
             35                  40                  45

Gly Lys Lys Leu Pro Leu Glu Val Leu Lys Glu Met Glu Ala Asn Ala
 50                  55                  60

Arg Lys Ala Gly Cys Thr Arg Gly Cys Leu Ile Cys Leu Ser His Ile
 65                  70                  75                  80

Lys Cys Thr Pro Lys Met Lys Lys Phe Ile Pro Gly Arg Cys His Thr
                 85                  90                  95

Tyr Glu Gly Asp Lys Glu Ser Ala Gln Gly Gly Ile Gly Glu Ala Ile
                100                 105                 110

Val Asp Ile Pro Glu Ile Pro Gly Phe Lys Asp Leu Glu Pro Met Glu
                115                 120                 125

Gln Phe Ile Ala Gln Val Asp Leu Cys Val Asp Cys Thr Thr Gly Cys
130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp
                180                 185
```

<210> SEQ ID NO 3
<211> LENGTH: 558
<212> TYPE: DNA
<213> ORGANISM: Gaussia princeps
<220> FEATURE:
<221> NAME/KEY: CDS
<222> LOCATION: (1)..(558)
<223> OTHER INFORMATION: SGLuc polynucleotide

<400> SEQUENCE: 3

```
atg gga gtc aaa gtt ctg ttt gcc ctg atc tgc atc gct gtg gcc gag       48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc       96
Ala Lys Pro Thr Glu Asn Asn Glu Asp Phe Asn Ile Val Ala Val Ala
                20                  25                  30 agc aac ttt gcg acc acg gat ctc gat gct gac cga ggg aag ttg ccc      144
Ser Asn Phe Ala Thr Thr Asp Leu Asp Ala Asp Arg Gly Lys Leu Pro
            35                  40                  45 ggc aag aag ctg ccg ctg gag gtg ctc aaa gag atg gaa gcc aat gcc      192
Gly Lys Lys Leu Pro Leu Glu Val Leu Lys Glu Met Glu Ala Asn Ala
        50                  55                  60 cgg aaa gct ggc tgc acc agg ggc tgt ctg atc tgc ctg tcc cac atc      240
Arg Lys Ala Gly Cys Thr Arg Gly Cys Leu Ile Cys Leu Ser His Ile
65                  70                  75                  80 aag tgc acg ccc aag atg aag aag tgg ctc cca gga cgc tgc cac acc      288
Lys Cys Thr Pro Lys Met Lys Lys Trp Leu Pro Gly Arg Cys His Thr
                85                  90                  95 tac gaa ggc gac aaa gag tcc gca cag ggc ggc ata ggc gag gcg atc      336
Tyr Glu Gly Asp Lys Glu Ser Ala Gln Gly Gly Ile Gly Glu Ala Ile
                100                 105                 110 gtc gat att cct gag att cct ggg ttc aag gac ttg gag cca atg gag      384
Val Asp Ile Pro Glu Ile Pro Gly Phe Lys Asp Leu Glu Pro Met Glu
            115                 120                 125 cag ttc atc gca cag gtc gat ctg tgt gtg gac tgc aca act ggc tgc      432
Gln Phe Ile Ala Gln Val Asp Leu Cys Val Asp Cys Thr Thr Gly Cys
        130                 135                 140 ctc aaa ggg ctt gcc aac gtg cag tgt tct gac ctg ctc aag aag tgg      480
Leu Lys Gly Leu Ala Asn Val Gln Cys Ser Asp Leu Leu Lys Lys Trp
145                 150                 155                 160 ctg ccg caa cgc tgt gcg acc ttt gcc agc aag atc cag ggc cag gtg      528
Leu Pro Gln Arg Cys Ala Thr Phe Ala Ser Lys Ile Gln Gly Gln Val
                165                 170                 175 gac aag atc aag ggg gcc ggt ggt gac taa                              558
Asp Lys Ile Lys Gly Ala Gly Gly Asp
                180                 185
```

<210> SEQ ID NO 4
<211> LENGTH: 185
<212> TYPE: PRT
<213> ORGANISM: Gaussia princeps

<400> SEQUENCE: 4

```
Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
                20                  25                  30

Ser Asn Phe Ala Thr Thr Asp Leu Asp Ala Asp Arg Gly Lys Leu Pro
            35                  40                  45

Gly Lys Lys Leu Pro Leu Glu Val Leu Lys Glu Met Glu Ala Asn Ala
```

```
                 50                  55                  60

Arg Lys Ala Gly Cys Thr Arg Gly Cys Leu Ile Cys Leu Ser His Ile
 65                  70                  75                  80

Lys Cys Thr Pro Lys Met Lys Lys Trp Leu Pro Gly Arg Cys His Thr
                 85                  90                  95

Tyr Glu Gly Asp Lys Glu Ser Ala Gln Gly Ile Gly Glu Ala Ile
                100                 105                 110

Val Asp Ile Pro Glu Ile Pro Gly Phe Lys Asp Leu Glu Pro Met Glu
                115                 120                 125

Gln Phe Ile Ala Gln Val Asp Leu Cys Val Asp Cys Thr Thr Gly Cys
                130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp
                180                 185

<210> SEQ ID NO 5
<211> LENGTH: 90
<212> TYPE: DNA
<213> ORGANISM: Artificial Sequence
<220> FEATURE:
<223> OTHER INFORMATION: Translation interrupter motif
<220> FEATURE:
<221> NAME/KEY: CDS
<222> LOCATION: (1)..(90)
<223> OTHER INFORMATION: Translation interrupter motif (TIM) DNA
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
```

<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t

<400> SEQUENCE: 5

```
nrn mrn nhn vmn nyn ryn rvn syn ghn arr car vyn ykn ary tty gay      48
Xaa Xaa Xaa Xaa Xaa Xaa Xaa Xaa Xaa Xaa Gln Xaa Xaa Xaa Phe Asp
1               5                   10                  15 ytn ytn aar ytn gcn ggn gay gtn gar tcn aay ccn ggn ccn              90
Leu Leu Lys Leu Ala Gly Asp Val Glu Xaa Asn Pro Gly Pro
            20                  25                  30
```

<210> SEQ ID NO 6
<211> LENGTH: 30
<212> TYPE: PRT
<213> ORGANISM: Artificial Sequence
<220> FEATURE:
<221> NAME/KEY: misc_feature
<222> LOCATION: (1)..(1)
<223> OTHER INFORMATION: The 'Xaa' at location 1 stands for Arg, Ser,
      Lys, Asn, Gly, Glu, Asp, Gln, His, Trp, Cys, or Tyr.
<220> FEATURE:
<221> NAME/KEY: misc_feature
<222> LOCATION: (2)..(2)
<223> OTHER INFORMATION: The 'Xaa' at location 2 stands for Arg, Ser,
      Lys, Asn, Gln, or His.
<220> FEATURE:
<221> NAME/KEY: misc_feature
<222> LOCATION: (3)..(3)
<223> OTHER INFORMATION: The 'Xaa' at location 3 stands for Lys, Asn,
      Thr, Ile, Met, Glu, Asp, Ala, Val, Gln, His, Pro, Leu, Tyr, Ser,
      or Phe.
<220> FEATURE:

-continued

```
<221> NAME/KEY: misc_feature
<222> LOCATION: (4)..(4)
<223> OTHER INFORMATION: The 'Xaa' at location 4 stands for Lys, Asn,
      Thr, Glu, Asp, Ala, Gln, His, or Pro.
<220> FEATURE:
<221> NAME/KEY: misc_feature
<222> LOCATION: (5)..(5)
<223> OTHER INFORMATION: The 'Xaa' at location 5 stands for Thr, Ile,
      Met, Ala, Val, Pro, Leu, Ser, or Phe.
<220> FEATURE:
<221> NAME/KEY: misc_feature
<222> LOCATION: (6)..(6)
<223> OTHER INFORMATION: The 'Xaa' at location 6 stands for Ala, Val,
      Thr, Ile, or Met.
<220> FEATURE:
<221> NAME/KEY: misc_feature
<222> LOCATION: (7)..(7)
<223> OTHER INFORMATION: The 'Xaa' at location 7 stands for Glu, Asp,
      Gly, Ala, Lys, Asn, Arg, Ser, or Thr.
<220> FEATURE:
<221> NAME/KEY: misc_feature
<222> LOCATION: (8)..(8)
<223> OTHER INFORMATION: The 'Xaa' at location 8 stands for Ala, Val,
      Pro, or Leu.
<220> FEATURE:
<221> NAME/KEY: misc_feature
<222> LOCATION: (9)..(9)
<223> OTHER INFORMATION: The 'Xaa' at location 9 stands for Glu, Asp,
      Ala, or Val.
<220> FEATURE:
<221> NAME/KEY: misc_feature
<222> LOCATION: (10)..(10)
<223> OTHER INFORMATION: The 'Xaa' at location 10 stands for Arg, or
      Lys.
<220> FEATURE:
<221> NAME/KEY: misc_feature
<222> LOCATION: (12)..(12)
<223> OTHER INFORMATION: The 'Xaa' at location 12 stands for Thr, Ile,
      Met, Ala, Val, Pro, or Leu.
<220> FEATURE:
<221> NAME/KEY: misc_feature
<222> LOCATION: (13)..(13)
<223> OTHER INFORMATION: The 'Xaa' at location 13 stands for Arg, Leu,
      Trp, Cys, or Phe.
<220> FEATURE:
<221> NAME/KEY: misc_feature
<222> LOCATION: (14)..(14)
<223> OTHER INFORMATION: The 'Xaa' at location 14 stands for Ser, or
      Asn.
<220> FEATURE:
<221> NAME/KEY: misc_feature
<222> LOCATION: (26)..(26)
<223> OTHER INFORMATION: The 'Xaa' at location 26 stands for Ser.
<220> FEATURE:
<223> OTHER INFORMATION: Synthetic Construct

<400> SEQUENCE: 6

Xaa Xaa Xaa Xaa Xaa Xaa Xaa Xaa Xaa Xaa Gln Xaa Xaa Xaa Phe Asp
1               5                   10                  15

Leu Leu Lys Leu Ala Gly Asp Val Glu Xaa Asn Pro Gly Pro
            20                  25                  30

<210> SEQ ID NO 7
<211> LENGTH: 57
<212> TYPE: DNA
<213> ORGANISM: Artificial Sequence
<220> FEATURE:
<223> OTHER INFORMATION: Translation interrupter motif 2
<220> FEATURE:
<221> NAME/KEY: CDS
<222> LOCATION: (1)..(57)
<220> FEATURE:
<221> NAME/KEY: misc_feature
<222> LOCATION: (3)..(3)
<223> OTHER INFORMATION: n is a, c, g, or t
<220> FEATURE:
```

<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t

<400> SEQUENCE: 7

```
ryn hbn ary wwn kmn ctn ctn mwn cdn gcn ggn gay rtn gar wsn aay

```
      Thr, Ile, Met, Pro, Leu, Trp, Cys, or Phe.
<220> FEATURE:
<221> NAME/KEY: misc_feature
<222> LOCATION: (3)..(3)
<223> OTHER INFORMATION: The 'Xaa' at location 3 stands for Ser, or Asn.
<220> FEATURE:
<221> NAME/KEY: misc_feature
<222> LOCATION: (4)..(4)
<223> OTHER INFORMATION: The 'Xaa' at location 4 stands for Lys, Asn,
      Ile, Met, Tyr, Leu, or Phe.
<220> FEATURE:
<221> NAME/KEY: misc_feature
<222> LOCATION: (5)..(5)
<223> OTHER INFORMATION: The 'Xaa' at location 5 stands for Glu, Asp,
      Ala, Tyr, or Ser.
<220> FEATURE:
<221> NAME/KEY: misc_feature
<222> LOCATION: (6)..(6)
<223> OTHER INFORMATION: The 'Xaa' at location 6 stands for Leu.
<220> FEATURE:
<221> NAME/KEY: misc_feature
<222> LOCATION: (7)..(7)
<223> OTHER INFORMATION: The 'Xaa' at location 7 stands for Leu.
<220> FEATURE:
<221> NAME/KEY: misc_feature
<222> LOCATION: (8)..(8)
<223> OTHER INFORMATION: The 'Xaa' at location 8 stands for Lys, Asn,
      Ile, Met, Gln, His, or Leu.
<220> FEATURE:
<221> NAME/KEY: misc_feature
<222> LOCATION: (9)..(9)
<223> OTHER INFORMATION: The 'Xaa' at location 9 stands for Gln, His,
      Arg, or Leu.
<220> FEATURE:
<221> NAME/KEY: misc_feature
<222> LOCATION: (13)..(13)
<223> OTHER INFORMATION: The 'Xaa' at location 13 stands for Val, Ile,
      or Met.
<220> FEATURE:
<223> OTHER INFORMATION: Synthetic Construct

<400> SEQUENCE: 8

Xaa Xaa Xaa Xaa Xaa Xaa Xaa Xaa Xaa Ala Gly Asp Xaa Glu Ser Asn
1               5                   10                  15

Pro Gly Pro

<210> SEQ ID NO 9
<211> LENGTH: 30
<212> TYPE: DNA
<213> ORGANISM: Artificial Sequence
<220> FEATURE:
<223> OTHER INFORMATION: Translation interrupter motif 3
<220> FEATURE:
<221> NAME/KEY: CDS
<222> LOCATION: (1)..(30)
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
```

```
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t

<400> SEQUENCE: 9 gcn ggn gay rtn gar wsn aay ccn ggn ccn                              30
Ala Gly Asp Xaa Glu Ser Asn Pro Gly Pro
1               5                   10

<210> SEQ ID NO 10
<211> LENGTH: 10
<212> TYPE: PRT
<213> ORGANISM: Artificial Sequence
<220> FEATURE:
<221> NAME/KEY: misc_feature
<222> LOCATION: (4)..(4)
<223> OTHER INFORMATION: The 'Xaa' at location 4 stands for Val, Ile, or
      Met.
<220> FEATURE:
<223> OTHER INFORMATION: Synthetic Construct

<400> SEQUENCE: 10

Ala Gly Asp Xaa Glu Ser Asn Pro Gly Pro
1               5                   10

<210> SEQ ID NO 11
<211> LENGTH: 42
<212> TYPE: DNA
<213> ORGANISM: Artificial Sequence
<220> FEATURE:
<223> OTHER INFORMATION: Translation interruptor 4
<220> FEATURE:
<221> NAME/KEY: CDS
<222> LOCATION: (1)..(42)
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (22)..(24)
<223> OTHER INFORMATION: n is a, c, g, or t
<220> FEATURE:
<221> NAME/KEY: misc_feature
<222> LOCATION: (28)..(30)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
```

<400> SEQUENCE: 11

```
ctn ctn nnn nnn gcn ggn gay nnn gar nnn aay ccn ggn ccn        42
Xaa Xaa Xaa Xaa Ala Gly Asp Xaa Glu Xaa Asn Pro Gly Pro
1               5                   10
```

<210> SEQ ID NO 12
<211> LENGTH: 14
<212> TYPE: PRT
<213> ORGANISM: Artificial Sequence
<220> FEATURE:
<221> NAME/KEY: misc_feature
<222> LOCATION: (1)..(1)
<223> OTHER INFORMATION: The 'Xaa' at location 1 stands for Leu.
<220> FEATURE:
<221> NAME/KEY: misc_feature
<222> LOCATION: (2)..(2)
<223> OTHER INFORMATION: The 'Xaa' at location 2 stands for Leu.
<220> FEATURE:
<221> NAME/KEY: misc_feature
<222> LOCATION: (3)..(3)
<223> OTHER INFORMATION: The 'Xaa' at location 3 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (4)..(4)
<223> OTHER INFORMATION: The 'Xaa' at location 4 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (8)..(8)
<223> OTHER INFORMATION: The 'Xaa' at location 8 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (10)..(10)
<223> OTHER INFORMATION: The 'Xaa' at location 10 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<223> OTHER INFORMATION: Synthetic Construct

<400> SEQUENCE: 12

```
Xaa Xaa Xaa Xaa Ala Gly Asp Xaa Glu Xaa Asn Pro Gly Pro
1               5                   10
```

<210> SEQ ID NO 13
<211> LENGTH: 24
<212> TYPE: DNA
<213> ORGANISM: Artificial Sequence
<220> FEATURE:
<223> OTHER INFORMATION: Translation interruptor sequence 5
<220> FEATURE:
<221> NAME/KEY: CDS
<222> LOCATION: (1)..(24)
<220> FEATURE:
<221> NAME/KEY: misc_feature
<222> LOCATION: (4)..(6)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature

```
<222> LOCATION: (24)..(24)
<223> OTHER INFORMATION: n is a, c, g, or t

<400> SEQUENCE: 13 gay nnn gar nnn aay ccn ggn ccn                                24
Asp Xaa Glu Xaa Asn Pro Gly Pro
1               5

<210> SEQ ID NO 14
<211> LENGTH: 8
<212> TYPE: PRT
<213> ORGANISM: Artificial Sequence
<220> FEATURE:
<221> NAME/KEY: misc_feature
<222> LOCATION: (2)..(2)
<223> OTHER INFORMATION: The 'Xaa' at location 2 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (4)..(4)
<223> OTHER INFORMATION: The 'Xaa' at location 4 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<223> OTHER INFORMATION: Synthetic Construct

<400> SEQUENCE: 14

Asp Xaa Glu Xaa Asn Pro Gly Pro
1               5

<210> SEQ ID NO 15
<211> LENGTH: 90
<212> TYPE: DNA
<213> ORGANISM: Foot-and-mouth disease virus
<220> FEATURE:
<221> NAME/KEY: CDS
<222> LOCATION: (1)..(90)
<223> OTHER INFORMATION: Delta-2A

<400> SEQUENCE: 15 cac aag caa aag atc att gca cca gca aag cag ctt ctg aat ttt gac    48
His Lys Gln Lys Ile Ile Ala Pro Ala Lys Gln Leu Leu Asn Phe Asp
1               5                   10                  15 ctg ctc aag ttg gcc gga gac gtt gag tcc aac cct gga ccc              90
Leu Leu Lys Leu Ala Gly Asp Val Glu Ser Asn Pro Gly Pro
            20                  25                  30

<210> SEQ ID NO 16
<211> LENGTH: 30
<212> TYPE: PRT
<213> ORGANISM: Foot-and-mouth disease virus

<400> SEQUENCE: 16

His Lys Gln Lys Ile Ile Ala Pro Ala Lys Gln Leu Leu Asn Phe Asp
1               5                   10                  15

Leu Leu Lys Leu Ala Gly Asp Val Glu Ser Asn Pro Gly Pro
            20                  25                  30

<210> SEQ ID NO 17
<211> LENGTH: 60
<212> TYPE: DNA
<213> ORGANISM: Foot-and-mouth disease virus
<220> FEATURE:
<221> NAME/KEY: CDS
<222> LOCATION: (1)..(60)
<223> OTHER INFORMATION: FMDV 2A polynucleotide

<400> SEQUENCE: 17
```

-continued

```
cag ctt ctg aat ttt gac ctg ctc aag ttg gcc gga gac gtt gag tcc    48
Gln Leu Leu Asn Phe Asp Leu Leu Lys Leu Ala Gly Asp Val Glu Ser
1               5                   10                  15 aac cct ggg ccc                                                    60
Asn Pro Gly Pro
            20
```

<210> SEQ ID NO 18
<211> LENGTH: 20
<212> TYPE: PRT
<213> ORGANISM: Foot-and-mouth disease virus

<400> SEQUENCE: 18

```
Gln Leu Leu Asn Phe Asp Leu Leu Lys Leu Ala Gly Asp Val Glu Ser
1               5                   10                  15

Asn Pro Gly Pro
            20
```

<210> SEQ ID NO 19
<211> LENGTH: 63
<212> TYPE: DNA
<213> ORGANISM: Bovine rhinitis virus A
<220> FEATURE:
<221> NAME/KEY: CDS
<222> LOCATION: (1)..(63)
<223> OTHER INFORMATION: Bovine rhinitis A 2A

<400> SEQUENCE: 19

```
tct ggt ata agc aac aag gac ctg cta ttg cag gcc ggt gat gtt gag    48
Ser Gly Ile Ser Asn Lys Asp Leu Leu Leu Gln Ala Gly Asp Val Glu
1               5                   10                  15 aca aac cct ggt ccc                                                63
Thr Asn Pro Gly Pro
            20
```

<210> SEQ ID NO 20
<211> LENGTH: 21
<212> TYPE: PRT
<213> ORGANISM: Bovine rhinitis virus A

<400> SEQUENCE: 20

```
Ser Gly Ile Ser Asn Lys Asp Leu Leu Leu Gln Ala Gly Asp Val Glu
1               5                   10                  15

Thr Asn Pro Gly Pro
            20
```

<210> SEQ ID NO 21
<211> LENGTH: 51
<212> TYPE: DNA
<213> ORGANISM: Equine rhinitis B
<220> FEATURE:
<221> NAME/KEY: CDS
<222> LOCATION: (1)..(51)
<223> OTHER INFORMATION: Equine rhinitis B 2A

<400> SEQUENCE: 21

```
aac ttt gac ctg ctc aaa ctg gca ggc gat gtg gaa tca aac cca ggc    48
Asn Phe Asp Leu Leu Lys Leu Ala Gly Asp Val Glu Ser Asn Pro Gly
1               5                   10                  15 ccc                                                                51
Pro
```

<210> SEQ ID NO 22
<211> LENGTH: 17

<212> TYPE: PRT
<213> ORGANISM: Equine rhinitis B

<400> SEQUENCE: 22

Asn Phe Asp Leu Leu Lys Leu Ala Gly Asp Val Glu Ser Asn Pro Gly
1               5                   10                  15

Pro

<210> SEQ ID NO 23
<211> LENGTH: 570
<212> TYPE: DNA
<213> ORGANISM: Sus scrofa
<220> FEATURE:
<221> NAME/KEY: CDS
<222> LOCATION: (1)..(570)
<223> OTHER INFORMATION: Porcine Interferon Alpha

<400> SEQUENCE: 23

```
atg gcc cca acc tca gcc ttc ctc acg gcc ctg gtg cta ctc agc tgc      48
Met Ala Pro Thr Ser Ala Phe Leu Thr Ala Leu Val Leu Leu Ser Cys
1               5                   10                  15 aat gcc atc tgc tct ctg ggc tgt gac ctg cct cag acc cac agc ctg      96
Asn Ala Ile Cys Ser Leu Gly Cys Asp Leu Pro Gln Thr His Ser Leu
                20                  25                  30 gct cac acc aga gcc ctg agg ctc ctg gca caa atg agg aga atc tct     144
Ala His Thr Arg Ala Leu Arg Leu Leu Ala Gln Met Arg Arg Ile Ser
            35                  40                  45 ccc ttc tcc tgc ctg gac cac aga agg gac ttt ggt tcc cct cat gag     192
Pro Phe Ser Cys Leu Asp His Arg Arg Asp Phe Gly Ser Pro His Glu
        50                  55                  60 gct ttt ggg ggc aac cag gtc cag aag gct caa gcc atg gct ctg gtg     240
Ala Phe Gly Gly Asn Gln Val Gln Lys Ala Gln Ala Met Ala Leu Val
65                  70                  75                  80 cat gag atg ctc cag cag acc ttc cag ctc ttc agc aca gag ggc tcg     288
His Glu Met Leu Gln Gln Thr Phe Gln Leu Phe Ser Thr Glu Gly Ser
                85                  90                  95 gct gct gcc tgg aat gag agc ctc ctg cac cag ttc tgc act gga ctg     336
Ala Ala Ala Trp Asn Glu Ser Leu Leu His Gln Phe Cys Thr Gly Leu
            100                 105                 110 gat cag cag ctc agg gac ctg gaa gcc tgt gtc atg cag gag gcg ggg     384
Asp Gln Gln Leu Arg Asp Leu Glu Ala Cys Val Met Gln Glu Ala Gly
        115                 120                 125 ctg gaa ggg acc ccc ctg ctg gag gag gac tcc atc ctg gct gtg agg     432
Leu Glu Gly Thr Pro Leu Leu Glu Glu Asp Ser Ile Leu Ala Val Arg
130                 135                 140 aaa tac ttc cac aga ctc acc ctc tat ctg caa gag aag agc tac agc     480
Lys Tyr Phe His Arg Leu Thr Leu Tyr Leu Gln Glu Lys Ser Tyr Ser
145                 150                 155                 160 ccc tgt gcc tgg gag atc gtc agg gca gaa gtc atg aga tcc ttc tct     528
Pro Cys Ala Trp Glu Ile Val Arg Ala Glu Val Met Arg Ser Phe Ser
                165                 170                 175 tcc tcc aga aac ctg caa gac aga ctc agg aag aag gag tga             570
Ser Ser Arg Asn Leu Gln Asp Arg Leu Arg Lys Lys Glu
            180                 185
```

<210> SEQ ID NO 24
<211> LENGTH: 189
<212> TYPE: PRT
<213> ORGANISM: Sus scrofa

<400> SEQUENCE: 24

Met Ala Pro Thr Ser Ala Phe Leu Thr Ala Leu Val Leu Leu Ser Cys

```
            1               5                  10                 15
          Asn Ala Ile Cys Ser Leu Gly Cys Asp Leu Pro Gln Thr His Ser Leu
                          20                 25                 30

Ala His Thr Arg Ala Leu Arg Leu Leu Ala Gln Met Arg Arg Ile Ser
                          35                 40                 45

Pro Phe Ser Cys Leu Asp His Arg Arg Asp Phe Gly Ser Pro His Glu
                          50                 55                 60

Ala Phe Gly Gly Asn Gln Val Gln Lys Ala Gln Ala Met Ala Leu Val
           65                  70                 75                 80

His Glu Met Leu Gln Gln Thr Phe Gln Leu Phe Ser Thr Glu Gly Ser
                          85                 90                 95

Ala Ala Ala Trp Asn Glu Ser Leu Leu His Gln Phe Cys Thr Gly Leu
                          100                105                110

Asp Gln Gln Leu Arg Asp Leu Glu Ala Cys Val Met Gln Glu Ala Gly
                          115                120                125

Leu Glu Gly Thr Pro Leu Leu Glu Glu Asp Ser Ile Leu Ala Val Arg
                          130                135                140

Lys Tyr Phe His Arg Leu Thr Leu Tyr Leu Gln Glu Lys Ser Tyr Ser
          145                 150                155                160

Pro Cys Ala Trp Glu Ile Val Arg Ala Glu Val Met Arg Ser Phe Ser
                          165                170                175

Ser Ser Arg Asn Leu Gln Asp Arg Leu Arg Lys Lys Glu
                          180                185

<210> SEQ ID NO 25
<211> LENGTH: 66
<212> TYPE: DNA
<213> ORGANISM: Sus scrofa
<220> FEATURE:
<221> NAME/KEY: CDS
<222> LOCATION: (1)..(66)
<223> OTHER INFORMATION: Porcine Interferon Alpha Secretion Peptide

<400> SEQUENCE: 25 atg gcc cca acc tca gcc ttc ctc acg gcc ctg gtg cta ctc agc tgc        48
Met Ala Pro Thr Ser Ala Phe Leu Thr Ala Leu Val Leu Leu Ser Cys
1               5                  10                 15 aat gcc atc tgc tct ctg                                                66
Asn Ala Ile Cys Ser Leu
            20

<210> SEQ ID NO 26
<211> LENGTH: 22
<212> TYPE: PRT
<213> ORGANISM: Sus scrofa

<400> SEQUENCE: 26

Met Ala Pro Thr Ser Ala Phe Leu Thr Ala Leu Val Leu Leu Ser Cys
1               5                  10                 15

Asn Ala Ile Cys Ser Leu
            20

<210> SEQ ID NO 27
<211> LENGTH: 69
<212> TYPE: DNA
<213> ORGANISM: Homo sapiens
<220> FEATURE:
<221> NAME/KEY: CDS
<222> LOCATION: (1)..(69)
<223> OTHER INFORMATION: Human Interferon Alpha Secretion peptide
```

```
<400> SEQUENCE: 27 atg gcc tcg ccc ttt gct tta ctg atg gtc ctg gtg gtg ctc agc tgc    48
Met Ala Ser Pro Phe Ala Leu Leu Met Val Leu Val Val Leu Ser Cys
1               5                   10                  15 aag tca agc tgc tct ccg ggc                                        69
Lys Ser Ser Cys Ser Pro Gly
            20

<210> SEQ ID NO 28
<211> LENGTH: 23
<212> TYPE: PRT
<213> ORGANISM: Homo sapiens

<400> SEQUENCE: 28

Met Ala Ser Pro Phe Ala Leu Leu Met Val Leu Val Val Leu Ser Cys
1               5                   10                  15

Lys Ser Ser Cys Ser Pro Gly
            20

<210> SEQ ID NO 29
<211> LENGTH: 63
<212> TYPE: DNA
<213> ORGANISM: Bos taurus
<220> FEATURE:
<221> NAME/KEY: CDS
<222> LOCATION: (1)..(63)
<223> OTHER INFORMATION: Bovine Interferon Beta Secretion Peptide

<400> SEQUENCE: 29 atg acc tac cgg tgc ctc ctc cag atg gtt ctc ctg ctg tgt ttc tcc    48
Met Thr Tyr Arg Cys Leu Leu Gln Met Val Leu Leu Leu Cys Phe Ser
1               5                   10                  15 acc aca gct ctt tcc                                                63
Thr Thr Ala Leu Ser
            20

<210> SEQ ID NO 30
<211> LENGTH: 21
<212> TYPE: PRT
<213> ORGANISM: Bos taurus

<400> SEQUENCE: 30

Met Thr Tyr Arg Cys Leu Leu Gln Met Val Leu Leu Leu Cys Phe Ser
1               5                   10                  15

Thr Thr Ala Leu Ser
            20

<210> SEQ ID NO 31
<211> LENGTH: 63
<212> TYPE: DNA
<213> ORGANISM: Sus scrofa
<220> FEATURE:
<221> NAME/KEY: CDS
<222> LOCATION: (1)..(63)
<223> OTHER INFORMATION: Porcine Interferon Beta Secretion Peptide

<400> SEQUENCE: 31 atg gct aac aag tgc atc ctc caa atc gct ctc ctg atg tgt ttc tcc    48
Met Ala Asn Lys Cys Ile Leu Gln Ile Ala Leu Leu Met Cys Phe Ser
1               5                   10                  15 acc aca gct ctt tcc                                                63
Thr Thr Ala Leu Ser
            20
```

```
<210> SEQ ID NO 32
<211> LENGTH: 21
<212> TYPE: PRT
<213> ORGANISM: Sus scrofa

<400> SEQUENCE: 32

Met Ala Asn Lys Cys Ile Leu Gln Ile Ala Leu Leu Met Cys Phe Ser
1               5                   10                  15

Thr Thr Ala Leu Ser
            20

<210> SEQ ID NO 33
<211> LENGTH: 63
<212> TYPE: DNA
<213> ORGANISM: Homo sapiens
<220> FEATURE:
<221> NAME/KEY: CDS
<222> LOCATION: (1)..(63)
<223> OTHER INFORMATION: Human Interferon Beta Secretion peptide

<400> SEQUENCE: 33 atg acc aac aag tgt ctc ctc caa att gct ctc ctg ttg tgc ttc tcc      48
Met Thr Asn Lys Cys Leu Leu Gln Ile Ala Leu Leu Leu Cys Phe Ser
1               5                   10                  15 acg aca gct ctt tcc                                                  63
Thr Thr Ala Leu Ser
            20

<210> SEQ ID NO 34
<211> LENGTH: 21
<212> TYPE: PRT
<213> ORGANISM: Homo sapiens

<400> SEQUENCE: 34

Met Thr Asn Lys Cys Leu Leu Gln Ile Ala Leu Leu Leu Cys Phe Ser
1               5                   10                  15

Thr Thr Ala Leu Ser
            20

<210> SEQ ID NO 35
<211> LENGTH: 69
<212> TYPE: DNA
<213> ORGANISM: Bos taurus
<220> FEATURE:
<221> NAME/KEY: CDS
<222> LOCATION: (1)..(69)
<223> OTHER INFORMATION: Bovine Interferon Gamma Secretion peptide

<400> SEQUENCE: 35 atg aaa tat aca agc tat ttc tta gct tta ctg ctc tgt ggg ctt ttg      48
Met Lys Tyr Thr Ser Tyr Phe Leu Ala Leu Leu Leu Cys Gly Leu Leu
1               5                   10                  15 ggt ttt tct ggt tct tat ggc                                          69
Gly Phe Ser Gly Ser Tyr Gly
            20

<210> SEQ ID NO 36
<211> LENGTH: 23
<212> TYPE: PRT
<213> ORGANISM: Bos taurus

<400> SEQUENCE: 36

Met Lys Tyr Thr Ser Tyr Phe Leu Ala Leu Leu Leu Cys Gly Leu Leu
1               5                   10                  15

Gly Phe Ser Gly Ser Tyr Gly
```

<210> SEQ ID NO 37
<211> LENGTH: 69
<212> TYPE: DNA
<213> ORGANISM: Sus scrofa
<220> FEATURE:
<221> NAME/KEY: CDS
<222> LOCATION: (1)..(69)
<223> OTHER INFORMATION: Porcine Interferon Gamma Secretion peptide

<400> SEQUENCE: 37

```
atg agt tat aca act tat ttc tta gct ttt cag ctt tgc gtg act ttg    48
Met Ser Tyr Thr Thr Tyr Phe Leu Ala Phe Gln Leu Cys Val Thr Leu
1               5                   10                  15 tgt ttt tct ggc tct tac tgc                                        69
Cys Phe Ser Gly Ser Tyr Cys
            20
```

<210> SEQ ID NO 38
<211> LENGTH: 23
<212> TYPE: PRT
<213> ORGANISM: Sus scrofa

<400> SEQUENCE: 38

```
Met Ser Tyr Thr Thr Tyr Phe Leu Ala Phe Gln Leu Cys Val Thr Leu
1               5                   10                  15

Cys Phe Ser Gly Ser Tyr Cys
            20
```

<210> SEQ ID NO 39
<211> LENGTH: 69
<212> TYPE: DNA
<213> ORGANISM: Homo sapiens
<220> FEATURE:
<221> NAME/KEY: CDS
<222> LOCATION: (1)..(69)
<223> OTHER INFORMATION: Human Interferon Gamma Secretion peptide

<400> SEQUENCE: 39

```
atg aaa tat aca agt tat atc ttg gct ttt cag ctc tgc atc gtt ttg    48
Met Lys Tyr Thr Ser Tyr Ile Leu Ala Phe Gln Leu Cys Ile Val Leu
1               5                   10                  15 ggt tct ctt ggc tgt tac tgc                                        69
Gly Ser Leu Gly Cys Tyr Cys
            20
```

<210> SEQ ID NO 40
<211> LENGTH: 23
<212> TYPE: PRT
<213> ORGANISM: Homo sapiens

<400> SEQUENCE: 40

```
Met Lys Tyr Thr Ser Tyr Ile Leu Ala Phe Gln Leu Cys Ile Val Leu
1               5                   10                  15

Gly Ser Leu Gly Cys Tyr Cys
            20
```

<210> SEQ ID NO 41
<211> LENGTH: 57
<212> TYPE: DNA
<213> ORGANISM: Bos taurus
<220> FEATURE:
<221> NAME/KEY: CDS
<222> LOCATION: (1)..(57)
<223> OTHER INFORMATION: Bovine Interferon Lambda Secretion peptide

```
<400> SEQUENCE: 41 atg gcc ccg ggc tgc acg ctg gtg ctg gtg ctg atg ctg acg acc gtg      48
Met Ala Pro Gly Cys Thr Leu Val Leu Val Leu Met Leu Thr Thr Val
1               5                   10                  15 gcg ctg agc                                                           57
Ala Leu Ser <210> SEQ ID NO 42
<211> LENGTH: 19
<212> TYPE: PRT
<213> ORGANISM: Bos taurus

<400> SEQUENCE: 42

Met Ala Pro Gly Cys Thr Leu Val Leu Val Leu Met Leu Thr Thr Val
1               5                   10                  15

Ala Leu Ser

<210> SEQ ID NO 43
<211> LENGTH: 48
<212> TYPE: DNA
<213> ORGANISM: Sus scrofa
<220> FEATURE:
<221> NAME/KEY: CDS
<222> LOCATION: (1)..(48)
<223> OTHER INFORMATION: Porcine Interferon Lambda Secretion peptide

<400> SEQUENCE: 43 atg gct aca gct tgg atc gtg gtg ctg gcg act gtg atg ctg gac ttg      48
Met Ala Thr Ala Trp Ile Val Val Leu Ala Thr Val Met Leu Asp Leu
1               5                   10                  15

<210> SEQ ID NO 44
<211> LENGTH: 16
<212> TYPE: PRT
<213> ORGANISM: Sus scrofa

<400> SEQUENCE: 44

Met Ala Thr Ala Trp Ile Val Val Leu Ala Thr Val Met Leu Asp Leu
1               5                   10                  15

<210> SEQ ID NO 45
<211> LENGTH: 45
<212> TYPE: DNA
<213> ORGANISM: Homo sapiens
<220> FEATURE:
<221> NAME/KEY: CDS
<222> LOCATION: (1)..(45)
<223> OTHER INFORMATION: Human Interferon Lambda Secretion peptide

<400> SEQUENCE: 45 atg gct gca gct tgg acc gtg gtg ctg gtg act ttg gtg cta ggc          45
Met Ala Ala Ala Trp Thr Val Val Leu Val Thr Leu Val Leu Gly
1               5                   10                  15

<210> SEQ ID NO 46
<211> LENGTH: 15
<212> TYPE: PRT
<213> ORGANISM: Homo sapiens

<400> SEQUENCE: 46

Met Ala Ala Ala Trp Thr Val Val Leu Val Thr Leu Val Leu Gly
1               5                   10                  15

<210> SEQ ID NO 47
```

<211> LENGTH: 1065
<212> TYPE: DNA
<213> ORGANISM: Sus scrofa
<220> FEATURE:
<221> NAME/KEY: CDS
<222> LOCATION: (1)..(1065)
<223> OTHER INFORMATION: Porcine SGLucON Alpha

<400> SEQUENCE: 47

```
atg gga gtc aaa gtt ctg ttt gcc ctg atc tgc atc gct gtg gcc gag     48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc     96
Ala Lys Pro Thr Glu Asn Asn Glu Asp Phe Asn Ile Val Ala Val Ala
            20                  25                  30 agc aac ttt gcg acc acg gat ctc gat gct gac cga ggg aag ttg ccc    144
Ser Asn Phe Ala Thr Thr Asp Leu Asp Ala Asp Arg Gly Lys Leu Pro
        35                  40                  45 ggc aag aag ctg ccg ctg gag gtg ctc aaa gag atg gaa gcc aat gcc    192
Gly Lys Lys Leu Pro Leu Glu Val Leu Lys Glu Met Glu Ala Asn Ala
    50                  55                  60 cgg aaa gct ggc tgc acc agg ggc tgt ctg atc tgc ctg tcc cac atc    240
Arg Lys Ala Gly Cys Thr Arg Gly Cys Leu Ile Cys Leu Ser His Ile
65                  70                  75                  80 aag tgc acg ccc aag atg aag aag tgg ctc cca gga cgc tgc cac acc    288
Lys Cys Thr Pro Lys Met Lys Lys Trp Leu Pro Gly Arg Cys His Thr
                85                  90                  95 tac gaa ggc gac aaa gag tcc gca cag ggc ggc ata ggc gag gcg atc    336
Tyr Glu Gly Asp Lys Glu Ser Ala Gln Gly Gly Ile Gly Glu Ala Ile
            100                 105                 110 gtc gat att cct gag att cct ggg ttc aag gac ttg gag cca atg gag    384
Val Asp Ile Pro Glu Ile Pro Gly Phe Lys Asp Leu Glu Pro Met Glu
        115                 120                 125 cag ttc atc gca cag gtc gat ctg tgt gtg gac tgc aca act ggc tgc    432
Gln Phe Ile Ala Gln Val Asp Leu Cys Val Asp Cys Thr Thr Gly Cys
    130                 135                 140 ctc aaa ggg ctt gcc aac gtg cag tgt tct gac ctg ctc aag aag tgg    480
Leu Lys Gly Leu Ala Asn Val Gln Cys Ser Asp Leu Leu Lys Lys Trp
145                 150                 155                 160 ctg ccg caa cgc tgt gcg acc ttt gcc agc aag atc cag ggc cag gtg    528
Leu Pro Gln Arg Cys Ala Thr Phe Ala Ser Lys Ile Gln Gly Gln Val
                165                 170                 175 gac aag atc aag ggg gcc ggt ggt gac ggg ccc ggg tgt gac ctg cct    576
Asp Lys Ile Lys Gly Ala Gly Gly Asp Gly Pro Gly Cys Asp Leu Pro
            180                 185                 190 cag acc cac agc ctg gct cac acc aga gcc ctg agg ctc ctg gca caa    624
Gln Thr His Ser Leu Ala His Thr Arg Ala Leu Arg Leu Leu Ala Gln
        195                 200                 205 atg agg aga atc tct ccc ttc tcc tgc ctg gac cac aga agg gac ttt    672
Met Arg Arg Ile Ser Pro Phe Ser Cys Leu Asp His Arg Arg Asp Phe
    210                 215                 220 ggt tcc cct cat gag gct ttt ggg ggc aac cag gtc cag aag gct caa    720
Gly Ser Pro His Glu Ala Phe Gly Gly Asn Gln Val Gln Lys Ala Gln
225                 230                 235                 240 gcc atg gct ctg gtg cat gag atg ctc cag cag acc ttc cag ctc ttc    768
Ala Met Ala Leu Val His Glu Met Leu Gln Gln Thr Phe Gln Leu Phe
                245                 250                 255 agc aca gag ggc tcg gct gct gcc tgg aat gag agc ctc ctg cac cag    816
Ser Thr Glu Gly Ser Ala Ala Ala Trp Asn Glu Ser Leu Leu His Gln
            260                 265                 270 ttc tgc act gga ctg gat cag cag ctc agg gac ctg gaa gcc tgt gtc    864
Phe Cys Thr Gly Leu Asp Gln Gln Leu Arg Asp Leu Glu Ala Cys Val
```

```
         Phe Cys Thr Gly Leu Asp Gln Gln Leu Arg Asp Leu Glu Ala Cys Val
                     275                 280                 285 atg cag gag gcg ggg ctg gaa ggg acc ccc ctg ctg gag gag gac tcc          912
Met Gln Glu Ala Gly Leu Glu Gly Thr Pro Leu Leu Glu Glu Asp Ser
        290                 295                 300 atc ctg gct gtg agg aaa tac ttc cac aga ctc acc ctc tat ctg caa          960
Ile Leu Ala Val Arg Lys Tyr Phe His Arg Leu Thr Leu Tyr Leu Gln
305                 310                 315                 320 gag aag agc tac agc ccc tgt gcc tgg gag atc gtc agg gca gaa gtc         1008
Glu Lys Ser Tyr Ser Pro Cys Ala Trp Glu Ile Val Arg Ala Glu Val
                325                 330                 335 atg aga tcc ttc tct tcc tcc aga aac ctg caa gac aga ctc agg aag         1056
Met Arg Ser Phe Ser Ser Ser Arg Asn Leu Gln Asp Arg Leu Arg Lys
            340                 345                 350 aag gag tga                                                             1065
Lys Glu <210> SEQ ID NO 48
<211> LENGTH: 354
<212> TYPE: PRT
<213> ORGANISM: Sus scrofa

<400> SEQUENCE: 48

Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
                20                  25                  30

Ser Asn Phe Ala Thr Thr Asp Leu Asp Ala Asp Arg Gly Lys Leu Pro
            35                  40                  45

Gly Lys Lys Leu Pro Leu Glu Val Leu Lys Glu Met Glu Ala Asn Ala
        50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Trp Leu Pro Gly Arg Cys His Thr
                85                  90                  95

Tyr Glu Gly Asp Lys Glu Ser Ala Gln Gly Gly Ile Gly Glu Ala Ile
                100                 105                 110

Val Asp Ile Pro Glu Ile Pro Gly Phe Lys Asp Leu Glu Pro Met Glu
            115                 120                 125

Gln Phe Ile Ala Gln Val Asp Leu Cys Val Asp Cys Thr Thr Gly Cys
        130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Asp Gly Pro Gly Cys Asp Leu Pro
            180                 185                 190

Gln Thr His Ser Leu Ala His Thr Arg Ala Leu Arg Leu Leu Ala Gln
        195                 200                 205

Met Arg Arg Ile Ser Pro Phe Ser Cys Leu Asp His Arg Arg Asp Phe
210                 215                 220

Gly Ser Pro His Glu Ala Phe Gly Gly Asn Val Gln Lys Ala Gln
225                 230                 235                 240

Ala Met Ala Leu Val His Glu Met Leu Gln Gln Thr Phe Gln Leu Phe
                245                 250                 255

Ser Thr Glu Gly Ser Ala Ala Ala Trp Asn Glu Ser Leu Leu His Gln
```

```
                260                 265                 270
Phe Cys Thr Gly Leu Asp Gln Gln Leu Arg Asp Leu Glu Ala Cys Val
                    275                 280                 285

Met Gln Glu Ala Gly Leu Glu Gly Thr Pro Leu Leu Glu Glu Asp Ser
            290                 295                 300

Ile Leu Ala Val Arg Lys Tyr Phe His Arg Leu Thr Leu Tyr Leu Gln
305                 310                 315                 320

Glu Lys Ser Tyr Ser Pro Cys Ala Trp Glu Ile Val Arg Ala Glu Val
                    325                 330                 335

Met Arg Ser Phe Ser Ser Ser Arg Asn Leu Gln Asp Arg Leu Arg Lys
            340                 345                 350

Lys Glu

<210> SEQ ID NO 49
<211> LENGTH: 570
<212> TYPE: DNA
<213> ORGANISM: Homo sapiens
<220> FEATURE:
<221> NAME/KEY: CDS
<222> LOCATION: (1)..(570)
<223> OTHER INFORMATION: Human Interferon Alpha

<400> SEQUENCE: 49 atg gcc tcg ccc ttt gct tta ctg atg gtc ctg gtg gtg ctc agc tgc        48
Met Ala Ser Pro Phe Ala Leu Leu Met Val Leu Val Val Leu Ser Cys
1               5                   10                  15 aag tca agc tgc tct ccg ggc tgt gat ctc cct gag acc cac agc ctg        96
Lys Ser Ser Cys Ser Pro Gly Cys Asp Leu Pro Glu Thr His Ser Leu
                20                  25                  30 gat aac agg agg acc ttg atg ctc ctg gca caa atg agc aga atc tct       144
Asp Asn Arg Arg Thr Leu Met Leu Leu Ala Gln Met Ser Arg Ile Ser
            35                  40                  45 cct tcc tcc tgt ctg atg gac aga cat gac ttt gga ttt ccc cag gag       192
Pro Ser Ser Cys Leu Met Asp Arg His Asp Phe Gly Phe Pro Gln Glu
        50                  55                  60 gag ttt gat ggc aac cag ttc cag aag gct cca gcc atc tct gtc ctc       240
Glu Phe Asp Gly Asn Gln Phe Gln Lys Ala Pro Ala Ile Ser Val Leu
65                  70                  75                  80 caa gag ctg atc cag cag atc ttc aac ctc ttt acc aca aaa gat tca       288
Gln Glu Leu Ile Gln Gln Ile Phe Asn Leu Phe Thr Thr Lys Asp Ser
                85                  90                  95 tct gct gct tgg gat gag gac ctc cta gac aaa ttc tgc acc gaa ctc       336
Ser Ala Ala Trp Asp Glu Asp Leu Leu Asp Lys Phe Cys Thr Glu Leu
            100                 105                 110 tac cag cag ctg aat gac ttg gaa gcc tgt gtg atg cag gag gag agg       384
Tyr Gln Gln Leu Asn Asp Leu Glu Ala Cys Val Met Gln Glu Glu Arg
        115                 120                 125 gtg gga gaa act ccc ctg atg aat gcg gac tcc atc ttg gct gtg aag       432
Val Gly Glu Thr Pro Leu Met Asn Ala Asp Ser Ile Leu Ala Val Lys
    130                 135                 140 aaa tac ttc cga aga atc act ctc tat ctg acg gag aag aaa tac agc       480
Lys Tyr Phe Arg Arg Ile Thr Leu Tyr Leu Thr Glu Lys Lys Tyr Ser
145                 150                 155                 160 cct tgt gcc tgg gag gtt gtc aga gca gaa atc gtg aga tcc ctc tct       528
Pro Cys Ala Trp Glu Val Val Arg Ala Glu Ile Val Arg Ser Leu Ser
                165                 170                 175 tta tca aca aac ttg caa gaa aga tta agg agg aag gaa taa               570
Leu Ser Thr Asn Leu Gln Glu Arg Leu Arg Arg Lys Glu
                180                 185
```

<210> SEQ ID NO 50
<211> LENGTH: 189
<212> TYPE: PRT
<213> ORGANISM: Homo sapiens

<400> SEQUENCE: 50

```
Met Ala Ser Pro Phe Ala Leu Leu Met Val Leu Val Leu Ser Cys
1               5                   10                  15

Lys Ser Ser Cys Ser Pro Gly Cys Asp Leu Pro Glu Thr His Ser Leu
            20                  25                  30

Asp Asn Arg Arg Thr Leu Met Leu Leu Ala Gln Met Ser Arg Ile Ser
            35                  40                  45

Pro Ser Ser Cys Leu Met Asp Arg His Asp Phe Gly Phe Pro Gln Glu
    50                  55                  60

Glu Phe Asp Gly Asn Gln Phe Gln Lys Ala Pro Ala Ile Ser Val Leu
65                  70                  75                  80

Gln Glu Leu Ile Gln Gln Ile Phe Asn Leu Phe Thr Thr Lys Asp Ser
                85                  90                  95

Ser Ala Ala Trp Asp Glu Asp Leu Leu Asp Lys Phe Cys Thr Glu Leu
            100                 105                 110

Tyr Gln Gln Leu Asn Asp Leu Glu Ala Cys Val Met Gln Glu Glu Arg
            115                 120                 125

Val Gly Glu Thr Pro Leu Met Asn Ala Asp Ser Ile Leu Ala Val Lys
    130                 135                 140

Lys Tyr Phe Arg Arg Ile Thr Leu Tyr Leu Thr Glu Lys Lys Tyr Ser
145                 150                 155                 160

Pro Cys Ala Trp Glu Val Val Arg Ala Glu Ile Val Arg Ser Leu Ser
                165                 170                 175

Leu Ser Thr Asn Leu Gln Glu Arg Leu Arg Arg Lys Glu
            180                 185
```

<210> SEQ ID NO 51
<211> LENGTH: 1056
<212> TYPE: DNA
<213> ORGANISM: Homo sapiens
<220> FEATURE:
<221> NAME/KEY: CDS
<222> LOCATION: (1)..(1056)
<223> OTHER INFORMATION: Human GlucON Alpha

<400> SEQUENCE: 51

```
atg gga gtc aaa gtt ctg ttt gcc ctg atc tgc atc gct gtg gcc gag    48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc    96
Ala Lys Pro Thr Glu Asn Asn Glu Asp Phe Asn Ile Val Ala Val Ala
            20                  25                  30 agc aac ttc gcg acc acg gat ctc gat gct gac cgc ggg aag ttg ccc    144
Ser Asn Phe Ala Thr Thr Asp Leu Asp Ala Asp Arg Gly Lys Leu Pro
        35                  40                  45 ggc aag aag ctg ccg ctg gag gtg ctc aaa gag atg gaa gcc aat gcc    192
Gly Lys Lys Leu Pro Leu Glu Val Leu Lys Glu Met Glu Ala Asn Ala
    50                  55                  60 cgg aaa gct ggc tgt acc agg ggc tgt ctg atc tgc ctg tcc cac atc    240
Arg Lys Ala Gly Cys Thr Arg Gly Cys Leu Ile Cys Leu Ser His Ile
65                  70                  75                  80 aag tgc acg ccc aag atg aag aag ttc atc cca gga cgc tgc cac acc    288
Lys Cys Thr Pro Lys Met Lys Lys Phe Ile Pro Gly Arg Cys His Thr
                85                  90                  95
```

-continued

| | | |
|---|---|---|
| tac gaa ggc gac aaa gag tcc gca cag ggc ggc ata ggc gag gcg atc<br>Tyr Glu Gly Asp Lys Glu Ser Ala Gln Gly Gly Ile Gly Glu Ala Ile<br>               100                     105                    110 | | 336 |
| gtc gac att cct gag att cct ggg ttc aag gac ttg gag ccc atg gag<br>Val Asp Ile Pro Glu Ile Pro Gly Phe Lys Asp Leu Glu Pro Met Glu<br>       115                     120                     125 | | 384 |
| cag ttc atc gca cag gtc gat ctg tgt gtg gac tgc aca act ggc tgc<br>Gln Phe Ile Ala Gln Val Asp Leu Cys Val Asp Cys Thr Thr Gly Cys<br>130                     135                     140 | | 432 |
| ctc aaa ggg ctt gcc aac gtg cag tgt tct gac ctg ctc aag aag tgg<br>Leu Lys Gly Leu Ala Asn Val Gln Cys Ser Asp Leu Leu Lys Lys Trp<br>145                    150                    155                  160 | | 480 |
| ctg ccg caa cgc tgt gcg acc ttt gcc agc aag atc cag ggc cag gtg<br>Leu Pro Gln Arg Cys Ala Thr Phe Ala Ser Lys Ile Gln Gly Gln Val<br>                     165                     170                     175 | | 528 |
| gac aag atc aag ggg gcc ggt ggt gac tgt gat ctc cct gag acc cac<br>Asp Lys Ile Lys Gly Ala Gly Gly Asp Cys Asp Leu Pro Glu Thr His<br>             180                     185                     190 | | 576 |
| agc ctg gat aac agg agg acc ttg atg ctc ctg gca caa atg agc aga<br>Ser Leu Asp Asn Arg Arg Thr Leu Met Leu Leu Ala Gln Met Ser Arg<br>       195                     200                     205 | | 624 |
| atc tct cct tcc tcc tgt ctg atg gac aga cat gac ttt gga ttt ccc<br>Ile Ser Pro Ser Ser Cys Leu Met Asp Arg His Asp Phe Gly Phe Pro<br>210                     215                     220 | | 672 |
| cag gag gag ttt gat ggc aac cag ttc cag aag gct cca gcc atc tct<br>Gln Glu Glu Phe Asp Gly Asn Gln Phe Gln Lys Ala Pro Ala Ile Ser<br>225                  230                    235                  240 | | 720 |
| gtc ctc caa gag ctg atc cag cag atc ttc aac ctc ttt acc aca aaa<br>Val Leu Gln Glu Leu Ile Gln Gln Ile Phe Asn Leu Phe Thr Thr Lys<br>                     245                     250                     255 | | 768 |
| gat tca tct gct gct tgg gat gag gac ctc cta gac aaa ttc tgc acc<br>Asp Ser Ser Ala Ala Trp Asp Glu Asp Leu Leu Asp Lys Phe Cys Thr<br>             260                     265                     270 | | 816 |
| gaa ctc tac cag cag ctg aat gac ttg gaa gcc tgt gtg atg cag gag<br>Glu Leu Tyr Gln Gln Leu Asn Asp Leu Glu Ala Cys Val Met Gln Glu<br>       275                     280                     285 | | 864 |
| gag agg gtg gga gaa act ccc ctg atg aat gcg gac tcc atc ttg gct<br>Glu Arg Val Gly Glu Thr Pro Leu Met Asn Ala Asp Ser Ile Leu Ala<br>290                     295                    300 | | 912 |
| gtg aag aaa tac ttc cga aga atc act ctc tat ctg acg gag aag aaa<br>Val Lys Lys Tyr Phe Arg Arg Ile Thr Leu Tyr Leu Thr Glu Lys Lys<br>305                    310                    315                  320 | | 960 |
| tac agc cct tgt gcc tgg gag gtt gtc aga gca gaa atc gtg aga tcc<br>Tyr Ser Pro Cys Ala Trp Glu Val Val Arg Ala Glu Ile Val Arg Ser<br>                     325                     330                     335 | | 1008 |
| ctc tct tta tca aca aac ttg caa gaa aga tta agg agg aag gaa taa<br>Leu Ser Leu Ser Thr Asn Leu Gln Glu Arg Leu Arg Arg Lys Glu<br>             340                     345                     350 | | 1056 |

<210> SEQ ID NO 52
<211> LENGTH: 351
<212> TYPE: PRT
<213> ORGANISM: Homo sapiens

<400> SEQUENCE: 52

Met Gly Val Lys Val Leu Phe Ala Leu Ile Cys Ile Ala Val Ala Glu
1               5                    10                    15

Ala Lys Pro Thr Glu Asn Asn Glu Asp Phe Asn Ile Val Ala Val Ala
                  20                     25                    30

```
Ser Asn Phe Ala Thr Thr Asp Leu Asp Ala Asp Arg Gly Lys Leu Pro
            35                  40                  45
Gly Lys Lys Leu Pro Leu Glu Val Leu Lys Glu Met Glu Ala Asn Ala
 50                  55                  60
Arg Lys Ala Gly Cys Thr Arg Gly Cys Leu Ile Cys Leu Ser His Ile
 65                  70                  75                  80
Lys Cys Thr Pro Lys Met Lys Lys Phe Ile Pro Gly Arg Cys His Thr
                85                  90                  95
Tyr Glu Gly Asp Lys Glu Ser Ala Gln Gly Gly Ile Gly Glu Ala Ile
                100                 105                 110
Val Asp Ile Pro Glu Ile Pro Gly Phe Lys Asp Leu Glu Pro Met Glu
            115                 120                 125
Gln Phe Ile Ala Gln Val Asp Leu Cys Val Asp Cys Thr Thr Gly Cys
130                 135                 140
Leu Lys Gly Leu Ala Asn Val Gln Cys Ser Asp Leu Leu Lys Lys Trp
145                 150                 155                 160
Leu Pro Gln Arg Cys Ala Thr Phe Ala Ser Lys Ile Gln Gly Gln Val
                165                 170                 175
Asp Lys Ile Lys Gly Ala Gly Gly Asp Cys Asp Leu Pro Glu Thr His
                180                 185                 190
Ser Leu Asp Asn Arg Arg Thr Leu Met Leu Leu Ala Gln Met Ser Arg
            195                 200                 205
Ile Ser Pro Ser Ser Cys Leu Met Asp Arg His Asp Phe Gly Phe Pro
210                 215                 220
Gln Glu Glu Phe Asp Gly Asn Gln Phe Gln Lys Ala Pro Ala Ile Ser
225                 230                 235                 240
Val Leu Gln Glu Leu Ile Gln Gln Ile Phe Asn Leu Phe Thr Thr Lys
                245                 250                 255
Asp Ser Ser Ala Ala Trp Asp Glu Asp Leu Leu Asp Lys Phe Cys Thr
                260                 265                 270
Glu Leu Tyr Gln Gln Leu Asn Asp Leu Glu Ala Cys Val Met Gln Glu
            275                 280                 285
Glu Arg Val Gly Glu Thr Pro Leu Met Asn Ala Asp Ser Ile Leu Ala
290                 295                 300
Val Lys Lys Tyr Phe Arg Arg Ile Thr Leu Tyr Leu Thr Glu Lys Lys
305                 310                 315                 320
Tyr Ser Pro Cys Ala Trp Glu Val Val Arg Ala Glu Ile Val Arg Ser
                325                 330                 335
Leu Ser Leu Ser Thr Asn Leu Gln Glu Arg Leu Arg Arg Lys Glu
            340                 345                 350

<210> SEQ ID NO 53
<211> LENGTH: 570
<212> TYPE: DNA
<213> ORGANISM: Bos taurus
<220> FEATURE:
<221> NAME/KEY: CDS
<222> LOCATION: (1)..(570)
<223> OTHER INFORMATION: Bovine Interferon Alpha

<400> SEQUENCE: 53 atg gcc cca gcc tgg tcc ttc ctg cta tcc ctg ttg ctg ctc agc tgc    48
Met Ala Pro Ala Trp Ser Phe Leu Leu Ser Leu Leu Leu Leu Ser Cys
1               5                   10                  15 aac gcc atc tgc tct ctg ggt tgc cac ctg cct cac acc cac agc ctg    96
Asn Ala Ile Cys Ser Leu Gly Cys His Leu Pro His Thr His Ser Leu
            20                  25                  30
```

```
gcc aac agg agg gtc ctg atg ctc ctg caa caa ctg aga agg gtc tcc      144
Ala Asn Arg Arg Val Leu Met Leu Leu Gln Gln Leu Arg Arg Val Ser
         35                  40                  45 cct tcc tcc tgc ctg cag gac aga aat gac ttc gaa ttc ctc cag gag      192
Pro Ser Ser Cys Leu Gln Asp Arg Asn Asp Phe Glu Phe Leu Gln Glu
 50                  55                  60 gct ctg ggt ggc agc cag ttg cag aag gct caa gcc atc tct gtg ctc      240
Ala Leu Gly Gly Ser Gln Leu Gln Lys Ala Gln Ala Ile Ser Val Leu
 65                  70                  75                  80 cac gag gtg acc cag cac acc ttc cag ctc ttc agc aca gag ggc tcg      288
His Glu Val Thr Gln His Thr Phe Gln Leu Phe Ser Thr Glu Gly Ser
                 85                  90                  95 ccc gcc acg tgg gac aag agc ctc ctg gac aag cta cgc gct gcg ctg      336
Pro Ala Thr Trp Asp Lys Ser Leu Leu Asp Lys Leu Arg Ala Ala Leu
            100                 105                 110 gat cag cag ctc act gac ctg caa gcc tgt ctg acg cag gag gag ggg      384
Asp Gln Gln Leu Thr Asp Leu Gln Ala Cys Leu Thr Gln Glu Glu Gly
        115                 120                 125 ctg cga ggg gct ccc ctg ctc aag gag gac tcc agc ctg gct gtg agg      432
Leu Arg Gly Ala Pro Leu Leu Lys Glu Asp Ser Ser Leu Ala Val Arg
    130                 135                 140 aaa tac ttc cac aga ctc act ctc tat ctg caa gag aag aga cac agc      480
Lys Tyr Phe His Arg Leu Thr Leu Tyr Leu Gln Glu Lys Arg His Ser
145                 150                 155                 160 cct tgt gcc tgg gag gtt gtc aga gca gaa gtc atg aga gcc ttc tct      528
Pro Cys Ala Trp Glu Val Val Arg Ala Glu Val Met Arg Ala Phe Ser
                165                 170                 175 tcc tca aca aac ttg cag gag agt ttc agg aga aag gac tga              570
Ser Ser Thr Asn Leu Gln Glu Ser Phe Arg Arg Lys Asp
            180                 185
```

<210> SEQ ID NO 54
<211> LENGTH: 189
<212> TYPE: PRT
<213> ORGANISM: Bos taurus

<400> SEQUENCE: 54

```
Met Ala Pro Ala Trp Ser Phe Leu Leu Ser Leu Leu Leu Leu Ser Cys
 1               5                  10                  15

Asn Ala Ile Cys Ser Leu Gly Cys His Leu Pro His Thr His Ser Leu
             20                  25                  30

Ala Asn Arg Arg Val Leu Met Leu Leu Gln Gln Leu Arg Arg Val Ser
         35                  40                  45

Pro Ser Ser Cys Leu Gln Asp Arg Asn Asp Phe Glu Phe Leu Gln Glu
 50                  55                  60

Ala Leu Gly Gly Ser Gln Leu Gln Lys Ala Gln Ala Ile Ser Val Leu
 65                  70                  75                  80

His Glu Val Thr Gln His Thr Phe Gln Leu Phe Ser Thr Glu Gly Ser
                 85                  90                  95

Pro Ala Thr Trp Asp Lys Ser Leu Leu Asp Lys Leu Arg Ala Ala Leu
            100                 105                 110

Asp Gln Gln Leu Thr Asp Leu Gln Ala Cys Leu Thr Gln Glu Glu Gly
        115                 120                 125

Leu Arg Gly Ala Pro Leu Leu Lys Glu Asp Ser Ser Leu Ala Val Arg
    130                 135                 140

Lys Tyr Phe His Arg Leu Thr Leu Tyr Leu Gln Glu Lys Arg His Ser
145                 150                 155                 160
```

```
            Pro Cys Ala Trp Glu Val Val Arg Ala Glu Val Met Arg Ala Phe Ser
                            165                 170                 175

Ser Ser Thr Asn Leu Gln Glu Ser Phe Arg Arg Lys Asp
                        180                 185

<210> SEQ ID NO 55
<211> LENGTH: 1056
<212> TYPE: DNA
<213> ORGANISM: Bos taurus
<220> FEATURE:
<221> NAME/KEY: CDS
<222> LOCATION: (1)..(1056)
<223> OTHER INFORMATION: Bovine GlucON Alpha

<400> SEQUENCE: 55 atg gga gtc aaa gtt ctg ttt gcc ctg atc tgc atc gct gtg gcc gag     48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc     96
Ala Lys Pro Thr Glu Asn Asn Glu Asp Phe Asn Ile Val Ala Val Ala
                20                  25                  30 agc aac ttc gcg acc acg gat ctc gat gct gac cgc ggg aag ttg ccc    144
Ser Asn Phe Ala Thr Thr Asp Leu Asp Ala Asp Arg Gly Lys Leu Pro
            35                  40                  45 ggc aag aag ctg ccg ctg gag gtg ctc aaa gag atg gaa gcc aat gcc    192
Gly Lys Lys Leu Pro Leu Glu Val Leu Lys Glu Met Glu Ala Asn Ala
        50                  55                  60 cgg aaa gct ggc tgc acc agg ggc tgt ctg atc tgc ctg tcc cac atc    240
Arg Lys Ala Gly Cys Thr Arg Gly Cys Leu Ile Cys Leu Ser His Ile
65                  70                  75                  80 aag tgc acg ccc aag atg aag aag ttc atc cca gga cgc tgc cac acc    288
Lys Cys Thr Pro Lys Met Lys Lys Phe Ile Pro Gly Arg Cys His Thr
                85                  90                  95 tac gaa ggc gac aaa gag tcc gca cag ggc ggc ata ggc gag gcg atc    336
Tyr Glu Gly Asp Lys Glu Ser Ala Gln Gly Gly Ile Gly Glu Ala Ile
            100                 105                 110 gtc gac att cct gag att cct ggg ttc aag gac ttg gag ccc atg gag    384
Val Asp Ile Pro Glu Ile Pro Gly Phe Lys Asp Leu Glu Pro Met Glu
        115                 120                 125 cag ttc atc gca cag gtc gat ctg tgt gtg gac tgc aca act ggc tgc    432
Gln Phe Ile Ala Gln Val Asp Leu Cys Val Asp Cys Thr Thr Gly Cys
    130                 135                 140 ctc aaa ggg ctt gcc aac gtg cag tgt tct gac ctg ctc aag aag tgg    480
Leu Lys Gly Leu Ala Asn Val Gln Cys Ser Asp Leu Leu Lys Lys Trp
145                 150                 155                 160 ctg ccg caa cgc tgt gcg acc ttt gcc agc aag atc cag ggc cag gtg    528
Leu Pro Gln Arg Cys Ala Thr Phe Ala Ser Lys Ile Gln Gly Gln Val
                165                 170                 175 gac aag atc aag ggg gcc ggt ggt gac tgc cac ctg cct cac acc cac    576
Asp Lys Ile Lys Gly Ala Gly Gly Asp Cys His Leu Pro His Thr His
            180                 185                 190 agc ctg gcc aac agg agg gtc ctg atg ctc ctg caa caa ctg aga agg    624
Ser Leu Ala Asn Arg Arg Val Leu Met Leu Leu Gln Gln Leu Arg Arg
        195                 200                 205 gtc tcc cct tcc tcc tgc ctg cag gac aga aat gac ttc gaa ttc ctc    672
Val Ser Pro Ser Ser Cys Leu Gln Asp Arg Asn Asp Phe Glu Phe Leu
    210                 215                 220 cag gag gct ctg ggt ggc agc cag ttg cag aag gct caa gcc atc tct    720
Gln Glu Ala Leu Gly Gly Ser Gln Leu Gln Lys Ala Gln Ala Ile Ser
225                 230                 235                 240 gtg ctc cac gag gtg acc cag cac acc ttc cag ctc ttc agc aca gag    768
```

```
Val Leu His Glu Val Thr Gln His Thr Phe Gln Leu Phe Ser Thr Glu
                245                 250                 255 ggc tcg ccc gcc acg tgg gac aag agc ctc ctg gac aag cta cgc gct        816
Gly Ser Pro Ala Thr Trp Asp Lys Ser Leu Leu Asp Lys Leu Arg Ala
            260                 265                 270 gcg ctg gat cag cag ctc act gac ctg caa gcc tgt ctg acg cag gag        864
Ala Leu Asp Gln Gln Leu Thr Asp Leu Gln Ala Cys Leu Thr Gln Glu
                275                 280                 285 gag ggg ctg cga ggg gct ccc ctg ctc aag gag gac tcc agc ctg gct        912
Glu Gly Leu Arg Gly Ala Pro Leu Leu Lys Glu Asp Ser Ser Leu Ala
            290                 295                 300 gtg agg aaa tac ttc cac aga ctc act ctc tat ctg caa gag aag aga        960
Val Arg Lys Tyr Phe His Arg Leu Thr Leu Tyr Leu Gln Glu Lys Arg
305                 310                 315                 320 cac agc cct tgt gcc tgg gag gtt gtc aga gca gaa gtc atg aga gcc       1008
His Ser Pro Cys Ala Trp Glu Val Val Arg Ala Glu Val Met Arg Ala
                325                 330                 335 ttc tct tcc tca aca aac ttg cag gag agt ttc agg aga aag gac tga       1056
Phe Ser Ser Ser Thr Asn Leu Gln Glu Ser Phe Arg Arg Lys Asp
            340                 345                 350

<210> SEQ ID NO 56
<211> LENGTH: 351
<212> TYPE: PRT
<213> ORGANISM: Bos taurus

<400> SEQUENCE: 56

Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
                20                  25                  30

Ser Asn Phe Ala Thr Thr Asp Leu Asp Ala Asp Arg Gly Lys Leu Pro
            35                  40                  45

Gly Lys Lys Leu Pro Leu Glu Val Leu Lys Glu Met Glu Ala Asn Ala
        50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Gly Ile Gly Glu Ala Ile
            100                 105                 110

Val Asp Ile Pro Glu Ile Pro Gly Phe Lys Asp Leu Glu Pro Met Glu
        115                 120                 125

Gln Phe Ile Ala Gln Val Asp Leu Cys Val Asp Cys Thr Thr Gly Cys
    130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp Cys His Leu Pro His Thr His
            180                 185                 190

Ser Leu Ala Asn Arg Arg Val Leu Met Leu Gln Gln Leu Arg Arg
        195                 200                 205

Val Ser Pro Ser Ser Cys Leu Gln Asp Arg Asn Asp Phe Glu Phe Leu
    210                 215                 220

Gln Glu Ala Leu Gly Gly Ser Gln Leu Gln Lys Ala Gln Ala Ile Ser
225                 230                 235                 240
```

```
Val Leu His Glu Val Thr Gln His Thr Phe Gln Leu Phe Ser Thr Glu
            245                 250                 255

Gly Ser Pro Ala Thr Trp Asp Lys Ser Leu Leu Asp Lys Leu Arg Ala
            260                 265                 270

Ala Leu Asp Gln Gln Leu Thr Asp Leu Gln Ala Cys Leu Thr Gln Glu
            275                 280                 285

Glu Gly Leu Arg Gly Ala Pro Leu Leu Lys Glu Asp Ser Ser Leu Ala
        290                 295                 300

Val Arg Lys Tyr Phe His Arg Leu Thr Leu Tyr Leu Gln Glu Lys Arg
305                 310                 315                 320

His Ser Pro Cys Ala Trp Glu Val Val Arg Ala Glu Val Met Arg Ala
                325                 330                 335

Phe Ser Ser Ser Thr Asn Leu Gln Glu Ser Phe Arg Arg Lys Asp
            340                 345                 350

<210> SEQ ID NO 57
<211> LENGTH: 564
<212> TYPE: DNA
<213> ORGANISM: Homo sapiens
<220> FEATURE:
<221> NAME/KEY: CDS
<222> LOCATION: (1)..(564)
<223> OTHER INFORMATION: Human Interferon Beta

<400> SEQUENCE: 57 atg acc aac aag tgt ctc ctc caa att gct ctc ctg ttg tgc ttc tcc      48
Met Thr Asn Lys Cys Leu Leu Gln Ile Ala Leu Leu Leu Cys Phe Ser
1               5                   10                  15 acg aca gct ctt tcc atg agc tac aac ttg ctt gga ttc cta caa aga      96
Thr Thr Ala Leu Ser Met Ser Tyr Asn Leu Leu Gly Phe Leu Gln Arg
            20                  25                  30 agc agc aat tgt cag tgt cag aag ctc ctg tgg caa ttg aat ggg agg     144
Ser Ser Asn Cys Gln Cys Gln Lys Leu Leu Trp Gln Leu Asn Gly Arg
        35                  40                  45 ctt gaa tac tgc ctc aag gac agg agg aac ttt gac atc cct gag gag     192
Leu Glu Tyr Cys Leu Lys Asp Arg Arg Asn Phe Asp Ile Pro Glu Glu
    50                  55                  60 att aag cag ctg cag cag ttc cag aag gag gac gcc gca gtg acc atc     240
Ile Lys Gln Leu Gln Gln Phe Gln Lys Glu Asp Ala Ala Val Thr Ile
65                  70                  75                  80 tat gag atg ctc cag aac atc ttt gct att ttc aga caa gat tca tcg     288
Tyr Glu Met Leu Gln Asn Ile Phe Ala Ile Phe Arg Gln Asp Ser Ser
                85                  90                  95 agc act ggc tgg aat gag act att gtt gag aac ctc ctg gct aat gtc     336
Ser Thr Gly Trp Asn Glu Thr Ile Val Glu Asn Leu Leu Ala Asn Val
            100                 105                 110 tat cat cag aga aac cat ctg aag aca gtc ctg gaa gaa aaa ctg gag     384
Tyr His Gln Arg Asn His Leu Lys Thr Val Leu Glu Glu Lys Leu Glu
        115                 120                 125 aaa gaa gat ttc acc agg gga aaa cgc atg agc agt ctg cac ctg aaa     432
Lys Glu Asp Phe Thr Arg Gly Lys Arg Met Ser Ser Leu His Leu Lys
    130                 135                 140 aga tat tat ggg agg att ctg cat tac ctg aag gcc aag gag gac agt     480
Arg Tyr Tyr Gly Arg Ile Leu His Tyr Leu Lys Ala Lys Glu Asp Ser
145                 150                 155                 160 cac tgt gcc tgg acc ata gtc aga gtg gaa atc cta agg aac ttt tac     528
His Cys Ala Trp Thr Ile Val Arg Val Glu Ile Leu Arg Asn Phe Tyr
                165                 170                 175 gtc att aac aga ctt aca ggt tac ctc cga aac tga                     564
Val Ile Asn Arg Leu Thr Gly Tyr Leu Arg Asn
```

Val Ile Asn Arg Leu Thr Gly Tyr Leu Arg Asn
            180                 185

<210> SEQ ID NO 58
<211> LENGTH: 187
<212> TYPE: PRT
<213> ORGANISM: Homo sapiens

<400> SEQUENCE: 58

Met Thr Asn Lys Cys Leu Leu Gln Ile Ala Leu Leu Cys Phe Ser
 1               5                  10                  15

Thr Thr Ala Leu Ser Met Ser Tyr Asn Leu Leu Gly Phe Leu Gln Arg
            20                  25                  30

Ser Ser Asn Cys Gln Cys Gln Lys Leu Leu Trp Gln Leu Asn Gly Arg
                35                  40                  45

Leu Glu Tyr Cys Leu Lys Asp Arg Arg Asn Phe Asp Ile Pro Glu Glu
    50                  55                  60

Ile Lys Gln Leu Gln Gln Phe Gln Lys Glu Asp Ala Ala Val Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Arg Asn His Leu Lys Thr Val Leu Glu Glu Lys Leu Glu
        115                 120                 125

Lys Glu Asp Phe Thr Arg Gly Lys Arg Met Ser Ser Leu His Leu Lys
    130                 135                 140

Arg Tyr Tyr Gly Arg Ile Leu His Tyr Leu Lys Ala Lys Glu Asp Ser
145                 150                 155                 160

His Cys Ala Trp Thr Ile Val Arg Val Glu Ile Leu Arg Asn Phe Tyr
                165                 170                 175

Val Ile Asn Arg Leu Thr Gly Tyr Leu Arg Asn
            180                 185

<210> SEQ ID NO 59
<211> LENGTH: 1056
<212> TYPE: DNA
<213> ORGANISM: Homo sapiens
<220> FEATURE:
<221> NAME/KEY: CDS
<222> LOCATION: (1)..(1056)
<223> OTHER INFORMATION: Human GlucON Beta

<400> SEQUENCE: 59 atg gga gtc aaa gtt ctg ttt gcc ctg atc tgc atc gct gtg gcc gag      48
Met Gly Val Lys Val Leu Phe Ala Leu Ile Cys Ile Ala Val Ala Glu
 1               5                  10                  15 gcc aag ccc acc gag aac aac gaa gac ttc aac atc gtg gcc gtg gcc      96
Ala Lys Pro Thr Glu Asn Asn Glu Asp Phe Asn Ile Val Ala Val Ala
            20                  25                  30 agc aac ttc gcg acc acg gat ctc gat gct gac cgc ggg aag ttg ccc     144
Ser Asn Phe Ala Thr Thr Asp Leu Asp Ala Asp Arg Gly Lys Leu Pro
        35                  40                  45 ggc aag aag ctg ccg ctg gag gtg ctc aaa gag atg gaa gcc aat gcc     192
Gly Lys Lys Leu Pro Leu Glu Val Leu Lys Glu Met Glu Ala Asn Ala
    50                  55                  60 cgg aaa gct ggc tgc acc agg ggc tgt ctg atc tgc ctg tcc cac atc     240
Arg Lys Ala Gly Cys Thr Arg Gly Cys Leu Ile Cys Leu Ser His Ile
65                  70                  75                  80

```
aag tgc acg ccc aag atg aag aag ttc atc cca gga cgc tgc cac acc   288
Lys Cys Thr Pro Lys Met Lys Lys Phe Ile Pro Gly Arg Cys His Thr
                85                  90                  95 tac gaa ggc gac aaa gag tcc gca cag ggc ggc ata ggc gag gcg atc   336
Tyr Glu Gly Asp Lys Glu Ser Ala Gln Gly Gly Ile Gly Glu Ala Ile
            100                 105                 110 gtc gac att cct gag att cct ggg ttc aag gac ttg gag ccc atg gag   384
Val Asp Ile Pro Glu Ile Pro Gly Phe Lys Asp Leu Glu Pro Met Glu
        115                 120                 125 cag ttc atc gca cag gtc gat ctg tgt gtg gac tgc aca act ggc tgc   432
Gln Phe Ile Ala Gln Val Asp Leu Cys Val Asp Cys Thr Thr Gly Cys
    130                 135                 140 ctc aaa ggg ctt gcc aac gtg cag tgt tct gac ctg ctc aag aag tgg   480
Leu Lys Gly Leu Ala Asn Val Gln Cys Ser Asp Leu Leu Lys Lys Trp
145                 150                 155                 160 ctg ccg caa cgc tgt gcg acc ttt gcc agc aag atc cag ggc cag gtg   528
Leu Pro Gln Arg Cys Ala Thr Phe Ala Ser Lys Ile Gln Gly Gln Val
                165                 170                 175 gac aag atc aag ggg gcc ggt ggt gac atg agc tac aac ttg ctt gga   576
Asp Lys Ile Lys Gly Ala Gly Gly Asp Met Ser Tyr Asn Leu Leu Gly
            180                 185                 190 ttc cta caa aga agc agc aat tgt cag tgt cag aag ctc ctg tgg caa   624
Phe Leu Gln Arg Ser Ser Asn Cys Gln Cys Gln Lys Leu Leu Trp Gln
        195                 200                 205 ttg aat ggg agg ctt gaa tac tgc ctc aag gac agg agg aac ttt gac   672
Leu Asn Gly Arg Leu Glu Tyr Cys Leu Lys Asp Arg Arg Asn Phe Asp
    210                 215                 220 atc cct gag gag att aag cag ctg cag cag ttc cag aag gag gac gcc   720
Ile Pro Glu Glu Ile Lys Gln Leu Gln Gln Phe Gln Lys Glu Asp Ala
225                 230                 235                 240 gca gtg acc atc tat gag atg ctc cag aac atc ttt gct att ttc aga   768
Ala Val Thr Ile Tyr Glu Met Leu Gln Asn Ile Phe Ala Ile Phe Arg
                245                 250                 255 caa gat tca tcg agc act ggc tgg aat gag act att gtt gag aac ctc   816
Gln Asp Ser Ser Ser Thr Gly Trp Asn Glu Thr Ile Val Glu Asn Leu
            260                 265                 270 ctg gct aat gtc tat cat cag aga aac cat ctg aag aca gtc ctg gaa   864
Leu Ala Asn Val Tyr His Gln Arg Asn His Leu Lys Thr Val Leu Glu
        275                 280                 285 gaa aaa ctg gag aaa gaa gat ttc acc agg gga aaa cgc atg agc agt   912
Glu Lys Leu Glu Lys Glu Asp Phe Thr Arg Gly Lys Arg Met Ser Ser
    290                 295                 300 ctg cac ctg aaa aga tat tat ggg agg att ctg cat tac ctg aag gcc   960
Leu His Leu Lys Arg Tyr Tyr Gly Arg Ile Leu His Tyr Leu Lys Ala
305                 310                 315                 320 aag gag gac agt cac tgt gcc tgg acc ata gtc aga gtg gaa atc cta  1008
Lys Glu Asp Ser His Cys Ala Trp Thr Ile Val Arg Val Glu Ile Leu
                325                 330                 335 agg aac ttt tac gtc att aac aga ctt aca ggt tac ctc cga aac tga  1056
Arg Asn Phe Tyr Val Ile Asn Arg Leu Thr Gly Tyr Leu Arg Asn
            340                 345                 350

<210> SEQ ID NO 60
<211> LENGTH: 351
<212> TYPE: PRT
<213> ORGANISM: Homo sapiens

<400> SEQUENCE: 60

Met Gly Val Lys Val Leu Phe Ala Leu Ile Cys Ile Ala Val Ala Glu
1               5                   10                  15
```

```
Ala Lys Pro Thr Glu Asn Asn Glu Asp Phe Asn Ile Val Ala Val Ala
                 20                  25                  30

Ser Asn Phe Ala Thr Thr Asp Leu Asp Ala Asp Arg Gly Lys Leu Pro
             35                  40                  45

Gly Lys Lys Leu Pro Leu Glu Val Leu Lys Glu Met Glu Ala Asn Ala
         50                  55                  60

Arg Lys Ala Gly Cys Thr Arg Gly Cys Leu Ile Cys Leu Ser His Ile
 65                  70                  75                  80

Lys Cys Thr Pro Lys Met Lys Lys Phe Ile Pro Gly Arg Cys His Thr
                 85                  90                  95

Tyr Glu Gly Asp Lys Glu Ser Ala Gln Gly Gly Ile Gly Glu Ala Ile
            100                 105                 110

Val Asp Ile Pro Glu Ile Pro Gly Phe Lys Asp Leu Glu Pro Met Glu
            115                 120                 125

Gln Phe Ile Ala Gln Val Asp Leu Cys Val Asp Cys Thr Thr Gly Cys
        130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp Met Ser Tyr Asn Leu Leu Gly
            180                 185                 190

Phe Leu Gln Arg Ser Ser Asn Cys Gln Cys Gln Lys Leu Leu Trp Gln
        195                 200                 205

Leu Asn Gly Arg Leu Glu Tyr Cys Leu Lys Asp Arg Arg Asn Phe Asp
210                 215                 220

Ile Pro Glu Glu Ile Lys Gln Leu Gln Gln Phe Gln Lys Glu Asp Ala
225                 230                 235                 240

Ala Val Thr Ile Tyr Glu Met Leu Gln Asn Ile Phe Ala Ile Phe Arg
                245                 250                 255

Gln Asp Ser Ser Ser Thr Gly Trp Asn Glu Thr Ile Val Glu Asn Leu
            260                 265                 270

Leu Ala Asn Val Tyr His Gln Arg Asn His Leu Lys Thr Val Leu Glu
        275                 280                 285

Glu Lys Leu Glu Lys Glu Asp Phe Thr Arg Gly Lys Arg Met Ser Ser
290                 295                 300

Leu His Leu Lys Arg Tyr Tyr Gly Arg Ile Leu His Tyr Leu Lys Ala
305                 310                 315                 320

Lys Glu Asp Ser His Cys Ala Trp Thr Ile Val Arg Val Glu Ile Leu
                325                 330                 335

Arg Asn Phe Tyr Val Ile Asn Arg Leu Thr Gly Tyr Leu Arg Asn
            340                 345                 350

<210> SEQ ID NO 61
<211> LENGTH: 561
<212> TYPE: DNA
<213> ORGANISM: Bos taurus
<220> FEATURE:
<221> NAME/KEY: CDS
<222> LOCATION: (1)..(561)
<223> OTHER INFORMATION: Bovine Interferon Beta

<400> SEQUENCE: 61 atg acc tac cgg tgc ctc ctc cag atg gtt ctc ctg ctg tgt ttc tcc     48
Met Thr Tyr Arg Cys Leu Leu Gln Met Val Leu Leu Leu Cys Phe Ser
 1               5                  10                  15
```

-continued

| | | |
|---|---|---|
| acc aca gct ctt tcc agg agc tac agc ttg ctt cga ttc caa caa cgt<br>Thr Thr Ala Leu Ser Arg Ser Tyr Ser Leu Leu Arg Phe Gln Gln Arg<br>                20                        25                        30 | | 96 |
| cag agc ctt aaa gag tgt cag aaa ctc ctg ggg cag tta cct tca act<br>Gln Ser Leu Lys Glu Cys Gln Lys Leu Leu Gly Gln Leu Pro Ser Thr<br>          35                        40                        45 | | 144 |
| cct caa cat tgc ctc gag gcc agg atg gac ttc cag atg cct gag gag<br>Pro Gln His Cys Leu Glu Ala Arg Met Asp Phe Gln Met Pro Glu Glu<br>        50                        55                        60 | | 192 |
| atg aag caa gaa cag cag ttc cag aag gaa gat gcc ata ttg gtc atg<br>Met Lys Gln Glu Gln Gln Phe Gln Lys Glu Asp Ala Ile Leu Val Met<br>65                        70                        75                        80 | | 240 |
| tat gag gtg ctc cag cac atc ttc ggc att ctc acc aga gac ttc tcc<br>Tyr Glu Val Leu Gln His Ile Phe Gly Ile Leu Thr Arg Asp Phe Ser<br>                        85                        90                        95 | | 288 |
| agc act ggc tgg tct gag acc atc atc gag gac ctc ctt gag gaa ctc<br>Ser Thr Gly Trp Ser Glu Thr Ile Ile Glu Asp Leu Leu Glu Glu Leu<br>                        100                        105                      110 | | 336 |
| tat ggg cag atg aat cgt ctg cag cca atc cag aag gaa ata atg cag<br>Tyr Gly Gln Met Asn Arg Leu Gln Pro Ile Gln Lys Glu Ile Met Gln<br>                  115                        120                      125 | | 384 |
| aag caa aac acc aca gcg gga gac acg atc gtt ccc cac cta ggg aaa<br>Lys Gln Asn Thr Thr Ala Gly Asp Thr Ile Val Pro His Leu Gly Lys<br>        130                        135                        140 | | 432 |
| tat tac ttc aac ctc atg cag tac ctg gag tcc aag gag tac gac agg<br>Tyr Tyr Phe Asn Leu Met Gln Tyr Leu Glu Ser Lys Glu Tyr Asp Arg<br>145                        150                        155                        160 | | 480 |
| tgt gcc tgg aca gtc gtg caa gtg caa ata ctc acg aac gtt tct ttc<br>Cys Ala Trp Thr Val Val Gln Val Gln Ile Leu Thr Asn Val Ser Phe<br>                  165                        170                      175 | | 528 |
| ctg atg aga cta aca ggt tac gtc cgt gac tga<br>Leu Met Arg Leu Thr Gly Tyr Val Arg Asp<br>        180                        185 | | 561 |

<210> SEQ ID NO 62
<211> LENGTH: 186
<212> TYPE: PRT
<213> ORGANISM: Bos taurus

<400> SEQUENCE: 62

Met Thr Tyr Arg Cys Leu Leu Gln Met Val Leu Leu Cys Phe Ser
1               5                   10                  15

Thr Thr Ala Leu Ser Arg Ser Tyr Ser Leu Leu Arg Phe Gln Gln Arg
                20                  25                  30

Gln Ser Leu Lys Glu Cys Gln Lys Leu Leu Gly Gln Leu Pro Ser Thr
            35                  40                  45

Pro Gln His Cys Leu Glu Ala Arg Met Asp Phe Gln Met Pro Glu Glu
        50                  55                  60

Met Lys Gln Glu Gln Gln Phe Gln Lys Glu Asp Ala Ile Leu Val Met
65                  70                  75                  80

Tyr Glu Val Leu Gln His Ile Phe Gly Ile Leu Thr Arg Asp Phe Ser
                85                  90                  95

Ser Thr Gly Trp Ser Glu Thr Ile Ile Glu Asp Leu Leu Glu Glu Leu
            100                 105                 110

Tyr Gly Gln Met Asn Arg Leu Gln Pro Ile Gln Lys Glu Ile Met Gln
        115                 120                 125

Lys Gln Asn Thr Thr Ala Gly Asp Thr Ile Val Pro His Leu Gly Lys
    130                 135                 140

```
Tyr Tyr Phe Asn Leu Met Gln Tyr Leu Glu Ser Lys Glu Tyr Asp Arg
145                 150                 155                 160

Cys Ala Trp Thr Val Val Gln Val Gln Ile Leu Thr Asn Val Ser Phe
                165                 170                 175

Leu Met Arg Leu Thr Gly Tyr Val Arg Asp
            180                 185

<210> SEQ ID NO 63
<211> LENGTH: 1053
<212> TYPE: DNA
<213> ORGANISM: Bos taurus
<220> FEATURE:
<221> NAME/KEY: CDS
<222> LOCATION: (1)..(1053)
<223> OTHER INFORMATION: GlucON Beta Bovine

<400> SEQUENCE: 63
```

| | | | | | | | | | | | | | | | | |
|---|---|---|---|---|---|---|---|---|---|---|---|---|---|---|---|---|
| atg | gga | gtc | aaa | gtt | ctg | ttt | gcc | ctg | atc | tgc | atc | gct | gtg | gcc | gag | 48 |
| Met | Gly | Val | Lys | Val | Leu | Phe | Ala | Leu | Ile | Cys | Ile | Ala | Val | Ala | Glu | |
| 1 | | | | 5 | | | | | 10 | | | | | 15 | | |
| gcc | aag | ccc | acc | gag | aac | aac | gaa | gac | ttc | aac | atc | gtg | gcc | gtg | gcc | 96 |
| Ala | Lys | Pro | Thr | Glu | Asn | Asn | Glu | Asp | Phe | Asn | Ile | Val | Ala | Val | Ala | |
| | | | 20 | | | | | 25 | | | | | 30 | | | |
| agc | aac | ttc | gcg | acc | acg | gat | ctc | gat | gct | gac | cgc | ggg | aag | ttg | ccc | 144 |
| Ser | Asn | Phe | Ala | Thr | Thr | Asp | Leu | Asp | Ala | Asp | Arg | Gly | Lys | Leu | Pro | |
| | | 35 | | | | | 40 | | | | | 45 | | | | |
| ggc | aag | aag | ctg | ccg | ctg | gag | gtg | ctc | aaa | gag | atg | gaa | gcc | aat | gcc | 192 |
| Gly | Lys | Lys | Leu | Pro | Leu | Glu | Val | Leu | Lys | Glu | Met | Glu | Ala | Asn | Ala | |
| 50 | | | | | 55 | | | | | 60 | | | | | | |
| cgg | aaa | gct | ggc | tgc | acc | agg | ggc | tgt | ctg | atc | tgc | ctg | tcc | cac | atc | 240 |
| Arg | Lys | Ala | Gly | Cys | Thr | Arg | Gly | Cys | Leu | Ile | Cys | Leu | Ser | His | Ile | |
| 65 | | | | | 70 | | | | | 75 | | | | | 80 | |
| aag | tgc | acg | ccc | aag | atg | aag | aag | ttc | atc | cca | gga | cgc | tgc | cac | acc | 288 |
| Lys | Cys | Thr | Pro | Lys | Met | Lys | Lys | Phe | Ile | Pro | Gly | Arg | Cys | His | Thr | |
| | | | | 85 | | | | | 90 | | | | | 95 | | |
| tac | gaa | ggc | gac | aaa | gag | tcc | gca | cag | ggc | ggc | ata | ggc | gag | gcg | atc | 336 |
| Tyr | Glu | Gly | Asp | Lys | Glu | Ser | Ala | Gln | Gly | Gly | Ile | Gly | Glu | Ala | Ile | |
| | | | 100 | | | | | 105 | | | | | 110 | | | |
| gtc | gac | att | cct | gag | att | cct | ggg | ttc | aag | gac | ttg | gag | ccc | atg | gag | 384 |
| Val | Asp | Ile | Pro | Glu | Ile | Pro | Gly | Phe | Lys | Asp | Leu | Glu | Pro | Met | Glu | |
| | | | 115 | | | | | 120 | | | | | 125 | | | |
| cag | ttc | atc | gca | cag | gtc | gat | ctg | tgt | gtg | gac | tgc | aca | act | ggc | tgc | 432 |
| Gln | Phe | Ile | Ala | Gln | Val | Asp | Leu | Cys | Val | Asp | Cys | Thr | Thr | Gly | Cys | |
| | | 130 | | | | | 135 | | | | | 140 | | | | |
| ctc | aaa | ggg | ctt | gcc | aac | gtg | cag | tgt | tct | gac | ctg | ctc | aag | aag | tgg | 480 |
| Leu | Lys | Gly | Leu | Ala | Asn | Val | Gln | Cys | Ser | Asp | Leu | Leu | Lys | Lys | Trp | |
| 145 | | | | | 150 | | | | | 155 | | | | | 160 | |
| ctg | ccg | caa | cgc | tgt | gcg | acc | ttt | gcc | agc | aag | atc | cag | ggc | cag | gtg | 528 |
| Leu | Pro | Gln | Arg | Cys | Ala | Thr | Phe | Ala | Ser | Lys | Ile | Gln | Gly | Gln | Val | |
| | | | | 165 | | | | | 170 | | | | | 175 | | |
| gac | aag | atc | aag | ggg | gcc | ggt | ggt | gac | agg | agc | tac | agc | ttg | ctt | cga | 576 |
| Asp | Lys | Ile | Lys | Gly | Ala | Gly | Gly | Asp | Arg | Ser | Tyr | Ser | Leu | Leu | Arg | |
| | | | 180 | | | | | 185 | | | | | 190 | | | |
| ttc | caa | caa | cgt | cag | agc | ctt | aaa | gag | tgt | cag | aaa | ctc | ctg | ggg | cag | 624 |
| Phe | Gln | Gln | Arg | Gln | Ser | Leu | Lys | Glu | Cys | Gln | Lys | Leu | Leu | Gly | Gln | |
| | | | 195 | | | | | 200 | | | | | 205 | | | |
| tta | cct | tca | act | cct | caa | cat | tgc | ctc | gag | gcc | agg | atg | gac | ttc | cag | 672 |
| Leu | Pro | Ser | Thr | Pro | Gln | His | Cys | Leu | Glu | Ala | Arg | Met | Asp | Phe | Gln | |
| | | 210 | | | | | 215 | | | | | 220 | | | | |
| atg | cct | gag | gag | atg | aag | caa | gaa | cag | cag | ttc | cag | aag | gaa | gat | gcc | 720 |
| Met | Pro | Glu | Glu | Met | Lys | Gln | Glu | Gln | Gln | Phe | Gln | Lys | Glu | Asp | Ala | |

```
                225                 230                 235                 240
ata ttg gtc atg tat gag gtc ctc cag cac atc ttc ggc att ctc acc        768
Ile Leu Val Met Tyr Glu Val Leu Gln His Ile Phe Gly Ile Leu Thr
                245                 250                 255 aga gac ttc tcc agc act ggc tgg tct gag acc atc atc gag gac ctc        816
Arg Asp Phe Ser Ser Thr Gly Trp Ser Glu Thr Ile Ile Glu Asp Leu
            260                 265                 270 ctt gag gaa ctc tat ggg cag atg aat cgt ctg cag cca atc cag aag        864
Leu Glu Glu Leu Tyr Gly Gln Met Asn Arg Leu Gln Pro Ile Gln Lys
        275                 280                 285 gaa ata atg cag aag caa aac acc aca gcg gga gac acg atc gtt ccc        912
Glu Ile Met Gln Lys Gln Asn Thr Thr Ala Gly Asp Thr Ile Val Pro
    290                 295                 300 cac cta ggg aaa tat tac ttc aac ctc atg cag tac ctg gag tcc aag        960
His Leu Gly Lys Tyr Tyr Phe Asn Leu Met Gln Tyr Leu Glu Ser Lys
305                 310                 315                 320 gag tac gac agg tgt gcc tgg aca gtc gtg caa gtg caa ata ctc acg       1008
Glu Tyr Asp Arg Cys Ala Trp Thr Val Val Gln Val Gln Ile Leu Thr
                325                 330                 335 aac gtt tct ttc ctg atg aga cta aca ggt tac gtc cgt gac tga           1053
Asn Val Ser Phe Leu Met Arg Leu Thr Gly Tyr Val Arg Asp
                340                 345                 350

<210> SEQ ID NO 64
<211> LENGTH: 350
<212> TYPE: PRT
<213> ORGANISM: Bos taurus

<400> SEQUENCE: 64

Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
        35                  40                  45

Gly Lys Lys Leu Pro Leu Glu Val Leu Lys Glu Met Glu Ala Asn Ala
    50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Gly Ile Gly Glu Ala Ile
            100                 105                 110

Val Asp Ile Pro Glu Ile Pro Gly Phe Lys Asp Leu Glu Pro Met Glu
        115                 120                 125

Gln Phe Ile Ala Gln Val Asp Leu Cys Val Asp Cys Thr Thr Gly Cys
    130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp Arg Ser Tyr Ser Leu Leu Arg
            180                 185                 190

Phe Gln Gln Arg Gln Ser Leu Lys Glu Cys Gln Lys Leu Leu Gly Gln
        195                 200                 205

Leu Pro Ser Thr Pro Gln His Cys Leu Glu Ala Arg Met Asp Phe Gln
    210                 215                 220
```

```
Met Pro Glu Glu Met Lys Gln Glu Gln Gln Phe Gln Lys Glu Asp Ala
225                 230                 235                 240

Ile Leu Val Met Tyr Glu Val Leu Gln His Ile Phe Gly Ile Leu Thr
                245                 250                 255

Arg Asp Phe Ser Ser Thr Gly Trp Ser Glu Thr Ile Ile Glu Asp Leu
            260                 265                 270

Leu Glu Glu Leu Tyr Gly Gln Met Asn Arg Leu Gln Pro Ile Gln Lys
        275                 280                 285

Glu Ile Met Gln Lys Gln Asn Thr Thr Ala Gly Asp Thr Ile Val Pro
    290                 295                 300

His Leu Gly Lys Tyr Tyr Phe Asn Leu Met Gln Tyr Leu Glu Ser Lys
305                 310                 315                 320

Glu Tyr Asp Arg Cys Ala Trp Thr Val Val Gln Val Gln Ile Leu Thr
                325                 330                 335

Asn Val Ser Phe Leu Met Arg Leu Thr Gly Tyr Val Arg Asp
            340                 345                 350

<210> SEQ ID NO 65
<211> LENGTH: 561
<212> TYPE: DNA
<213> ORGANISM: Sus scrofa
<220> FEATURE:
<221> NAME/KEY: CDS
<222> LOCATION: (1)..(561)
<223> OTHER INFORMATION: Porcine Interferon Beta

<400> SEQUENCE: 65 atg gct aac aag tgc atc ctc caa atc gct ctc ctg atg tgt ttc tcc       48
Met Ala Asn Lys Cys Ile Leu Gln Ile Ala Leu Leu Met Cys Phe Ser
1               5                   10                  15 acc aca gct ctt tcc atg agc tat gat gtg ctt cga tac caa caa agg      96
Thr Thr Ala Leu Ser Met Ser Tyr Asp Val Leu Arg Tyr Gln Gln Arg
            20                  25                  30 agc agc aat ttg gca tgt cag aag ctc ctg gga cag ttg cct ggg act     144
Ser Ser Asn Leu Ala Cys Gln Lys Leu Leu Gly Gln Leu Pro Gly Thr
        35                  40                  45 cct caa tat tgc ctc gaa gat agg atg aac ttt gag gtc cct gag gag     192
Pro Gln Tyr Cys Leu Glu Asp Arg Met Asn Phe Glu Val Pro Glu Glu
    50                  55                  60 att atg caa cca cca caa ttc cag aag gaa gat gca gta ttg att atc     240
Ile Met Gln Pro Pro Gln Phe Gln Lys Glu Asp Ala Val Leu Ile Ile
65                  70                  75                  80 cac gag atg ctc cag cag atc ttc ggc att ctc aga aga aat ttc tct     288
His Glu Met Leu Gln Gln Ile Phe Gly Ile Leu Arg Arg Asn Phe Ser
                85                  90                  95 agc act ggc tgg aat gaa acc gtc att aag act atc ctt gtg gaa ctt     336
Ser Thr Gly Trp Asn Glu Thr Val Ile Lys Thr Ile Leu Val Glu Leu
            100                 105                 110 gat ggg cag atg gat gac ctg gag aca atc ctg gag gaa atc atg gag     384
Asp Gly Gln Met Asp Asp Leu Glu Thr Ile Leu Glu Glu Ile Met Glu
        115                 120                 125 gag gaa aat ttc ccc agg gga gac atg acc att ctt cac ctg aag aaa     432
Glu Glu Asn Phe Pro Arg Gly Asp Met Thr Ile Leu His Leu Lys Lys
    130                 135                 140 tat tac ttg agc att ctg cag tac ctg aag tcc aag gag tac aga agc     480
Tyr Tyr Leu Ser Ile Leu Gln Tyr Leu Lys Ser Lys Glu Tyr Arg Ser
145                 150                 155                 160 tgt gcc tgg aca gtc gtc caa gtg gaa atc ctc agg aac ttt tct ttc     528
Cys Ala Trp Thr Val Val Gln Val Glu Ile Leu Arg Asn Phe Ser Phe
```

```
                       165                 170                 175
ctt aac aga ctt aca gat tac ctc cgg aac tga                          561
Leu Asn Arg Leu Thr Asp Tyr Leu Arg Asn
            180                 185

<210> SEQ ID NO 66
<211> LENGTH: 186
<212> TYPE: PRT
<213> ORGANISM: Sus scrofa

<400> SEQUENCE: 66

Met Ala Asn Lys Cys Ile Leu Gln Ile Ala Leu Leu Met Cys Phe Ser
1               5                   10                  15

Thr Thr Ala Leu Ser Met Ser Tyr Asp Val Leu Arg Tyr Gln Gln Arg
            20                  25                  30

Ser Ser Asn Leu Ala Cys Gln Lys Leu Leu Gly Gln Leu Pro Gly Thr
        35                  40                  45

Pro Gln Tyr Cys Leu Glu Asp Arg Met Asn Phe Glu Val Pro Glu Glu
    50                  55                  60

Ile Met Gln Pro Pro Gln Phe Gln Lys Glu Asp Ala Val Leu Ile Ile
65                  70                  75                  80

His Glu Met Leu Gln Gln Ile Phe Gly Ile Leu Arg Arg Asn Phe Ser
                85                  90                  95

Ser Thr Gly Trp Asn Glu Thr Val Ile Lys Thr Ile Leu Val Glu Leu
            100                 105                 110

Asp Gly Gln Met Asp Asp Leu Glu Thr Ile Leu Glu Glu Ile Met Glu
        115                 120                 125

Glu Glu Asn Phe Pro Arg Gly Asp Met Thr Ile Leu His Leu Lys Lys
    130                 135                 140

Tyr Tyr Leu Ser Ile Leu Gln Tyr Leu Lys Ser Lys Glu Tyr Arg Ser
145                 150                 155                 160

Cys Ala Trp Thr Val Val Gln Val Glu Ile Leu Arg Asn Phe Ser Phe
                165                 170                 175

Leu Asn Arg Leu Thr Asp Tyr Leu Arg Asn
            180                 185

<210> SEQ ID NO 67
<211> LENGTH: 1059
<212> TYPE: DNA
<213> ORGANISM: Sus scrofa
<220> FEATURE:
<221> NAME/KEY: CDS
<222> LOCATION: (1)..(1059)
<223> OTHER INFORMATION: GLucON Beta porcine

<400> SEQUENCE: 67 atg gga gtc aaa gtt ctg ttt gcc ctg atc tgc atc gct gtg gcc gag    48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc    96
Ala Lys Pro Thr Glu Asn Asn Glu Asp Phe Asn Ile Val Ala Val Ala
            20                  25                  30 agc aac ttc gcg acc acg gat ctc gat gct gac cgc ggg aag ttg ccc   144
Ser Asn Phe Ala Thr Thr Asp Leu Asp Ala Asp Arg Gly Lys Leu Pro
        35                  40                  45 ggc aag aag ctg ccg ctg gag gtg ctc aaa gag atg gaa gcc aat gcc   192
Gly Lys Lys Leu Pro Leu Glu Val Leu Lys Glu Met Glu Ala Asn Ala
    50                  55                  60 cgg aaa gct ggc tgc acc agg ggc tgt ctg atc tgc ctg tcc cac atc   240
```

|  |  |
|---|---|
| Arg Lys Ala Gly Cys Thr Arg Gly Cys Leu Ile Cys Leu Ser His Ile<br>65                        70                    75                  80 |  |
| aag tgc acg ccc aag atg aag aag ttc atc cca gga cgc tgc cac acc<br>Lys Cys Thr Pro Lys Met Lys Lys Phe Ile Pro Gly Arg Cys His Thr<br>                      85                    90                    95 | 288 |
| tac gaa ggc gac aaa gag tcc gca cag ggc ggc ata ggc gag gcg atc<br>Tyr Glu Gly Asp Lys Glu Ser Ala Gln Gly Gly Ile Gly Glu Ala Ile<br>                100                  105                  110 | 336 |
| gtc gac att cct gag att cct ggg ttc aag gac ttg gag ccc atg gag<br>Val Asp Ile Pro Glu Ile Pro Gly Phe Lys Asp Leu Glu Pro Met Glu<br>           115                  120                  125 | 384 |
| cag ttc atc gca cag gtc gat ctg tgt gtg gac tgc aca act ggc tgc<br>Gln Phe Ile Ala Gln Val Asp Leu Cys Val Asp Cys Thr Thr Gly Cys<br>130                    135                  140 | 432 |
| ctc aaa ggg ctt gcc aac gtg cag tgt tct gac ctg ctc aag aag tgg<br>Leu Lys Gly Leu Ala Asn Val Gln Cys Ser Asp Leu Leu Lys Lys Trp<br>145                    150                  155                  160 | 480 |
| ctg ccg caa cgc tgt gcg acc ttt gcc agc aag atc cag ggc cag gtg<br>Leu Pro Gln Arg Cys Ala Thr Phe Ala Ser Lys Ile Gln Gly Gln Val<br>                  165                  170                  175 | 528 |
| gac aag atc aag ggg gcc ggt ggt gac ggg ccc atg agc tat gat gtg<br>Asp Lys Ile Lys Gly Ala Gly Gly Asp Gly Pro Met Ser Tyr Asp Val<br>                180                  185                  190 | 576 |
| ctt cga tac caa caa agg agc agc aat ttg gca tgt cag aag ctc ctg<br>Leu Arg Tyr Gln Gln Arg Ser Ser Asn Leu Ala Cys Gln Lys Leu Leu<br>           195                  200                  205 | 624 |
| gga cag ttg cct ggg act cct caa tat tgc ctc gaa gat agg atg aac<br>Gly Gln Leu Pro Gly Thr Pro Gln Tyr Cys Leu Glu Asp Arg Met Asn<br>210                    215                  220 | 672 |
| ttt gag gtc cct gag gag att atg caa cca cca caa ttc cag aag gaa<br>Phe Glu Val Pro Glu Glu Ile Met Gln Pro Pro Gln Phe Gln Lys Glu<br>225                    230                  235                  240 | 720 |
| gat gca gta ttg att atc cac gag atg ctc cag cag atc ttc ggc att<br>Asp Ala Val Leu Ile Ile His Glu Met Leu Gln Gln Ile Phe Gly Ile<br>                245                  250                  255 | 768 |
| ctc aga aga aat ttc tct agc act ggc tgg aat gaa acc gtc att aag<br>Leu Arg Arg Asn Phe Ser Ser Thr Gly Trp Asn Glu Thr Val Ile Lys<br>           260                  265                  270 | 816 |
| act atc ctt gtg gaa ctt gat ggg cag atg gat gac ctg gag aca atc<br>Thr Ile Leu Val Glu Leu Asp Gly Gln Met Asp Asp Leu Glu Thr Ile<br>                275                  280                  285 | 864 |
| ctg gag gaa atc atg gag gag gaa aat ttc ccc agg gga gac atg acc<br>Leu Glu Glu Ile Met Glu Glu Glu Asn Phe Pro Arg Gly Asp Met Thr<br>290                    295                  300 | 912 |
| att ctt cac ctg aag aaa tat tac ttg agc att ctg cag tac ctg aag<br>Ile Leu His Leu Lys Lys Tyr Tyr Leu Ser Ile Leu Gln Tyr Leu Lys<br>305                    310                  315                  320 | 960 |
| tcc aag gag tac aga agc tgt gcc tgg aca gtc gtc caa gtg gaa atc<br>Ser Lys Glu Tyr Arg Ser Cys Ala Trp Thr Val Val Gln Val Glu Ile<br>                325                  330                  335 | 1008 |
| ctc agg aac ttt tct ttc ctt aac aga ctt aca gat tac ctc cgg aac<br>Leu Arg Asn Phe Ser Phe Leu Asn Arg Leu Thr Asp Tyr Leu Arg Asn<br>           340                  345                  350 | 1056 |
| tga | 1059 |

<210> SEQ ID NO 68
<211> LENGTH: 352
<212> TYPE: PRT
<213> ORGANISM: Sus scrofa

<400> SEQUENCE: 68

```
Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
        35                  40                  45

Gly Lys Lys Leu Pro Leu Glu Val Leu Lys Glu Met Glu Ala Asn Ala
    50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Gly Ile Gly Glu Ala Ile
            100                 105                 110

Val Asp Ile Pro Glu Ile Pro Gly Phe Lys Asp Leu Glu Pro Met Glu
        115                 120                 125

Gln Phe Ile Ala Gln Val Asp Leu Cys Val Asp Cys Thr Thr Gly Cys
    130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp Gly Pro Met Ser Tyr Asp Val
            180                 185                 190

Leu Arg Tyr Gln Gln Arg Ser Ser Asn Leu Ala Cys Gln Lys Leu Leu
        195                 200                 205

Gly Gln Leu Pro Gly Thr Pro Gln Tyr Cys Leu Glu Asp Arg Met Asn
    210                 215                 220

Phe Glu Val Pro Glu Glu Ile Met Gln Pro Pro Gln Phe Gln Lys Glu
225                 230                 235                 240

Asp Ala Val Leu Ile Ile His Glu Met Leu Gln Gln Ile Phe Gly Ile
                245                 250                 255

Leu Arg Arg Asn Phe Ser Ser Thr Gly Trp Asn Glu Thr Val Ile Lys
            260                 265                 270

Thr Ile Leu Val Glu Leu Asp Gly Gln Met Asp Asp Leu Glu Thr Ile
        275                 280                 285

Leu Glu Glu Ile Met Glu Glu Asn Phe Pro Arg Gly Asp Met Thr
    290                 295                 300

Ile Leu His Leu Lys Lys Tyr Tyr Leu Ser Ile Leu Gln Tyr Leu Lys
305                 310                 315                 320

Ser Lys Glu Tyr Arg Ser Cys Ala Trp Thr Val Val Gln Val Glu Ile
                325                 330                 335

Leu Arg Asn Phe Ser Phe Leu Asn Arg Leu Thr Asp Tyr Leu Arg Asn
            340                 345                 350
```

<210> SEQ ID NO 69
<211> LENGTH: 1062
<212> TYPE: DNA
<213> ORGANISM: Sus scrofa
<220> FEATURE:
<221> NAME/KEY: CDS
<222> LOCATION: (1)..(1062)
<223> OTHER INFORMATION: SGLucON Beta porcine

<400> SEQUENCE: 69

```
atg gga gtc aaa gtt ctg ttt gcc ctg atc tgc atc gct gtg gcc gag        48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc        96
Ala Lys Pro Thr Glu Asn Asn Glu Asp Phe Asn Ile Val Ala Val Ala
            20                  25                  30 agc aac ttt gcg acc acg gat ctc gat gct gac cga ggg aag ttg ccc        144
Ser Asn Phe Ala Thr Thr Asp Leu Asp Ala Asp Arg Gly Lys Leu Pro
        35                  40                  45 ggc aag aag ctg ccg ctg gag gtg ctc aaa gag atg gaa gcc aat gcc        192
Gly Lys Lys Leu Pro Leu Glu Val Leu Lys Glu Met Glu Ala Asn Ala
50                  55                  60 cgg aaa gct ggc tgc acc agg ggc tgt ctg atc tgc ctg tcc cac atc        240
Arg Lys Ala Gly Cys Thr Arg Gly Cys Leu Ile Cys Leu Ser His Ile
65                  70                  75                  80 aag tgc acg ccc aag atg aag aag tgg ctc cca gga cgc tgc cac acc        288
Lys Cys Thr Pro Lys Met Lys Lys Trp Leu Pro Gly Arg Cys His Thr
                85                  90                  95 tac gaa ggc gac aaa gag tcc gca cag ggc ggc ata ggc gag gcg atc        336
Tyr Glu Gly Asp Lys Glu Ser Ala Gln Gly Gly Ile Gly Glu Ala Ile
            100                 105                 110 gtc gat att cct gag att cct ggg ttc aag gac ttg gag cca atg gag        384
Val Asp Ile Pro Glu Ile Pro Gly Phe Lys Asp Leu Glu Pro Met Glu
        115                 120                 125 cag ttc atc gca cag gtc gat ctg tgt gtg gac tgc aca act ggc tgc        432
Gln Phe Ile Ala Gln Val Asp Leu Cys Val Asp Cys Thr Thr Gly Cys
130                 135                 140 ctc aaa ggg ctt gcc aac gtg cag tgt tct gac ctg ctc aag aag tgg        480
Leu Lys Gly Leu Ala Asn Val Gln Cys Ser Asp Leu Leu Lys Lys Trp
145                 150                 155                 160 ctg ccg caa cgc tgt gcg acc ttt gcc agc aag atc cag ggc cag gtg        528
Leu Pro Gln Arg Cys Ala Thr Phe Ala Ser Lys Ile Gln Gly Gln Val
                165                 170                 175 gac aag atc aag ggg gcc ggt ggt gac ggg ccc ggg atg agc tat gat        576
Asp Lys Ile Lys Gly Ala Gly Gly Asp Gly Pro Gly Met Ser Tyr Asp
            180                 185                 190 gtg ctt cga tac caa caa agg agc agc aat ttg gca tgt cag aag ctc        624
Val Leu Arg Tyr Gln Gln Arg Ser Ser Asn Leu Ala Cys Gln Lys Leu
        195                 200                 205 ctg gga cag ttg cct ggg act cct caa tat tgc ctc gaa gat agg atg        672
Leu Gly Gln Leu Pro Gly Thr Pro Gln Tyr Cys Leu Glu Asp Arg Met
210                 215                 220 aac ttt gag gtc cct gag gag att atg caa cca cca caa ttc cag aag        720
Asn Phe Glu Val Pro Glu Glu Ile Met Gln Pro Pro Gln Phe Gln Lys
225                 230                 235                 240 gaa gat gca gta ttg att atc cac gag atg ctc cag cag atc ttc ggc        768
Glu Asp Ala Val Leu Ile Ile His Glu Met Leu Gln Gln Ile Phe Gly
                245                 250                 255 att ctc aga aga aat ttc tct agc act ggc tgg aat gaa acc gtc att        816
Ile Leu Arg Arg Asn Phe Ser Ser Thr Gly Trp Asn Glu Thr Val Ile
            260                 265                 270 aag act atc ctt gtg gaa ctt gat ggg cag atg gat gac ctg gag aca        864
Lys Thr Ile Leu Val Glu Leu Asp Gly Gln Met Asp Asp Leu Glu Thr
        275                 280                 285 atc ctg gag gaa atc atg gag gag gaa aat ttc ccc agg gga gac atg        912
Ile Leu Glu Glu Ile Met Glu Glu Glu Asn Phe Pro Arg Gly Asp Met
290                 295                 300 acc att ctt cac ctg aag aaa tat tac ttg agc att ctg cag tac ctg        960
Thr Ile Leu His Leu Lys Lys Tyr Tyr Leu Ser Ile Leu Gln Tyr Leu
```

```
                       305                 310                 315                 320
aag tcc aag gag tac aga agc tgt gcc tgg aca gtc gtc caa gtg gaa       1008
Lys Ser Lys Glu Tyr Arg Ser Cys Ala Trp Thr Val Val Gln Val Glu
                325                 330                 335 atc ctc agg aac ttt tct ttc ctt aac aga ctt aca gat tac ctc cgg       1056
Ile Leu Arg Asn Phe Ser Phe Leu Asn Arg Leu Thr Asp Tyr Leu Arg
            340                 345                 350 aac tga                                                                1062
Asn

<210> SEQ ID NO 70
<211> LENGTH: 353
<212> TYPE: PRT
<213> ORGANISM: Sus scrofa

<400> SEQUENCE: 70

Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
                20                  25                  30

Ser Asn Phe Ala Thr Thr Asp Leu Asp Ala Asp Arg Gly Lys Leu Pro
            35                  40                  45

Gly Lys Lys Leu Pro Leu Glu Val Leu Lys Glu Met Glu Ala Asn Ala
50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Trp Leu Pro Gly Arg Cys His Thr
                85                  90                  95

Tyr Glu Gly Asp Lys Glu Ser Ala Gln Gly Gly Ile Gly Glu Ala Ile
                100                 105                 110

Val Asp Ile Pro Glu Ile Pro Gly Phe Lys Asp Leu Glu Pro Met Glu
            115                 120                 125

Gln Phe Ile Ala Gln Val Asp Leu Cys Val Asp Cys Thr Thr Gly Cys
130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp Gly Pro Gly Met Ser Tyr Asp
                180                 185                 190

Val Leu Arg Tyr Gln Gln Arg Ser Ser Asn Leu Ala Cys Gln Lys Leu
            195                 200                 205

Leu Gly Gln Leu Pro Gly Thr Pro Gln Tyr Cys Leu Glu Asp Arg Met
210                 215                 220

Asn Phe Glu Val Pro Glu Glu Ile Met Gln Pro Gln Phe Gln Lys
225                 230                 235                 240

Glu Asp Ala Val Leu Ile Ile His Glu Met Leu Gln Gln Ile Phe Gly
                245                 250                 255

Ile Leu Arg Arg Asn Phe Ser Ser Thr Gly Trp Asn Glu Thr Val Ile
            260                 265                 270

Lys Thr Ile Leu Val Glu Leu Asp Gly Gln Met Asp Asp Leu Glu Thr
        275                 280                 285

Ile Leu Glu Glu Ile Met Glu Glu Asn Phe Pro Arg Gly Asp Met
290                 295                 300

Thr Ile Leu His Leu Lys Lys Tyr Tyr Leu Ser Ile Leu Gln Tyr Leu
```

```
                305                 310                 315                 320
Lys Ser Lys Glu Tyr Arg Ser Cys Ala Trp Thr Val Val Gln Val Glu
                    325                 330                 335

Ile Leu Arg Asn Phe Ser Phe Leu Asn Arg Leu Thr Asp Tyr Leu Arg
                340                 345                 350

Asn
```

```
<210> SEQ ID NO 71
<211> LENGTH: 501
<212> TYPE: DNA
<213> ORGANISM: Homo sapiens
<220> FEATURE:
<221> NAME/KEY: CDS
<222> LOCATION: (1)..(501)
<223> OTHER INFORMATION: Human Interferon Gamma

<400> SEQUENCE: 71 atg aaa tat aca agt tat atc ttg gct ttt cag ctc tgc atc gtt ttg        48
Met Lys Tyr Thr Ser Tyr Ile Leu Ala Phe Gln Leu Cys Ile Val Leu
1               5                   10                  15 ggt tct ctt ggc tgt tac tgc cag gac cca tat gta aaa gaa gca gaa        96
Gly Ser Leu Gly Cys Tyr Cys Gln Asp Pro Tyr Val Lys Glu Ala Glu
            20                  25                  30 aac ctt aag aaa tat ttt aat gca ggt cat tca gat gta gcg gat aat       144
Asn Leu Lys Lys Tyr Phe Asn Ala Gly His Ser Asp Val Ala Asp Asn
        35                  40                  45 gga act ctt ttc tta ggc att ttg aag aat tgg aaa gag gag agt gac       192
Gly Thr Leu Phe Leu Gly Ile Leu Lys Asn Trp Lys Glu Glu Ser Asp
    50                  55                  60 aga aaa ata atg cag agc caa att gtc tcc ttt tac ttc aaa ctt ttt       240
Arg Lys Ile Met Gln Ser Gln Ile Val Ser Phe Tyr Phe Lys Leu Phe
65                  70                  75                  80 aaa aac ttt aaa gat gac cag agc atc caa aag agt gtg gag acc atc       288
Lys Asn Phe Lys Asp Asp Gln Ser Ile Gln Lys Ser Val Glu Thr Ile
                85                  90                  95 aag gaa gac atg aat gtc aag ttt ttc aat agc aac aaa aag aaa cga       336
Lys Glu Asp Met Asn Val Lys Phe Phe Asn Ser Asn Lys Lys Lys Arg
            100                 105                 110 gat gac ttc gaa aag ctg act aat tat tcg gta act gac ttg aat gtc       384
Asp Asp Phe Glu Lys Leu Thr Asn Tyr Ser Val Thr Asp Leu Asn Val
        115                 120                 125 caa cgc aaa gca ata cat gaa ctc atc caa gtg atg gct gaa ctg tcg       432
Gln Arg Lys Ala Ile His Glu Leu Ile Gln Val Met Ala Glu Leu Ser
    130                 135                 140 cca gca gct aaa aca ggg aag cga aaa agg agt cag atg ctg ttt cga       480
Pro Ala Ala Lys Thr Gly Lys Arg Lys Arg Ser Gln Met Leu Phe Arg
145                 150                 155                 160 ggt cga aga gca tcc cag taa                                           501
Gly Arg Arg Ala Ser Gln
                165

<210> SEQ ID NO 72
<211> LENGTH: 166
<212> TYPE: PRT
<213> ORGANISM: Homo sapiens

<400> SEQUENCE: 72

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30
```

```
Asn Leu Lys Lys Tyr Phe Asn Ala Gly His Ser Asp Val Ala Asp Asn
         35                  40                  45

Gly Thr Leu Phe Leu Gly Ile Leu Lys Asn Trp Lys Glu Glu Ser Asp
 50                  55                  60

Arg Lys Ile Met Gln Ser Gln Ile Val Ser Phe Tyr Phe Lys Leu Phe
 65                  70                  75                  80

Lys Asn Phe Lys Asp Asp Gln Ser Ile Gln Lys Ser Val Glu Thr Ile
                 85                  90                  95

Lys Glu Asp Met Asn Val Lys Phe Phe Asn Ser Asn Lys Lys Lys Arg
                100                 105                 110

Asp Asp Phe Glu Lys Leu Thr Asn Tyr Ser Val Thr Asp Leu Asn Val
             115                 120                 125

Gln Arg Lys Ala Ile His Glu Leu Ile Gln Val Met Ala Glu Leu Ser
        130                 135                 140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 73
<211> LENGTH: 987
<212> TYPE: DNA
<213> ORGANISM: Homo sapiens
<220> FEATURE:
<221> NAME/KEY: CDS
<222> LOCATION: (1)..(987)
<223> OTHER INFORMATION: Human GlucON Gamma

<400> SEQUENCE: 73 atg gga gtc aaa gtt ctg ttt gcc ctg atc tgc atc gct gtg gcc gag    48
Met Gly Val Lys Val Leu Phe Ala Leu Ile Cys Ile Ala Val Ala Glu
 1               5                  10                  15 gcc aag ccc acc gag aac aac gaa gac ttc aac atc gtg gcc gtg gcc    96
Ala Lys Pro Thr Glu Asn Asn Glu Asp Phe Asn Ile Val Ala Val Ala
             20                  25                  30 agc aac ttc gcg acc acg gat ctc gat gct gac cgc ggg aag ttg ccc   144
Ser Asn Phe Ala Thr Thr Asp Leu Asp Ala Asp Arg Gly Lys Leu Pro
         35                  40                  45 ggc aag aag ctg ccg ctg gag gtg ctc aaa gag atg gaa gcc aat gcc   192
Gly Lys Lys Leu Pro Leu Glu Val Leu Lys Glu Met Glu Ala Asn Ala
 50                  55                  60 cgg aaa gct ggc tgc acc agg ggc tgt ctg atc tgc ctg tcc cac atc   240
Arg Lys Ala Gly Cys Thr Arg Gly Cys Leu Ile Cys Leu Ser His Ile
 65                  70                  75                  80 aag tgc acg ccc aag atg aag aag ttc atc cca gga cgc tgc cac acc   288
Lys Cys Thr Pro Lys Met Lys Lys Phe Ile Pro Gly Arg Cys His Thr
                 85                  90                  95 tac gaa ggc gac aaa gag tcc gca cag ggc ggc ata ggc gag gcg atc   336
Tyr Glu Gly Asp Lys Glu Ser Ala Gln Gly Gly Ile Gly Glu Ala Ile
            100                 105                 110 gtc gac att cct gag att cct ggg ttc aag gac ttg gag ccc atg gag   384
Val Asp Ile Pro Glu Ile Pro Gly Phe Lys Asp Leu Glu Pro Met Glu
        115                 120                 125 cag ttc atc gca cag gtc gat ctg tgt gtg gac tgc aca act ggc tgc   432
Gln Phe Ile Ala Gln Val Asp Leu Cys Val Asp Cys Thr Thr Gly Cys
    130                 135                 140 ctc aaa ggg ctt gcc aac gtg cag tgt tct gac ctg ctc aag aag tgg   480
Leu Lys Gly Leu Ala Asn Val Gln Cys Ser Asp Leu Leu Lys Lys Trp
145                 150                 155                 160
```

-continued

| | | |
|---|---|---|
| ctg ccg caa cgc tgt gcg acc ttt gcc agc aag atc cag ggc cag gtg<br>Leu Pro Gln Arg Cys Ala Thr Phe Ala Ser Lys Ile Gln Gly Gln Val<br>                  165                      170                   175 | 528 |
| gac aag atc aag ggg gcc ggt ggt gac cag gac cca tat gta aaa gaa<br>Asp Lys Ile Lys Gly Ala Gly Gly Asp Gln Asp Pro Tyr Val Lys Glu<br>        180                      185                      190 | 576 |
| gca gaa aac ctt aag aaa tat ttt aat gca ggt cat tca gat gta gcg<br>Ala Glu Asn Leu Lys Lys Tyr Phe Asn Ala Gly His Ser Asp Val Ala<br>                  195                      200                   205 | 624 |
| gat aat gga act ctt ttc tta ggc att ttg aag aat tgg aaa gag gag<br>Asp Asn Gly Thr Leu Phe Leu Gly Ile Leu Lys Asn Trp Lys Glu Glu<br>210                      215                      220 | 672 |
| agt gac aga aaa ata atg cag agc caa att gtc tcc ttt tac ttc aaa<br>Ser Asp Arg Lys Ile Met Gln Ser Gln Ile Val Ser Phe Tyr Phe Lys<br>225                      230                      235                   240 | 720 |
| ctt ttt aaa aac ttt aaa gat gac cag agc atc caa aag agt gtg gag<br>Leu Phe Lys Asn Phe Lys Asp Asp Gln Ser Ile Gln Lys Ser Val Glu<br>                  245                      250                   255 | 768 |
| acc atc aag gaa gac atg aat gtc aag ttt ttc aat agc aac aaa aag<br>Thr Ile Lys Glu Asp Met Asn Val Lys Phe Phe Asn Ser Asn Lys Lys<br>260                      265                      270 | 816 |
| aaa cga gat gac ttc gaa aag ctg act aat tat tcg gta act gac ttg<br>Lys Arg Asp Asp Phe Glu Lys Leu Thr Asn Tyr Ser Val Thr Asp Leu<br>        275                      280                      285 | 864 |
| aat gtc caa cgc aaa gca ata cat gaa ctc atc caa gtg atg gct gaa<br>Asn Val Gln Arg Lys Ala Ile His Glu Leu Ile Gln Val Met Ala Glu<br>                  290                      295                   300 | 912 |
| ctg tcg cca gca gct aaa aca ggg aag cga aaa agg agt cag atg ctg<br>Leu Ser Pro Ala Ala Lys Thr Gly Lys Arg Lys Arg Ser Gln Met Leu<br>305                      310                      315                   320 | 960 |
| ttt cga ggt cga aga gca tcc cag taa<br>Phe Arg Gly Arg Arg Ala Ser Gln<br>        325 | 987 |

<210> SEQ ID NO 74
<211> LENGTH: 328
<212> TYPE: PRT
<213> ORGANISM: Homo sapiens

<400> SEQUENCE: 74

Met Gly Val Lys Val Leu Phe Ala Leu Ile Cys Ile Ala Val Ala Glu
1                   5                    10                   15

Ala Lys Pro Thr Glu Asn Asn Glu Asp Phe Asn Ile Val Ala Val Ala
               20                   25                  30

Ser Asn Phe Ala Thr Thr Asp Leu Asp Ala Asp Arg Gly Lys Leu Pro
        35                   40                   45

Gly Lys Lys Leu Pro Leu Glu Val Leu Lys Glu Met Glu Ala Asn Ala
50                     55                   60

Arg Lys Ala Gly Cys Thr Arg Gly Cys Leu Ile Cys Leu Ser His Ile
65                     70                   75                   80

Lys Cys Thr Pro Lys Met Lys Lys Phe Ile Pro Gly Arg Cys His Thr
               85                   90                  95

Tyr Glu Gly Asp Lys Glu Ser Ala Gln Gly Gly Ile Gly Glu Ala Ile
            100                  105                  110

Val Asp Ile Pro Glu Ile Pro Gly Phe Lys Asp Leu Glu Pro Met Glu
        115                    120                  125

Gln Phe Ile Ala Gln Val Asp Leu Cys Val Asp Cys Thr Thr Gly Cys
130                     135                   140

```
Leu Lys Gly Leu Ala Asn Val Gln Cys Ser Asp Leu Leu Lys Trp
145                 150                 155                 160

Leu Pro Gln Arg Cys Ala Thr Phe Ala Ser Lys Ile Gln Gly Gln Val
            165                 170                 175

Asp Lys Ile Lys Gly Ala Gly Gly Asp Gln Asp Pro Tyr Val Lys Glu
            180                 185                 190

Ala Glu Asn Leu Lys Lys Tyr Phe Asn Ala Gly His Ser Asp Val Ala
            195                 200                 205

Asp Asn Gly Thr Leu Phe Leu Gly Ile Leu Lys Asn Trp Lys Glu Glu
            210                 215                 220

Ser Asp Arg Lys Ile Met Gln Ser Gln Ile Val Ser Phe Tyr Phe Lys
225                 230                 235                 240

Leu Phe Lys Asn Phe Lys Asp Asp Gln Ser Ile Gln Lys Ser Val Glu
            245                 250                 255

Thr Ile Lys Glu Asp Met Asn Val Lys Phe Phe Asn Ser Asn Lys Lys
            260                 265                 270

Lys Arg Asp Asp Phe Glu Lys Leu Thr Asn Tyr Ser Val Thr Asp Leu
            275                 280                 285

Asn Val Gln Arg Lys Ala Ile His Glu Leu Ile Gln Val Met Ala Glu
            290                 295                 300

Leu Ser Pro Ala Ala Lys Thr Gly Lys Arg Lys Arg Ser Gln Met Leu
305                 310                 315                 320

Phe Arg Gly Arg Arg Ala Ser Gln
                325

<210> SEQ ID NO 75
<211> LENGTH: 501
<212> TYPE: DNA
<213> ORGANISM: Bos taurus
<220> FEATURE:
<221> NAME/KEY: CDS
<222> LOCATION: (1)..(501)
<223> OTHER INFORMATION: 75)Bovine Interferon Gamma

<400> SEQUENCE: 75 atg aaa tat aca agc tat ttc tta gct tta ctg ctc tgt ggg ctt ttg      48
Met Lys Tyr Thr Ser Tyr Phe Leu Ala Leu Leu Leu Cys Gly Leu Leu
1               5                   10                  15 ggt ttt tct ggt tct tat ggc cag ggc caa ttt ttt aga gaa ata gaa      96
Gly Phe Ser Gly Ser Tyr Gly Gln Gly Gln Phe Phe Arg Glu Ile Glu
            20                  25                  30 aac tta aag gag tat ttt aat gca agc agc cca gat gta gct aag ggt     144
Asn Leu Lys Glu Tyr Phe Asn Ala Ser Ser Pro Asp Val Ala Lys Gly
        35                  40                  45 ggg cct ctc ttc tca gaa att ttg aag aat tgg aaa gat gaa agt gac     192
Gly Pro Leu Phe Ser Glu Ile Leu Lys Asn Trp Lys Asp Glu Ser Asp
50                  55                  60 aaa aaa att att cag agc caa att gtc tcc ttc tac ttc aaa ctc ttt     240
Lys Lys Ile Ile Gln Ser Gln Ile Val Ser Phe Tyr Phe Lys Leu Phe
65                  70                  75                  80 gaa aac ctc aaa gat aac cag gtc att caa agg agc atg gat atc atc     288
Glu Asn Leu Lys Asp Asn Gln Val Ile Gln Arg Ser Met Asp Ile Ile
            85                  90                  95 aag caa gac atg ttt cag aag ttc ttg aat ggc agc tct gag aaa ctg     336
Lys Gln Asp Met Phe Gln Lys Phe Leu Asn Gly Ser Ser Glu Lys Leu
            100                 105                 110 gag gac ttc aaa aag ctg att caa att ccg gtg gat gat ctg cag atc     384
Glu Asp Phe Lys Lys Leu Ile Gln Ile Pro Val Asp Asp Leu Gln Ile
```

```
                115             120             125
cag cgc aaa gcc ata aat gaa ctc atc aaa gtg atg aat gac ctg tca       432
Gln Arg Lys Ala Ile Asn Glu Leu Ile Lys Val Met Asn Asp Leu Ser
        130             135             140 cca aaa tct aac ctc aga aag cgg aag aga agt cag aat ctc ttt cga       480
Pro Lys Ser Asn Leu Arg Lys Arg Lys Arg Ser Gln Asn Leu Phe Arg
145             150             155             160 ggc cgg aga gca tca acg taa                                           501
Gly Arg Arg Ala Ser Thr
                165

<210> SEQ ID NO 76
<211> LENGTH: 166
<212> TYPE: PRT
<213> ORGANISM: Bos taurus

<400> SEQUENCE: 76

Met Lys Tyr Thr Ser Tyr Phe Leu Ala Leu Leu Leu Cys Gly Leu Leu
1               5                   10                  15

Gly Phe Ser Gly Ser Tyr Gly Gln Gly Gln Phe Arg Glu Ile Glu
            20                  25                  30

Asn Leu Lys Glu Tyr Phe Asn Ala Ser Ser Pro Asp Val Ala Lys Gly
        35                  40                  45

Gly Pro Leu Phe Ser Glu Ile Leu Lys Asn Trp Lys Asp Glu Ser Asp
    50                  55                  60

Lys Lys Ile Ile Gln Ser Gln Ile Val Ser Phe Tyr Phe Lys Leu Phe
65                  70                  75                  80

Glu Asn Leu Lys Asp Asn Gln Val Ile Gln Arg Ser Met Asp Ile Ile
                85                  90                  95

Lys Gln Asp Met Phe Gln Lys Phe Leu Asn Gly Ser Ser Glu Lys Leu
            100                 105                 110

Glu Asp Phe Lys Lys Leu Ile Gln Ile Pro Val Asp Asp Leu Gln Ile
        115                 120                 125

Gln Arg Lys Ala Ile Asn Glu Leu Ile Lys Val Met Asn Asp Leu Ser
    130                 135                 140

Pro Lys Ser Asn Leu Arg Lys Arg Lys Arg Ser Gln Asn Leu Phe Arg
145                 150                 155                 160

Gly Arg Arg Ala Ser Thr
                165

<210> SEQ ID NO 77
<211> LENGTH: 993
<212> TYPE: DNA
<213> ORGANISM: Bos taurus
<220> FEATURE:
<221> NAME/KEY: CDS
<222> LOCATION: (1)..(993)
<223> OTHER INFORMATION: Bovine GlucON Gamma

<400> SEQUENCE: 77 atg gga gtc aaa gtt ctg ttt gcc ctg atc tgc atc gct gtg gcc gag       48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc       96
Ala Lys Pro Thr Glu Asn Asn Glu Asp Phe Asn Ile Val Ala Val Ala
            20                  25                  30 agc aac ttc gcg acc acg gat ctc gat gct gac cgc ggg aag ttg ccc      144
Ser Asn Phe Ala Thr Thr Asp Leu Asp Ala Asp Arg Gly Lys Leu Pro
        35                  40                  45
```

```
ggc aag aag ctg ccg ctg gag gtg ctc aaa gag atg gaa gcc aat gcc     192
Gly Lys Lys Leu Pro Leu Glu Val Leu Lys Glu Met Glu Ala Asn Ala
 50              55                  60 cgg aaa gct ggc tgc acc agg ggc tgt ctg atc tgc ctg tcc cac atc     240
Arg Lys Ala Gly Cys Thr Arg Gly Cys Leu Ile Cys Leu Ser His Ile
 65              70                  75                  80 aag tgc acg ccc aag atg aag aag ttc atc cca gga cgc tgc cac acc     288
Lys Cys Thr Pro Lys Met Lys Lys Phe Ile Pro Gly Arg Cys His Thr
                 85                  90                  95 tac gaa ggc gac aaa gag tcc gca cag ggc ggc ata ggc gag gcg atc     336
Tyr Glu Gly Asp Lys Glu Ser Ala Gln Gly Gly Ile Gly Glu Ala Ile
            100                 105                 110 gtt gac att cct gag att cct ggg ttc aag gac ttg gag ccc atg gag     384
Val Asp Ile Pro Glu Ile Pro Gly Phe Lys Asp Leu Glu Pro Met Glu
        115                 120                 125 cag ttc atc gca cag gtc gat ctg tgt gtg gac tgc aca act ggc tgc     432
Gln Phe Ile Ala Gln Val Asp Leu Cys Val Asp Cys Thr Thr Gly Cys
130                 135                 140 ctc aaa ggg ctt gcc aac gtg cag tgt tct gac ctg ctc aag aag tgg     480
Leu Lys Gly Leu Ala Asn Val Gln Cys Ser Asp Leu Leu Lys Lys Trp
145                 150                 155                 160 ctg ccg caa cgc tgt gcg acc ttt gcc agc aag atc cag ggc cag gtg     528
Leu Pro Gln Arg Cys Ala Thr Phe Ala Ser Lys Ile Gln Gly Gln Val
                165                 170                 175 gac aag atc aag ggg gca ggt ggt gac ggg ccc cag ggc caa ttt ttt     576
Asp Lys Ile Lys Gly Ala Gly Gly Asp Gly Pro Gln Gly Gln Phe Phe
            180                 185                 190 aga gaa ata gaa aac tta aag gag tat ttt aat gca agt agc cca gat     624
Arg Glu Ile Glu Asn Leu Lys Glu Tyr Phe Asn Ala Ser Ser Pro Asp
        195                 200                 205 gta gct aag ggt ggg cct ctc ttc tca gaa att ttg aag aat tgg aaa     672
Val Ala Lys Gly Gly Pro Leu Phe Ser Glu Ile Leu Lys Asn Trp Lys
210                 215                 220 gat gaa agt gac aaa aaa att att cag agc caa att gtc tcc ttc tac     720
Asp Glu Ser Asp Lys Lys Ile Ile Gln Ser Gln Ile Val Ser Phe Tyr
225                 230                 235                 240 ttc aaa ctc ttt gaa aac ctc aaa gat aac cag gtc att caa agg agc     768
Phe Lys Leu Phe Glu Asn Leu Lys Asp Asn Gln Val Ile Gln Arg Ser
                245                 250                 255 atg gat ata atc aag caa gac atg ttt cag aag ttc ttg aat ggc agc     816
Met Asp Ile Ile Lys Gln Asp Met Phe Gln Lys Phe Leu Asn Gly Ser
            260                 265                 270 tct gag aaa ctg gag gac ttc aaa aag ctg att caa att ccg gtg gat     864
Ser Glu Lys Leu Glu Asp Phe Lys Lys Leu Ile Gln Ile Pro Val Asp
        275                 280                 285 gat ctc cag atc cag cgc aaa gcc ata aat gaa ctc atc aaa gtg atg     912
Asp Leu Gln Ile Gln Arg Lys Ala Ile Asn Glu Leu Ile Lys Val Met
290                 295                 300 aat gac ctg tca cca aaa tct aac ctc aga aag cgg aag aga agt cag     960
Asn Asp Leu Ser Pro Lys Ser Asn Leu Arg Lys Arg Lys Arg Ser Gln
305                 310                 315                 320 aat ctc ttt cga ggc cgg aga gca tca acg taa                         993
Asn Leu Phe Arg Gly Arg Arg Ala Ser Thr
                325                 330
```

<210> SEQ ID NO 78
<211> LENGTH: 330
<212> TYPE: PRT
<213> ORGANISM: Bos taurus

<400> SEQUENCE: 78

Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
                20                  25                  30

Ser Asn Phe Ala Thr Thr Asp Leu Asp Ala Asp Arg Gly Lys Leu Pro
            35                  40                  45

Gly Lys Lys Leu Pro Leu Glu Val Leu Lys Glu Met Glu Ala Asn Ala
    50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Gly Ile Gly Glu Ala Ile
                100                 105                 110

Val Asp Ile Pro Glu Ile Pro Gly Phe Lys Asp Leu Glu Pro Met Glu
            115                 120                 125

Gln Phe Ile Ala Gln Val Asp Leu Cys Val Asp Cys Thr Thr Gly Cys
    130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Asp Gly Pro Gln Gly Gln Phe Phe
                180                 185                 190

Arg Glu Ile Glu Asn Leu Lys Glu Tyr Phe Asn Ala Ser Ser Pro Asp
            195                 200                 205

Val Ala Lys Gly Gly Pro Leu Phe Ser Glu Ile Leu Lys Asn Trp Lys
    210                 215                 220

Asp Glu Ser Asp Lys Lys Ile Ile Gln Ser Gln Ile Val Ser Phe Tyr
225                 230                 235                 240

Phe Lys Leu Phe Glu Asn Leu Lys Asp Asn Gln Val Ile Gln Arg Ser
                245                 250                 255

Met Asp Ile Ile Lys Gln Asp Met Phe Gln Lys Phe Leu Asn Gly Ser
                260                 265                 270

Ser Glu Lys Leu Glu Asp Phe Lys Lys Leu Ile Gln Ile Pro Val Asp
            275                 280                 285

Asp Leu Gln Ile Gln Arg Lys Ala Ile Asn Glu Leu Ile Lys Val Met
    290                 295                 300

Asn Asp Leu Ser Pro Lys Ser Asn Leu Arg Lys Arg Lys Arg Ser Gln
305                 310                 315                 320

Asn Leu Phe Arg Gly Arg Arg Ala Ser Thr
                325                 330

<210> SEQ ID NO 79
<211> LENGTH: 501
<212> TYPE: DNA
<213> ORGANISM: Sus scrofa
<220> FEATURE:
<221> NAME/KEY: CDS
<222> LOCATION: (1)..(501)
<223> OTHER INFORMATION: Porcine Interferon Gamma

<400> SEQUENCE: 79 atg agt tat aca act tat ttc tta gct ttt cag ctt tgc gtg act ttg    48
Met Ser Tyr Thr Thr Tyr Phe Leu Ala Phe Gln Leu Cys Val Thr Leu
1               5                   10                  15

-continued

```
tgt ttt tct ggc tct tac tgc cag gcg ccc ttt ttt aaa gaa ata acg      96
Cys Phe Ser Gly Ser Tyr Cys Gln Ala Pro Phe Phe Lys Glu Ile Thr
            20                  25                  30 atc cta aag gac tat ttt aat gca agt acc tca gat gta cct aat ggt     144
Ile Leu Lys Asp Tyr Phe Asn Ala Ser Thr Ser Asp Val Pro Asn Gly
        35                  40                  45 gga cct ctt ttc tta gaa att ttg aag aat tgg aaa gag gag agt gac     192
Gly Pro Leu Phe Leu Glu Ile Leu Lys Asn Trp Lys Glu Glu Ser Asp
    50                  55                  60 aaa aaa ata att cag agc caa att gtc tcc ttc tac ttc aaa ttc ttt     240
Lys Lys Ile Ile Gln Ser Gln Ile Val Ser Phe Tyr Phe Lys Phe Phe
65                  70                  75                  80 gaa atc ttc aaa gat aac cag gcc att caa agg agc atg gat gtg atc     288
Glu Ile Phe Lys Asp Asn Gln Ala Ile Gln Arg Ser Met Asp Val Ile
                85                  90                  95 aag caa gac atg ttt cag agg ttc cta aat ggt agc tct ggg aaa ctg     336
Lys Gln Asp Met Phe Gln Arg Phe Leu Asn Gly Ser Ser Gly Lys Leu
            100                 105                 110 aat gac ttc gaa aag ctg att aaa att ccg gta gat aat ctg cag atc     384
Asn Asp Phe Glu Lys Leu Ile Lys Ile Pro Val Asp Asn Leu Gln Ile
        115                 120                 125 cag cgc aaa gcc atc agt gaa ctc atc aaa gtg atg aat gat ctg tca     432
Gln Arg Lys Ala Ile Ser Glu Leu Ile Lys Val Met Asn Asp Leu Ser
    130                 135                 140 cca aga tct aac cta aga aag cgg aag aga agt cag act atg ttc caa     480
Pro Arg Ser Asn Leu Arg Lys Arg Lys Arg Ser Gln Thr Met Phe Gln
145                 150                 155                 160 ggc cag aga gca tca aaa taa                                         501
Gly Gln Arg Ala Ser Lys
                165

<210> SEQ ID NO 80
<211> LENGTH: 166
<212> TYPE: PRT
<213> ORGANISM: Sus scrofa

<400> SEQUENCE: 80

Met Ser Tyr Thr Thr Tyr Phe Leu Ala Phe Gln Leu Cys Val Thr Leu
1               5                   10                  15

Cys Phe Ser Gly Ser Tyr Cys Gln Ala Pro Phe Phe Lys Glu Ile Thr
            20                  25                  30

Ile Leu Lys Asp Tyr Phe Asn Ala Ser Thr Ser Asp Val Pro Asn Gly
        35                  40                  45

Gly Pro Leu Phe Leu Glu Ile Leu Lys Asn Trp Lys Glu Glu Ser Asp
    50                  55                  60

Lys Lys Ile Ile Gln Ser Gln Ile Val Ser Phe Tyr Phe Lys Phe Phe
65                  70                  75                  80

Glu Ile Phe Lys Asp Asn Gln Ala Ile Gln Arg Ser Met Asp Val Ile
                85                  90                  95

Lys Gln Asp Met Phe Gln Arg Phe Leu Asn Gly Ser Ser Gly Lys Leu
            100                 105                 110

Asn Asp Phe Glu Lys Leu Ile Lys Ile Pro Val Asp Asn Leu Gln Ile
        115                 120                 125

Gln Arg Lys Ala Ile Ser Glu Leu Ile Lys Val Met Asn Asp Leu Ser
    130                 135                 140

Pro Arg Ser Asn Leu Arg Lys Arg Lys Arg Ser Gln Thr Met Phe Gln
145                 150                 155                 160
```

Gly Gln Arg Ala Ser Lys
                165

<210> SEQ ID NO 81
<211> LENGTH: 987
<212> TYPE: DNA
<213> ORGANISM: Sus scrofa
<220> FEATURE:
<221> NAME/KEY: CDS
<222> LOCATION: (1)..(987)
<223> OTHER INFORMATION: Porcine GLucON Gamma

<400> SEQUENCE: 81

| | | | | | | | | | | | | | | | | |
|---|---|---|---|---|---|---|---|---|---|---|---|---|---|---|---|---|
| atg | gga | gtc | aaa | gtt | ctg | ttt | gcc | ctg | atc | tgc | atc | gct | gtg | gcc | gag | 48 |
| Met | Gly | Val | Lys | Val | Leu | Phe | Ala | Leu | Ile | Cys | Ile | Ala | Val | Ala | Glu | |
| 1 | | | | 5 | | | | | 10 | | | | | 15 | | |

| gcc | aag | ccc | acc | gag | aac | aac | gaa | gac | ttc | aac | atc | gtg | gcc | gtg | gcc | 96 |
|---|---|---|---|---|---|---|---|---|---|---|---|---|---|---|---|---|
| Ala | Lys | Pro | Thr | Glu | Asn | Asn | Glu | Asp | Phe | Asn | Ile | Val | Ala | Val | Ala | |
| | | | 20 | | | | | 25 | | | | | 30 | | | |

| agc | aac | ttc | gcg | acc | acg | gat | ctc | gat | gct | gac | cgc | ggg | aag | ttg | ccc | 144 |
|---|---|---|---|---|---|---|---|---|---|---|---|---|---|---|---|---|
| Ser | Asn | Phe | Ala | Thr | Thr | Asp | Leu | Asp | Ala | Asp | Arg | Gly | Lys | Leu | Pro | |
| | 35 | | | | | 40 | | | | | 45 | | | | | |

| ggc | aag | aag | ctg | ccg | ctg | gag | gtg | ctc | aaa | gag | atg | gaa | gcc | aat | gcc | 192 |
|---|---|---|---|---|---|---|---|---|---|---|---|---|---|---|---|---|
| Gly | Lys | Lys | Leu | Pro | Leu | Glu | Val | Leu | Lys | Glu | Met | Glu | Ala | Asn | Ala | |
| 50 | | | | | 55 | | | | | 60 | | | | | | |

| cgg | aaa | gct | ggc | tgc | acc | agg | ggc | tgt | ctg | atc | tgc | ctg | tcc | cac | atc | 240 |
|---|---|---|---|---|---|---|---|---|---|---|---|---|---|---|---|---|
| Arg | Lys | Ala | Gly | Cys | Thr | Arg | Gly | Cys | Leu | Ile | Cys | Leu | Ser | His | Ile | |
| 65 | | | | 70 | | | | | 75 | | | | | 80 | | |

| aag | tgc | acg | ccc | aag | atg | aag | aag | ttc | atc | cca | gga | cgc | tgc | cac | acc | 288 |
|---|---|---|---|---|---|---|---|---|---|---|---|---|---|---|---|---|
| Lys | Cys | Thr | Pro | Lys | Met | Lys | Lys | Phe | Ile | Pro | Gly | Arg | Cys | His | Thr | |
| | | | | 85 | | | | | 90 | | | | | 95 | | |

| tac | gaa | ggc | gac | aaa | gag | tcc | gca | cag | ggc | ggc | ata | ggc | gag | gcg | atc | 336 |
|---|---|---|---|---|---|---|---|---|---|---|---|---|---|---|---|---|
| Tyr | Glu | Gly | Asp | Lys | Glu | Ser | Ala | Gln | Gly | Gly | Ile | Gly | Glu | Ala | Ile | |
| | | | 100 | | | | | 105 | | | | | 110 | | | |

| gtc | gac | att | cct | gag | att | cct | ggg | ttc | aag | gac | ttg | gag | ccc | atg | gag | 384 |
|---|---|---|---|---|---|---|---|---|---|---|---|---|---|---|---|---|
| Val | Asp | Ile | Pro | Glu | Ile | Pro | Gly | Phe | Lys | Asp | Leu | Glu | Pro | Met | Glu | |
| | | 115 | | | | | 120 | | | | | 125 | | | | |

| cag | ttc | atc | gca | cag | gtc | gat | ctg | tgt | gtg | gac | tgc | aca | act | ggc | tgc | 432 |
|---|---|---|---|---|---|---|---|---|---|---|---|---|---|---|---|---|
| Gln | Phe | Ile | Ala | Gln | Val | Asp | Leu | Cys | Val | Asp | Cys | Thr | Thr | Gly | Cys | |
| 130 | | | | | 135 | | | | | 140 | | | | | | |

| ctc | aaa | ggg | ctt | gcc | aac | gtg | cag | tgt | tct | gac | ctg | ctc | aag | aag | tgg | 480 |
|---|---|---|---|---|---|---|---|---|---|---|---|---|---|---|---|---|
| Leu | Lys | Gly | Leu | Ala | Asn | Val | Gln | Cys | Ser | Asp | Leu | Leu | Lys | Lys | Trp | |
| 145 | | | | | 150 | | | | | 155 | | | | | 160 | |

| ctg | ccg | caa | cgc | tgt | gcg | acc | ttt | gcc | agc | aag | atc | cag | ggc | cag | gtg | 528 |
|---|---|---|---|---|---|---|---|---|---|---|---|---|---|---|---|---|
| Leu | Pro | Gln | Arg | Cys | Ala | Thr | Phe | Ala | Ser | Lys | Ile | Gln | Gly | Gln | Val | |
| | | | 165 | | | | | 170 | | | | | 175 | | | |

| gac | aag | atc | aag | ggg | gcc | ggt | ggt | gac | cag | gcg | ccc | ttt | ttt | aaa | gaa | 576 |
|---|---|---|---|---|---|---|---|---|---|---|---|---|---|---|---|---|
| Asp | Lys | Ile | Lys | Gly | Ala | Gly | Gly | Asp | Gln | Ala | Pro | Phe | Phe | Lys | Glu | |
| | | | 180 | | | | | 185 | | | | | 190 | | | |

| ata | acg | atc | cta | aag | gac | tat | ttt | aat | gca | agt | acc | tca | gat | gta | cct | 624 |
|---|---|---|---|---|---|---|---|---|---|---|---|---|---|---|---|---|
| Ile | Thr | Ile | Leu | Lys | Asp | Tyr | Phe | Asn | Ala | Ser | Thr | Ser | Asp | Val | Pro | |
| | | 195 | | | | | 200 | | | | | 205 | | | | |

| aat | ggt | gga | cct | ctt | ttc | tta | gaa | att | ttg | aag | aat | tgg | aaa | gag | gag | 672 |
|---|---|---|---|---|---|---|---|---|---|---|---|---|---|---|---|---|
| Asn | Gly | Gly | Pro | Leu | Phe | Leu | Glu | Ile | Leu | Lys | Asn | Trp | Lys | Glu | Glu | |
| | 210 | | | | | 215 | | | | | 220 | | | | | |

| agt | gac | aaa | aaa | ata | att | cag | agc | caa | att | gtc | tcc | ttc | tac | ttc | aaa | 720 |
|---|---|---|---|---|---|---|---|---|---|---|---|---|---|---|---|---|
| Ser | Asp | Lys | Lys | Ile | Ile | Gln | Ser | Gln | Ile | Val | Ser | Phe | Tyr | Phe | Lys | |
| 225 | | | | | 230 | | | | | 235 | | | | | 240 | |

| ttc | ttt | gaa | atc | ttc | aaa | gat | aac | cag | gcc | att | caa | agg | agc | atg | gat | 768 |
|---|---|---|---|---|---|---|---|---|---|---|---|---|---|---|---|---|
| Phe | Phe | Glu | Ile | Phe | Lys | Asp | Asn | Gln | Ala | Ile | Gln | Arg | Ser | Met | Asp | |
| | | | | 245 | | | | | 250 | | | | | 255 | | |

| | |
|---|---|
| gtg atc aag caa gac atg ttt cag agg ttc cta aat ggt agc tct ggg<br>Val Ile Lys Gln Asp Met Phe Gln Arg Phe Leu Asn Gly Ser Ser Gly<br>260             265                 270 | 816 |
| aaa ctg aat gac ttc gaa aag ctg att aaa att ccg gta gat aat ctg<br>Lys Leu Asn Asp Phe Glu Lys Leu Ile Lys Ile Pro Val Asp Asn Leu<br>    275                 280                 285 | 864 |
| cag atc cag cgc aaa gcc atc agt gaa ctc atc aaa gtg atg aat gat<br>Gln Ile Gln Arg Lys Ala Ile Ser Glu Leu Ile Lys Val Met Asn Asp<br>290             295                 300 | 912 |
| ctg tca cca aga tct aac cta aga aag cgg aag aga agt cag act atg<br>Leu Ser Pro Arg Ser Asn Leu Arg Lys Arg Lys Arg Ser Gln Thr Met<br>305             310                 315                 320 | 960 |
| ttc caa ggc cag aga gca tca aaa taa<br>Phe Gln Gly Gln Arg Ala Ser Lys<br>                325 | 987 |

<210> SEQ ID NO 82
<211> LENGTH: 328
<212> TYPE: PRT
<213> ORGANISM: Sus scrofa

<400> SEQUENCE: 82

```
Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
        35                  40                  45

Gly Lys Lys Leu Pro Leu Glu Val Leu Lys Glu Met Glu Ala Asn Ala
    50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Ile Gly Glu Ala Ile
            100                 105                 110

Val Asp Ile Pro Glu Ile Pro Gly Phe Lys Asp Leu Glu Pro Met Glu
        115                 120                 125

Gln Phe Ile Ala Gln Val Asp Leu Cys Val Asp Cys Thr Thr Gly Cys
    130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Asp Gln Ala Pro Phe Phe Lys Glu
            180                 185                 190

Ile Thr Ile Leu Lys Asp Tyr Phe Asn Ala Ser Thr Ser Asp Val Pro
        195                 200                 205

Asn Gly Gly Pro Leu Phe Leu Glu Ile Leu Lys Asn Trp Lys Glu Glu
    210                 215                 220

Ser Asp Lys Lys Ile Ile Gln Ser Gln Ile Val Ser Phe Tyr Phe Lys
225                 230                 235                 240

Phe Phe Glu Ile Phe Lys Asp Asn Gln Ala Ile Gln Arg Ser Met Asp
                245                 250                 255

Val Ile Lys Gln Asp Met Phe Gln Arg Phe Leu Asn Gly Ser Ser Gly
            260                 265                 270
```

```
Lys Leu Asn Asp Phe Glu Lys Leu Ile Lys Ile Pro Val Asp Asn Leu
            275                 280                 285

Gln Ile Gln Arg Lys Ala Ile Ser Glu Leu Ile Lys Val Met Asn Asp
        290                 295                 300

Leu Ser Pro Arg Ser Asn Leu Arg Lys Arg Lys Arg Ser Gln Thr Met
305                 310                 315                 320

Phe Gln Gly Gln Arg Ala Ser Lys
                325

<210> SEQ ID NO 83
<211> LENGTH: 588
<212> TYPE: DNA
<213> ORGANISM: Bos taurus
<220> FEATURE:
<221> NAME/KEY: CDS
<222> LOCATION: (1)..(588)
<223> OTHER INFORMATION: Bovine Interferon Lambda IL29

<400> SEQUENCE: 83 atg gcc ccg ggc tgc acg ctg gtg ctg gtg ctg atg ctg acg acc gtg    48
Met Ala Pro Gly Cys Thr Leu Val Leu Val Leu Met Leu Thr Thr Val
1               5                   10                  15 gcg ctg agc agg aca gga gca gtt cct gtg ccc tct gcc ccc agg gcc    96
Ala Leu Ser Arg Thr Gly Ala Val Pro Val Pro Ser Ala Pro Arg Ala
                20                  25                  30 ctc cca cct gcc agg ggc tgc cac gtg gcc cag ttc aag tct ctg tcc    144
Leu Pro Pro Ala Arg Gly Cys His Val Ala Gln Phe Lys Ser Leu Ser
            35                  40                  45 cct caa gag ctg cag gcc ttc aag acg gcc agg gat gcc ttt gaa gac    192
Pro Gln Glu Leu Gln Ala Phe Lys Thr Ala Arg Asp Ala Phe Glu Asp
        50                  55                  60 tcg ttc ttg cca aag gac tgg gac tgc agc acc cac ctt ttc ccc agg    240
Ser Phe Leu Pro Lys Asp Trp Asp Cys Ser Thr His Leu Phe Pro Arg
65                  70                  75                  80 acc cgg gac ctg aag cac ctg cag gtg tgg gag cgc cct gtg gct ctg    288
Thr Arg Asp Leu Lys His Leu Gln Val Trp Glu Arg Pro Val Ala Leu
                85                  90                  95 gag gca gag ctg gcc ctg aca ctg acg gtc ctg gag gcc atg gct aac    336
Glu Ala Glu Leu Ala Leu Thr Leu Thr Val Leu Glu Ala Met Ala Asn
                100                 105                 110 tca tcc ctg ggc cac agc ctg gag cag ccc ctt ctc acg ctg cag aac    384
Ser Ser Leu Gly His Ser Leu Glu Gln Pro Leu Leu Thr Leu Gln Asn
            115                 120                 125 atc cac tcc aag ctc cag gcc tgt gtc cca gct cag ccc aca gca agc    432
Ile His Ser Lys Leu Gln Ala Cys Val Pro Ala Gln Pro Thr Ala Ser
        130                 135                 140 tcc agg ccc cgg ggc cgc ctc cac cac tgg ctg cac cgc ctc cag gag    480
Ser Arg Pro Arg Gly Arg Leu His His Trp Leu His Arg Leu Gln Glu
145                 150                 155                 160 gcc cgg aag gag tcc cag gac tgc ctc gaa gcc tct gtg atg ttc aac    528
Ala Arg Lys Glu Ser Gln Asp Cys Leu Glu Ala Ser Val Met Phe Asn
                165                 170                 175 ctc ctc cgc ctc ctc acc cgg gac ctg aaa tgt gtt gcc agc gga gac    576
Leu Leu Arg Leu Leu Thr Arg Asp Leu Lys Cys Val Ala Ser Gly Asp
                180                 185                 190 cag tgt gtc tga                                                    588
Gln Cys Val
        195

<210> SEQ ID NO 84
<211> LENGTH: 195
```

```
<212> TYPE: PRT
<213> ORGANISM: Bos taurus

<400> SEQUENCE: 84

Met Ala Pro Gly Cys Thr Leu Val Leu Val Leu Met Leu Thr Thr Val
1               5                   10                  15

Ala Leu Ser Arg Thr Gly Ala Val Pro Val Pro Ser Ala Pro Arg Ala
            20                  25                  30

Leu Pro Pro Ala Arg Gly Cys His Val Ala Gln Phe Lys Ser Leu Ser
            35                  40                  45

Pro Gln Glu Leu Gln Ala Phe Lys Thr Ala Arg Asp Ala Phe Glu Asp
        50                  55                  60

Ser Phe Leu Pro Lys Asp Trp Asp Cys Ser Thr His Leu Phe Pro Arg
65                  70                  75                  80

Thr Arg Asp Leu Lys His Leu Gln Val Trp Glu Arg Pro Val Ala Leu
                85                  90                  95

Glu Ala Glu Leu Ala Leu Thr Leu Thr Val Leu Glu Ala Met Ala Asn
            100                 105                 110

Ser Ser Leu Gly His Ser Leu Glu Gln Pro Leu Leu Thr Leu Gln Asn
        115                 120                 125

Ile His Ser Lys Leu Gln Ala Cys Val Pro Ala Gln Pro Thr Ala Ser
    130                 135                 140

Ser Arg Pro Arg Gly Arg Leu His His Trp Leu His Arg Leu Gln Glu
145                 150                 155                 160

Ala Arg Lys Glu Ser Gln Asp Cys Leu Glu Ala Ser Val Met Phe Asn
                165                 170                 175

Leu Leu Arg Leu Leu Thr Arg Asp Leu Lys Cys Val Ala Ser Gly Asp
            180                 185                 190

Gln Cys Val
        195

<210> SEQ ID NO 85
<211> LENGTH: 1092
<212> TYPE: DNA
<213> ORGANISM: Bos taurus
<220> FEATURE:
<221> NAME/KEY: CDS
<222> LOCATION: (1)..(1092)
<223> OTHER INFORMATION: Bovine GLucON Lambda

<400> SEQUENCE: 85 atg gga gtc aaa gtt ctg ttt gcc ctg atc tgc atc gct gtg gcc gag     48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc     96
Ala Lys Pro Thr Glu Asn Asn Glu Asp Phe Asn Ile Val Ala Val Ala
            20                  25                  30 agc aac ttc gcg acc acg gat ctc gat gct gac cgc ggg aag ttg ccc    144
Ser Asn Phe Ala Thr Thr Asp Leu Asp Ala Asp Arg Gly Lys Leu Pro
        35                  40                  45 ggc aag aag ctg ccg ctg gag gtg ctc aaa gag atg gaa gcc aat gcc    192
Gly Lys Lys Leu Pro Leu Glu Val Leu Lys Glu Met Glu Ala Asn Ala
    50                  55                  60 cgg aaa gct ggc tgc acc agg ggc tgt ctg atc tgc ctg tcc cac atc    240
Arg Lys Ala Gly Cys Thr Arg Gly Cys Leu Ile Cys Leu Ser His Ile
65                  70                  75                  80 aag tgc acg ccc aag atg aag aag ttc atc cca gga cgc tgc cac acc    288
Lys Cys Thr Pro Lys Met Lys Lys Phe Ile Pro Gly Arg Cys His Thr
                85                  90                  95
```

| | | |
|---|---|---|
| tac gaa ggc gac aaa gag tcc gca cag ggc ggc ata ggc gag gcg atc<br>Tyr Glu Gly Asp Lys Glu Ser Ala Gln Gly Gly Ile Gly Glu Ala Ile<br>100                        105                     110 | | 336 |
| gtt gac att cct gag att cct ggg ttc aag gac ttg gag ccc atg gag<br>Val Asp Ile Pro Glu Ile Pro Gly Phe Lys Asp Leu Glu Pro Met Glu<br>          115                     120                     125 | | 384 |
| cag ttc atc gca cag gtc gat ctg tgt gtg gac tgc aca act ggc tgc<br>Gln Phe Ile Ala Gln Val Asp Leu Cys Val Asp Cys Thr Thr Gly Cys<br>130                        135                     140 | | 432 |
| ctc aaa ggg ctt gcc aac gtg cag tgt tct gac ctg ctc aag aag tgg<br>Leu Lys Gly Leu Ala Asn Val Gln Cys Ser Asp Leu Leu Lys Lys Trp<br>145                        150                     155                     160 | | 480 |
| ctg ccg caa cgc tgt gcg acc ttt gcc agc aag atc cag ggc cag gtg<br>Leu Pro Gln Arg Cys Ala Thr Phe Ala Ser Lys Ile Gln Gly Gln Val<br>                          165                     170                     175 | | 528 |
| gac aag atc aag ggg gcc ggt ggt gac ggg ccc agg aca gga gca gtt<br>Asp Lys Ile Lys Gly Ala Gly Gly Asp Gly Pro Arg Thr Gly Ala Val<br>          180                     185                     190 | | 576 |
| cct gtg ccc tct gcc ccc agg gca ctc cca cct gcc agg ggc tgc cac<br>Pro Val Pro Ser Ala Pro Arg Ala Leu Pro Pro Ala Arg Gly Cys His<br>                    195                     200                     205 | | 624 |
| gtg gcc cag ttc aag tct ctg tcc cct caa gag ctg caa gcc ttc aag<br>Val Ala Gln Phe Lys Ser Leu Ser Pro Gln Glu Leu Gln Ala Phe Lys<br>210                        215                     220 | | 672 |
| acg gcc agg gat gcc ttt gaa gac tcg ttc ttg ccg aag gac tgg gac<br>Thr Ala Arg Asp Ala Phe Glu Asp Ser Phe Leu Pro Lys Asp Trp Asp<br>225                        230                     235                     240 | | 720 |
| tgt agc acc cac ctt ttc ccc agg aca cga gac ctg aag cac ctg caa<br>Cys Ser Thr His Leu Phe Pro Arg Thr Arg Asp Leu Lys His Leu Gln<br>                          245                     250                     255 | | 768 |
| gtg tgg gag cgc cct gtg gct ctg gag gca gag ctg gcc ctg aca ctg<br>Val Trp Glu Arg Pro Val Ala Leu Glu Ala Glu Leu Ala Leu Thr Leu<br>          260                     265                     270 | | 816 |
| acg gtc ctg gag gca atg gct aac tca tcc ctg ggc cac agc ctg gag<br>Thr Val Leu Glu Ala Met Ala Asn Ser Ser Leu Gly His Ser Leu Glu<br>                    275                     280                     285 | | 864 |
| cag ccc ctt ctc acg ctg caa aac atc cac tcc aag ctc cag gcc tgt<br>Gln Pro Leu Leu Thr Leu Gln Asn Ile His Ser Lys Leu Gln Ala Cys<br>290                        295                     300 | | 912 |
| gtc cca gct cag ccc aca gca agc tcc aga ccc cga ggc cgc ctc cac<br>Val Pro Ala Gln Pro Thr Ala Ser Ser Arg Pro Arg Gly Arg Leu His<br>305                        310                     315                     320 | | 960 |
| cac tgg ctg cac cgc ctc caa gag gcc cgg aag gag tcc cag gac tgc<br>His Trp Leu His Arg Leu Gln Glu Ala Arg Lys Glu Ser Gln Asp Cys<br>                          325                     330                     335 | | 1008 |
| ctc gaa gcc tct gtg atg ttc aac ctc ctc cgc ctc ctc acc cga gac<br>Leu Glu Ala Ser Val Met Phe Asn Leu Leu Arg Leu Leu Thr Arg Asp<br>          340                     345                     350 | | 1056 |
| ctg aaa tgt gtt gcc agc gga gac cag tgt gtc tga<br>Leu Lys Cys Val Ala Ser Gly Asp Gln Cys Val<br>                   355                     360 | | 1092 |

<210> SEQ ID NO 86
<211> LENGTH: 363
<212> TYPE: PRT
<213> ORGANISM: Bos taurus

<400> SEQUENCE: 86

Met Gly Val Lys Val Leu Phe Ala Leu Ile Cys Ile Ala Val Ala Glu
1                  5                       10                     15

Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
        35                  40                  45

Gly Lys Lys Leu Pro Leu Glu Val Leu Lys Glu Met Glu Ala Asn Ala
    50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Gly Ile Gly Glu Ala Ile
            100                 105                 110

Val Asp Ile Pro Glu Ile Pro Gly Phe Lys Asp Leu Glu Pro Met Glu
        115                 120                 125

Gln Phe Ile Ala Gln Val Asp Leu Cys Val Asp Cys Thr Thr Gly Cys
130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp Gly Pro Arg Thr Gly Ala Val
            180                 185                 190

Pro Val Pro Ser Ala Pro Arg Ala Leu Pro Pro Ala Arg Gly Cys His
        195                 200                 205

Val Ala Gln Phe Lys Ser Leu Ser Pro Gln Glu Leu Gln Ala Phe Lys
210                 215                 220

Thr Ala Arg Asp Ala Phe Glu Asp Ser Phe Leu Pro Lys Asp Trp Asp
225                 230                 235                 240

Cys Ser Thr His Leu Phe Pro Arg Thr Arg Asp Leu Lys His Leu Gln
                245                 250                 255

Val Trp Glu Arg Pro Val Ala Leu Glu Ala Glu Leu Ala Leu Thr Leu
            260                 265                 270

Thr Val Leu Glu Ala Met Ala Asn Ser Ser Leu Gly His Ser Leu Glu
        275                 280                 285

Gln Pro Leu Leu Thr Leu Gln Asn Ile His Ser Lys Leu Gln Ala Cys
290                 295                 300

Val Pro Ala Gln Pro Thr Ala Ser Ser Arg Pro Arg Gly Arg Leu His
305                 310                 315                 320

His Trp Leu His Arg Leu Gln Glu Ala Arg Lys Glu Ser Gln Asp Cys
                325                 330                 335

Leu Glu Ala Ser Val Met Phe Asn Leu Leu Arg Leu Leu Thr Arg Asp
            340                 345                 350

Leu Lys Cys Val Ala Ser Gly Asp Gln Cys Val
        355                 360

<210> SEQ ID NO 87
<211> LENGTH: 603
<212> TYPE: DNA
<213> ORGANISM: Homo sapiens
<220> FEATURE:
<221> NAME/KEY: CDS
<222> LOCATION: (1)..(603)
<223> OTHER INFORMATION: Human Interferon Lambda 1 (IL29)

<400> SEQUENCE: 87

| | | | | | | | | | | | | | | | | |
|---|---|---|---|---|---|---|---|---|---|---|---|---|---|---|---|---|
| atg | gct | gca | gct | tgg | acc | gtg | gtg | ctg | gtg | act | ttg | gtg | cta | ggc | ttg | 48 |
| Met | Ala | Ala | Ala | Trp | Thr | Val | Val | Leu | Val | Thr | Leu | Val | Leu | Gly | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gcc | gtg | gca | ggc | cct | gtc | ccc | act | tcc | aag | ccc | acc | aca | act | ggg | aag | 96 |
| Ala | Val | Ala | Gly | Pro | Val | Pro | Thr | Ser | Lys | Pro | Thr | Thr | Thr | Gly | Lys | |
| | | | 20 | | | | 25 | | | | | 30 | | | | |

| | | | | | | | | | | | | | | | | |
|---|---|---|---|---|---|---|---|---|---|---|---|---|---|---|---|---|
| ggc | tgc | cac | att | ggc | agg | ttc | aaa | tct | ctg | tca | cca | cag | gag | cta | gcg | 144 |
| Gly | Cys | His | Ile | Gly | Arg | Phe | Lys | Ser | Leu | Ser | Pro | Gln | Glu | Leu | Ala | |
| | | 35 | | | | | 40 | | | | | 45 | | | | |

| | | | | | | | | | | | | | | | | |
|---|---|---|---|---|---|---|---|---|---|---|---|---|---|---|---|---|
| agc | ttc | aag | aag | gcc | agg | gac | gcc | ttg | gaa | gag | tca | ctc | aag | ctg | aaa | 192 |
| Ser | Phe | Lys | Lys | Ala | Arg | Asp | Ala | Leu | Glu | Glu | Ser | Leu | Lys | Leu | Lys | |
| 50 | | | | | 55 | | | | | 60 | | | | | | |

| | | | | | | | | | | | | | | | | |
|---|---|---|---|---|---|---|---|---|---|---|---|---|---|---|---|---|
| aac | tgg | agt | tgc | agc | tct | cct | gtc | ttc | ccc | ggg | aat | tgg | gac | ctg | agg | 240 |
| Asn | Trp | Ser | Cys | Ser | Ser | Pro | Val | Phe | Pro | Gly | Asn | Trp | Asp | Leu | Arg | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ctt | ctc | cag | gtg | agg | gag | cgc | cct | gtg | gcc | ttg | gag | gct | gag | ctg | gcc | 288 |
| Leu | Leu | Gln | Val | Arg | Glu | Arg | Pro | Val | Ala | Leu | Glu | Ala | Glu | Leu | Ala | |
| | | | | 85 | | | | | 90 | | | | | 95 | | |

| | | | | | | | | | | | | | | | | |
|---|---|---|---|---|---|---|---|---|---|---|---|---|---|---|---|---|
| ctg | acg | ctg | aag | gtc | ctg | gag | gcc | gct | gct | ggc | cca | gcc | ctg | gag | gac | 336 |
| Leu | Thr | Leu | Lys | Val | Leu | Glu | Ala | Ala | Ala | Gly | Pro | Ala | Leu | Glu | Asp | |
| | | | 100 | | | | | 105 | | | | | 110 | | | |

| | | | | | | | | | | | | | | | | |
|---|---|---|---|---|---|---|---|---|---|---|---|---|---|---|---|---|
| gtc | cta | gac | cag | ccc | ctt | cac | acc | ctg | cac | cac | atc | ctc | tcc | cag | ctc | 384 |
| Val | Leu | Asp | Gln | Pro | Leu | His | Thr | Leu | His | His | Ile | Leu | Ser | Gln | Leu | |
| | | 115 | | | | | 120 | | | | | 125 | | | | |

| | | | | | | | | | | | | | | | | |
|---|---|---|---|---|---|---|---|---|---|---|---|---|---|---|---|---|
| cag | gcc | tgt | atc | cag | cct | cag | ccc | aca | gca | ggg | ccc | agg | ccc | cgg | ggc | 432 |
| Gln | Ala | Cys | Ile | Gln | Pro | Gln | Pro | Thr | Ala | Gly | Pro | Arg | Pro | Arg | Gly | |
| | 130 | | | | | 135 | | | | | 140 | | | | | |

| | | | | | | | | | | | | | | | | |
|---|---|---|---|---|---|---|---|---|---|---|---|---|---|---|---|---|
| cgc | ctc | cac | cac | tgg | ctg | cac | cgg | ctc | cag | gag | gcc | ccc | aaa | aag | gag | 480 |
| Arg | Leu | His | His | Trp | Leu | His | Arg | Leu | Gln | Glu | Ala | Pro | Lys | Lys | Glu | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| tcc | gct | ggc | tgc | ctg | gag | gca | tct | gtc | acc | ttc | aac | ctc | ttc | cgc | ctc | 528 |
| Ser | Ala | Gly | Cys | Leu | Glu | Ala | Ser | Val | Thr | Phe | Asn | Leu | Phe | Arg | Leu | |
| | | | | 165 | | | | | 170 | | | | | 175 | | |

| | | | | | | | | | | | | | | | | |
|---|---|---|---|---|---|---|---|---|---|---|---|---|---|---|---|---|
| ctc | acg | cga | gac | ctc | aaa | tat | gtg | gcc | gat | ggg | aac | ctg | tgt | ctg | aga | 576 |
| Leu | Thr | Arg | Asp | Leu | Lys | Tyr | Val | Ala | Asp | Gly | Asn | Leu | Cys | Leu | Arg | |
| | | | 180 | | | | | 185 | | | | | 190 | | | |

| | | | | | | | | |
|---|---|---|---|---|---|---|---|---|
| acg | tca | acc | cac | cct | gag | tcc | acc | tga | 603 |
| Thr | Ser | Thr | His | Pro | Glu | Ser | Thr | | |
| | | 195 | | | | | 200 | | |

<210> SEQ ID NO 88
<211> LENGTH: 200
<212> TYPE: PRT
<213> ORGANISM: Homo sapiens

<400> SEQUENCE: 88

Met Ala Ala Ala Trp Thr Val Val Leu Val Thr Leu Val Leu Gly Leu
1               5                   10                  15

Ala Val Ala Gly Pro Val Pro Thr Ser Lys Pro Thr Thr Thr Gly Lys
            20                  25                  30

Gly Cys His Ile Gly Arg Phe Lys Ser Leu Ser Pro Gln Glu Leu Ala
        35                  40                  45

Ser Phe Lys Lys Ala Arg Asp Ala Leu Glu Glu Ser Leu Lys Leu Lys
50                  55                  60

Asn Trp Ser Cys Ser Ser Pro Val Phe Pro Gly Asn Trp Asp Leu Arg
65                  70                  75                  80

Leu Leu Gln Val Arg Glu Arg Pro Val Ala Leu Glu Ala Glu Leu Ala
            85                  90                  95

Leu Thr Leu Lys Val Leu Glu Ala Ala Ala Gly Pro Ala Leu Glu Asp

```
                 100                 105                 110
Val Leu Asp Gln Pro Leu His Thr Leu His His Ile Leu Ser Gln Leu
        115                 120                 125

Gln Ala Cys Ile Gln Pro Gln Pro Thr Ala Gly Pro Arg Pro Arg Gly
130                 135                 140

Arg Leu His His Trp Leu His Arg Leu Gln Glu Ala Pro Lys Lys Glu
145                 150                 155                 160

Ser Ala Gly Cys Leu Glu Ala Ser Val Thr Phe Asn Leu Phe Arg Leu
                165                 170                 175

Leu Thr Arg Asp Leu Lys Tyr Val Ala Asp Gly Asn Leu Cys Leu Arg
                180                 185                 190

Thr Ser Thr His Pro Glu Ser Thr
                195                 200

<210> SEQ ID NO 89
<211> LENGTH: 1113
<212> TYPE: DNA
<213> ORGANISM: Homo sapiens
<220> FEATURE:
<221> NAME/KEY: CDS
<222> LOCATION: (1)..(1113)
<223> OTHER INFORMATION: Human GlucON Lambda

<400> SEQUENCE: 89 atg gga gtc aaa gtt ctg ttt gcc ctg atc tgc atc gct gtg gcc gag     48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc     96
Ala Lys Pro Thr Glu Asn Asn Glu Asp Phe Asn Ile Val Ala Val Ala
                20                  25                  30 agc aac ttc gcg acc acg gat ctc gat gct gac cgc ggg aag ttg ccc    144
Ser Asn Phe Ala Thr Thr Asp Leu Asp Ala Asp Arg Gly Lys Leu Pro
            35                  40                  45 ggc aag aag ctg ccg ctg gag gtg ctc aaa gag atg gaa gcc aat gcc    192
Gly Lys Lys Leu Pro Leu Glu Val Leu Lys Glu Met Glu Ala Asn Ala
        50                  55                  60 cgg aaa gct ggc tgc acc agg ggc tgt ctg atc tgc ctg tcc cac atc    240
Arg Lys Ala Gly Cys Thr Arg Gly Cys Leu Ile Cys Leu Ser His Ile
65                  70                  75                  80 aag tgc acg ccc aag atg aag aag ttc atc cca gga cgc tgc cac acc    288
Lys Cys Thr Pro Lys Met Lys Lys Phe Ile Pro Gly Arg Cys His Thr
                85                  90                  95 tac gaa ggc gac aaa gag tcc gca cag ggc ggc ata ggc gag gcg atc    336
Tyr Glu Gly Asp Lys Glu Ser Ala Gln Gly Gly Ile Gly Glu Ala Ile
            100                 105                 110 gtc gac att cct gag att cct ggg ttc aag gac ttg gag ccc atg gag    384
Val Asp Ile Pro Glu Ile Pro Gly Phe Lys Asp Leu Glu Pro Met Glu
        115                 120                 125 cag ttc atc gca cag gtc gat ctg tgt gtg gac tgc aca act ggc tgc    432
Gln Phe Ile Ala Gln Val Asp Leu Cys Val Asp Cys Thr Thr Gly Cys
130                 135                 140 ctc aaa ggg ctt gcc aac gtg cag tgt tct gac ctg ctc aag aag tgg    480
Leu Lys Gly Leu Ala Asn Val Gln Cys Ser Asp Leu Leu Lys Lys Trp
145                 150                 155                 160 ctg ccg caa cgc tgt gcg acc ttt gcc agc aag atc cag ggc cag gtg    528
Leu Pro Gln Arg Cys Ala Thr Phe Ala Ser Lys Ile Gln Gly Gln Val
                165                 170                 175 gac aag atc aag ggg gcc ggt ggt gac ttg gcc gtg gca ggc cct gtc    576
Asp Lys Ile Lys Gly Ala Gly Gly Asp Leu Ala Val Ala Gly Pro Val
            180                 185                 190
```

| | | | | | | | | | | | | | | | | |
|---|---|---|---|---|---|---|---|---|---|---|---|---|---|---|---|---|
| ccc | act | tcc | aag | ccc | acc | aca | act | ggg | aag | ggc | tgc | cac | att | ggc | agg | 624 |
| Pro | Thr | Ser | Lys | Pro | Thr | Thr | Thr | Gly | Lys | Gly | Cys | His | Ile | Gly | Arg | |
| | | 195 | | | | 200 | | | | | 205 | | | | | |
| ttc | aaa | tct | ctg | tca | cca | cag | gag | cta | gcg | agc | ttc | aag | aag | gcc | agg | 672 |
| Phe | Lys | Ser | Leu | Ser | Pro | Gln | Glu | Leu | Ala | Ser | Phe | Lys | Lys | Ala | Arg | |
| | 210 | | | | | 215 | | | | | 220 | | | | | |
| gac | gcc | ttg | gaa | gag | tca | ctc | aag | ctg | aaa | aac | tgg | agt | tgc | agc | tct | 720 |
| Asp | Ala | Leu | Glu | Glu | Ser | Leu | Lys | Leu | Lys | Asn | Trp | Ser | Cys | Ser | Ser | |
| 225 | | | | | 230 | | | | | 235 | | | | | 240 | |
| cct | gtc | ttc | ccc | ggg | aat | tgg | gac | ctg | agg | ctt | ctc | cag | gtg | agg | gag | 768 |
| Pro | Val | Phe | Pro | Gly | Asn | Trp | Asp | Leu | Arg | Leu | Leu | Gln | Val | Arg | Glu | |
| | | | | 245 | | | | | 250 | | | | | 255 | | |
| cgc | cct | gtg | gcc | ttg | gag | gct | gag | ctg | gcc | ctg | acg | ctg | aag | gtc | ctg | 816 |
| Arg | Pro | Val | Ala | Leu | Glu | Ala | Glu | Leu | Ala | Leu | Thr | Leu | Lys | Val | Leu | |
| | | | 260 | | | | | 265 | | | | | 270 | | | |
| gag | gcc | gct | gct | ggc | cca | gcc | ctg | gag | gac | gtc | cta | gac | cag | ccc | ctt | 864 |
| Glu | Ala | Ala | Ala | Gly | Pro | Ala | Leu | Glu | Asp | Val | Leu | Asp | Gln | Pro | Leu | |
| | | 275 | | | | | 280 | | | | | 285 | | | | |
| cac | acc | ctg | cac | cac | atc | ctc | tcc | cag | ctc | cag | gcc | tgt | atc | cag | cct | 912 |
| His | Thr | Leu | His | His | Ile | Leu | Ser | Gln | Leu | Gln | Ala | Cys | Ile | Gln | Pro | |
| | 290 | | | | | 295 | | | | | 300 | | | | | |
| cag | ccc | aca | gca | ggg | ccc | agg | ccc | cgg | ggc | cgc | ctc | cac | cac | tgg | ctg | 960 |
| Gln | Pro | Thr | Ala | Gly | Pro | Arg | Pro | Arg | Gly | Arg | Leu | His | His | Trp | Leu | |
| 305 | | | | | 310 | | | | | 315 | | | | | 320 | |
| cac | cgg | ctc | cag | gag | gcc | ccc | aaa | aag | gag | tcc | gct | ggc | tgc | ctg | gag | 1008 |
| His | Arg | Leu | Gln | Glu | Ala | Pro | Lys | Lys | Glu | Ser | Ala | Gly | Cys | Leu | Glu | |
| | | | | 325 | | | | | 330 | | | | | 335 | | |
| gca | tct | gtc | acc | ttc | aac | ctc | ttc | cgc | ctc | ctc | acg | cga | gac | ctc | aaa | 1056 |
| Ala | Ser | Val | Thr | Phe | Asn | Leu | Phe | Arg | Leu | Leu | Thr | Arg | Asp | Leu | Lys | |
| | | | 340 | | | | | 345 | | | | | 350 | | | |
| tat | gtg | gcc | gat | ggg | aac | ctg | tgt | ctg | aga | acg | tca | acc | cac | cct | gag | 1104 |
| Tyr | Val | Ala | Asp | Gly | Asn | Leu | Cys | Leu | Arg | Thr | Ser | Thr | His | Pro | Glu | |
| | | 355 | | | | | 360 | | | | | 365 | | | | |
| tcc | acc | tga | | | | | | | | | | | | | | 1113 |
| Ser | Thr | | | | | | | | | | | | | | | |
| | 370 | | | | | | | | | | | | | | | |

<210> SEQ ID NO 90
<211> LENGTH: 370
<212> TYPE: PRT
<213> ORGANISM: Homo sapiens

<400> SEQUENCE: 90

Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
        35                  40                  45

Gly Lys Lys Leu Pro Leu Glu Val Leu Lys Met Glu Ala Asn Ala
    50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Gly Ile Gly Glu Ala Ile
            100                 105                 110

Val Asp Ile Pro Glu Ile Pro Gly Phe Lys Asp Leu Glu Pro Met Glu

```
                115                 120                 125
Gln Phe Ile Ala Gln Val Asp Leu Cys Val Asp Cys Thr Thr Gly Cys
130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Asp Leu Ala Val Ala Gly Pro Val
                180                 185                 190

Pro Thr Ser Lys Pro Thr Thr Gly Lys Gly Cys His Ile Gly Arg
                195                 200                 205

Phe Lys Ser Leu Ser Pro Gln Glu Leu Ala Ser Phe Lys Lys Ala Arg
210                 215                 220

Asp Ala Leu Glu Glu Ser Leu Lys Leu Lys Asn Trp Ser Cys Ser Ser
225                 230                 235                 240

Pro Val Phe Pro Gly Asn Trp Asp Leu Arg Leu Leu Gln Val Arg Glu
                245                 250                 255

Arg Pro Val Ala Leu Glu Ala Glu Leu Ala Leu Thr Leu Lys Val Leu
                260                 265                 270

Glu Ala Ala Gly Pro Ala Leu Glu Asp Val Leu Asp Gln Pro Leu
                275                 280                 285

His Thr Leu His His Ile Leu Ser Gln Leu Gln Ala Cys Ile Gln Pro
290                 295                 300

Gln Pro Thr Ala Gly Pro Arg Pro Gly Arg Leu His His Trp Leu
305                 310                 315                 320

His Arg Leu Gln Glu Ala Pro Lys Lys Glu Ser Ala Gly Cys Leu Glu
                325                 330                 335

Ala Ser Val Thr Phe Asn Leu Phe Arg Leu Leu Thr Arg Asp Leu Lys
                340                 345                 350

Tyr Val Ala Asp Gly Asn Leu Cys Leu Arg Thr Ser Thr His Pro Glu
                355                 360                 365

Ser Thr
    370

<210> SEQ ID NO 91
<211> LENGTH: 576
<212> TYPE: DNA
<213> ORGANISM: Sus scrofa
<220> FEATURE:
<221> NAME/KEY: CDS
<222> LOCATION: (1)..(576)
<223> OTHER INFORMATION: Porcine Interferon Lambda 1 (IL29

<400> SEQUENCE: 91 atg gct aca gct tgg atc gtg gtg ctg gcg act gtg atg ctg gac ttg      48
Met Ala Thr Ala Trp Ile Val Val Leu Ala Thr Val Met Leu Asp Leu
1               5                   10                  15 gcc aga gct ggc cct gtc ccc act ttc aag ccc acc aca acc agg aag      96
Ala Arg Ala Gly Pro Val Pro Thr Phe Lys Pro Thr Thr Thr Arg Lys
            20                  25                  30 ggc tgc cac atg ggc cag ttc caa tct ctg tca cca cag gag ctg aag     144
Gly Cys His Met Gly Gln Phe Gln Ser Leu Ser Pro Gln Glu Leu Lys
        35                  40                  45 ggc ttc aag aaa gcc aag gat gct ttg gaa gag tca ctc tca ctg aag     192
Gly Phe Lys Lys Ala Lys Asp Ala Leu Glu Glu Ser Leu Ser Leu Lys
    50                  55                  60 aac tgg agc tgc agc tct ccc ctc ttc ccc agg acc cgg gac ctg agg     240
```

```
Asn Trp Ser Cys Ser Ser Pro Leu Phe Pro Arg Thr Arg Asp Leu Arg
 65                  70                  75                  80 cag ctg cag gtg tgg gag cgc ctc gtg gcc tta gag gct gag cta gac      288
Gln Leu Gln Val Trp Glu Arg Leu Val Ala Leu Glu Ala Glu Leu Asp
                 85                  90                  95 ttg act ctg aag gtc cta agg gcc gcg gct gac tca tcc ctg ggg gtc      336
Leu Thr Leu Lys Val Leu Arg Ala Ala Ala Asp Ser Ser Leu Gly Val
             100                 105                 110 acc ctg gac cag cca ctt cgc acg ctg cat cac atc cac gtc gaa ctt      384
Thr Leu Asp Gln Pro Leu Arg Thr Leu His His Ile His Val Glu Leu
         115                 120                 125 cag gct tgc atc agg gct cag ccc acg gca gga tcc cgg ctc cag ggc      432
Gln Ala Cys Ile Arg Ala Gln Pro Thr Ala Gly Ser Arg Leu Gln Gly
     130                 135                 140 cgc ctc aac cac tgg ctg cac cgg ctc caa gaa gcc aca aag aaa gag      480
Arg Leu Asn His Trp Leu His Arg Leu Gln Glu Ala Thr Lys Lys Glu
145                 150                 155                 160 tcc caa ggc tgc ctt gag gcc tct gtg aca ttc aac ctc ttc cac ctc      528
Ser Gln Gly Cys Leu Glu Ala Ser Val Thr Phe Asn Leu Phe His Leu
                165                 170                 175 ctc gta agg gac ctg aga agt gtt acc agt gga gac ttg cac atc tga      576
Leu Val Arg Asp Leu Arg Ser Val Thr Ser Gly Asp Leu His Ile
            180                 185                 190
```

<210> SEQ ID NO 92
<211> LENGTH: 191
<212> TYPE: PRT
<213> ORGANISM: Sus scrofa

<400> SEQUENCE: 92

```
Met Ala Thr Ala Trp Ile Val Val Leu Ala Thr Val Met Leu Asp Leu
  1               5                  10                  15

Ala Arg Ala Gly Pro Val Pro Thr Phe Lys Pro Thr Thr Arg Lys
             20                  25                  30

Gly Cys His Met Gly Gln Phe Gln Ser Leu Ser Pro Gln Glu Leu Lys
         35                  40                  45

Gly Phe Lys Lys Ala Lys Asp Ala Leu Glu Glu Ser Leu Ser Leu Lys
     50                  55                  60

Asn Trp Ser Cys Ser Ser Pro Leu Phe Pro Arg Thr Arg Asp Leu Arg
 65                  70                  75                  80

Gln Leu Gln Val Trp Glu Arg Leu Val Ala Leu Glu Ala Glu Leu Asp
                 85                  90                  95

Leu Thr Leu Lys Val Leu Arg Ala Ala Ala Asp Ser Ser Leu Gly Val
            100                 105                 110

Thr Leu Asp Gln Pro Leu Arg Thr Leu His His Ile His Val Glu Leu
        115                 120                 125

Gln Ala Cys Ile Arg Ala Gln Pro Thr Ala Gly Ser Arg Leu Gln Gly
    130                 135                 140

Arg Leu Asn His Trp Leu His Arg Leu Gln Glu Ala Thr Lys Lys Glu
145                 150                 155                 160

Ser Gln Gly Cys Leu Glu Ala Ser Val Thr Phe Asn Leu Phe His Leu
                165                 170                 175

Leu Val Arg Asp Leu Arg Ser Val Thr Ser Gly Asp Leu His Ile
            180                 185                 190
```

<210> SEQ ID NO 93
<211> LENGTH: 1083
<212> TYPE: DNA

```
<213> ORGANISM: Sus scrofa
<220> FEATURE:
<221> NAME/KEY: CDS
<222> LOCATION: (1)..(1083)
<223> OTHER INFORMATION: Porcine GLucON Lambda

<400> SEQUENCE: 93 atg gga gtc aaa gtt ctg ttt gcc ctg atc tgc atc gct gtg gcc gag      48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc      96
Ala Lys Pro Thr Glu Asn Asn Glu Asp Phe Asn Ile Val Ala Val Ala
                20                  25                  30 agc aac ttc gcg acc acg gat ctc gat gct gac cgc ggg aag ttg ccc     144
Ser Asn Phe Ala Thr Thr Asp Leu Asp Ala Asp Arg Gly Lys Leu Pro
            35                  40                  45 ggc aag aag ctg ccg ctg gag gtg ctc aaa gag atg gaa gcc aat gcc     192
Gly Lys Lys Leu Pro Leu Glu Val Leu Lys Glu Met Glu Ala Asn Ala
        50                  55                  60 cgg aaa gct ggc tgc acc agg ggc tgt ctg atc tgc ctg tcc cac atc     240
Arg Lys Ala Gly Cys Thr Arg Gly Cys Leu Ile Cys Leu Ser His Ile
65                  70                  75                  80 aag tgc acg ccc aag atg aag aag ttc atc cca gga cgc tgc cac acc     288
Lys Cys Thr Pro Lys Met Lys Lys Phe Ile Pro Gly Arg Cys His Thr
                85                  90                  95 tac gaa ggc gac aaa gag tcc gca cag ggc ggc ata ggc gag gcg atc     336
Tyr Glu Gly Asp Lys Glu Ser Ala Gln Gly Gly Ile Gly Glu Ala Ile
                100                 105                 110 gtc gac att cct gag att cct ggg ttc aag gac ttg gag ccc atg gag     384
Val Asp Ile Pro Glu Ile Pro Gly Phe Lys Asp Leu Glu Pro Met Glu
            115                 120                 125 cag ttc atc gca cag gtc gat ctg tgt gtg gac tgc aca act ggc tgc     432
Gln Phe Ile Ala Gln Val Asp Leu Cys Val Asp Cys Thr Thr Gly Cys
        130                 135                 140 ctc aaa ggg ctt gcc aac gtg cag tgt tct gac ctg ctc aag aag tgg     480
Leu Lys Gly Leu Ala Asn Val Gln Cys Ser Asp Leu Leu Lys Lys Trp
145                 150                 155                 160 ctg ccg caa cgc tgt gcg acc ttt gcc agc aag atc cag ggc cag gtg     528
Leu Pro Gln Arg Cys Ala Thr Phe Ala Ser Lys Ile Gln Gly Gln Val
                165                 170                 175 gac aag atc aag ggg gcc ggt ggt gac gcc aga gct ggc cct gtc ccc     576
Asp Lys Ile Lys Gly Ala Gly Gly Asp Ala Arg Ala Gly Pro Val Pro
            180                 185                 190 act ttc aag ccc acc aca acc agg aag ggc tgc cac atg ggc cag ttc     624
Thr Phe Lys Pro Thr Thr Thr Arg Lys Gly Cys His Met Gly Gln Phe
        195                 200                 205 caa tct ctg tca cca cag gag ctg aag ggc ttc aag aaa gcc aag gat     672
Gln Ser Leu Ser Pro Gln Glu Leu Lys Gly Phe Lys Lys Ala Lys Asp
    210                 215                 220 gct ttg gaa gag tca ctc tca ctg aag aac tgg agc tgc agc tct ccc     720
Ala Leu Glu Glu Ser Leu Ser Leu Lys Asn Trp Ser Cys Ser Ser Pro
225                 230                 235                 240 ctc ttc ccc agg acc cgg gac ctg agg cag ctg cag gtg tgg gag cgc     768
Leu Phe Pro Arg Thr Arg Asp Leu Arg Gln Leu Gln Val Trp Glu Arg
                245                 250                 255 ctc gtg gcc tta gag gct gag cta gac ttg act ctg aag gtc cta agg     816
Leu Val Ala Leu Glu Ala Glu Leu Asp Leu Thr Leu Lys Val Leu Arg
            260                 265                 270 gcc gcg gct gac tca tcc ctg ggg gtc acc ctg gac cag cca ctt cgc     864
Ala Ala Ala Asp Ser Ser Leu Gly Val Thr Leu Asp Gln Pro Leu Arg
        275                 280                 285
```

```
acg ctg cat cac atc cac gtc gaa ctt cag gct tgc atc agg gct cag      912
Thr Leu His His Ile His Val Glu Leu Gln Ala Cys Ile Arg Ala Gln
    290                 295                 300 ccc acg gca gga tcc cgg ctc cag ggc cgc ctc aac cac tgg ctg cac      960
Pro Thr Ala Gly Ser Arg Leu Gln Gly Arg Leu Asn His Trp Leu His
305                 310                 315                 320 cgg ctc caa gaa gcc aca aag aaa gag tcc caa ggc tgc ctt gag gcc     1008
Arg Leu Gln Glu Ala Thr Lys Lys Glu Ser Gln Gly Cys Leu Glu Ala
                    325                 330                 335 tct gtg aca ttc aac ctc ttc cac ctc ctc gta agg gac ctg aga agt     1056
Ser Val Thr Phe Asn Leu Phe His Leu Leu Val Arg Asp Leu Arg Ser
                340                 345                 350 gtt acc agt gga gac ttg cac atc tga                                 1083
Val Thr Ser Gly Asp Leu His Ile
            355                 360

<210> SEQ ID NO 94
<211> LENGTH: 360
<212> TYPE: PRT
<213> ORGANISM: Sus scrofa

<400> SEQUENCE: 94

Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
        35                  40                  45

Gly Lys Lys Leu Pro Leu Glu Val Leu Lys Glu Met Glu Ala Asn Ala
    50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Gly Ile Gly Glu Ala Ile
            100                 105                 110

Val Asp Ile Pro Glu Ile Pro Gly Phe Lys Asp Leu Glu Pro Met Glu
        115                 120                 125

Gln Phe Ile Ala Gln Val Asp Leu Cys Val Asp Cys Thr Thr Gly Cys
    130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Asp Ala Arg Ala Gly Pro Val Pro
            180                 185                 190

Thr Phe Lys Pro Thr Thr Thr Arg Lys Gly Cys His Met Gly Gln Phe
        195                 200                 205

Gln Ser Leu Ser Pro Gln Glu Leu Lys Gly Phe Lys Lys Ala Lys Asp
    210                 215                 220

Ala Leu Glu Glu Ser Leu Ser Leu Lys Asn Trp Ser Cys Ser Ser Pro
225                 230                 235                 240

Leu Phe Pro Arg Thr Arg Asp Leu Arg Gln Leu Gln Val Trp Glu Arg
                245                 250                 255

Leu Val Ala Leu Glu Ala Glu Leu Asp Leu Thr Leu Lys Val Leu Arg
            260                 265                 270
```

Ala Ala Ala Asp Ser Ser Leu Gly Val Thr Leu Asp Gln Pro Leu Arg
            275                 280                 285

Thr Leu His His Ile His Val Glu Leu Gln Ala Cys Ile Arg Ala Gln
        290                 295                 300

Pro Thr Ala Gly Ser Arg Leu Gln Gly Arg Leu Asn His Trp Leu His
305                 310                 315                 320

Arg Leu Gln Glu Ala Thr Lys Lys Glu Ser Gln Gly Cys Leu Glu Ala
            325                 330                 335

Ser Val Thr Phe Asn Leu Phe His Leu Leu Val Arg Asp Leu Arg Ser
            340                 345                 350

Val Thr Ser Gly Asp Leu His Ile
            355                 360

<210> SEQ ID NO 95
<211> LENGTH: 13
<212> TYPE: DNA
<213> ORGANISM: Artificial Sequence
<220> FEATURE:
<223> OTHER INFORMATION: Kozak Sequence
<220> FEATURE:
<221> NAME/KEY: misc_feature
<222> LOCATION: (7)..(7)
<223> OTHER INFORMATION: R is A or G

<400> SEQUENCE: 95
gccgccrcca tgg                                                            13

<210> SEQ ID NO 96
<211> LENGTH: 5670
<212> TYPE: DNA
<213> ORGANISM: Artificial Sequence
<220> FEATURE:
<223> OTHER INFORMATION: pTarget Empty Vector

<400> SEQUENCE: 96
tcaatattgg ccattagcca tattattcat tggttatata gcataaatca atattggcta        60
ttggccattg catacgttgt atctatatca taatatgtac atttatattg gctcatgtcc       120
aatatgaccg ccatgttggc attgattatt gactagttat taatagtaat caattacggg       180
gtcattagtt catagcccat atatggagtt ccgcgttaca taacttacgg taaatggccc       240
gcctggctga ccgcccaacg acccccgccc attgacgtca ataatgacgt atgttcccat       300
agtaacgcca tagggacttt ccattgacg tcaatgggtg gagtatttac ggtaaactgc        360
ccacttggca gtacatcaag tgtatcatat gccaagtccg cccctattg acgtcaatga        420 cggtaaatgg cccgcctggc attatgccca gtacatgacc ttacgggact ttcctacttg       480
gcagtacatc tacgtattag tcatcgctat taccatggtg atgcggtttt ggcagtacac       540
caatgggcgt ggatagcggt ttgactcacg ggatttcca gtctccacc ccattgacgt         600 caatgggagt ttgttttggc accaaaatca acgggacttt ccaaaatgtc gtaacaactg       660
cgatcgcccg ccccgttgac gcaaatgggc ggtaggcgtg tacggtggga ggtctatata       720
agcagagctc gtttagtgaa ccgtcagatc actagaagct ttattgcggt agtttatcac       780
agttaaattg ctaacgcagt cagtgcttct gacacaacag tctcgaactt aagctgcagt       840
gactctctta aggtagcctt gcagaagttg gtcgtgaggc actgggcagg taagtatcaa       900
ggttacaaga caggtttaag gagaccaata gaaactgggc ttgtcgagac agagaagact       960
cttgcgtttc tgataggcac ctattggtct tactgacatc cactttgcct ttctctccac      1020

```
aggtgtccac tcccagttca attacagctc ttaaaaattg gatctccatt cgccattcag  1080
gctgcgcaac tgctgggaag gacgatcaga gcgggcctct tcgctattac gccagctggc  1140
gaaagggacg tggcaagcaa ggcgattaag ttgagttacg ccaggatttt cccagtcacg  1200
acgttgtaaa acgacggcca gagaattata atacgactca ctatagggcg aattcggatc  1260
cttgctagcc tcgagacgcg tgatatcttt cccggggta ccgtcgactg cggccgcgaa  1320
ttccaagctt gagtattcta tcgtgtcacc taaataactt ggcgtaatca tggtcatatc  1380
tgtttcctgt gtgaaattgt tatccgctca caattccaca acatacga gccggaagca  1440
taaagtgtaa agcctggggt gcctaatgag tgagctaact cacattaatt gcgttgcgcg  1500
atgcttccat tttgtgaggg ttaatgcttc gagaagacat gataagatac attgatgagt  1560
ttggacaaac cacaacaaga atgcagtgaa aaaaatgctt tatttgtgaa atttgtgatg  1620
ctattgcttt atttgtaacc attataagct gcaataaaca agttaacaac aacaattgca  1680
ttcattttat gtttcaggtt caggggggaga tgtgggaggt ttttaaagc aagtaaaacc  1740
tctacaaatg tggtaaaatc cgataaggat cgattccgga gcctgaatgg cgaatggacg  1800
cgccctgtag cggcgcatta agcgcggcgg gtgtggtggt tacgcgcacg tgaccgctac  1860
acttgccagc gccctagcgc ccgctccttt cgctttcttc ccttcctttc tcgccacgtt  1920
cgccggcttt ccccgtcaag ctctaaatcg ggggctccct ttagggttcc gatttagtgc  1980
tttacggcac ctcgacccca aaaaacttga ttagggtgat ggttcacgta gtgggccatc  2040
gccctgatag acggtttttc gccctttgac gttggagtcc acgttcttta atagtggact  2100
cttgttccaa actggaacaa cactcaaccc tatctcggtc tattcttttg atttataagg  2160
gattttgccg atttcggcct attggttaaa aaatgagctg atttaacaaa aatttaacgc  2220
gaattttaac aaaatattaa cgcttacaat ttcgcctgtg taccttctga ggcggaaaga  2280
accagctgtg aatgtgtgt cagttagggt gtggaaagtc cccaggctcc ccagcaggca  2340
gaagtatgca aagcatgcat ctcaattagt cagcaaccag gtgtggaaag tccccaggct  2400
ccccagcagg cagaagtatg caaagcatgc atctcaatta gtcagcaacc atagtcccgc  2460
ccctaactcc gcccatcccg cccctaactc cgcccagttc cgcccattct ccgccccatg  2520
gctgactaat tttttttatt tatgcagagg ccgaggccgc ctcggcctct gagctattcc  2580
agaagtagtg aggaggcttt tttggaggcc taggcttttg caaaaagctt gattcttctg  2640
acacaacagt ctcgaactta aggctagagc caccatgatt gaacaagatg gattgcacgc  2700
aggttctccg gccgcttggg tggagaggct attcggctat gactgggcac aacagacaat  2760
cggctgctct gatgccgccg tgttccggct gtcagcgcag gggcgcccgg ttcttttgt  2820
caagaccgac ctgtccggtg ccctgaatga actgcaggac gaggcagcgc ggctatcgtg  2880
gctggccacg acgggcgttc cttgcgcagc tgtgctcgac gttgtcactg aagcgggaag  2940
ggactggctg ctattgggcg aagtgccggg gcaggatctc ctgtcatctc accttgctcc  3000
tgccgagaaa gtatccatca tggctgatgc aatgcggcgg ctgcatacgc ttgatccggc  3060
tacctgccca ttcgaccacc aagcgaaaca tcgcatcgag cgagcacgta ctcggatgga  3120
agccggtctt gtcgatcagg atgatctgga cgaagagcat caggggctcg cgccagccga  3180
actgttcgcc aggctcaagg cgcgcatgcc cgacggcgag gatctcgtcg tgacccatgg  3240
cgatgcctgc ttgccgaata tcatggtgga aaatggccgc ttttctggat tcatcgactg  3300
tggccggctg ggtgtggcgg accgctatca ggacatagcg ttggctaccc gtgatattgc  3360
tgaagagctt ggcggcgaat gggctgaccg cttcctcgtg ctttacggta tcgccgctcc  3420
```

```
cgattcgcag cgcatcgcct tctatcgcct tcttgacgag ttcttctgag cgggactctg    3480
gggttcgaaa tgaccgacca agcgacgccc aacctgccat cacgatggcc gcaataaaat    3540
atctttattt tcattacatc tgtgtgttgg ttttttgtgt gaagatccgc gtatggtgca    3600
ctctcagtac aatctgctct gatgccgcat agttaagcca gccccgacac ccgccaacac    3660
ccgctgacgc gccctgacgg gcttgtctgc tcccggcatc cgcttacaga caagctgtga    3720
ccgtctccgg gagctgcatg tgtcagaggt tttcaccgtc atcaccgaaa cgcgcgagac    3780
gaaagggcct cgtgatacgc ctatttttat aggttaatgt catgataata atggtttctt    3840
agacgtcagg tggcacttttt cggggaaatg tgcgcggaac ccctatttgt ttatttttct    3900
aaatacattc aaatatgtat ccgctcatga caataaacc ctgataaatg cttcaataat    3960
attgaaaaag gaagagtatg agtattcaac atttccgtgt cgcccttatt ccctttttttg    4020
cggcattttg ccttcctgtt tttgctcacc cagaaacgct ggtgaaagta aaagatgctg    4080
aagatcagtt gggtgcacga gtgggttaca tcgaactgga tctcaacagc ggtaagatcc    4140
ttgagagttt tcgccccgaa gaacgttttc caatgatgag cacttttaaa gttctgctat    4200
gtggcgcggt attatcccgt attgacgccg ggcaagagca actcggtcgc cgcatacact    4260
attctcagaa tgacttggtt gagtactcac cagtcacaga aaagcatctt acggatggca    4320
tgacagtaag agaattatgc agtgctgcca taaccatgag tgataacact gcggccaact    4380
tacttctgac aacgatcgga ggaccgaagg agctaaccgc ttttttgcac aacatggggg    4440
atcatgtaac tcgccttgat cgttgggaac cggagctgaa tgaagccata ccaaacgacg    4500
agcgtgacac cacgatgcct gtagcaatgg caacaacgtt gcgcaaacta ttaactggcg    4560
aactacttac tctagcttcc cggcaacaat taatagactg gatggaggcg gataaagttg    4620
caggaccact tctgcgctcg gcccttccgg ctggctggtt tattgctgat aaatctggag    4680
ccggtgagcg tgggtctcgc ggtatcattg cagcactggg gccagatggt aagccctccc    4740
gtatcgtagt tatctacacg acggggagtc aggcaactat ggatgaacga atagacaga    4800
tcgctgagat aggtgcctca ctgattaagc attggtaact gtcagaccaa gtttactcat    4860
atatacttta gattgattta aaacttcatt tttaatttaa aaggatctag gtgaagatcc    4920
tttttgataa tctcatgacc aaaatccctt aacgtgagtt ttcgttccac tgagcgtcag    4980
accccgtaga aaagatcaaa ggatcttctt gagatccttt ttttctgcgc gtaatctgct    5040
gcttgcaaac aaaaaaacca ccgctaccag cggtggtttg tttgccggat caagagctac    5100
caactctttt tccgaaggta actggcttca gcagagcgca gataccaaat actgtccttc    5160
tagtgtagcc gtagttaggc caccacttca agaactctgt agcaccgcct acatacctcg    5220
ctctgctaat cctgttacca gtggctgctg ccagtggcga taagtcgtgt cttaccgggt    5280
tggactcaag acgatagtta ccggataagg cgcagcggtc gggctgaacg gggggttcgt    5340
gcacacagcc cagcttggag cgaacgacct acaccgaact gagatacta cagcgtgagc    5400
tatgagaaag cgccacgctt cccgaaggga gaaaggcgga caggtatccg gtaagcggca    5460
gggtcggaac aggagagcgc acgagggagc ttccaggggg aaacgcctgg tatctttata    5520
gtcctgtcgg gtttcgccac ctctgacttg agcgtcgatt tttgtgatgc tcgtcagggg    5580
ggcggagcct atggaaaaac gccagcaacg cggccttttt acggttcctg gccttttgct    5640
ggccttttgc tcacatggct cgacagatct                                     5670
```

<210> SEQ ID NO 97

<211> LENGTH: 6884
<212> TYPE: DNA
<213> ORGANISM: Artificial Sequence
<220> FEATURE:
<223> OTHER INFORMATION: pTarget IFNa-d1D2A-SGluc (-1M)

<400> SEQUENCE: 97

| | | | | | |
|---|---|---|---|---|---|
| tcaatattgg | ccattagcca | tattattcat | tggttatata | gcataaatca | atattggcta | 60 |
| ttggccattg | catacgttgt | atctatatca | taatatgtac | atttatattg | gctcatgtcc | 120 |
| aatatgaccg | ccatgttggc | attgattatt | gactagttat | taatagtaat | caattacggg | 180 |
| gtcattagtt | catagcccat | atatggagtt | ccgcgttaca | taacttacgg | taaatggccc | 240 |
| gcctggctga | ccgcccaacg | accccgccc | attgacgtca | ataatgacgt | atgttcccat | 300 |
| agtaacgcca | atagggactt | tccattgacg | tcaatgggtg | gagtatttac | ggtaaactgc | 360 |
| ccacttggca | gtacatcaag | tgtatcatat | gccaagtccg | cccctattg | acgtcaatga | 420 |
| cggtaaatgg | cccgcctggc | attatgccca | gtacatgacc | ttacgggact | ttcctacttg | 480 |
| gcagtacatc | tacgtattag | tcatcgctat | taccatggtg | atgcggtttt | ggcagtacac | 540 |
| caatgggcgt | ggatagcggt | ttgactcacg | gggatttcca | agtctccacc | ccattgacgt | 600 |
| caatgggagt | ttgttttggc | accaaaatca | acgggacttt | ccaaaatgtc | gtaacaactg | 660 |
| cgatcgcccg | ccccgttgac | gcaaatgggc | ggtaggcgtg | tacggtggga | ggtctatata | 720 |
| agcagagctc | gtttagtgaa | ccgtcagatc | actagaagct | ttattgcggt | agtttatcac | 780 |
| agttaaattg | ctaacgcagt | cagtgcttct | gacacaacag | tctcgaactt | aagctgcagt | 840 |
| gactctctta | aggtagcctt | gcagaagttg | gtcgtgaggc | actgggcagg | taagtatcaa | 900 |
| ggttacaaga | caggtttaag | gagaccaata | gaaactgggc | ttgtcgagac | agagaagact | 960 |
| cttgcgtttc | tgataggcac | ctattggtct | tactgacatc | cactttgcct | ttctctccac | 1020 |
| aggtgtccac | tcccagttca | attacagctc | ttaaaaattg | gatctccatt | cgccattcag | 1080 |
| gctgcgcaac | tgctgggaag | gacgatcaga | gcgggcctct | tcgctattac | gccagctggc | 1140 |
| gaaagggacg | tggcaagcaa | ggcgattaag | ttgagttacg | ccaggatttt | cccagtcacg | 1200 |
| acgttgtaaa | acgacggcca | gagaattata | atacgactca | ctatagggcg | aattcggatc | 1260 |
| cttgctagcg | ccgccaccat | ggccccaacc | tcagccttcc | tcacggccct | ggtgctactc | 1320 |
| agctgcaatg | ccatctgctc | tctgggctgt | gacctgcctc | agacccacag | cctggctcac | 1380 |
| accagagccc | tgaggctcct | ggcacaaatg | aggagaatct | ctcccttctc | ctgcctggac | 1440 |
| cacgaaggg | actttggttc | ccctcatgag | gcttttgggg | caaccaggt | ccagaaggct | 1500 |
| caagccatgg | ctctggtgca | tgagatgctc | cagcagacct | ccagctctt | cagcacagag | 1560 |
| ggctcggctg | ctgcctggaa | tgagagcctc | ctgcaccagt | tctgcactgg | actggatcag | 1620 |
| cagctcaggg | acctggaagc | ctgtgtcatg | caggaggcgg | ggctggaagg | accccctg | 1680 |
| ctggaggagg | actccatcct | ggctgtgagg | aaatacttcc | acagactcac | cctctatctg | 1740 |
| caagagaaga | gctacagccc | ctgtgcctgg | gagatcgtca | gggcagaagt | catgagatcc | 1800 |
| ttctcttcct | ccagaaacct | gcaagacaga | ctcaggaaga | aggagctcga | gacgcgtgat | 1860 |
| tgcgccgcca | ccatgagcca | aagcaaaag | atcattgcac | cagcaaagca | gcttctgaat | 1920 |
| tttgacctgc | tcaagttggc | cggagacgtt | gagtccaacc | ctgggcccgg | agtcaaagtt | 1980 |
| ctgtttgccc | tgatctgcat | cgctgtggc | gaggccaagc | ccaccgagaa | caacgaagac | 2040 |
| ttcaacatcg | tggccgtggc | cagcaacttt | gcgaccacgg | atctcgatgc | tgaccgaggg | 2100 |
| aagttgcccg | gcaagaagct | gccgctggag | gtgctcaaag | agatggaagc | caatgcccgg | 2160 |

```
aaagctggct gcaccagggg ctgtctgatc tgcctgtccc acatcaagtg cacgcccaag    2220
atgaagaagt ggctcccagg acgctgccac acctacgaag gcgacaaaga gtccgcacag    2280
ggcggcatag gcgaggcgat cgtcgatatt cctgagattc ctgggttcaa ggacttggag    2340
ccaatggagc agttcatcgc acaggtcgat ctgtgtgtgg actgcacaac tggctgcctc    2400
aaagggcttg ccaacgtgca gtgttcagac ctgctcaaga gtggctgccg caacgctgt     2460 gcgacctttg ccagcaagat ccagggccag gtggacaaga tcaaggggc cggtggtgac     2520 taagcggccg cgaattccaa gcttgagtat tctatcgtgt cacctaaata acttggcgta    2580
atcatggtca tatctgtttc ctgtgtgaaa ttgttatccg ctcacaattc cacacaacat    2640
acgagccgga agcataaagt gtaaagcctg gggtgcctaa tgagtgagct aactcacatt    2700
aattgcgttg cgcgatgctt ccattttgtg agggttaatg cttcgagaag acatgataag    2760
atacattgat gagtttggac aaaccacaac aagaatgcag tgaaaaaaat gctttatttg    2820
tgaaatttgt gatgctattg ctttatttgt aaccattata agctgcaata acaagttaa     2880 caacaacaat tgcattcatt ttatgtttca ggttcagggg gagatgtggg aggtttttta    2940
aagcaagtaa aacctctaca aatgtggtaa aatccgataa ggatcgattc cggagcctga    3000
atggcgaatg gacgcgccct gtagcggcgc attaagcgcg gcgggtgtgg tggttacgcg    3060
cacgtgaccg ctacacttgc cagcgcccta gcgcccgctc ctttcgcttt cttcccttcc    3120
tttctcgcca cgttcgccgg cttccccgt caagctctaa atcggggggct ccctttaggg     3180 ttccgattta gtgctttacg gcacctcgac cccaaaaaac ttgattaggg tgatggttca    3240
cgtagtgggc catcgccctg atagacggtt tttcgccctt gacgttgga gtccacgttc     3300 tttaatagtg gactcttgtt ccaaactgga acaacactca accctatctc ggtctattct    3360
tttgatttat aagggatttt gccgatttcg gcctattggt taaaaaatga gctgatttaa    3420
caaaaattta acgcgaattt taacaaaata ttaacgctta caatttcgcc tgtgtacctt    3480
ctgaggcgga aagaaccagc tgtggaatgt gtgtcagtta gggtgtggaa agtccccagg    3540
ctccccagca ggcagaagta tgcaaagcat gcatctcaat tagtcagcaa ccaggtgtgg    3600
aaagtcccca ggctccccag caggcagaag tatgcaaagc atgcatctca attagtcagc    3660
aaccatagtc cgcccctaa ctccgcccat cccgccccta actccgccca gttccgccca    3720
ttctccgccc catggctgac taattttttt tatttatgca gaggccgagg ccgcctcggc    3780
ctctgagcta ttccagaagt agtgaggagg cttttttgga ggcctaggct tttgcaaaaa    3840
gcttgattct tctgacacaa cagtctcgaa cttaaggcta gagccaccat gattgaacaa    3900
gatggattgc acgcaggttc tccggccgct tgggtggaga ggctattcgg ctatgactgg    3960
gcacaacaga caatcggctg ctctgatgcc gccgtgttcc ggctgtcagc gcaggggcgc    4020
ccggttcttt ttgtcaagac cgacctgtcc ggtgccctga tgaactgca ggacgaggca     4080 gcgcggctat cgtggctggc cacgacgggc gttccttgcg cagctgtgct cgacgttgtc    4140
actgaagcgg gaagggactg gctgctattg ggcgaagtgc cggggcagga tctcctgtca    4200
tctcaccttg ctcctgccga gaaagtatcc atcatggctg atgcaatgcg gcggctgcat    4260
acgcttgatc cggctacctg cccattcgac caccaagcga aacatcgcat cgagcgagca    4320
cgtactcgga tggaagccgg tcttgtcgat caggatgatc tggacgaaga gcatcagggg    4380
ctcgcgccag ccgaactgtt cgccaggctc aaggcgcgca tgcccgacgg cgaggatctc    4440
gtcgtgaccc atggcgatgc ctgcttgccg aatatcatgg tggaaaatgg ccgcttttct    4500
```

```
ggattcatcg actgtggccg gctgggtgtg gcggaccgct atcaggacat agcgttggct      4560
acccgtgata ttgctgaaga gcttggcggc gaatgggctg accgcttcct cgtgctttac      4620
ggtatcgccg ctcccgattc gcagcgcatc gccttctatc gccttcttga cgagttcttc      4680
tgagcgggac tctggggttc gaaatgaccg accaagcgac gcccaacctg ccatcacgat      4740
ggccgcaata aaatatcttt attttcatta catctgtgtg ttggttttt gtgtgaagat      4800 ccgcgtatgg tgcactctca gtacaatctg ctctgatgcc gcatagttaa gccagccccg      4860
acacccgcca acacccgctg acgcgccctg acgggcttgt ctgctcccgg catccgctta      4920
cagacaagct gtgaccgtct ccgggagctg catgtgtcag aggttttcac cgtcatcacc      4980
gaaacgcgcg agacgaaagg gcctcgtgat acgcctattt ttataggtta atgtcatgat      5040
aataatggtt tcttagacgt caggtggcac ttttcgggga atgtgcgcg gaaccccctat      5100 ttgtttattt ttctaaatac attcaaatat gtatccgctc atgagacaat aaccctgata      5160
aatgcttcaa taatattgaa aaggaagag tatgagtatt caacatttcc gtgtcgccct      5220
tattcccttt tttgcggcat tttgccttcc tgttttgct cacccagaaa cgctggtgaa      5280
agtaaaagat gctgaagatc agttgggtgc acgagtgggt tacatcgaac tggatctcaa      5340
cagcggtaag atccttgaga gttttcgccc cgaagaacgt tttccaatga tgagcacttt      5400
taaagttctg ctatgtggcg cggtattatc ccgtattgac gccgggcaag agcaactcgg      5460
tcgccgcata cactattctc agaatgactt ggttgagtac tcaccagtca cagaaaagca      5520
tcttacggat ggcatgacag taagagaatt atgcagtgct gccataacca tgagtgataa      5580
cactgcggcc aacttacttc tgacaacgat cggaggaccg aaggagctaa ccgcttttt      5640 gcacaacatg ggggatcatg taactcgcct tgatcgttgg gaaccggagc tgaatgaagc      5700
cataccaaac gacgagcgtg acaccacgat gcctgtagca atggcaacaa cgttgcgcaa      5760
actattaact ggcgaactac ttactctagc ttcccggcaa caattaatag actggatgga      5820
ggcggataaa gttgcaggac cacttctgcg ctcggccctt ccggctggct ggtttattgc      5880
tgataaatct ggagccggtg agcgtgggtc tcgcggtatc attgcagcac tggggccaga      5940
tggtaagccc tcccgtatcg tagttatcta cacgacgggg agtcaggcaa ctatggatga      6000
acgaaataga cagatcgctg agataggtgc ctcactgatt aagcattggt aactgtcaga      6060
ccaagtttac tcatatatac tttagattga tttaaaactt catttttaat ttaaaaggat      6120
ctaggtgaag atcctttttg ataatctcat gaccaaaatc ccttaacgtg agttttcgtt      6180
ccactgagcg tcagaccccg tagaaaagat caaaggatct tcttgagatc ctttttttct      6240
gcgcgtaatc tgctgcttgc aaacaaaaaa accaccgcta ccagcggtgg tttgtttgcc      6300
ggatcaagag ctaccaactc ttttccgaa ggtaactggc ttcagcagag cgcagatacc      6360
aaatactgtc cttctagtgt agccgtagtt aggccaccac ttcaagaact ctgtagcacc      6420
gcctacatac ctcgctctgc taatcctgtt accagtggct gctgccagtg gcgataagtc      6480
gtgtcttacc gggttggact caagacgata gttaccggat aaggcgcagc ggtcgggctg      6540
aacggggggt tcgtgcacac agcccagctt ggagcgaacg acctacaccg aactgagata      6600 cctacacgt gagctatgag aaagcgccac gcttcccgaa gggagaaagg cggacaggta      6660
tccggtaagc ggcagggtcg gaacaggaga gcgcacgagg gagcttccag ggggaaacgc      6720
ctggtatctt tatagtcctg tcgggtttcg ccacctctga cttgagcgtc gatttttgtg      6780
atgctcgtca gggggggcgga gcctatggaa aaacgccagc aacgcggcct ttttacggtt      6840
cctggccttt tgctggcctt ttgctcacat ggctcgacag atct                       6884
```

<210> SEQ ID NO 98
<211> LENGTH: 6864
<212> TYPE: DNA
<213> ORGANISM: Artificial Sequence
<220> FEATURE:
<223> OTHER INFORMATION: pTarget SGLuc-d1D2A-IFNa

<400> SEQUENCE: 98

| | | | | | |
|---|---|---|---|---|---|
| tcaatattgg | ccattagcca | tattattcat | tggttatata | gcataaatca | atattggcta | 60 |
| ttggccattg | catacgttgt | atctatatca | taatatgtac | atttatattg | gctcatgtcc | 120 |
| aatatgaccg | ccatgttggc | attgattatt | gactagttat | taatagtaat | caattacggg | 180 |
| gtcattagtt | catagcccat | atatggagtt | ccgcgttaca | taacttacgg | taaatggccc | 240 |
| gcctggctga | ccgcccaacg | acccccgccc | attgacgtca | ataatgacgt | atgttcccat | 300 |
| agtaacgcca | atagggactt | tccattgacg | tcaatgggtg | gagtatttac | ggtaaactgc | 360 |
| ccacttggca | gtacatcaag | tgtatcatat | gccaagtccg | cccctattg | acgtcaatga | 420 |
| cggtaaatgg | cccgcctggc | attatgccca | gtacatgacc | ttacgggact | ttcctacttg | 480 |
| gcagtacatc | tacgtattag | tcatcgctat | taccatggtg | atgcggtttt | ggcagtacac | 540 |
| caatgggcgt | ggatagcggt | ttgactcacg | gggatttcca | agtctccacc | ccattgacgt | 600 |
| caatgggagt | ttgttttggc | accaaaatca | acgggacttt | ccaaaatgtc | gtaacaactg | 660 |
| cgatcgcccg | ccccgttgac | gcaaatgggc | ggtaggcgtg | tacggtggga | ggtctatata | 720 |
| agcagagctc | gtttagtgaa | ccgtcagatc | actagaagct | ttattgcggt | agtttatcac | 780 |
| agttaaattg | ctaacgcagt | cagtgcttct | gacacaacag | tctcgaactt | aagctgcagt | 840 |
| gactctctta | aggtagcctt | gcagaagttg | gtcgtgaggc | actgggcagg | taagtatcaa | 900 |
| ggttacaaga | caggtttaag | gagaccaata | gaaactgggc | ttgtcgagac | agagaagact | 960 |
| cttgcgtttc | tgataggcac | ctattggtct | tactgacatc | cactttgcct | ttctctccac | 1020 |
| aggtgtccac | tcccagttca | attacagctc | ttaaaaattg | gatctccatt | cgccattcag | 1080 |
| gctgcgcaac | tgctgggaag | gacgatcaga | gcgggcctct | tcgctattac | gccagctggc | 1140 |
| gaaagggacg | tggcaagcaa | ggcgattaag | ttgagttacg | ccaggatttt | cccagtcacg | 1200 |
| acgttgtaaa | acgacggcca | gagaattata | atacgactca | ctatagggcg | aattcggatc | 1260 |
| cttggcgtgc | gccgccacca | tgggagtcaa | agttctgttt | gccctgatct | gcatcgctgt | 1320 |
| ggccgaggcc | aagcccaccg | agaacaacga | agacttcaac | atcgtggccg | tggccagcaa | 1380 |
| cttcgcgacc | acggatctcg | atgctgaccg | cgggaagttg | cccggcaaga | agctgccgct | 1440 |
| ggaggtgctc | aaagagatgg | aagccaatgc | ccggaaagct | ggctgcacca | ggggctgtct | 1500 |
| gatctgcctg | tcccacatca | gtgcacgcc | caagatgaag | aagtggctcc | caggacgctg | 1560 |
| ccacacctac | gaaggcgaca | aagagtccgc | acagggcggc | ataggcgagg | cgatcgtcga | 1620 |
| cattcctgag | attcctgggt | tcaaggactt | ggagcccatg | gagcagttca | tcgcacaggt | 1680 |
| cgatctgtgt | gtggactgca | caactggctg | cctcaaaggg | cttgccaacg | tgcagtgttc | 1740 |
| tgacctgctc | aagaagtggc | tgccgcaacg | ctgtgcgacc | tttgccagca | agatccaggg | 1800 |
| ccaggtggac | aagatcaagg | gggccggtgg | tgacgctagc | acaagcaaa | agatcattgc | 1860 |
| accagcaaag | cagcttctga | attttgacct | gctcaagttg | gccggagacg | ttgagtccaa | 1920 |
| ccctggaccc | gggatggccc | caacctcagc | cttcctcacg | gccctggtgc | tactcagctg | 1980 |
| caatgccatc | tgctctctgg | gctgtgacct | gcctcagacc | cacagcctgg | ctcacaccag | 2040 |

```
agccctgagg ctcctggcac aaatgaggag aatctctccc ttctcctgcc tggaccacag    2100
aagggacttt ggttcccctc atgaggcttt tgggggcaac caggtccaga aggctcaagc    2160
catggctctg gtgcatgaga tgctccagca gaccttccag ctcttcagca cagagggctc    2220
ggctgctgcc tggaatgaga gcctcctgca ccagttctgc actggactgg atcagcagct    2280
cagggacctg gaagcctgtg tcatgcagga ggcggggctg gaagggaccc cctgctggga    2340
ggaggactcc atcctggctg tgaggaaata cttccacaga ctcaccctct atctgcaaga    2400
gaagagctac agccctgtg cctgggagat cgtcagggca gaagtcatga gatccttctc    2460
ttcctccaga aacctgcaag acagactcag gaagaaggag tgagcggccg cgaattccaa    2520
gcttgagtat tctatcgtgt cacctaaata acttggcgta atcatggtca tatctgtttc    2580
ctgtgtgaaa ttgttatccg ctcacaattc cacacaacat acgagccgga agcataaagt    2640
gtaaagcctg gggtgcctaa tgagtgagct aactcacatt aattgcgttg cgcgatgctt    2700
ccattttgtg agggttaatg cttcgagaag acatgataag atacattgat gagtttggac    2760
aaaccacaac aagaatgcag tgaaaaaaat gctttatttg tgaaatttgt gatgctattg    2820
ctttatttgt aaccattata agctgcaata acaagttaa caacaacaat tgcattcatt    2880
ttatgtttca ggttcagggg gagatgtggg aaggtttttta aagcaagtaa aacctctaca    2940
aatgtggtaa atccgataa ggatcgattc cggagcctga atggcgaatg gacgcgccct    3000
gtagcggcgc attaagcgcg gcgggtgtgg tggttacgcg cacgtgaccg ctacacttgc    3060
cagcgcccta gcgcccgctc ctttcgcttt cttcccttcc tttctcgcca cgttcgccgg    3120
ctttccccgt caagctctaa atcggggct ccctttaggg ttccgattta gtgctttacg    3180
gcacctcgac cccaaaaaac ttgattaggg tgatggttca cgtagtgggc catcgccctg    3240
atagacggtt tttcgccctt tgacgttgga gtccacgttc tttaatagtg gactcttgtt    3300
ccaaactgga acaacactca accctatctc ggtctattct tttgatttat aagggatttt    3360
gccgatttcg gcctattggt taaaaaatga gctgatttaa caaaaattta acgcgaattt    3420
taacaaaata ttaacgctta caatttcgcc tgtgtacctt ctgaggcgga agaaccagc    3480 tgtggaatgt gtgtcagtta gggtgtggaa agtccccagg ctccccagca ggcagaagta    3540
tgcaaagcat gcatctcaat tagtcagcaa ccaggtgtgg aaagtcccca ggctccccag    3600
caggcagaag tatgcaaagc atgcatctca attagtcagc aaccatagtc ccgcccctaa    3660
ctccgcccat cccgccccta actccgccca gttccgccca ttctccgccc catggctgac    3720 taatttttt tatttatgca gaggccgagg ccgcctcggc ctctgagcta ttccagaagt    3780
agtgaggagg ctttttgga ggcctaggct tttgcaaaaa gcttgattct tctgacacaa    3840
cagtctcgaa cttaaggcta gagccaccat gattgaacaa gatggattgc acgcaggttc    3900
tccggccgct tgggtggaga ggctattcgg ctatgactgg gcacaacaga caatcggctg    3960
ctctgatgcc gccgtgttcc ggctgtcagc gcaggggcgc ccggttcttt ttgtcaagac    4020
cgacctgtcc ggtgccctga tgaactgca ggacgaggca gcgcggctat cgtggctggc    4080
cacgacgggc gttccttgcg cagctgtgct cgacgttgtc actgaagcgg gaagggactg    4140
gctgctattg ggcgaagtgc cggggcagga tctcctgtca tctcaccttg ctcctgccga    4200
gaaagtatcc atcatggctg atgcaatgcg gcggctgcat acgcttgatc cggctacctg    4260
cccattcgac caccaagcga aacatcgcat cgagcgagca cgtactcgga tggaagccgg    4320
tcttgtcgat caggatgatc tggacgaaga gcatcagggg ctcgcgccag ccgaactgtt    4380
cgccaggctc aaggcgcgca tgcccgacgg cgaggatctc gtcgtgaccc atggcgatgc    4440
```

```
ctgcttgccg aatatcatgg tggaaaatgg ccgcttttct ggattcatcg actgtggccg    4500
gctgggtgtg gcggaccgct atcaggacat agcgttggct acccgtgata ttgctgaaga    4560
gcttggcggc gaatgggctg accgcttcct cgtgctttac ggtatcgccg ctcccgattc    4620
gcagcgcatc gccttctatc gccttcttga cgagttcttc tgagcgggac tctggggttc    4680
gaaatgaccg accaagcgac gcccaacctg ccatcacgat ggccgcaata aaatatcttt    4740
attttcatta catctgtgtg ttggttttttt gtgtgaagat ccgcgtatgg tgcactctca    4800
gtacaatctg ctctgatgcc gcatagttaa gccagccccg cacccgcca acccgctg      4860
acgcgccctg acgggcttgt ctgctcccgg catccgctta cagacaagct gtgaccgtct    4920
ccgggagctg catgtgtcag aggttttcac cgtcatcacc gaaacgcgcg agacgaaagg    4980
gcctcgtgat acgcctattt ttataggtta atgtcatgat aataatggtt tcttagacgt    5040
caggtggcac ttttcgggga atgtgcgcg gaacccctat ttgtttattt ttctaaatac     5100
attcaaatat gtatccgctc atgagacaat aaccctgata aatgcttcaa taatattgaa    5160
aaaggaagag tatgagtatt caacatttcc gtgtcgccct tattccctttt tttgcggcat   5220
tttgccttcc tgttttttgct cacccagaaa cgctggtgaa agtaaaagat gctgaagatc   5280
agttgggtgc acgagtgggt tacatcgaac tggatctcaa cagcggtaag atccttgaga   5340
gttttcgccc cgaagaacgt tttccaatga tgagcacttt taaagttctg ctatgtggcg   5400
cggtattatc ccgtattgac gccgggcaag agcaactcgg tcgccgcata cactattctc   5460
agaatgactt ggttgagtac tcaccagtca cagaaaagca tcttacggat ggcatgacag   5520
taagagaatt atgcagtgct gccataacca tgagtgataa cactgcggcc aacttacttc   5580
tgacaacgat cggaggaccg aaggagctaa ccgcttttt gcacaacatg ggggatcatg    5640
taactcgcct tgatcgttgg gaaccggagc tgaatgaagc cataccaaac gacgagcgtg   5700
acaccacgat gcctgtagca atggcaacaa cgttgcgcaa actattaact ggcgaactac   5760
ttactctagc ttcccggcaa caattaatag actggatgga ggcggataaa gttgcaggac   5820
cacttctgcg ctcggccctt ccggctggct ggtttattgc tgataaatct ggagccggtg   5880
agcgtgggtc tcgcggtatc attgcagcac tggggccaga tggtaagccc tcccgtatcg   5940
tagttatcta cacgacgggg agtcaggcaa ctatggatga acgaaataga cagatcgctg   6000
agataggtgc ctcactgatt aagcattggt aactgtcaga ccaagtttac tcatatatac   6060
tttagattga tttaaaactt cattttaat ttaaaaggat ctaggtgaag atcctttttg    6120
ataatctcat gaccaaaatc ccttaacgtg agttttcgtt ccactgagcg tcagaccccg   6180
tagaaaagat caaaggatct tcttgagatc cttttttttct gcgcgtaatc tgctgcttgc   6240
aaacaaaaaa accaccgcta ccagcggtgg tttgtttgcc ggatcaagag ctaccaactc   6300
ttttttccgaa ggtaactggc ttcagcagag cgcagatacc aaatactgtc cttctagtgt   6360
agccgtagtt aggccaccac ttcaagaact ctgtagcacc gcctacatac ctcgctctgc   6420
taatcctgtt accagtggct gctgccagtg gcgataagtc gtgtcttacc gggttggact   6480
caagacgata gttaccggat aaggcgcagc ggtcgggctg aacggggggt tcgtgcacac   6540
agcccagctt ggagcgaacg acctacaccg aactgagata cctacagcgt gagctatgag   6600
aaagcgccac gcttcccgaa gggagaaagg cggacaggta tccggtaagc ggcagggtcg   6660
gaacaggaga gcgcacgagg gagcttccag ggggaaacgc ctggtatctt tatagtcctg   6720
tcgggtttcg ccacctctga cttgagcgtc gatttttgtg atgctcgtca ggggggcgga   6780
```

```
gcctatggaa aaacgccagc aacgcggcct ttttacggtt cctggccttt tgctggcctt    6840
ttgctcacat ggctcgacag atct                                           6864

<210> SEQ ID NO 99
<211> LENGTH: 6106
<212> TYPE: DNA
<213> ORGANISM: Artificial Sequence
<220> FEATURE:
<223> OTHER INFORMATION: pTarget Histone H3

<400> SEQUENCE: 99
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg accccgcccc attgacgtca ataatgacgt atgttcccat     300
agtaacgcca atagggactt tccattgacg tcaatgggtg gagtatttac ggtaaactgc     360
ccacttggca gtacatcaag tgtatcatat gccaagtccg cccctattg acgtcaatga      420 cggtaaatgg cccgcctggc attatgccca gtacatgacc ttacgggact ttcctacttg     480
gcagtacatc tacgtattag tcatcgctat taccatggtg atgcggtttt ggcagtacac     540
caatgggcgt ggatagcggt ttgactcacg ggatttccaa gtctccacc ccattgacgt      600 caatgggagt ttgttttggc accaaaatca acgggacttt ccaaaatgtc gtaacaactg     660
cgatcgcccg ccccgttgac gcaaatgggc ggtaggcgtg tacggtggga ggtctatata     720
agcagagctc gtttagtgaa ccgtcagatc actagaagct ttattgcggt agtttatcac     780
agttaaattg ctaacgcagt cagtgcttct gacacaacag tctcgaactt aagctgcagt     840
gactctctta aggtagcctt gcagaagttg gtcgtgaggc actgggcagg taagtatcaa     900
ggttacaaga caggtttaag gagaccaata gaaactgggc ttgtcgagac agagaagact     960
cttgcgtttc tgataggcac ctattggtct tactgacatc cactttgcct ttctctccac    1020
aggtgtccac tcccagttca attacagctc ttaaaaattg gatctccatt cgccattcag    1080
gctgcgcaac tgctgggaag gacgatcaga gcgggcctct tcgctattac gccagctggc    1140
gaaagggacg tggcaagcaa ggcgattaag ttgagttacg ccaggatttt cccagtcacg    1200
acgttgtaaa acgacggcca gagaattata atacgactca ctatagggcg aattcggatc    1260
cttgctagcc tcgagacgcg tgataaggag ctcgagccac catggctcgt acaaagcaga    1320
ctgcccgcaa atcgaccggt ggtaaagcac cgaggaagca actcgctaca aaagccgctc    1380
gcaagagtgc gccctctact ggagggtga agaaacctca tcgttacagg cctggtactg     1440
tggcactccg tgaaattaga cgttatcaga agtccactga acttctgatt cgcaaacttc    1500
ccttccagcg tctggtgcgg gaaattgctc aggacttcaa aacagatctg cgcttccaga    1560
gtgcagctat tggtgctttg caggaggcaa gtgaggccta tctggttggc cttttttgaag    1620 acaccaacct gtgtgctatc catgccaaac gtgtaacaat tatgccaaaa gacatccagc    1680
tagcacgccg catacgtgga gaacgtgctt aaggtaacca atctttcccg ggggtaccgt    1740
cgactgcggc cgcgaattcc aagcttgagt attctatcgt gtcacctaaa taacttggcg    1800
taatcatggt catatctgtt tcctgtgtga aattgttatc cgctcacaat tccacacaac    1860
atacgagccg gaagcataaa gtgtaaagcc tggggtgcct aatgagtgag ctaactcaca    1920
ttaattgcgt tgcgcgatgc ttccattttg tgagggttaa tgcttcgaga agacatgata    1980
```

```
agatacattg atgagtttgg acaaaccaca acaagaatgc agtgaaaaaa atgctttatt    2040
tgtgaaattt gtgatgctat tgctttattt gtaaccatta taagctgcaa taaacaagtt    2100
aacaacaaca attgcattca ttttatgttt caggttcagg gggagatgtg ggaggttttt    2160
taaagcaagt aaaacctcta caaatgtggt aaaatccgat aaggatcgat tccggagcct    2220
gaatggcgaa tggacgcgcc ctgtagcggc gcattaagcg cggcgggtgt ggtggttacg    2280
cgcacgtgac cgctacactt gccagcgccc tagcgcccgc tcctttcgct ttcttccctt    2340
cctttctcgc cacgttcgcc ggctttcccc gtcaagctct aaatcggggg ctcccttag    2400
ggttccgatt tagtgcttta cggcacctcg accccaaaaa acttgattag ggtgatggtt    2460
cacgtagtgg gccatcgccc tgatagacgg ttttttcgccc tttgacgttg gagtccacgt    2520
tctttaatag tggactcttg ttccaaactg aacaacact caaccctatc tcggtctatt    2580
cttttgattt ataagggatt ttgccgattt cggcctattg gttaaaaaat gagctgattt    2640
aacaaaaatt taacgcgaat tttaacaaaa tattaacgct tacaatttcg cctgtgtacc    2700
ttctgaggcg gaaagaacca gctgtggaat gtgtgtcagt tagggtgtgg aaagtcccca    2760
ggctccccag caggcagaag tatgcaaagc atgcatctca attagtcagc aaccaggtgt    2820
ggaaagtccc caggctcccc agcaggcaga agtatgcaaa gcatgcatct caattagtca    2880
gcaaccatag tcccgcccct aactccgccc atcccgcccc taactccgcc cagttccgcc    2940
cattctccgc cccatggctg actaattttt tttatttatg cagaggccga ggccgcctcg    3000
gcctctgagc tattccagaa gtagtgagga ggcttttttg gaggcctagg cttttgcaaa    3060
aagcttgatt cttctgacac aacagtctcg aacttaaggc tagagccacc atgattgaac    3120
aagatggatt gcacgcaggt tctccggccg cttgggtgga gaggctattc ggctatgact    3180
gggcacaaca gacaatcggc tgctctgatg ccgccgtgtt ccggctgtca gcgcagggc    3240
gcccggttct ttttgtcaag accgacctgt ccggtgccct gaatgaactg caggacgagg    3300
cagcgcggct atcgtggctg gccacgacgg gcgttccttg cgcagctgtg ctcgacgttg    3360
tcactgaagc gggaagggac tggctgctat tgggcgaagt gccggggcag gatctcctgt    3420
catctcacct tgctcctgcc gagaaagtat ccatcatggc tgatgcaatg cggcggctgc    3480
atacgcttga tccggctacc tgcccattcg accaccaagc gaaacatcgc atcgagcgag    3540
cacgtactcg gatggaagcc ggtcttgtcg atcaggatga tctggacgaa gagcatcagg    3600
ggctcgcgcc agccgaactg ttcgccaggc tcaaggcgcg catgcccgac ggcgaggatc    3660
tcgtcgtgac ccatggcgat gcctgcttgc cgaatatcat ggtggaaaat ggccgctttt    3720
ctggattcat cgactgtggc cggctgggtg tggcggaccg ctatcaggac atagcgttgg    3780
ctacccgtga tattgctgaa gagcttggcg gcgaatgggc tgaccgcttc ctcgtgcttt    3840
acggtatcgc cgctcccgat tcgcagcgca tcgccttcta tcgccttctt gacgagttct    3900
tctgagcggg actctggggt tcgaaatgac cgaccaagcg acgcccaacc tgccatcacg    3960
atggccgcaa taaaatatct ttattttcat tacatctgtg tgttggtttt ttgtgtgaag    4020
atccgcgtat ggtgcactct cagtacaatc tgctctgatg ccgcatagtt aagccagccc    4080
cgacacccgc caacacccgc tgacgcgccc tgacgggctt gtctgctccc ggcatccgct    4140
tacagacaag ctgtgaccgt ctccgggagc tgcatgtgtc agaggttttc accgtcatca    4200
ccgaaacgcg cgagacgaaa gggcctcgtg atacgcctat ttttataggt taatgtcatg    4260
ataataatgg tttcttagac gtcaggtggc acttttcggg gaaatgtgcg cggaacccct    4320
```

```
atttgtttat ttttctaaat acattcaaat atgtatccgc tcatgagaca ataaccctga      4380
taaatgcttc aataatattg aaaaggaag agtatgagta ttcaacattt ccgtgtcgcc       4440
cttattccct tttttgcggc attttgcctt cctgttttg ctcacccaga aacgctggtg       4500
aaagtaaaag atgctgaaga tcagttgggt gcacgagtgg gttacatcga actggatctc     4560
aacagcggta agatccttga gagttttcgc cccgaagaac gttttccaat gatgagcact     4620
tttaaagttc tgctatgtgg cgcggtatta tcccgtattg acgccgggca agagcaactc     4680
ggtcgccgca tacactattc tcagaatgac ttggttgagt actcaccagt cacagaaaag     4740
catcttacgg atggcatgac agtaagagaa ttatgcagtg ctgccataac catgagtgat     4800
aacactgcgg ccaacttact tctgacaacg atcggaggac cgaaggagct aaccgctttt     4860
ttgcacaaca tgggggatca tgtaactcgc cttgatcgtt gggaaccgga gctgaatgaa     4920
gccataccaa acgacgagcg tgacaccacg atgcctgtag caatggcaac aacgttgcgc    4980
aaactattaa ctggcgaact acttactcta gcttcccggc aacaattaat agactggatg     5040
gaggcggata aagttgcagg accacttctg cgctcggccc ttccggctgg ctggtttatt     5100
gctgataaat ctggagccgg tgagcgtggg tctcgcggta tcattgcagc actggggcca    5160
gatggtaagc cctcccgtat cgtagttatc tacacgacgg ggagtcaggc aactatggat    5220
gaacgaaata gacagatcgc tgagataggt gcctcactga ttaagcattg gtaactgtca    5280
gaccaagttt actcatatat actttagatt gatttaaaac ttcattttta atttaaaagg    5340
atctaggtga agatcctttt tgataatctc atgaccaaaa tcccttaacg tgagttttcg    5400
ttccactgag cgtcagaccc cgtagaaaag atcaaaggat cttcttgaga tcctttttt     5460 ctgcgcgtaa tctgctgctt gcaaacaaaa aaaccaccgc taccagcggt ggtttgtttg    5520
ccggatcaag agctaccaac tcttttccg aaggtaactg gcttcagcag agcgcagata     5580
ccaaatactg tccttctagt gtagccgtag ttaggccacc acttcaagaa ctctgtagca    5640
ccgcctacat acctcgctct gctaatcctg ttaccagtgg ctgctgccag tggcgataag    5700
tcgtgtctta ccgggttgga ctcaagacga tagttaccgg ataaggcgca gcggtcgggc    5760
tgaacggggg gttcgtgcac acagcccagc ttggagcgaa cgacctacac cgaactgaga    5820
tacctacagc gtgagctatg agaaagcgcc acgcttcccg aagggagaaa ggcggacagg    5880
tatccggtaa gcggcagggt cggaacagga gagcgcacga gggagcttcc agggggaaac    5940
gcctggtatc tttatagtcc tgtcgggttt cgccacctct gacttgagcg tcgatttttg    6000
tgatgctcgt caggggggcg gagcctatgg aaaaacgcca gcaacgcggc ctttttacgg    6060
ttcctggcct tttgctggcc ttttgctcac atggctcgac agatct                   6106

<210> SEQ ID NO 100
<211> LENGTH: 6696
<212> TYPE: DNA
<213> ORGANISM: Artificial Sequence
<220> FEATURE:
<223> OTHER INFORMATION: pTarget SGLucON Alpha Porcine

<400> SEQUENCE: 100
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg    180
gtcattagtt catagcccat atatggagtt ccgcgttaca taacttacgg taaatggccc    240
gcctggctga ccgcccaacg acccccgccc attgacgtca ataatgacgt atgttcccat    300
```

```
agtaacgcca ataggggactt tccattgacg tcaatgggtg gagtatttac ggtaaactgc    360
ccacttggca gtacatcaag tgtatcatat gccaagtccg cccctattg acgtcaatga     420
cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt ttgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaaaattg gatctccatt cgccattcag   1080
gctgcgcaac tgctgggaag gacgatcaga gcgggcctct tcgctattac gccagctggc   1140
gaaagggacg tggcaagcaa ggcgattaag ttgagttacg ccaggatttt cccagtcacg   1200
acgttgtaaa acgacggcca gagaattata atacgactca ctatagggcg aattcgctag   1260
cgccgccacc atgggagtca agttctgtt tgccctgatc tgcatcgctg tggccgaggc    1320
caagcccacc gagaacaacg aagacttcaa catcgtggcc gtggccagca actttgcgac   1380
cacggatctc gatgctgacc gagggaagtt gcccggcaag aagctgccgc tggaggtgct   1440
caaagagatg gaagccaatg cccggaaagc tggctgcacc aggggctgtc tgatctgcct   1500
gtcccacatc aagtgcacgc ccaagatgaa gaagtggctc ccaggacgct gccacaccta   1560
cgaaggcgac aaagagtccg cacagggcgg cataggcgag gcgatcgtcg atattcctga   1620
gattcctggg ttcaaggact ggagccaat ggagcagttc atcgcacagg tcgatctgtg    1680
tgtggactgc acaactggct gcctcaaagg gcttgccaac gtgcagtgtt ctgacctgct   1740
caagaagtgg ctgccgcaac gctgtgcgac ctttgccagc aagatccagg gccaggtgga   1800
caagatcaag ggggccggtg gtgacgggcc cgggtgtgac ctgcctcaga cccacagcct   1860
ggctcacacc agagccctga ggctcctggc acaaatgagg agaatctctc ccttctcctg   1920
cctggaccac agaagggact ttggttcccc tcatgaggct tttggggggca accaggtcca   1980
gaaggctcaa gccatggctc tggtgcatga gatgctccag cagaccttcc agctcttcag   2040
cacagagggc tcggctgctg cctggaatga gagcctcctg caccagttct gcactggact   2100
ggatcagcag ctcagggacc tggaagcctg tgtcatgcag gaggcgggc tggaagggac    2160
cccctgctg gaggaggact ccatcctggc tgtgaggaaa tacttccaca gactcaccct    2220
ctatctgcaa gagaagagct acagccctg tgcctgggag atcgtcaggg cagaagtcat    2280
gagatccttc tcttcctcca gaaacctgca agacagactc aggaagaagg agtgagcggc   2340
cgcgaattcc aagcttgagt attctatcgt gtcacctaaa taacttggcg taatcatggt   2400
catatctgtt tcctgtgtga aattgttatc cgctcacaat tccacacaac atacgagccg   2460
gaagcataaa gtgtaaagcc tggggtgcct aatgagtgag ctaactcaca ttaattgcgt   2520
tgcgcgatgt ttccatttg tgagggttaa gcttcgaga agacatgata agatacattg     2580
atgagtttgg acaaaccaca acaagaatgc agtgaaaaaa atgctttatt tgtgaaattt   2640
```

```
gtgatgctat tgctttattt gtaaccatta taagctgcaa taaacaagtt aacaacaaca    2700
attgcattca ttttatgttt caggttcagg gggagatgtg ggaggttttt taaagcaagt    2760
aaaacctcta caaatgtggt aaaatccgat aaggatcgat tccggagcct gaatggcgaa    2820
tggacgcgcc ctgtagcggc gcattaagcg cggcgggtgt ggtggttacg cgcacgtgac    2880
cgctacactt gccagcgccc tagcgcccgc tcctttcgct ttcttccctt cctttctcgc    2940
cacgttcgcc ggctttcccc gtcaagctct aaatcggggg ctcccttag ggttccgatt     3000 tagtgcttta cggcacctcg accccaaaaa acttgattag ggtgatggtt cacgtagtgg    3060
gccatcgccc tgatagacgg ttttcgccc tttgacgttg gagtccacgt tctttaatag     3120
tggactcttg ttccaaactg gaacaacact caaccctatc tcggtctatt cttttgattt    3180
ataagggatt ttgccgattt cggcctattg gttaaaaaat gagctgattt aacaaaaatt    3240
taacgcgaat tttaacaaaa tattaacgct tacaatttcg cctgtgtacc ttctgaggcg    3300
gaaagaacca gctgtggaat gtgtgtcagt tagggtgtgg aaagtcccca ggctccccag    3360
caggcagaag tatgcaaagc atgcatctca attagtcagc aaccaggtgt ggaaagtccc    3420
caggctcccc agcaggcaga agtatgcaaa gcatgcatct caattagtca gcaaccatag    3480
tcccgcccct aactccgccc atcccgcccc taactccgcc cagttccgcc cattctccgc    3540
cccatggctg actaatttt tttatttatg cagaggccga ggccgcctcg gcctctgagc     3600
tattccagaa gtagtgagga ggcttttttg gaggcctagg cttttgcaaa aagcttgatt    3660
cttctgacac aacagtctcg aacttaaggc tagagccacc atgattgaac aagatggatt    3720
gcacgcaggt tctccggccg cttgggtgga gaggctattc ggctatgact gggcacaaca    3780
gacaatcggc tgctctgatg ccgccgtgtt ccggctgtca gcgcaggggc gcccggttct    3840
ttttgtcaag accgacctgt ccggtgccct gaatgaactg caggacgagg cagcgcggct    3900
atcgtggctg gccacgacgg gcgttccttg cgcagctgtg ctcgacgttg tcactgaagc    3960
gggaagggac tggctgctat tgggcgaagt gccggggcag gatctcctgt catctcacct    4020
tgctcctgcc gagaaagtat ccatcatggc tgatgcaatg cggcggctgc atacgcttga    4080
tccggctacc tgcccattcg accaccaagc gaaacatcgc atcgagcgag cacgtactcg    4140
gatggaagcc ggtcttgtcg atcaggatga tctggacgaa gagcatcagg ggctcgcgcc    4200
agccgaactg ttcgccaggc tcaaggcgcg catgcccgac ggcgaggatc tcgtcgtgac    4260
ccatggcgat gcctgcttgc cgaatatcat ggtggaaaat ggccgctttt ctggattcat    4320
cgactgtggc cggctgggtg tggcggaccg ctatcaggac atagcgttgg ctacccgtga    4380
tattgctgaa gagcttggcg gcgaatgggc tgaccgcttc ctcgtgcttt acggtatcgc    4440
cgctcccgat tcgcagcgca tcgccttcta tcgccttctt gacgagttct tctgagcggg    4500
actctggggt tcgaaatgac cgaccaagcg acgcccaacc tgccatcacg atggccgcaa    4560
taaaatatct ttattttcat tacatctgtg tgttggtttt ttgtgtgaag atccgcgtat    4620
ggtgcactct cagtacaatc tgctctgatg ccgcatagtt aagccagccc cgacacccgc    4680
caacacccgc tgacgcgccc tgacgggctt gtctgctccc ggcatccgct tacagacaag    4740
ctgtgaccgt ctccgggagc tgcatgtgtc agaggttttc accgtcatca ccgaaacgcg    4800
cgagacgaaa gggcctcgtg atacgcctat ttttataggt taatgtcatg ataataatgg    4860
tttcttagac gtcaggtggc acttttcggg gaaatgtgcg cggaacccct atttgtttat    4920
ttttctaaat acattcaaat atgtatccgc tcatgagaca ataaccctga taaatgcttc    4980
aataatattg aaaaaggaag agtatgagta ttcaacattt ccgtgtcgcc cttattccct    5040
```

```
tttttgcggc attttgcctt cctgttttg ctcacccaga aacgctggtg aaagtaaaag    5100
atgctgaaga tcagttgggt gcacgagtgg gttacatcga actggatctc aacagcggta   5160
agatccttga gagttttcgc cccgaagaac gttttccaat gatgagcact tttaaagttc   5220
tgctatgtgg cgcggtatta tcccgtattg acgccgggca agagcaactc ggtcgccgca   5280
tacactattc tcagaatgac ttggttgagt actcaccagt cacagaaaag catcttacgg   5340
atggcatgac agtaagagaa ttatgcagtg ctgccataac catgagtgat aacactgcgg   5400
ccaacttact tctgacaacg atcggaggac cgaaggagct aaccgctttt ttgcacaaca   5460
tgggggatca tgtaactcgc cttgatcgtt gggaaccgga gctgaatgaa gccataccaa   5520
acgacgagcg tgacaccacg atgcctgtag caatggcaac aacgttgcgc aaactattaa   5580
ctggcgaact acttactcta gcttcccggc aacaattaat agactggatg gaggcggata   5640
aagttgcagg accacttctg cgctcggccc ttccggctgg ctggtttatt gctgataaat   5700
ctggagccgg tgagcgtggg tctcgcggta tcattgcagc actggggcca gatggtaagc   5760
cctcccgtat cgtagttatc tacacgacgg ggagtcaggc aactatggat gaacgaaata   5820
gacagatcgc tgagataggt gcctcactga ttaagcattg gtaactgtca gaccaagttt   5880
actcatatat actttagatt gatttaaaac ttcattttta atttaaaagg atctaggtga   5940
agatcctttt tgataatctc atgaccaaaa tcccttaacg tgagttttcg ttccactgag   6000
cgtcagaccc cgtagaaaag atcaaaggat cttcttgaga tcctttttt ctgcgcgtaa    6060
tctgctgctt gcaaacaaaa aaaccaccgc taccagcggt ggtttgtttg ccggatcaag   6120
agctaccaac tctttttccg aaggtaactg gcttcagcag agcgcagata ccaaatactg   6180
tccttctagt gtagccgtag ttaggccacc acttcaagaa ctctgtagca ccgcctacat   6240
acctcgctct gctaatcctg ttaccagtgg ctgctgccag tggcgataag tcgtgtctta   6300
ccgggttgga ctcaagacga tagttaccgg ataaggcgca gcggtcgggc tgaacggggg   6360
gttcgtgcac acagcccagc ttggagcgaa cgacctacac cgaactgaga tacctacagc   6420
gtgagctatg agaaagcgcc acgcttcccg aagggagaaa ggcggacagg tatccggtaa   6480
gcggcagggt cggaacagga gagcgcacga gggagcttcc agggggaaac gcctggtatc   6540
tttatagtcc tgtcgggttt cgccacctct gacttgagcg tcgatttttg tgatgctcgt   6600
caggggggcg gagcctatgg aaaaacgcca gcaacgcggc ctttttacgg ttcctggcct   6660
tttgctggcc ttttgctcac atggctcgac agatct                            6696
```

<210> SEQ ID NO 101
<211> LENGTH: 6693
<212> TYPE: DNA
<213> ORGANISM: Artificial Sequence
<220> FEATURE:
<223> OTHER INFORMATION: pTarget GLucON Beta Porcine

<400> SEQUENCE: 101

```
tcaatattgg ccattagcca tattattcat tggttatata gcataaatca atattggcta    60
ttggccattg catacgttgt atctatatca taatatgtac atttatattg gctcatgtcc   120
aatatgaccg ccatgttggc attgattatt gactagttat taatagtaat caattacggg   180
gtcattagtt catagcccat atatggagtt ccgcgttaca taacttacgg taaatggccc   240
gcctggctga ccgcccaacg acccccgccc attgacgtca ataatgacgt atgttcccat   300
agtaacgcca atagggactt tccattgacg tcaatgggtg gagtatttac ggtaaactgc   360
```

```
ccacttggca gtacatcaag tgtatcatat gccaagtccg cccccctattg acgtcaatga    420
cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt ttgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaaaattg gatctccatt cgccattcag   1080
gctgcgcaac tgctgggaag gacgatcaga gcgggcctct tcgctattac gccagctggc   1140
gaaagggacg tggcaagcaa ggcgattaag ttgagttacg ccaggatttt cccagtcacg   1200
acgttgtaaa acgacggcca gagaattata atacgactca ctatagggcg aattcgctag   1260
cgccgccacc atgggagtca aagttctgtt tgccctgatc tgcatcgctg tggccgaggc   1320
caagcccacc gagaacaacg aagacttcaa catcgtggcc gtggccagca actttgcgac   1380
cacggatctc gatgctgacc gagggaagtt gcccggcaag aagctgccgc tggaggtgct   1440
caaagagatg gaagccaatg cccggaaagc tggctgcacc aggggctgtc tgatctgcct   1500
gtcccacatc aagtgcacgc ccaagatgaa gaagtggctc ccaggacgct gccacaccta   1560
cgaaggcgac aaagagtccg cacagggcgg cataggcgag gcgatcgtcg atattcctga   1620
gattcctggg ttcaaggact tggagccaat ggagcagttc atcgcacagg tcgatctgtg   1680
tgtggactgc acaactggct gcctcaaagg gcttgccaac gtgcagtgtt ctgacctgct   1740
caagaagtgg ctgccgcaac gctgtgcgac cttttccagc aagatccagg ccaggtgga   1800
caagatcaag ggggccggtg gtgacgggcc cgggatgagc tatgatgtgc ttcgatacca   1860
acaaaggagc agcaatttgg catgtcagaa gctcctggga cagttgcctg ggactcctca   1920
atattgcctc gaagatagga tgaactttga ggtccctgag gagattatgc aaccaccaca   1980
attccagaag gaagatgcag tattgattat ccacgagatg ctccagcaga tcttcggcat   2040
tctcagaaga aatttctcta gcactggctg gaatgaaacc gtcattaaga ctatccttgt   2100
ggaacttgat gggcagatgg atgacctgga gacaatcctg gaggaaatca tggaggagga   2160
aaatttcccc aggggagaca tgaccattct tcacctgaag aaatattact tgagcattct   2220
gcagtacctg aagtccaagg agtacagaag ctgtgcctgg acagtcgtcc aagtggaaat   2280
cctcaggaac ttttctttcc ttaacagact tacagattac ctccggaact gagcggccgc   2340
gaattccaag cttgagtatt ctatcgtgtc acctaaataa cttggcgtaa tcatggtcat   2400
atctgtttcc tgtgtgaaat tgttatccgc tcacaattcc acacaacata cgagccggaa   2460
gcataaagtg taaagcctgg ggtgcctaat gagtgagcta actcacatta attgcgttgc   2520
gcgatgcttc cattttgtga gggttaatgc ttcgagaaga catgataaga tacattgatg   2580
agtttggaca aaccacaaca agaatgcagt gaaaaaaatg ctttatttgt gaaatttgtg   2640
atgctattgc tttatttgta accattataa gctgcaataa acaagttaac aacaacaatt   2700
gcattcattt tatgtttcag gttcaggggg agatgtggga ggttttttaa agcaagtaaa   2760
```

```
acctctacaa atgtggtaaa atccgataag gatcgattcc ggagcctgaa tggcgaatgg    2820
acgcgccctg tagcggcgca ttaagcgcgg cgggtgtggt ggttacgcgc acgtgaccgc    2880
tacacttgcc agcgccctag cgcccgctcc tttcgctttc ttcccttcct ttctcgccac    2940
gttcgccggc tttccccgtc aagctctaaa tcggggggctc cctttagggt tccgatttag    3000
tgctttacgg cacctcgacc ccaaaaaact tgattagggt gatggttcac gtagtgggcc    3060
atcgccctga tagacggttt ttcgcccttt gacgttggag tccacgttct ttaatagtgg    3120
actcttgttc caaactggaa caacactcaa ccctatctcg gtctattctt ttgatttata    3180
agggattttg ccgatttcgg cctattggtt aaaaaatgag ctgatttaac aaaaatttaa    3240
cgcgaatttt aacaaaatat taacgcttac aatttcgcct gtgtaccttc tgaggcggaa    3300
agaaccagct gtggaatgtg tgtcagttag ggtgtggaaa gtccccaggc tccccagcag    3360
gcagaagtat gcaaagcatg catctcaatt agtcagcaac caggtgtgga aagtccccag    3420
gctcccccagc aggcagaagt atgcaaagca tgcatctcaa ttagtcagca accatagtcc    3480
cgcccctaac tccgcccatc ccgcccctaa ctccgcccag ttccgcccat tctccgcccc    3540
atggctgact aatttttttt atttatgcag aggccgaggc cgcctcggcc tctgagctat    3600
tccagaagta gtgaggaggc ttttttggag gcctaggctt ttgcaaaaag cttgattctt    3660
ctgacacaac agtctcgaac ttaaggctag agccaccatg attgaacaag atggattgca    3720
cgcaggttct ccggccgctt gggtggagag gctattcggc tatgactggg cacaacagac    3780
aatcggctgc tctgatgccg ccgtgttccg gctgtcagcg caggggcgcc cggttctttt    3840
tgtcaagacc gacctgtccg gtgccctgaa tgaactgcag gacgaggcag cgcggctatc    3900
gtggctggcc acgacgggcg ttccttgcgc agctgtgctc gacgttgtca ctgaagcggg    3960
aagggactgg ctgctattgg gcgaagtgcc ggggcaggat ctcctgtcat ctcaccttgc    4020
tcctgccgag aaagtatcca tcatggctga tgcaatgcgg cggctgcata cgcttgatcc    4080
ggctacctgc ccattcgacc accaagcgaa acatcgcatc gagcgagcac gtactcggat    4140
ggaagccggt cttgtcgatc aggatgatct ggacgaagag catcaggggc tcgcgccagc    4200
cgaactgttc gccaggctca aggcgcgcat gcccgacggc gaggatctcg tcgtgaccca    4260
tggcgatgcc tgcttgccga atatcatggt ggaaaatggc cgcttttctg gattcatcga    4320
ctgtggccgg ctgggtgtgg cggaccgcta tcaggacata gcgttggcta cccgtgatat    4380
tgctgaagag cttggcggcg aatgggctga ccgcttcctc gtgctttacg gtatcgccgc    4440
tcccgattcg cagcgcatcg ccttctatcg ccttcttgac gagttcttct gagcgggact    4500
ctggggttcg aaatgaccga ccaagcgacg cccaacctgc catcacgatg gccgcaataa    4560
aatatcttta ttttcattac atctgtgtgt tggttttttg tgtgaagatc cgcgtatggt    4620
gcactctcag tacaatctgc tctgatgccg catagttaag ccagccccga cacccgccaa    4680
cacccgctga cgcgccctga cgggcttgtc tgctcccggc atccgcttac agacaagctg    4740
tgaccgtctc cgggagctgc atgtgtcaga ggttttcacc gtcatcaccg aaacgcgcga    4800
gacgaaaggg cctcgtgata cgcctatttt tataggttaa tgtcatgata taatggtttc    4860
cttagacgtc aggtggcact tttcggggaa atgtgcgcgg aacccctatt tgtttatttt    4920
tctaaataca ttcaaatatg tatccgctca tgagacaata accctgataa atgcttcaat    4980
aatattgaaa aaggaagagt atgagtattc aacatttccg tgtcgccctt attccctttt    5040
ttgcggcatt ttgccttcct gtttttgctc acccagaaac gctggtgaaa gtaaaagatg    5100
```

```
ctgaagatca gttgggtgca cgagtgggtt acatcgaact ggatctcaac agcggtaaga      5160
tccttgagag ttttcgcccc gaagaacgtt ttccaatgat gagcactttt aaagttctgc      5220
tatgtggcgc ggtattatcc cgtattgacg ccgggcaaga gcaactcggt cgccgcatac      5280
actattctca gaatgacttg gttgagtact caccagtcac agaaaagcat cttacggatg      5340
gcatgacagt aagagaatta tgcagtgctg ccataaccat gagtgataac actgcggcca      5400
acttacttct gacaacgatc ggaggaccga aggagctaac cgcttttttg cacaacatgg      5460
gggatcatgt aactcgcctt gatcgttggg aaccggagct gaatgaagcc ataccaaacg      5520
acgagcgtga caccacgatg cctgtagcaa tggcaacaac gttgcgcaaa ctattaactg      5580
gcgaactact tactctagct tcccggcaac aattaataga ctggatggag gcggataaag      5640
ttgcaggacc acttctgcgc tcggcccttc cggctggctg gtttattgct gataaatctg      5700
gagccggtga gcgtgggtct cgcggtatca ttgcagcact ggggccagat ggtaagccct      5760
cccgtatcgt agttatctac acgacgggga gtcaggcaac tatggatgaa cgaaatagac      5820
agatcgctga gataggtgcc tcactgatta agcattggta actgtcagac caagtttact      5880
catatatact ttagattgat ttaaaacttc atttttaatt taaaaggatc taggtgaaga      5940
tcctttttga taatctcatg accaaaatcc cttaacgtga gttttcgttc cactgagcgt      6000
cagaccccgt agaaaagatc aaaggatctt cttgagatcc ttttttttctg cgcgtaatct      6060 gctgcttgca acaaaaaaa ccaccgctac cagcggtggt ttgtttgccg gatcaagagc      6120
taccaactct ttttccgaag gtaactggct tcagcagagc gcagatacca aatactgtcc      6180
ttctagtgta gccgtagtta ggccaccact tcaagaactc tgtagcaccg cctacatacc      6240
tcgctctgct aatcctgtta ccagtggctg ctgccagtgg cgataagtcg tgtcttaccg      6300
ggttggactc aagacgatag ttaccggata aggcgcagcg gtcgggctga acggggggtt      6360
cgtgcacaca gcccagcttg gagcgaacga cctacaccga actgagatac ctacagcgtg      6420
agctatgaga aagcgccacg cttcccgaag ggagaaaggc ggacaggtat ccggtaagcg      6480
gcagggtcgg aacaggagag cgcacgaggg agcttccagg gggaaacgcc tggtatcttt      6540
atagtcctgt cgggtttcgc cacctctgac ttgagcgtcg attttttgtga tgctcgtcag      6600 ggggggcggag cctatggaaa aacgccagca acgcggcctt tttacggttc ctggccttttt     6660 gctggccttt tgctcacatg gctcgacaga tct                                  6693
```

<210> SEQ ID NO 102
<211> LENGTH: 6624
<212> TYPE: DNA
<213> ORGANISM: Artificial Sequence
<220> FEATURE:
<223> OTHER INFORMATION: pTarget GLucON Gamma Bovine

<400> SEQUENCE: 102

```
tcaatattgg ccattagcca tattattcat tggttatata gcataaatca atattggcta        60
ttggccattg catacgttgt atctatatca taatatgtac atttatattg gctcatgtcc       120
aatatgaccg ccatgttggc attgattatt gactagttat taatagtaat caattacggg       180
gtcattagtt catagcccat atatggagtt ccgcgttaca taacttacgg taaatggccc       240
gcctggctga ccgcccaacg acccccgccc attgacgtca ataatgacgt atgttcccat       300
agtaacgcca atagggactt tccattgacg tcaatgggtg gagtatttac ggtaaactgc       360
ccacttggca gtacatcaag tgtatcatat gccaagtccg ccccctattg acgtcaatga       420
cggtaaatgg cccgcctggc attatgccca gtacatgacc ttacgggact ttcctacttg       480
```

```
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt tgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaaaattg gatctccatt cgccattcag   1080
gctgcgcaac tgctgggaag gacgatcaga gcgggcctct tcgctattac gccagctggc   1140 gaagggacg tggcaagcaa ggcgattaag ttgagttacg ccaggatttt cccagtcacg   1200
acgttgtaaa acgacggcca gagaattata atacgactca ctatagggcg aattcgctag   1260
cgccgccacc atgggagtca agttctgtt tgccctgatc tgcatcgctg tggccgaggc   1320
caagcccacc gagaacaacg aagacttcaa catcgtggcc gtggccagca actttgcgac   1380
cacggatctc gatgctgacc gagggaagtt gcccggcaag aagctgccgc tggaggtgct   1440
caaagagatg gaagccaatg cccggaaagc tggctgcacc aggggctgtc tgatctgcct   1500
gtcccacatc aagtgcacgc ccaagatgaa gaagtggctc ccaggacgct gccacaccta   1560
cgaaggcgac aaagagtccg cacagggcgg cataggcgag gcgatcgtcg atattcctga   1620
gattcctggg ttcaaggact ggagccaat ggagcagttc atcgcacagg tcgatctgtg   1680
tgtggactgc acaactggct gcctcaaagg gcttgccaac gtgcagtgtt ctgacctgct   1740
caagaagtgg ctgccgcaac gctgtgcgac cttttgccagc aagatccagg ccaggtgga   1800 caagatcaag ggggccggtg gtgacgggcc ccagggccaa ttttttagag aaatagaaaa   1860
cttaaaggag tattttaatg caagtagccc agatgtagct aagggtgggc ctctcttctc   1920 agaaatttg aagaattgga aagatgaaag tgacaaaaaa attattcaga gccaaattgt   1980
ctccttctac ttcaaactct ttgaaaacct caaagataac caggtcattc aaaggagcat   2040
ggatataatc aagcaagaca tgtttcagaa gttcttgaat ggcagctctg agaaactgga   2100
ggacttcaaa aagctgattc aaattccggt ggatgatctc cagatccagc gcaaagccat   2160
aaatgaactc atcaaagtga tgaatgacct gtcaccaaaa tctaacctca gaaagcggaa   2220
gagaagtcag aatctctttc gaggccggag agcatcaacg taagcggccg cgaattccaa   2280
gcttgagtat tctatcgtgt cacctaaata acttggcgta atcatggtca tatctgtttc   2340
ctgtgtgaaa ttgttatccg ctcacaattc cacacaacat acgagccgga agcataaagt   2400
gtaaagcctg gggtgcctaa tgagtgagct aactcacatt aattgcgttg cgcgatgctt   2460 ccatttgtg agggttaatg cttcgagaag acatgataag atacattgat gagtttggac   2520
aaaccacaac aagaatgcag tgaaaaaaat gctttatttg tgaaatttgt gatgctattg   2580
ctttatttgt aaccattata agctgcaata acaagttaa caacaacaat tgcattcatt   2640
ttatgtttca ggttcagggg gagatgtggg aggtttttta aagcaagtaa aacctctaca   2700
aatgtggtaa aatccgataa ggatcgattc cggagcctga atggcgaatg gacgcgccct   2760
gtagcggcgc attaagcgcg gcgggtgtgg tggttacgcg cacgtgaccg ctacacttgc   2820
```

```
cagcgccta gcgcccgctc ctttcgcttt cttcccttcc tttctcgcca cgttcgccgg      2880
cttcccccgt caagctctaa atcgggggct cccttaggg ttccgattta gtgctttacg       2940
gcacctcgac cccaaaaaac ttgattaggg tgatggttca cgtagtgggc catcgccctg      3000
atagacggtt tttcgccctt tgacgttgga gtccacgttc tttaatagtg gactcttgtt      3060
ccaaactgga acaacactca accctatctc ggtctattct tttgatttat aagggatttt      3120
gccgatttcg gcctattggt taaaaaatga gctgatttaa caaaaattta cgcgaatt       3180 taacaaaata ttaacgctta caatttcgcc tgtgtaccct ctgaggcgga agaaccagc      3240 tgtggaatgt gtgtcagtta gggtgtggaa agtccccagg ctccccagca ggcagaagta     3300
tgcaaagcat gcatctcaat tagtcagcaa ccaggtgtgg aaagtcccca ggctccccag     3360
caggcagaag tatgcaaagc atgcatctca attagtcagc aaccatagtc ccgcccctaa     3420
ctccgcccat cccgccccta actccgccca gttccgccca ttctccgccc catggctgac    3480 taatttttt tatttatgca gaggccgagg ccgcctcggc ctctgagcta ttccagaagt     3540
agtgaggagg ctttttgga ggcctaggct tttgcaaaaa gcttgattct tctgacacaa     3600
cagtctcgaa cttaaggcta gagccaccat gattgaacaa gatggattgc acgcaggttc    3660 tccgccgct tgggtggaga ggctattcgg ctatgactgg gcacaacaga caatcggctg     3720
ctctgatgcc gccgtgttcc ggctgtcagc gcaggggcgc ccggttcttt tgtcaagac    3780 cgacctgtcc ggtgccctga tgaactgca ggacgaggca gcgcggctat cgtggctggc    3840
cacgacgggc gttccttgcg cagctgtgct cgacgttgtc actgaagcgg aagggactg    3900 gctgctattg ggcgaagtgc cggggcagga tctcctgtca tctcaccttg ctcctgccga    3960
gaaagtatcc atcatggctg atgcaatgcg gcggctgcat acgcttgatc cggctacctg    4020
cccattcgac caccaagcga aacatcgcat cgagcgagca cgtactcgga tggaagccgg    4080
tcttgtcgat caggatgatc tggacgaaga gcatcagggg ctcgcgccag ccgaactgtt    4140
cgccaggctc aaggcgcgca tgcccgacgg cgaggatctc gtcgtgaccc atggcgatgc    4200
ctgcttgccg aatatcatgg tggaaaatgg ccgcttttct ggattcatcg actgtggccg    4260
gctgggtgtg gcggaccgct atcaggacat agcgttggct acccgtgata ttgctgaaga    4320
gcttggcggc gaatgggctg accgcttcct cgtgctttac ggtatcgccg ctcccgattc    4380
gcagcgcatc gccttctatc gccttcttga cgagttcttc tgagcgggac tctgggttc    4440 gaaatgaccg accaagcgac gcccaacctg ccatcacgat ggccgcaata aaatatcttt    4500
attttcatta catctgtgtg ttggtttttt gtgtgaagat ccgcgtatgg tgcactctca    4560
gtacaatctg ctctgatgcc gcatagttaa gccagccccg acacccgcca cacccgctg    4620 acgcgccctg acgggcttgt ctgctcccgg catccgctta cagacaagct gtgaccgtct    4680
ccgggagctg catgtgtcag aggttttcac cgtcatcacc gaaacgcgcg agacgaaagg    4740
gcctcgtgat acgcctattt ttataggtta atgtcatgat aataatggtt tcttagacgt    4800
caggtggcac ttttcgggga atgtgcgcg gaacccctat ttgtttattt ttctaaatac    4860
attcaaatat gtatccgctc atgagacaat aaccctgata aatgcttcaa taatattgaa    4920
aaaggaagag tatgagtatt caacatttcc gtgtcgccct tattccctt tttgcggcat    4980 tttgccttcc tgtttttgct cacccagaaa cgctggtgaa agtaaaagat gctgaagatc    5040
agttgggtgc acgagtgggt tacatcgaac tggatctcaa cagcggtaag atccttgaga    5100
gttttcgccc cgaagaacgt tttccaatga tgagcacttt taaagttctg ctatgtggcg    5160
cggtattatc ccgtattgac gccgggcaag agcaactcgg tcgccgcata cactattctc    5220
```

```
agaatgactt ggttgagtac tcaccagtca cagaaaagca tcttacggat ggcatgacag    5280
taagagaatt atgcagtgct gccataacca tgagtgataa cactgcggcc aacttacttc    5340
tgacaacgat cggaggaccg aaggagctaa ccgcttttt gcacaacatg ggggatcatg     5400
taactcgcct tgatcgttgg aaccggagc tgaatgaagc cataccaaac gacgagcgtg     5460
acaccacgat gcctgtagca atggcaacaa cgttgcgcaa actattaact ggcgaactac    5520
ttactctagc ttcccggcaa caattaatag actggatgga ggcggataaa gttgcaggac    5580
cacttctgcg ctcggccctt ccggctggct ggtttattgc tgataaatct ggagccggtg    5640
agcgtgggtc tcgcggtatc attgcagcac tggggccaga tggtaagccc tcccgtatcg    5700
tagttatcta cacgacgggg agtcaggcaa ctatggatga acgaaataga cagatcgctg    5760
agataggtgc ctcactgatt aagcattggt aactgtcaga ccaagtttac tcatatatac    5820
tttagattga tttaaaactt cattttaat ttaaaggat ctaggtgaag atccttttg       5880 ataatctcat gaccaaaatc ccttaacgtg agttttcgtt ccactgagcg tcagacccg     5940 tagaaaagat caaaggatct tcttgagatc cttttttct gcgcgtaatc tgctgcttgc     6000
aaacaaaaaa accaccgcta ccagcggtgg tttgtttgcc ggatcaagag ctaccaactc    6060 ttttccgaa ggtaactggc ttcagcagag cgcagatacc aaatactgtc cttctagtgt     6120
agccgtagtt aggccaccac ttcaagaact ctgtagcacc gcctacatac ctcgctctgc    6180
taatcctgtt accagtggct gctgccagtg gcgataagtc gtgtcttacc gggttggact    6240
caagacgata gttaccggat aaggcgcagc ggtcgggctg aacggggggt tcgtgcacac    6300
agcccagctt ggagcgaacg acctacaccg aactgagata cctacagcgt gagctatgag    6360
aaagcgccac gcttcccgaa gggagaaagg cggacaggta tccggtaagc ggcagggtcg    6420
gaacaggaga gcgcacgagg gagcttccag ggggaaacgc ctggtatctt tatagtcctg    6480
tcgggtttcg ccacctctga cttgagcgtc gatttttgtg atgctcgtca ggggggcgga    6540
gcctatggaa aaacgccagc aacgcggcct ttttacggtt cctggccttt tgctggcctt    6600
ttgctcacat ggctcgacag atct                                           6624
```

<210> SEQ ID NO 103  
<211> LENGTH: 6723  
<212> TYPE: DNA  
<213> ORGANISM: Artificial Sequence  
<220> FEATURE:  
<223> OTHER INFORMATION: pTarget GLucON Lambda Bovine

<400> SEQUENCE: 103

```
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg accccgccc attgacgtca taatgacgt atgttcccat       300 agtaacgcca atagggactt tccattgacg tcaatgggtg gagtatttac ggtaaactgc     360
ccacttggca gtacatcaag tgtatcatat gccaagtccg cccctattg acgtcaatga     420 cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca agtctccacc ccattgacgt    600
```

```
caatgggagt tgttttggc accaaaatca acgggacttt ccaaaatgtc gtaacaactg     660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaaaattg gatctccatt cgccattcag   1080
gctgcgcaac tgctgggaag gacgatcaga gcgggcctct tcgctattac gccagctggc   1140
gaaagggacg tggcaagcaa ggcgattaag ttgagttacg ccaggatttt cccagtcacg   1200
acgttgtaaa acgacggcca gagaattata atacgactca ctatagggcg aattcgctag   1260
cgccgccacc atgggagtca agttctgtt tgccctgatc tgcatcgctg tggccgaggc   1320
caagcccacc gagaacaacg aagacttcaa catcgtggcc gtggccagca ctttgcgac    1380 cacggatctc gatgctgacc gagggaagtt gcccggcaag aagctgccgc tggaggtgct   1440
caaagagatg gaagccaatg cccggaaagc tggctgcacc aggggctgtc tgatctgcct   1500
gtcccacatc aagtgcacgc ccaagatgaa gaagtggctc ccaggacgct gccacaccta   1560
cgaaggcgac aaagagtccg cacagggcgg catagcgag gcgatcgtcg atattcctga    1620
gattcctggg ttcaaggact tggagccaat ggagcagttc atcgcacagg tcgatctgtg   1680
tgtggactgc acaactggct gcctcaaagg gcttgccaac gtgcagtgtt ctgacctgct   1740
caagaagtgg ctgccgcaac gctgtgcgac cttgccagc aagatccagg ccaggtgga    1800 caagatcaag ggggccggtg gtgacgggcc aggacagga gcagttcctg tgccctctgc    1860
ccccagggcc ctcccacctg ccaggggctg ccacgtggcc cagttcaagt ctctgtcccc   1920
tcaagagctg caggccttca agacggccag ggatgccttt gaagactcgt tcttgccaaa   1980
ggactgggac tgcagcaccc acctttcccc caggaccccgg gacctgaagc acctgcaggt   2040
gtgggagcgc cctgtggctc tggaggcaga gctggccctg acactgacgg tcctggaggc   2100
catggctaac tcatccctgg ccacagcct ggagcagccc cttctcacgc tgcagaacat    2160
ccactccaag ctccaggcct gtgtcccagc tcagcccaca gcaagctcca ggccccgggg   2220
ccgcctccac cactggctgc accgcctcca ggaggcccgg aaggagtccc aggactgcct   2280
cgaagcctct gtgatgttca acctcctccg cctcctcacc cgggacctga atgtgttgc    2340 cagcggagac cagtgtgtct gagcggccgc gaattccaag cttgagtatt ctatcgtgtc   2400
acctaaataa cttggcgtaa tcatggtcat atctgtttcc tgtgtgaaat tgttatccgc   2460
tcacaattcc acacaacata cgagccggaa gcataaagtg taaagcctgg ggtgcctaat   2520
gagtgagcta actcacatta attgcgttgc gcgatgcttc cattttgtga gggttaatgc    2580
ttcgagaaga catgataaga tacattgatg agtttggaca aaccacaaca agaatgcagt    2640
gaaaaaaatg ctttatttgt gaaatttgtg atgctattgc tttatttgta accattataa    2700
gctgcaataa acaagttaac aacaacaatt gcattcattt tatgtttcag gttcaggggg   2760
agatgtggga ggttttttaa agcaagtaaa acctctacaa atgtggtaaa atccgataag   2820
gatcgattcc ggagcctgaa tggcgaatgg acgcgccctg tagcggcgca ttaagcgcgg    2880
cgggtgtggt ggttacgcgc acgtgaccgc tacacttgcc agcgccctag cgcccgctcc    2940
tttcgctttc ttcccttcct ttctcgccac gttcgccggc tttccccgtc aagctctaaa    3000
```

```
tcggggctc cctttagggt tccgatttag tgctttacgg cacctcgacc ccaaaaaact   3060
tgattagggt gatggttcac gtagtgggcc atcgccctga tagacggttt ttcgcccttt   3120
gacgttggag tccacgttct ttaatagtgg actcttgttc caaactggaa caacactcaa   3180
ccctatctcg gtctattctt ttgatttata agggattttg ccgatttcgg cctattggtt   3240
aaaaaatgag ctgatttaac aaaaatttaa cgcgaatttt aacaaaatat taacgcttac   3300
aatttcgcct gtgtaccttc tgaggcgaaa agaaccagct gtggaatgtg tgtcagttag   3360
ggtgtggaaa gtccccaggc tccccagcag gcagaagtat gcaaagcatg catctcaatt   3420
agtcagcaac caggtgtgga agtccccag gctcccagc aggcagaagt atgcaaagca   3480
tgcatctcaa ttagtcagca accatagtcc cgcccctaac tccgcccatc ccgcccctaa   3540
ctccgcccag ttccgcccat tctccgcccc atggctgact aattttttt atttatgcag   3600
aggccgaggc cgcctcggcc tctgagctat tccagaagta gtgaggaggc ttttttggag   3660
gcctaggctt ttgcaaaaag cttgattctt ctgacacaac agtctcgaac ttaaggctag   3720
agccaccatg attgaacaag atggattgca cgcaggttct ccggccgctt gggtggagag   3780
gctattcggc tatgactggg cacaacagac aatcggctgc tctgatgccg ccgtgttccg   3840
gctgtcagcg caggggcgcc cggttctttt tgtcaagacc gacctgtccg gtgccctgaa   3900
tgaactgcag gacgaggcag cgcggctatc gtggctggcc acgacgggcg ttccttgcgc   3960
agctgtgctc gacgttgtca ctgaagcggg aagggactgg ctgctattgg gcgaagtgcc   4020
ggggcaggat ctcctgtcat ctcaccttgc tcctgccgag aaagtatcca tcatggctga   4080
tgcaatgcgg cggctgcata cgcttgatcc ggctacctgc ccattcgacc accaagcgaa   4140
acatcgcatc gagcgagcac gtactcggat ggaagccggt cttgtcgatc aggatgatct   4200
ggacgaagag catcaggggc tcgcgccagc cgaactgttc gccaggctca aggcgcgcat   4260
gcccgacggc gaggatctcg tcgtgaccca tggcgatgcc tgcttgccga atatcatggt   4320
ggaaaatggc cgcttttctg gattcatcga ctgtggccgg ctgggtgtgg cggaccgcta   4380
tcaggacata gcgttggcta cccgtgatat tgctgaagag cttggcggcg aatgggctga   4440
ccgcttcctc gtgctttacg gtatcgccgc tcccgattcg cagcgcatcg ccttctatcg   4500
ccttcttgac gagttcttct gagcgggact ctggggttcg aaatgaccga ccaagcgacg   4560
cccaacctgc catcacgatg gccgcaataa aatatcttta ttttcattac atctgtgtgt   4620
tggttttttg tgtgaagatc cgcgtatggt gcactctcag tacaatctgc tctgatgccg   4680
catagttaag ccagccccga cacccgccaa cacccgctga cgcgccctga cgggcttgtc   4740
tgctcccggc atccgcttac agacaagctg tgaccgtctc cgggagctgc atgtgtcaga   4800
ggttttcacc gtcatcaccg aaacgcgcga cgcgaagggg cctcgtgata cgcctatttt   4860
tataggttaa tgtcatgata ataatggttt cttagacgtc aggtggcact tttcggggaa   4920
atgtgcgcg aacccctatt tgtttatttt tctaaataca ttcaaatatg tatccgctca   4980
tgagacaata accctgataa atgcttcaat aatattgaaa aggaagagt atgagtattc   5040
aacatttccg tgtcgccctt attccctttt tgcggcatt tgccttcct gttttgctc   5100
acccagaaac gctggtgaaa gtaaaagatg ctgaagatca gttgggtgca cgagtgggtt   5160
acatcgaact ggatctcaac agcggtaaga tccttgagag ttttcgcccc gaagaacgtt   5220
ttccaatgat gagcactttt aaagttctgc tatgtgcgc ggtattatcc cgtattgacg   5280
ccgggcaaga gcaactcggt cgccgcatac actattctca gaatgacttg gttgagtact   5340
```

```
caccagtcac agaaaagcat cttacggatg gcatgacagt aagagaatta tgcagtgctg    5400
ccataaccat gagtgataac actgcggcca acttacttct gacaacgatc ggaggaccga    5460
aggagctaac cgcttttttg cacaacatgg gggatcatgt aactcgcctt gatcgttggg    5520
aaccggagct gaatgaagcc ataccaaacg acgagcgtga caccacgatg cctgtagcaa    5580
tggcaacaac gttgcgcaaa ctattaactg gcgaactact tactctagct tcccggcaac    5640
aattaataga ctggatggag gcggataaag ttgcaggacc acttctgcgc tcggcccttc    5700
cggctggctg gtttattgct gataaatctg gagccggtga gcgtgggtct cgcggtatca    5760
ttgcagcact ggggccagat ggtaagccct cccgtatcgt agttatctac acgacgggga    5820
gtcaggcaac tatggatgaa cgaaatagac agatcgctga gataggtgcc tcactgatta    5880
agcattggta actgtcagac caagtttact catatatact ttagattgat ttaaaacttc    5940 attttaatt taaaaggatc taggtgaaga tcctttttga taatctcatg accaaaatcc    6000
cttaacgtga gttttcgttc cactgagcgt cagaccccgt agaaaagatc aaaggatctt    6060
cttgagatcc ttttttctg cgcgtaatct gctgcttgca acaaaaaaa ccaccgctac    6120 cagcggtggt ttgtttgccg gatcaagagc taccaactct ttttccgaag gtaactggct    6180
tcagcagagc gcagatacca atactgtcc ttctagtgta gccgtagtta ggccaccact    6240
tcaagaactc tgtagcaccg cctacatacc tcgctctgct aatcctgtta ccagtggctg    6300
ctgccagtgg cgataagtcg tgtcttaccg ggttggactc aagacgatag ttaccggata    6360
aggcgcagcg gtcgggctga acggggggtt cgtgcacaca gcccagcttg gagcgaacga    6420
cctacaccga actgagatac ctacagcgtg agctatgaga agcgccacg cttcccgaag    6480 ggagaaaggc ggacaggtat ccggtaagcg gcagggtcgg aacaggagag cgcacgaggg    6540
agcttccagg gggaaacgcc tggtatcttt atagtcctgt cgggtttcgc cacctctgac    6600
ttgagcgtcg atttttgtga tgctcgtcag ggggcggag cctatggaaa aacgccagca    6660
acgcggcctt tttacggttc ctggcctttt gctggccttt tgctcacatg gctcgacaga    6720
tct                                                                  6723
```

<210> SEQ ID NO 104
<211> LENGTH: 6201
<212> TYPE: DNA
<213> ORGANISM: Artificial Sequence
<220> FEATURE:
<223> OTHER INFORMATION: pTarget porcine interferon alpha

<400> SEQUENCE: 104

```
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca aacttacgg taaatggccc      240 gcctggctga ccgcccaacg acccccgccc attgacgtca ataatgacgt atgttcccat     300
agtaacgcca tagggacttt ccattgacg tcaatgggtg gagtatttac ggtaaactgc      360
ccacttggca gtacatcaag tgtatcatat gccaagtccg cccctattg acgtcaatga     420 cggtaaatgg cccgcctggc attatgccca gtacatgacc ttacgggact tcctacttg     480 gcagtacatc tacgtattag tcatcgctat taccatggtg atgcggtttt ggcagtacac     540
caatgggcgt ggatagcggt ttgactcacg gggatttcca gtctccacc ccattgacgt     600 caatgggagt ttgttttggc accaaaatca acgggacttt ccaaaatgtc gtaacaactg     660
```

```
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac    1020
aggtgtccac tcccagttca attacagctc ttaaaaattg gatctccatt cgccattcag    1080
gctgcgcaac tgctgggaag gacgatcaga gcgggcctct tcgctattac gccagctggc    1140
gaaagggacg tggcaagcaa ggcgattaag ttgagttacg ccaggatttt cccagtcacg    1200
acgttgtaaa acgacggcca gagaattata atacgactca ctatagggcg gatccgctag    1260
cgccgccacc atggccccaa cctcagcctt cctcacggcc ctggtgctac tcagctgcaa    1320
tgccatctgc tctctgggct gtgacctgcc tcagacccac agcctggctc acaccagagc    1380
cctgaggctc ctggcacaaa tgaggagaat ctctcccttc cctgcctgg accacagaag     1440 ggactttggt tcccctcatg aggcttttgg gggcaaccag gtccagaagg ctcaagccat    1500
ggctctggtg catgagatgc tccagcagac cttccagctc ttcagcacag agggctcggc    1560
tgctgcctgg aatgagagcc tcctgcacca gttctgcact ggactggatc agcagctcag    1620
ggacctggaa gcctgtgtca tgcaggaggc ggggctggaa gggaccccccc tgctggagga   1680 ggactccatc ctggctgtga ggaaatactt ccacagactc acccctctatc tgcaagagaa   1740 gagctacagc ccctgtgcct gggagatcgt cagggcagaa gtcatgagat ccttctcttc    1800
ctccagaaac ctgcaagaca gactcaggaa gaaggagtga gcggccgcga attccaagct    1860
tgagtattct atcgtgtcac ctaaataact tggcgtaatc atggtcatat ctgtttcctg    1920
tgtgaaattg ttatccgctc acaattccac acaacatacg agccgaagc ataaagtgta     1980 aagcctgggg tgcctaatga gtgagctaac tcacattaat tgcgttgcgc gatgcttcca    2040
ttttgtgagg gttaatgctt cgagaagaca tgataagata cattgatgag tttggacaaa    2100
ccacaacaag aatgcagtga aaaaaatgct ttatttgtga aatttgtgat gctattgctt    2160
tatttgtaac cattataagc tgcaataaac aagttaacaa caacaattgc attcatttta    2220
tgtttcaggt tcaggggggag atgtgggagg ttttttaaag caagtaaaac ctctacaaat   2280
gtggtaaaat ccgataagga tcgattccgg agcctgaatg gcgaatggac gcgccctgta    2340
gcggcgcatt aagcgcggcg ggtgtggtgg ttacgcgcac gtgaccgcta cacttgccag    2400
cgccctagcg cccgctcctt tcgctttctt cccttccttt ctcgccacgt tcgccggctt    2460
tccccgtcaa gctctaaatc gggggctccc tttagggttc cgatttagtg ctttacggca    2520
cctcgacccc aaaaaacttg attagggtga tggttcacgt agtgggccat cgccctgata    2580
gacggttttt cgccctttga cgttggagtc acgttctttt aatagtggac tcttgttcca    2640
aactggaaca cactcaacc ctatctcggt ctattctttt gatttataag ggattttgcc     2700
gatttcggcc tattggttaa aaaatgagct gatttaacaa aaatttaacg cgaattttaa    2760
caaaatatta cgcttacaa tttcgcctgt gtaccttctg aggcggaaag aaccagctgt     2820
ggaatgtgtg tcagttaggg tgtggaaagt ccccaggctc cccagcaggc agaagtatgc    2880
aaagcatgca tctcaattag tcagcaacca ggtgtggaaa gtcccaggc tccccagcag     2940 gcagaagtat gcaaagcatg catctcaatt agtcagcaac catagtcccg cccctaactc    3000
```

```
cgcccatccc gccccctaact ccgcccagtt ccgcccattc tccgcccccat ggctgactaa   3060 tttttttat ttatgcagag gccgaggccg cctcggcctc tgagctattc cagaagtagt     3120
gaggaggctt ttttggaggc ctaggctttt gcaaaaagct tgattcttct gacacaacag    3180
tctcgaactt aaggctagag ccaccatgat tgaacaagat ggattgcacg caggttctcc    3240
ggccgcttgg gtggagaggc tattcggcta tgactgggca caacagacaa tcggctgctc    3300
tgatgccgcc gtgttccggc tgtcagcgca ggggcgcccg gttcttttg tcaagaccga     3360 cctgtccggt gccctgaatg aactgcagga cgaggcagcg cggctatcgt ggctggccac    3420
gacgggcgtt ccttgcgcag ctgtgctcga cgttgtcact gaagcgggaa gggactggct    3480
gctattgggc gaagtgccgg ggcaggatct cctgtcatct caccttgctc ctgccgagaa    3540
agtatccatc atggctgatg caatgcggcg gctgcatacg cttgatccgg ctacctgccc    3600
attcgaccac caagcgaaac atcgcatcga gcgagcacgt actcggatgg aagccggtct    3660
tgtcgatcag gatgatctgg acgaagagca tcagggggctc gcgccagccg aactgttcgc    3720
caggctcaag gcgcgcatgc ccgacggcga ggatctcgtc gtgacccatg gcgatgcctg    3780
cttgccgaat atcatggtgg aaaatggccg cttttctgga ttcatcgact gtggccggct    3840
gggtgtggcg gaccgctatc aggacatagc gttggctacc cgtgatattg ctgaagagct    3900
tggcggcgaa tgggctgacc gcttcctcgt gctttacggt atcgccgctc ccgattcgca    3960
gcgcatcgcc ttctatcgcc ttcttgacga gttcttctga gcgggactct ggggttcgaa    4020
atgaccgacc aagcgacgcc caacctgcca tcacgatggc cgcaataaaa tatctttatt    4080
ttcattacat ctgtgtgttg gttttttgtg tgaagatccg cgtatggtgc actctcagta    4140
caatctgctc tgatgccgca tagttaagcc agccccgaca cccgccaaca cccgctgacg    4200
cgccctgacg ggcttgtctg ctcccggcat ccgcttacag acaagctgtg accgtctccg    4260
ggagctgcat gtgtcagagg ttttcaccgt catcaccgaa acgcgcgaga cgaaagggcc    4320
tcgtgatacg cctatttta taggttaatg tcatgataat aatggtttct tagacgtcag    4380
gtggcacttt tcggggaaat gtgcgcggaa cccctatttg tttatttttc taaatacatt    4440
caaatatgta tccgctcatg agacaataac cctgataaat gcttcaataa tattgaaaaa    4500
ggaagagtat gagtattcaa catttccgtg tcgcccttat tcccttttt gcggcatttt     4560 gccttcctgt ttttgctcac ccagaaacgc tggtgaaagt aaaagatgct gaagatcagt    4620
tgggtgcacg agtgggttac atcgaactgg atctcaacag cggtaagatc cttgagagtt    4680
ttcgccccga agaacgtttt ccaatgatga gcacttttaa agttctgcta tgtggcgcgg    4740
tattatcccg tattgacgcc gggcaagagc aactcggtcg ccgcatacac tattctcaga    4800
atgacttggt tgagtactca ccagtcacag aaaagcatct tacgatggc atgacagtaa     4860 gagaattatg cagtgctgcc ataaccatga gtgataacac tgcggccaac ttacttctga    4920
caacgatcgg aggaccgaag gagctaaccg cttttttgca caacatgggg gatcatgtaa    4980
ctcgccttga tcgttgggaa ccggagctga atgaagccat accaaacgac gagcgtgaca    5040
ccacgatgcc tgtagcaatg gcaacaacgt tgcgcaaact attaactggc gaactactta    5100
ctctagcttc ccggcaacaa ttaatagact ggatggaggc ggataaagtt gcaggaccac    5160
ttctgcgctc ggcccttccg gctggctggt ttattgctga taaatctgga gccggtgagc    5220
gtgggtctcg cggtatcatt gcagcactgg ggccagatgg taagccctcc cgtatcgtag    5280
ttatctacac gacggggagt caggcaacta tggatgaacg aaatagacag atcgctgaga    5340
taggtgcctc actgattaag cattggtaac tgtcagacca agtttactca tatatacttt    5400
```

```
agattgattt aaaacttcat ttttaattta aaaggatcta ggtgaagatc cttttttgata    5460 atctcatgac caaaatccct taacgtgagt tttcgttcca ctgagcgtca gaccccgtag    5520
aaaagatcaa aggatcttct tgagatcctt ttttttctgcg cgtaatctgc tgcttgcaaa    5580
caaaaaaacc accgctacca gcggtggttt gtttgccgga tcaagagcta ccaactcttt    5640
ttccgaaggt aactggcttc agcagagcgc agataccaaa tactgtcctt ctagtgtagc    5700
cgtagttagg ccaccacttc aagaactctg tagcaccgcc tacatacctc gctctgctaa    5760
tcctgttacc agtggctgct gccagtggcg ataagtcgtg tcttaccggg ttggactcaa    5820
gacgatagtt accggataag cgcagcggt cgggctgaac ggggggttcg tgcacacagc     5880
ccagcttgga gcgaacgacc tacaccgaac tgagatacct acagcgtgag ctatgagaaa    5940
gcgccacgct tcccgaaggg agaaaggcgg acaggtatcc ggtaagcggc agggtcggaa    6000
caggagagcg cacgagggag cttccagggg gaaacgcctg gtatctttat agtcctgtcg    6060
ggtttcgcca cctctgactt gagcgtcgat ttttgtgatg ctcgtcaggg gggcggagcc    6120
tatggaaaaa cgccagcaac gcggccttt tacggttcct ggccttttgc tggccttttg     6180
ctcacatggc tcgacagatc t                                               6201
```

<210> SEQ ID NO 105
<211> LENGTH: 6192
<212> TYPE: DNA
<213> ORGANISM: Artificial Sequence
<220> FEATURE:
<223> OTHER INFORMATION: pTarget Porcine Interferon Beta

<400> SEQUENCE: 105

```
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg accccgccc attgacgtca ataatgacgt atgttcccat     300
agtaacgcca tagggacttt tccattgacg tcaatgggtg gagtatttac ggtaaactgc     360
ccacttggca gtacatcaag tgtatcatat gccaagtccg ccccctattg acgtcaatga     420
cggtaaatgg cccgcctggc attatgccca gtacatgacc ttacgggact ttcctacttg     480
gcagtacatc tacgtattag tcatcgctat taccatggtg atgcggtttt ggcagtacac     540
caatgggcgt ggatagcggt ttgactcacg gggatttcca agtctccacc ccattgacgt     600
caatgggagt ttgttttggc accaaaatca acgggacttt ccaaaatgtc gtaacaactg     660
cgatcgcccg ccccgttgac gcaaatgggc ggtaggcgtg tacggtggga ggtctatata     720
agcagagctc gtttagtgaa ccgtcagatc actagaagct ttattgcggt agtttatcac     780
agttaaattg ctaacgcagt cagtgcttct gacacaacag tctcgaactt aagctgcagt     840
gactctctta aggtagcctt gcagaagttg gtcgtgaggc actgggcagg taagtatcaa     900
ggttacaaga caggtttaag gagaccaata gaaactgggc ttgtcgagac agagaagact     960
cttgcgtttc tgataggcac ctattggtct tactgacatc cactttgcct ttctctccac    1020
aggtgtccac tcccagttca attacagctc ttaaaaattg gatctccatt cgccattcag    1080
gctgcgcaac tgctgggaag gacgatcaga gcgggcctct tcgctattac gccagctggc    1140
gaaagggacg tggcaagcaa ggcgattaag ttgagttacg ccaggatttt cccagtcacg    1200
```

```
acgttgtaaa acgacggcca gagaattata atacgactca ctatagggcg gatccgctag      1260
cgccgccacc atggctaaca agtgcatcct ccaaatcgct ctcctgatgt gtttctccac      1320
cacagctctt tccatgagct atgatgtgct tcgataccaa caaaggagca gcaatttggc      1380
atgtcagaag ctcctgggac agttgcctgg gactcctcaa tattgcctcg aagataggat      1440
gaactttgag gtccctgagg agattatgca accaccacaa ttccagaagg aagatgcagt      1500
attgattatc cacgagatgc tccagcagat cttcggcatt tcagaagaa atttctctag       1560 cactggctgg aatgaaaccg tcattaagac tatccttgtg gaacttgatg gcagatgga       1620 tgacctggag acaatcctgg aggaaatcat ggaggaggaa aatttcccca ggggagacat      1680
gaccattctt cacctgaaga aatattactt gagcattctg cagtacctga agtccaagga      1740
gtacagaagc tgtgcctgga cagtcgtcca agtggaaatc ctcaggaact tttcttcctt     1800
taacagactt acagattacc tccggaactg agcggccgcg aattccaagc ttgagtattc      1860
tatcgtgtca cctaaataac ttggcgtaat catggtcata tctgtttcct gtgtgaaatt     1920
gttatccgct cacaattcca cacaacatac gagccggaag cataaagtgt aaagcctggg     1980
gtgcctaatg agtgagctaa ctcacattaa ttgcgttgcg cgatgcttcc attttgtgag     2040
ggttaatgct tcgagaagac atgataagat acattgatga gtttggacaa accacaacaa     2100
gaatgcagtg aaaaaaatgc tttatttgtg aaatttgtga tgctattgct ttatttgtaa     2160
ccattataag ctgcaataaa caagttaaca acaacaattg cattcatttt atgtttcagg     2220
ttcaggggga gatgtgggag gttttttaaa gcaagtaaaa cctctacaaa tgtggtaaaa     2280
tccgataagg atcgattccg gagcctgaat ggcgaatgga cgcgccctgt agcggcgcat     2340
taagcgcggc gggtgtggtg gttacgcgca cgtgaccgct acacttgcca gcgccctagc     2400
gcccgctcct ttcgctttct tcccttcctt tctcgccacg ttcgccggct ttccccgtca     2460
agctctaaat cgggggctcc ctttagggtt ccgatttagt gctttacggc acctcgaccc     2520
caaaaaactt gattagggtg atggttcacg tagtgggcca tcgccctgat agacggtttt     2580
tcgccctttg acgttggagt ccacgttctt taatagtgga ctcttgttcc aaactggaac     2640
aacactcaac cctatctcgg tctattcttt tgatttataa gggattttgc cgatttcggc     2700
ctattggtta aaaaatgagc tgatttaaca aaaatttaac gcgaatttta acaaaatatt     2760
aacgcttaca atttcgcctg tgtaccttct gaggcggaaa gaaccagctg tggaatgtgt     2820
gtcagttagg gtgtggaaag tccccaggct ccccagcagg cagaagtatg caaagcatgc     2880
atctcaatta gtcagcaacc aggtgtggaa agtcccagg ctccccagca ggcagaagta      2940
tgcaaagcat gcatctcaat tagtcagcaa ccatagtccc gcccctaact ccgcccatcc     3000
cgcccctaac tccgcccagt tccgcccatt ctccgcccca tggctgacta atttttttta     3060
tttatgcaga ggccgaggcc gcctcggcct ctgagctatt ccagaagtag tgaggaggct     3120
tttttggagg cctaggcttt tgcaaaaagc ttgattcttc tgacacaaca gtctcgaact     3180
taaggctaga gccaccatga ttgaacaaga tggattgcac gcaggttctc cggccgcttg     3240
ggtggagagg ctattcggct atgactgggc acaacagaca atcggctgct ctgatgccgc     3300
cgtgttccgg ctgtcagcgc aggggcgccc ggttcttttt gtcaagaccg acctgtccgg     3360
tgccctgaat gaactgcagg acgaggcagc gcggctatcg tggctggcca cgacgggcgt     3420
tccttgcgca gctgtgctcg acgttgtcac tgaagcggga agggactggc tgctattggg     3480
cgaagtgccg gggcaggatc tcctgtcatc tcaccttgct cctgccgaga aagtatccat     3540
catggctgat gcaatgcggc ggctgcatac gcttgatccg gctacctgcc cattcgacca     3600
```

```
ccaagcgaaa catcgcatcg agcgagcacg tactcggatg gaagccggtc ttgtcgatca    3660
ggatgatctg gacgaagagc atcaggggct cgcgccagcc gaactgttcg ccaggctcaa    3720
ggcgcgcatg cccgacggcg aggatctcgt cgtgacccat ggcgatgcct gcttgccgaa    3780
tatcatggtg gaaaatggcc gcttttctgg attcatcgac tgtggccggc tgggtgtggc    3840
ggaccgctat caggacatag cgttggctac ccgtgatatt gctgaagagc ttggcggcga    3900
atgggctgac cgcttcctcg tgctttacgg tatcgccgct cccgattcgc agcgcatcgc    3960
cttctatcgc cttcttgacg agttcttctg agcgggactc tggggttcga atgaccgac     4020
caagcgacgc ccaacctgcc atcacgatgg ccgcaataaa atatctttat tttcattaca    4080
tctgtgtgtt ggttttttgt gtgaagatcc gcgtatggtg cactctcagt acaatctgct    4140
ctgatgccga atagttaagc cagccccgac acccgccaac acccgctgac gcgccctgac    4200
gggcttgtct gctcccggca tccgcttaca gacaagctgt gaccgtctcc gggagctgca    4260
tgtgtcagag gttttcaccg tcatcaccga acgcgcgag acgaaagggc ctcgtgatac     4320
gcctattttt ataggttaat gtcatgataa taatggtttc ttagacgtca ggtggcactt    4380
ttcggggaaa tgtgcgcgga acccctattt gtttattttt ctaaatacat tcaaatatgt    4440
atccgctcat gagacaataa ccctgataaa tgcttcaata atattgaaaa aggaagagta    4500
tgagtattca acatttccgt gtcgccctta ttccctttttt tgcggcattt tgccttcctg    4560
tttttgctca cccagaaacg ctggtgaaag taaaagatgc tgaagatcag ttgggtgcac    4620
gagtgggtta catcgaactg gatctcaaca gcggtaagat ccttgagagt tttcgccccg    4680
aagaacgttt tccaatgatg agcacttttta aagttctgct atgtggcgcg gtattatccc    4740
gtattgacgc cgggcaagag caactcggtc gccgcataca ctattctcag aatgacttgg    4800
ttgagtactc accagtcaca gaaaagcatc ttacggatgg catgacagta agagaattat    4860
gcagtgctgc cataaccatg agtgataaca ctgcggccaa cttacttctg acaacgatcg    4920
gaggaccgaa ggagctaacc gcttttttgc acaacatggg ggatcatgta actcgccttg    4980
atcgttggga accggagctg aatgaagcca taccaaacga cgagcgtgac caccgatgc     5040
ctgtagcaat ggcaacaacg ttgcgcaaac tattaactgg cgaactactt actctagctt    5100
cccggcaaca attaatagac tggatggagg cggataaagt tgcaggacca cttctgcgct    5160
cggcccttcc ggctggctgg tttattgctg ataaatctgg agccggtgag cgtgggtctc    5220
gcggtatcat tgcagcactg gggccagatg gtaagccctc ccgtatcgta gttatctaca    5280
cgacggggag tcaggcaact atggatgaac gaaatagaca gatcgctgag ataggtgcct    5340
cactgattaa gcattggtaa ctgtcagacc aagtttactc atatatactt tagattgatt    5400
taaaacttca ttttttaattt aaaaggatct aggtgaagat cctttttgat aatctcatga    5460
ccaaaatccc ttaacgtgag ttttcgttcc actgagcgtc agaccccgta gaaaagatca    5520
aaggatcttc ttgagatcct ttttttctgc gcgtaatctg ctgcttgcaa acaaaaaaac    5580
caccgctacc agcggtggtt tgtttgccgg atcaagagct accaactctt tttccgaagg    5640
taactggctt cagcagagcg cagataccaa atactgtcct tctagtgtag ccgtagttag    5700
gccaccactt caagaactct gtagcaccgc ctacatacct cgctctgcta atcctgttac    5760
cagtggctgc tgccagtggc gataagtcgt gtcttaccgg gttggactca agacgatagt    5820
taccggataa ggcgcagcgg tcgggctgaa cggggggttc gtgcacacag cccagcttgg    5880
agcgaacgac ctacaccgaa ctgagatacc tacagcgtga gctatgagaa agcgccacgc    5940
```

```
ttcccgaagg gagaaaggcg gacaggtatc cggtaagcgg cagggtcgga acaggagagc    6000
gcacgaggga gcttccaggg ggaaacgcct ggtatcttta tagtcctgtc gggtttcgcc    6060
acctctgact tgagcgtcga ttttgtgat gctcgtcagg ggggcggagc ctatggaaaa    6120
acgccagcaa cgcggccttt ttacggttcc tggccttttg ctggcctttt gctcacatgg    6180
ctcgacagat ct                                                        6192

<210> SEQ ID NO 106
<211> LENGTH: 6124
<212> TYPE: DNA
<213> ORGANISM: Artificial Sequence
<220> FEATURE:
<223> OTHER INFORMATION: pTarget Bovine Interferon Gamma

<400> SEQUENCE: 106
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca aacttacgg taaatggccc      240 gcctggctga ccgcccaacg accccgcc attgacgtca ataatgacgt atgttcccat      300
agtaacgcca atagggactt tccattgacg tcaatgggtg gagtatttac ggtaaactgc     360
ccacttggca gtacatcaag tgtatcatat gccaagtccg cccctattg acgtcaatga     420 cggtaaatgg cccgcctggc attatgccca gtacatgacc ttacgggact ttcctacttg     480
gcagtacatc tacgtattag tcatcgctat taccatggtg atgcggtttt ggcagtacac     540
caatgggcgt ggatagcggt ttgactcacg gggatttcca agtctccacc ccattgacgt     600
caatgggagt ttgttttggc accaaaatca acgggacttt ccaaaatgtc gtaacaactg     660
cgatcgcccg ccccgttgac gcaaatgggc ggtaggcgtg tacggtggga ggtctatata     720
agcagagctc gtttagtgaa ccgtcagatc actagaagct ttattgcggt agtttatcac     780
agttaaattg ctaacgcagt cagtgcttct gacacaacag tctcgaactt aagctgcagt     840
gactctctta aggtagcctt gcagaagttg gtcgtgaggc actgggcagg taagtatcaa     900
ggttacaaga caggtttaag gagaccaata gaaactgggc ttgtcgagac agagaagact     960
cttgcgtttc tgataggcac ctattggtct tactgcatc cactttgcct ttctctccac    1020
aggtgtccac tcccagttca attacagctc ttaaaaattg gatctccatt cgccattcag    1080
gctgcgcaac tgctgggaag gacgatcaga gcgggcctct cgctattac gccagctggc    1140 gaaagggacg tggcaagcaa ggcgattaag ttgagttacg ccaggatttt cccagtcacg    1200
acgttgtaaa acgacggcca gagaattata atacgactca ctatagggcg gatccgctag    1260
cgccgccacc atgaaatata aagctatt cttagcttta ctgctctgtg gcttttggg     1320 tttttctggt tcttatggcc agggccaatt ttttagagaa atagaaaact taaggagta     1380 ttttaatgca agtagcccag atgtagctaa gggtgggcct ctcttctcag aaattttgaa    1440
gaattggaaa gatgaaagtg acaaaaaaat tattcagagc caaattgtct ccttctactt    1500
caaactcttt gaaaacctca agataaacca ggtcattcaa aggagcatgg atataatcaa    1560
gcaagacatg tttcagaagt tcttgaatgg cagctctgag aaactggagg acttcaaaaa    1620
gctgattcaa attccggtgg atgatctcca gatccagcgc aaagccataa atgaactcat    1680
caaagtgatg aatgacctgt caccaaaatc taacctcaga aagcggaaga gaagtcagaa    1740
tctctttcga ggccggagag catcaacgta agaattccaa gcttgagtat tctatcgtgt    1800
```

```
cacctaaata acttggcgta atcatggtca tatctgtttc ctgtgtgaaa ttgttatccg    1860
ctcacaattc cacacaacat acgagccgga agcataaagt gtaaagcctg ggtgcctaa    1920 tgagtgagct aactcacatt aattgcgttg cgcgatgctt ccattttgtg agggttaatg    1980
cttcgagaag acatgataag atacattgat gagtttggac aaaccacaac aagaatgcag    2040
tgaaaaaaat gctttatttg tgaaatttgt gatgctattg ctttatttgt aaccattata    2100
agctgcaata aacaagttaa caacaacaat tgcattcatt ttatgtttca ggttcagggg    2160
gagatgtggg aggttttta aagcaagtaa aacctctaca aatgtggtaa aatccgataa    2220
ggatcgattc cggagcctga atggcgaatg acgcgccct gtagcggcgc attaagcgcg    2280
gcgggtgtgg tggttacgcg cacgtgaccg ctacacttgc cagcgcccta gcgcccgctc    2340
ctttcgcttt cttcccttcc tttctcgcca cgttcgccgg ctttccccgt caagctctaa    2400
atcgggggct ccctttaggg ttccgattta gtgctttacg gcacctcgac cccaaaaaac    2460
ttgattaggg tgatggttca cgtagtgggc catcgccctg atagacggtt tttcgccctt    2520
tgacgttgga gtccacgttc tttaatagtg gactcttgtt ccaaactgga acaacactca    2580
accctatctc ggtctattct tttgatttat aagggatttt gccgatttcg gcctattggt    2640
taaaaaatga gctgatttaa caaaaattta acgcgaattt taacaaaata ttaacgctta    2700
caatttcgcc tgtgtaccct ctgaggcgga aagaaccagc tgtggaatgt gtgtcagtta    2760
gggtgtggaa agtccccagg ctccccagca ggcagaagta tgcaaagcat gcatctcaat    2820
tagtcagcaa ccaggtgtgg aaagtcccca ggctccccag caggcagaag tatgcaaagc    2880
atgcatctca attagtcagc aaccatagtc ccgcccctaa ctccgcccat cccgcccta    2940 actccgccca gttccgccca ttctccgccc catggctgac taatttttt tatttatgca    3000 gaggccgagg ccgcctcggc ctctgagcta ttccagaagt agtgaggagg cttttttgga    3060
ggcctaggct tttgcaaaaa gcttgattct tctgacacaa cagtctcgaa cttaaggcta    3120
gagccaccat gattgaacaa gatggattgc acgcaggttc tccggccgct tgggtggaga    3180
ggctattcgg ctatgactgg gcacaacaga caatcggctg ctctgatgcc gccgtgttcc    3240
ggctgtcagc gcaggggcgc ccggttcttt ttgtcaagac cgacctgtcc ggtgccctga    3300
atgaactgca ggacgaggca gcgcggctat cgtggctggc cacgacgggc gttccttgcg    3360
cagctgtgct cgacgttgtc actgaagcgg gaagggactg gctgctattg ggcgaagtgc    3420
cggggcagga tctcctgtca tctcaccttg ctcctgccga gaaagtatcc atcatggctg    3480
atgcaatgcg gcggctgcat acgcttgatc cggctacctg cccattcgac caccaagcga    3540
aacatcgcat cgagcgagca cgtactcgga tggaagccgg tcttgtcgat caggatgatc    3600
tggacgaaga gcatcagggg ctcgcgccag ccgaactgtt cgccaggctc aaggcgcgca    3660
tgcccgacgg cgaggatctc gtcgtgaccc atggcgatgc ctgcttgccg aatatcatgg    3720
tggaaaatgg ccgcttttct ggattcatcg actgtggccg ctgggtgtg gcggaccgct    3780 atcaggacat agcgttggct acccgtgata ttgctgaaga gcttggcggc gaatgggctg    3840
accgcttcct cgtgctttac ggtatcgccg ctcccgattc gcagcgcatc gccttctatc    3900
gccttcttga cgagttcttc tgagcgggac tctggggttc gaaatgaccg accaagcgac    3960
gcccaacctg ccatcacgat ggccgcaata aaatatcttt attttcatta catctgtgtg    4020
ttggtttttt gtgtgaagat ccgcgtatgg tgcactctca gtacaatctg ctctgatgcc    4080
gcatagttaa gccagccccg acacccgcca acacccgctg acgcgccctg acgggcttgt    4140
```

```
ctgctcccgg catccgctta cagacaagct gtgaccgtct ccgggagctg catgtgtcag    4200
aggttttcac cgtcatcacc gaaacgcgcg agacgaaagg gcctcgtgat acgcctattt    4260
ttataggtta atgtcatgat aataatggtt tcttagacgt caggtggcac ttttcgggga    4320
aatgtgcgcg gaacccctat ttgtttattt ttctaaatac attcaaatat gtatccgctc    4380
atgagacaat aaccctgata aatgcttcaa taatattgaa aaaggaagag tatgagtatt    4440
caacatttcc gtgtcgccct tattccctttt tttgcggcat tttgccttcc tgttttttgct    4500 cacccagaaa cgctggtgaa agtaaaagat gctgaagatc agttgggtgc acgagtgggt    4560
tacatcgaac tggatctcaa cagcggtaag atccttgaga gttttcgccc cgaagaacgt    4620
tttccaatga tgagcacttt taaagttctg ctatgtggcg cggtattatc ccgtattgac    4680
gccgggcaag agcaactcgg tcgccgcata cactattctc agaatgactt ggttgagtac    4740
tcaccagtca cagaaaagca tcttacggat ggcatgacag taagagaatt atgcagtgct    4800
gccataacca tgagtgataa cactgcggcc aacttacttc tgacaacgat cggaggaccg    4860
aaggagctaa ccgcttttt gcacaacatg ggggatcatg taactcgcct tgatcgttgg    4920
gaaccggagc tgaatgaagc cataccaaac gacgagcgtg acaccacgat gcctgtagca    4980
atggcaacaa cgttgcgcaa actattaact ggcgaactac ttactctagc ttcccggcaa    5040
caattaatag actggatgga ggcggataaa gttgcaggac cacttctgcg ctcggccctt    5100
ccggctggct ggtttattgc tgataaatct ggagccggtg agcgtgggtc tcgcggtatc    5160
attgcagcac tggggccaga tggtaagccc tcccgtatcg tagttatcta cacgacgggg    5220
agtcaggcaa ctatggatga acgaaataga cagatcgctg agataggtgc ctcactgatt    5280
aagcattggt aactgtcaga ccaagtttac tcatatatac tttagattga tttaaaactt    5340
catttttaat ttaaaaggat ctaggtgaag atcctttttg ataatctcat gaccaaaatc    5400
ccttaacgtg agttttcgtt ccactgagcg tcagaccccg tagaaaagat caaaggatct    5460
tcttgagatc ctttttttct gcgcgtaatc tgctgcttgc aaacaaaaaa accaccgcta    5520
ccagcggtgg tttgtttgcc ggatcaagag ctaccaactc tttttccgaa ggtaactggc    5580
ttcagcagag cgcagatacc aaatactgtc cttctagtgt agccgtagtt aggccaccac    5640
ttcaagaact ctgtagcacc gcctacatac ctcgctctgc taatcctgtt accagtggct    5700
gctgccagtg gcgataagtc gtgtcttacc gggttggact caagacgata gttaccggat    5760
aaggcgcagc ggtcgggctg aacggggggt tcgtgcacac agcccagctt ggagcgaacg    5820
acctacaccg aactgagata cctacagcgt gagctatgag aaagcgccac gcttcccgaa    5880
gggagaaagg cggacaggta tccggtaagc ggcagggtcg aacaggaga gcgcacgagg    5940 gagcttccag ggggaaacgc ctggtatctt tatagtcctg tcgggtttcg ccacctctga    6000
cttgagcgtc gatttttgtg atgctcgtca ggggggcgga gcctatggaa aaacgccagc    6060
aacgcggcct ttttacggtt cctggccttt tgctggcctt tgctcacat ggctcgacag    6120 atct                                                                6124
```

<210> SEQ ID NO 107
<211> LENGTH: 6210
<212> TYPE: DNA
<213> ORGANISM: Artificial Sequence
<220> FEATURE:
<223> OTHER INFORMATION: pTarget Bovine Interferon Lambda

<400> SEQUENCE: 107

```
tcaatattgg ccattagcca tattattcat tggttatata gcataaatca atattggcta     60
```

-continued

```
ttggccattg catacgttgt atctatatca taatatgtac atttatattg gctcatgtcc    120
aatatgaccg ccatgttggc attgattatt gactagttat taatagtaat caattacggg    180
gtcattagtt catagcccat atatggagtt ccgcgttaca taacttacgg taaatggccc    240
gcctggctga ccgcccaacg acccccgccc attgacgtca ataatgacgt atgttcccat    300
agtaacgcca tagggacttt ccattgacg tcaatgggtg gagtatttac ggtaaactgc     360
ccacttggca gtacatcaag tgtatcatat gccaagtccg cccctattg acgtcaatga     420 cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca gtctccacc ccattgacgt     600 caatgggagt ttgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaaaattg gatctccatt cgccattcag   1080
gctgcgcaac tgctgggaag gacgatcaga gcgggcctct tcgctattac gccagctggc   1140
gaaagggacg tggcaagcaa ggcgattaag ttgagttacg ccaggatttt cccagtcacg   1200
acgttgtaaa acgacggcca gagaattata atacgactca ctatagggcg gatccggcgc   1260
gccgccacca tggccccagg ctgcacgctg gtgctggtgc tgatgctgac gaccgtggcg   1320
ctgagcagga caggagcagt tcctgtgccc tctgccccca gggcactccc acctgccagg   1380
ggctgccacg tggcccagtt caagtctctg tcccctcaag agctgcaagc cttcaagacg   1440
gccagggatg cctttgaaga ctcgttcttg ccgaaggact gggactgtag cacccacctt   1500
ttccccagga cacgagacct gaagcacctg caagtgtggg agcgccctgt ggctctggag   1560
gcagagctgg ccctgacact gacggtcctg gaggcaatgg ctaactcatc cctgggccac   1620
agcctggagc agccccttct cacgctgcaa aacatccact ccaagctcca ggcctgtgtc   1680
ccagctcagc ccacagcaag ctccagaccc cgaggccgcc tccaccactg gctgcaccgc   1740
ctccaagagg cccggaagga gtcccaggac tgcctcgaag cctctgtgat gttcaacctc   1800
ctccgcctcc tcacccgaga cctgaaatgt gttgccagcg agaccagtg tgtctgagaa    1860 ttccaagctt gagtattcta tcgtgtcacc taaataactt ggcgtaatca tggtcatatc   1920
tgtttcctgt gtgaaattgt tatccgctca caattccaca caacatacga gccggaagca   1980
taaagtgtaa agcctggggt gcctaatgag tgagctaact cacattaatt gcgttgcgcg   2040
atgcttccat tttgtgaggg ttaatgcttc gagaagacat gataagatac attgatgagt   2100
ttggacaaac cacaacaaga atgcagtgaa aaaaatgctt tatttgtgaa atttgtgatg   2160
ctattgcttt atttgtaacc attataagct gcaataaaca agttaacaac aacaattgca   2220
ttcattttat gtttcaggtt cagggggaga tgtgggaggt tttttaaagc aagtaaaacc   2280
tctacaaatg tggtaaaatc cgataaggat cgattccgga gcctgaatgg cgaatggacg   2340
cgccctgtag cggcgcatta agcgcggcgg gtgtggtggt tacgcgcacg tgaccgctac   2400
```

```
acttgccagc gccctagcgc ccgctccttt cgctttcttc ccttcctttc tcgccacgtt   2460
cgccggcttt ccccgtcaag ctctaaatcg ggggctccct ttagggttcc gatttagtgc   2520
tttacggcac ctcgacccca aaaaacttga ttagggtgat ggttcacgta gtgggccatc   2580
gccctgatag acggtttttc gcccttttgac gttggagtcc acgttcttta atagtggact   2640
cttgttccaa actggaacaa cactcaaccc tatctcggtc tattcttttg atttataagg   2700
gattttgccg atttcggcct attggttaaa aaatgagctg atttaacaaa aatttaacgc   2760
gaattttaac aaaatattaa cgcttacaat ttcgcctgtg taccttctga ggcggaaaga   2820
accagctgtg gaatgtgtgt cagttagggt gtggaaagtc cccaggctcc ccagcaggca   2880
gaagtatgca aagcatgcat ctcaattagt cagcaaccag gtgtggaaag tccccaggct   2940
ccccagcagg cagaagtatg caaagcatgc atctcaatta gtcagcaacc atagtcccgc   3000
ccctaactcc gcccatcccg ccctaactc cgcccagttc cgcccattct ccgccccatg   3060
gctgactaat ttttttatt tatgcagagg ccgaggccgc ctcggcctct gagctattcc   3120
agaagtagtg aggaggcttt tttggaggcc taggcttttg caaaaagctt gattcttctg   3180
acacaacagt ctcgaactta aggctagagc caccatgatt gaacaagatg gattgcacgc   3240
aggttctccg gccgcttggg tggagaggct attcggctat gactgggcac aacagacaat   3300
cggctgctct gatgccgccg tgttccggct gtcagcgcag gggcgcccgg ttcttttttgt   3360
caagaccgac ctgtccggtg ccctgaatga actgcaggac gaggcagcgc ggctatcgtg   3420
gctggccacg acgggcgttc cttgcgcagc tgtgctcgac gttgtcactg aagcgggaag   3480
ggactggctg ctattgggcg aagtgccggg gcaggatctc ctgtcatctc accttgctcc   3540
tgccgagaaa gtatccatca tggctgatgc aatgcggcgg ctgcatacgc ttgatccggc   3600
tacctgccca ttcgaccacc aagcgaaaca tcgcatcgag cgagcacgta ctcggatgga   3660
agccggtctt gtcgatcagg atgatctgga cgaagagcat caggggctcg cgccagccga   3720
actgttcgcc aggctcaagg cgcgcatgcc cgacggcgag gatctcgtcg tgacccatgg   3780
cgatgcctgc ttgccgaata tcatggtgga aaatggccgc ttttctggat tcatcgactg   3840
tggccggctg ggtgtggcgg accgctatca ggacatagcg ttggctaccc gtgatattgc   3900
tgaagagctt ggcggcgaat gggctgaccg cttcctcgtg ctttacggta tcgccgctcc   3960
cgattcgcag cgcatcgcct tctatcgcct tcttgacgag ttcttctgag cgggactctg   4020
gggttcgaaa tgaccgacca agcgacgccc aacctgccat cacgatggcc gcaataaaat   4080
atctttattt tcattacatc tgtgtgttgg ttttttgtgt gaagatccgc gtatggtgca   4140
ctctcagtac aatctgctct gatgccgcat agttaagcca gccccgacac ccgccaacac   4200
ccgctgacgc gccctgacgg gcttgtctgc tcccggcatc cgcttacaga caagctgtga   4260
ccgtctccgg gagctgcatg tgtcagaggt tttcaccgtc atcaccgaaa cgcgcgagac   4320
gaaagggcct cgtgatacgc ctatttttat aggttaatgt catgataata atggtttctt   4380
agacgtcagg tggcacttt cggggaaatg tgcgcggaac ccctatttgt ttatttttct   4440
aaatacattc aaatatgtat ccgctcatga caataaacc tgataaaatg cttcaataat   4500
attgaaaaag gaagagtatg agtattcaac atttccgtgt cgcccttatt cccttttttg   4560
cggcattttg ccttcctgtt tttgctcacc cagaaacgct ggtgaaagta aaagatgctg   4620
aagatcagtt gggtgcacga gtgggttaca tcgaactgga tctcaacagc ggtaagatcc   4680
ttgagagttt tcgccccgaa gaacgttttc caatgatgag cacttttaaa gttctgctat   4740
gtggcgcggt attatcccgt attgacgccg ggcaagagca actcggtcgc cgcatacact   4800
```

```
attctcagaa tgacttggtt gagtactcac cagtcacaga aaagcatctt acggatggca    4860
tgacagtaag agaattatgc agtgctgcca taaccatgag tgataacact gcggccaact    4920
tacttctgac aacgatcgga ggaccgaagg agctaaccgc ttttttgcac aacatggggg    4980
atcatgtaac tcgccttgat cgttgggaac cggagctgaa tgaagccata ccaaacgacg    5040
agcgtgacac cacgatgcct gtagcaatgg caacaacgtt gcgcaaacta ttaactggcg    5100
aactacttac tctagcttcc cggcaacaat taatagactg gatggaggcg ataaagttg     5160 caggaccact tctgcgctcg gcccttccgg ctggctggtt tattgctgat aaatctggag    5220
ccggtgagcg tgggtctcgc ggtatcattg cagcactggg gccagatggt aagccctccc    5280
gtatcgtagt tatctacacg acggggagtc aggcaactat ggatgaacga atagacaga    5340 tcgctgagat aggtgcctca ctgattaagc attggtaact gtcagaccaa gtttactcat    5400
atatacttta gattgattta aaacttcatt tttaatttaa aaggatctag gtgaagatcc    5460
tttttgataa tctcatgacc aaaatccctt aacgtgagtt ttcgttccac tgagcgtcag    5520
accccgtaga aagatcaaa ggatcttctt gagatccttt ttttctgcgc gtaatctgct    5580
gcttgcaaac aaaaaaacca ccgctaccag cggtggtttg tttgccggat caagagctac    5640
caactctttt tccgaaggta actggcttca gcagagcgca gataccaaat actgtccttc    5700
tagtgtagcc gtagttaggc caccacttca agaactctgt agcaccgcct acatacctcg    5760
ctctgctaat cctgttacca gtggctgctg ccagtggcga taagtcgtgt cttaccgggt    5820
tggactcaag acgatagtta ccggataagg cgcagcggtc gggctgaacg gggggttcgt    5880
gcacacagcc cagcttggag cgaacgacct acaccgaact gagatacctt cagcgtgagc    5940
tatgagaaag cgccacgctt cccgaaggga gaaaggcgga caggtatccg gtaagcggca    6000
gggtcggaac aggagagcgc acgagggagc ttccagggggg aaacgcctgg tatctttata    6060
gtcctgtcgg gtttcgccac ctctgacttg agcgtcgatt tttgtgatgc tcgtcagggg    6120
ggcggagcct atggaaaaac gccagcaacg cggcctttttt acggttcctg ccttttgct    6180 ggccttttgc tcacatggct cgacagatct                                    6210
```

<210> SEQ ID NO 108
<211> LENGTH: 6314
<212> TYPE: DNA
<213> ORGANISM: Artificial Sequence
<220> FEATURE:
<223> OTHER INFORMATION: pTarget d1D2A-SGluc (-1M)

<400> SEQUENCE: 108

```
tcaatattgg ccattagcca tattattcat tggttatata gcataaatca atattggcta     60
ttggccattg catacgttgt atctatatca taatatgtac atttatattg gctcatgtcc    120
aatatgaccg ccatgttggc attgattatt gactagttat taatagtaat caattacggg    180
gtcattagtt catagcccat atatggagtt ccgcgttaca taacttacgg taaatggccc    240
gcctggctga ccgcccaacg acccccgccc attgacgtca ataatgacgt atgttcccat    300
agtaacgcca atagggactt tccattgacg tcaatgggtg gagtatttac ggtaaactgc    360
ccacttggca gtacatcaag tgtatcatat gccaagtccg cccctattg acgtcaatga     420 cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca agtctccacc ccattgacgt    600
```

```
caatgggagt tgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaaaattg gatctccatt cgccattcag   1080
gctgcgcaac tgctgggaag gacgatcaga gcgggcctct tcgctattac gccagctggc   1140
gaaagggacg tggcaagcaa ggcgattaag ttgagttacg ccaggatttt cccagtcacg   1200
acgttgtaaa acgacggcca gagaattata atacgactca ctataggcg aattcggatc    1260 cttgctagcc tcgagctcga gacgcgtgat tgcgccgcca ccatgagcca aagcaaaag    1320 atcattgcac cagcaaagca gcttctgaat tttgacctgc tcaagttggc cggagacgtt   1380
gagtccaacc ctgggcccgg agtcaaagtt ctgtttgccc tgatctgcat cgctgtggcc   1440
gaggccaagc ccaccgagaa caacgaagac ttcaacatcg tggccgtggc cagcaacttt   1500
gcgaccacgg atctcgatgc tgaccgaggg aagttgcccg gcaagaagct gccgctggag   1560
gtgctcaaag agatggaagc caatgcccgg aaagctggct gcaccagggg ctgtctgatc   1620
tgcctgtccc acatcaagtg cacgcccaag atgaagaagt ggctcccagg acgctgccac   1680
acctacgaag gcgacaaaga gtccgcacag ggcggcatag gcgaggcgat cgtcgatatt   1740
cctgagattc ctgggttcaa ggacttggag ccaatggagc agttcatcgc acaggtcgat   1800
ctgtgtgtgg actgcacaac tggctgcctc aaagggcttg ccaacgtgca gtgttcagac   1860
ctgctcaaga gtggctgccg caacgctgt gcgacctttg ccagcaagat ccagggccag   1920
gtggacaaga tcaaggggc cggtggtgac taagcggccg cgaattccaa gcttgagtat   1980
tctatcgtgt cacctaaata acttggcgta atcatggtca tatctgtttc ctgtgtgaaa   2040
ttgttatccg ctcacaattc cacacaacat acgagccgga agcataaagt gtaaagcctg   2100
gggtgcctaa tgagtgagct aactcacatt aattgcgttg cgcgatgctt ccattttgtg   2160
agggttaatg cttcgagaag acatgataag atacattgat gagtttggac aaaccacaac   2220
aagaatgcag tgaaaaaaat gctttatttg tgaaatttgt gatgctattg ctttatttgt   2280
aaccattata agctgcaata aacaagttaa caacaacaat tgcattcatt ttatgtttca   2340
ggttcagggg gagatgtggg aggtttttta agcaagtaa aacctctaca aatgtggtaa   2400
aatccgataa ggatcgattc cggagcctga atggcgaatg gacgcgccct gtagcggcgc   2460
attaagcgcg gcgggtgtgg tggttacgcg cacgtgaccg ctacacttgc cagcgcccta   2520
gcgcccgctc ctttcgcttt cttcccttcc tttctcgcca cgttcgccgg ctttccccgt   2580
caagctctaa atcgggggct ccctttaggg ttccgattta gtgctttacg gcacctcgac   2640
cccaaaaaac ttgattaggg tgatggttca cgtagtgggc catcgccctg atagacggtt   2700
tttcgccctt tgacgttgga gtccacgttc tttaatagtg gactcttgtt ccaaactgga   2760
acaacactca accctatctc ggtctattct tttgatttat aagggatttt gccgatttcg   2820
gcctattggt taaaaaatga gctgatttaa caaaaattta acgcgaattt taacaaaata   2880
ttaacgctta caatttcgcc tgtgtacctt ctgaggcgga agaaccagc tgtggaatgt    2940 gtgtcagtta gggtgtggaa agtccccagg ctccccagca ggcagaagta tgcaaagcat   3000
```

```
gcatctcaat tagtcagcaa ccaggtgtgg aaagtcccca ggctccccag caggcagaag    3060
tatgcaaagc atgcatctca attagtcagc aaccatagtc ccgcccctaa ctccgcccat    3120
cccgcccta  actccgccca gttccgccca ttctccgccc catggctgac taattttttt    3180
tatttatgca gaggccgagg ccgcctcggc tctgagctca ttccagaagt agtgaggagg    3240
cttttttgga ggcctaggct tttgcaaaaa gcttgattct tctgacacaa cagtctcgaa    3300
cttaaggcta gagccaccat gattgaacaa gatggattgc acgcaggttc tccggccgct    3360
tgggtggaga ggctattcgg ctatgactgg gcacaacaga caatcggctg ctctgatgcc    3420
gccgtgttcc ggctgtcagc gcaggggcgc ccggttcttt ttgtcaagac cgacctgtcc    3480
ggtgccctga atgaactgca ggacgaggca gcgcggctat cgtggctggc cacgacgggc    3540
gttccttgcg cagctgtgct cgacgttgtc actgaagcgg gaagggactg gctgctattg    3600
ggcgaagtgc cggggcagga tcctcctgtca tctcaccttg ctcctgccga aaagtatcc    3660
atcatggctg atgcaatgcg gcggctgcat acgcttgatc cggctacctg cccattcgac    3720
caccaagcga aacatcgcat cgagcgagca cgtactcgga tggaagccgg tcttgtcgat    3780
caggatgatc tggacgaaga gcatcagggg ctcgcgccag ccgaactgtt cgccaggctc    3840
aaggcgcgca tgcccgacgg cgaggatctc gtcgtgaccc atggcgatgc ctgcttgccg    3900
aatatcatgg tggaaaatgg ccgcttttct ggattcatcg actgtggccg gctgggtgtg    3960
gcggaccgct atcaggacat agcgttggct acccgtgata ttgctgaaga gcttggcggc    4020
gaatgggctg accgcttcct cgtgctttac ggtatcgccg ctcccgattc gcagcgcatc    4080
gccttctatc gccttcttga cgagttcttc tgagcgggac tctggggttc gaaatgaccg    4140
accaagcgac gcccaacctg ccatcacgat ggccgcaata aaatatcttt attttcatta    4200
catctgtgtg ttggtttttt gtgtgaagat ccgcgtatgg tgcactctca gtacaatctg    4260
ctctgatgcc gcatagttaa gccagccccg acacccgcca cacccgctg  acgcgccctg    4320
acgggcttgt ctgctcccgg catccgctta cagacaagct gtgaccgtct ccgggagctg    4380
catgtgtcag aggttttcac cgtcatcacc gaaacgcgcg agacgaaagg gcctcgtgat    4440
acgcctattt ttataggtta atgtcatgat aataatggtt tcttagacgt caggtggcac    4500
ttttcgggga aatgtgcgcg gaaccccta  ttgtttattt ttctaaatac attcaaatat    4560
gtatccgctc atgagacaat aaccctgata aatgcttcaa taatattgaa aaaggaagag    4620
tatgagtatt caacatttcc gtgtcgccct tattcccttt tttgcggcat tttgccttcc    4680
tgttttgct  cacccagaaa cgctggtgaa agtaaaagat gctgaagatc agttgggtgc    4740
acgagtgggt tacatcgaac tggatctcaa cagcggtaag atccttgaga gttttcgccc    4800
cgaagaacgt tttccaatga tgagcacttt taaagttctg ctatgtggcg cggtattatc    4860
ccgtattgac gccgggcaag agcaactcgg tcgccgcata cactattctc agaatgactt    4920
ggttgagtac tcaccagtca cagaaaagca tcttacggat ggcatgacag taagagaatt    4980
atgcagtgct gccataacca tgagtgataa cactgcggcc aacttacttc tgacaacgat    5040
cggaggaccg aaggagctaa ccgcttttttt gcacaacatg ggggatcatg taactcgcct    5100
tgatcgttgg gaaccggagc tgaatgaagc cataccaaac gacgagcgtg acaccacgat    5160
gcctgtagca atggcaacaa cgttgcgcaa actattaact ggcgaactac ttactctagc    5220
ttcccggcaa caattaatag actggatgga ggcggataaa gttgcaggac cacttctgcg    5280
ctcggccctt ccggctggct ggtttattgc tgataaatct ggagccggtg agcgtgggtc    5340
```

| | | |
|---|---|---|
| tcgcggtatc attgcagcac tgggccaga tggtaagccc tcccgtatcg tagttatcta | 5400 | |
| cacgacgggg agtcaggcaa ctatggatga acgaaataga cagatcgctg agataggtgc | 5460 | |
| ctcactgatt aagcattggt aactgtcaga ccaagtttac tcatatatac tttagattga | 5520 | |
| tttaaaactt cattttaat ttaaaaggat ctaggtgaag atccttttg ataatctcat | 5580 | |
| gaccaaaatc ccttaacgtg agtttttcgtt ccactgagcg tcagaccccg tagaaaagat | 5640 | |
| caaaggatct tcttgagatc cttttttct gcgcgtaatc tgctgcttgc aaacaaaaaa | 5700 | |
| accaccgcta ccagcggtgg tttgtttgcc ggatcaagag ctaccaactc tttttccgaa | 5760 | |
| ggtaactggc ttcagcagag cgcagatacc aaatactgtc cttctagtgt agccgtagtt | 5820 | |
| aggccaccac ttcaagaact ctgtagcacc gcctacatac ctcgctctgc taatcctgtt | 5880 | |
| accagtggct gctgccagtg gcgataagtc gtgtcttacc gggttggact caagacgata | 5940 | |
| gttaccggat aaggcgcagc ggtcgggctg aacgggggt tcgtgcacac agcccagctt | 6000 | |
| ggagcgaacg acctacaccg aactgagata cctacagcgt gagctatgag aaagcgccac | 6060 | |
| gcttcccgaa gggagaaagg cggacaggta tccggtaagc ggcagggtcg gaacaggaga | 6120 | |
| gcgcacgagg gagcttccag ggggaaacgc ctggtatctt tatagtcctg tcgggtttcg | 6180 | |
| ccacctctga cttgagcgtc gatttttgtg atgctcgtca ggggggcgga gcctatggaa | 6240 | |
| aaacgccagc aacgcggcct ttttacggtt cctggccttt tgctggcctt ttgctcacat | 6300 | |
| ggctcgacag atct | 6314 | |

<210> SEQ ID NO 109
<211> LENGTH: 6319
<212> TYPE: DNA
<213> ORGANISM: Artificial Sequence
<220> FEATURE:
<223> OTHER INFORMATION: pTarget SGLuc-d1D2A

<400> SEQUENCE: 109

| | | |
|---|---|---|
| tcaatattgg ccattagcca tattattcat tggttatata gcataaatca atattggcta | 60 | |
| ttggccattg catacgttgt atctatatca taatatgtac atttatattg gctcatgtcc | 120 | |
| aatatgaccg ccatgttggc attgattatt gactagttat taatagtaat caattacggg | 180 | |
| gtcattagtt catagcccat atatggagtt ccgcgttaca taacttacgg taaatggccc | 240 | |
| gcctggctga ccgcccaacg acccccgccc attgacgtca ataatgacgt atgttcccat | 300 | |
| agtaacgcca atagggactt tccattgacg tcaatgggtg gagtatttac ggtaaactgc | 360 | |
| ccacttggca gtacatcaag tgtatcatat gccaagtccg cccctattg acgtcaatga | 420 | |
| cggtaaatgg cccgcctggc attatgccca gtacatgacc ttacgggact ttcctacttg | 480 | |
| gcagtacatc tacgtattag tcatcgctat taccatggtg atgcggtttt ggcagtacac | 540 | |
| caatgggcgt ggatagcggt ttgactcacg ggatttcca gtctccacc ccattgacgt | 600 | |
| caatgggagt ttgttttggc accaaaatca acgggacttt ccaaaatgtc gtaacaactg | 660 | |
| cgatcgcccg ccccgttgac gcaaatgggc ggtaggcgtg tacggtggga ggtctatata | 720 | |
| agcagagctc gtttagtgaa ccgtcagatc actagaagct ttattgcggt agtttatcac | 780 | |
| agttaaattg ctaacgcagt cagtgcttct gacacaacag tctcgaactt aagctgcagt | 840 | |
| gactctctta aggtagcctt gcagaagttg gtcgtgaggc actgggcagg taagtatcaa | 900 | |
| ggttacaaga caggtttaag gagaccaata gaaactgggc ttgtcgagac agagaagact | 960 | |
| cttgcgtttc tgataggcac ctattggtct tactgacatc cactttgcct ttctctccac | 1020 | |
| aggtgtccac tcccagttca attacagctc ttaaaaattg gatctccatt cgccattcag | 1080 | |

-continued

```
gctgcgcaac tgctgggaag gacgatcaga gcgggcctct tcgctattac gccagctggc   1140
gaaagggacg tggcaagcaa ggcgattaag ttgagttacg ccaggatttt cccagtcacg   1200
acgttgtaaa acgacggcca gagaattata atacgactca ctatagggcg aattcggatc   1260
cttgctagcc tcgagacgcg tgatatcttt ggcgcgccgc caccatggga gtcaaagttc   1320
tgtttgccct gatctgcatc gctgtggccg aggccaagcc caccgagaac aacgaagact   1380
tcaacatcgt ggccgtggcc agcaacttcg cgaccacgtg tctcgatgct gaccgcggga   1440
agttgcccgg caagaagctg ccgctggagg tgctcaaaga gatggaagcc aatgcccgga   1500
aagctggctg caccaggggc tgtctgatct gcctgtccca catcaagtgc acgcccaaga   1560
tgaagaagtg gctcccagga cgctgccaca cctacgaagg cgacaaagag tccgcacagg   1620
gcggcatagg cgaggcgatc gtcgacattc tgagattcc tggggttcaag acttggagc   1680
ccatggagca gttcatcgca caggtcgatc tgtgtgtgga ctgcacaact ggctgcctca   1740
aagggcttgc caacgtgcag tgttctgacc tgctcaagaa gtggctgccg caacgctgtg   1800
cgacctttgc cagcaagatc cagggccagg tggacaagat caagggggcc ggtggtgacg   1860
ctagccacaa gcaaaagatc attgcaccag caaagcagct tctgaatttt gacctgctca   1920
agttggccgg agacgttgag tccaaccctg acccggggc ggccgcgaat tccaagcttg   1980
agtattctat cgtgtcacct aaataacttg gcgtaatcat ggtcatatct gtttcctgtg   2040
tgaaattgtt atccgctcac aattccacac aacatacgag ccggaagcat aaagtgtaaa   2100
gcctggggtg cctaatgagt gagctaactc acattaattg cgttgcgcga tgcttccatt   2160
ttgtgagggt taatgcttcg agaagacatg ataagataca ttgatgagtt tggacaaacc   2220
acaacaagaa tgcagtgaaa aaaatgcttt atttgtgaaa tttgtgatgc tattgcttta   2280
tttgtaacca ttataagctg caataaacaa gttaacaaca caattgcat tcattttatg   2340
tttcaggttc aggggagat gtgggaggtt ttttaaagca agtaaaacct ctacaaatgt   2400
ggtaaaatcc gataaggatc gattccggag cctgaatggc gaatggacgc gccctgtagc   2460
ggcgcattaa gcgcggcggg tgtggtggtt acgcgcacgt gaccgctaca cttgccagcg   2520
ccctagcgcc cgctcctttc gctttcttcc cttcctttct cgccacgttc gccggctttc   2580
cccgtcaagc tctaaatcgg gggctccctt tagggttccg atttagtgct ttacggcacc   2640
tcgacccaa aaaacttgat tagggtgatg gttcacgtag tgggccatcg ccctgataga   2700
cggtttttcg ccctttgacg ttggagtcca cgttctttaa tagtggactc ttgttccaaa   2760
ctggaacaac actcaaccct atctcggtct attcttttga tttataaggg attttgccga   2820
tttcggccta ttggttaaaa aatgagctga tttaacaaaa atttaacgcg aattttaaca   2880
aaatattaac gcttacaatt tcgcctgtgt accttctgag gcggaaagaa ccagctgtgg   2940
aatgtgtgtc agttagggtg tggaaagtcc ccaggctccc cagcaggcag aagtatgcaa   3000
agcatgcatc tcaattagtc agcaaccagg tgtggaaagt ccccaggctc cccagcaggc   3060
agaagtatgc aaagcatgca tctcaattag tcagcaacca tagtcccgcc cctaactccg   3120
cccatcccgc ccctaactcc gcccagttcc gcccattctc cgccccatgg ctgactaatt   3180
ttttttattt atgcagaggc cgaggccgcc tcggcctctg agctattcca gaagtagtga   3240
ggaggctttt ttggaggcct aggcttttgc aaaaagcttg attcttctga cacaacagtc   3300
tcgaacttaa ggctagagcc accatgattg aacaagatgg attgcacgca ggttctccgg   3360
ccgcttgggt ggagaggcta ttcggctatg actgggcaca acagacaatc ggctgctctg   3420
```

-continued

```
atgccgccgt gttccggctg tcagcgcagg ggcgcccggt tcttttgtc aagaccgacc       3480
tgtccggtgc cctgaatgaa ctgcaggacg aggcagcgcg gctatcgtgg ctggccacga       3540
cgggcgttcc ttgcgcagct gtgctcgacg ttgtcactga agcgggaagg gactggctgc       3600
tattgggcga agtgccgggg caggatctcc tgtcatctca ccttgctcct gccgagaaag       3660
tatccatcat ggctgatgca atgcggcggc tgcatacgct tgatccggct acctgcccat       3720
tcgaccacca agcgaaacat cgcatcgagc gagcacgtac tcggatggaa gccggtcttg       3780
tcgatcagga tgatctggac gaagagcatc aggggctcgc gccagccgaa ctgttcgcca       3840
ggctcaaggc gcgcatgccc gacggcgagg atctcgtcgt gacccatggc gatgcctgct       3900
tgccgaatat catggtggaa aatggccgct tttctggatt catcgactgt ggccggctgg       3960
gtgtggcgga ccgctatcag gacatagcgt tggctacccg tgatattgct gaagagcttg       4020
gcggcgaatg ggctgaccgc ttcctcgtgc tttacggtat cgccgctccc gattcgcagc       4080
gcatcgcctt ctatcgcctt cttgacgagt tcttctgagc gggactctgg ggttcgaaat       4140
gaccgaccaa gcgacgccca acctgccatc acgatggccg caataaaata tctttatttt       4200
cattacatct gtgtgttggt tttttgtgtg aagatccgcg tatggtgcac tctcagtaca       4260
atctgctctg atgccgcata gttaagccag ccccgacacc cgccaacacc cgctgacgcg       4320
ccctgacggg cttgtctgct cccggcatcc gcttacagac aagctgtgac cgtctccggg       4380
agctgcatgt gtcagaggtt ttcaccgtca tcaccgaaac gcgcgagacg aaagggcctc       4440
gtgatacgcc tattttata ggttaatgtc atgataataa tggtttctta cgtcaggt         4500
ggcactttc ggggaaatgt gcgcggaacc cctatttgtt tatttttcta atacattca        4560
aatatgtatc cgctcatgag acaataaccc tgataaatgc ttcaataata ttgaaaaagg       4620
aagagtatga gtattcaaca tttccgtgtc gcccttattc ccttttttgc ggcatttgc       4680
cttcctgttt ttgctcaccc agaaacgctg gtgaaagtaa agatgctga agatcagttg       4740
ggtgcacgag tgggttacat cgaactggat ctcaacagcg gtaagatcct tgagagttt       4800
cgccccgaag aacgttttcc aatgatgagc acttttaaag ttctgctatg tggcgcggta       4860
ttatcccgta ttgacgccgg gcaagagcaa ctcggtcgcc gcatacacta ttctcagaat       4920
gacttggttg agtactcacc agtcacagaa aagcatctta cggatggcat gacagtaaga       4980
gaattatgca gtgctgccat aaccatgagt gataacactg cggccaactt acttctgaca       5040
acgatcggag gaccgaagga gctaaccgct tttttgcaca acatgggga tcatgtaact       5100
cgccttgatc gttgggaacc ggagctgaat gaagccatac caaacgacga gcgtgacacc       5160
acgatgcctg tagcaatggc aacaacgttg cgcaaactat taactggcga actacttact       5220
ctagcttccc ggcaacaatt aatagactgg atggaggcgg ataaagttgc aggaccactt       5280
ctgcgctcgg cccttccggc tggctggttt attgctgata atctggagc cggtgagcgt       5340
gggtctcgcg gtatcattgc agcactgggg ccagatggta agccctcccg tatcgtagtt       5400
atctacacga cggggagtca ggcaactatg gatgaacgaa atagacagat cgctgagata       5460
ggtgcctcac tgattaagca ttggtaactg tcagaccaag tttactcata tatactttag       5520
attgatttaa aacttcattt ttaatttaaa aggatctagg tgaagatcct ttttgataat       5580
ctcatgacca aaatccctta acgtgagttt tcgttccact gagcgtcaga ccccgtagaa       5640
aagatcaaag gatcttcttg agatcctttt tttctgcgcg taatctgctg cttgcaaaca       5700
aaaaaccac cgctaccagc ggtggtttgt ttgccggatc aagagctacc aactcttttt       5760
ccgaaggtaa ctggcttcag cagagcgcag ataccaaata ctgtccttct agtgtagccg       5820
```

```
tagttaggcc accacttcaa gaactctgta gcaccgccta catacctcgc tctgctaatc    5880
ctgttaccag tggctgctgc cagtggcgat aagtcgtgtc ttaccgggtt ggactcaaga    5940
cgatagttac cggataaggc gcagcggtcg ggctgaacgg ggggttcgtg cacacagccc    6000
agcttggagc gaacgaccta caccgaactg agatacctac agcgtgagct atgagaaagc    6060
gccacgcttc ccgaagggag aaaggcggac aggtatccgg taagcggcag ggtcggaaca    6120
ggagagcgca cgagggagct tccaggggga aacgcctggt atctttatag tcctgtcggg    6180
tttcgccacc tctgacttga gcgtcgattt ttgtgatgct cgtcaggggg cggagccta    6240 tggaaaaacg ccagcaacgc ggcctttta cggttcctgg ccttttgctg gccttttgct    6300
cacatggctc gacagatct                                                 6319
```

<210> SEQ ID NO 110
<211> LENGTH: 993
<212> TYPE: DNA
<213> ORGANISM: Bos taurus
<220> FEATURE:
<221> NAME/KEY: CDS
<222> LOCATION: (1)..(993)
<223> OTHER INFORMATION: SGlucON Bovine gamma

<400> SEQUENCE: 110

```
atg gga gtc aaa gtt ctg ttt gcc ctg atc tgc atc gct gtg gcc gag      48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc      96
Ala Lys Pro Thr Glu Asn Asn Glu Asp Phe Asn Ile Val Ala Val Ala
            20                  25                  30 agc aac ttt gcg acc acg gat ctc gat gct gac cga ggg aag ttg ccc     144
Ser Asn Phe Ala Thr Thr Asp Leu Asp Ala Asp Arg Gly Lys Leu Pro
        35                  40                  45 ggc aag aag ctg ccg ctg gag gtg ctc aaa gag atg gaa gcc aat gcc     192
Gly Lys Lys Leu Pro Leu Glu Val Leu Lys Glu Met Glu Ala Asn Ala
    50                  55                  60 cgg aaa gct ggc tgc acc agg ggc tgt ctg atc tgc ctg tcc cac atc     240
Arg Lys Ala Gly Cys Thr Arg Gly Cys Leu Ile Cys Leu Ser His Ile
65                  70                  75                  80 aag tgc acg ccc aag atg aag aag tgg ctc cca gga cgc tgc cac acc     288
Lys Cys Thr Pro Lys Met Lys Lys Trp Leu Pro Gly Arg Cys His Thr
                85                  90                  95 tac gaa ggc gac aaa gag tcc gca cag ggc ggc ata ggc gag gcg atc     336
Tyr Glu Gly Asp Lys Glu Ser Ala Gln Gly Gly Ile Gly Glu Ala Ile
            100                 105                 110 gtc gat att cct gag att cct ggg ttc aag gac ttg gag cca atg gag     384
Val Asp Ile Pro Glu Ile Pro Gly Phe Lys Asp Leu Glu Pro Met Glu
        115                 120                 125 cag ttc atc gca cag gtc gat ctg tgt gtg gac tgc aca act ggc tgc     432
Gln Phe Ile Ala Gln Val Asp Leu Cys Val Asp Cys Thr Thr Gly Cys
    130                 135                 140 ctc aaa ggg ctt gcc aac gtg cag tgt tct gac ctg ctc aag aag tgg     480
Leu Lys Gly Leu Ala Asn Val Gln Cys Ser Asp Leu Leu Lys Lys Trp
145                 150                 155                 160 ctg ccg caa cgc tgt gcg acc ttt gcc agc aag atc cag ggc cag gtg     528
Leu Pro Gln Arg Cys Ala Thr Phe Ala Ser Lys Ile Gln Gly Gln Val
                165                 170                 175 gac aag atc aag ggg gcc ggt ggt gac ggg ccc cag ggc caa ttt ttt     576
Asp Lys Ile Lys Gly Ala Gly Gly Asp Gly Pro Gln Gly Gln Phe Phe
            180                 185                 190
```

| | | |
|---|---|---|
| aga gaa ata gaa aac tta aag gag tat ttt aat gca agt agc cca gat<br>Arg Glu Ile Glu Asn Leu Lys Glu Tyr Phe Asn Ala Ser Ser Pro Asp<br>            195                       200                   205 | | 624 |
| gta gct aag ggt ggg cct ctc ttc tca gaa att ttg aag aat tgg aaa<br>Val Ala Lys Gly Gly Pro Leu Phe Ser Glu Ile Leu Lys Asn Trp Lys<br>210                       215                       220 | | 672 |
| gat gaa agt gac aaa aaa att att cag agc caa att gtc tcc ttc tac<br>Asp Glu Ser Asp Lys Lys Ile Ile Gln Ser Gln Ile Val Ser Phe Tyr<br>225                     230                       235                 240 | | 720 |
| ttc aaa ctc ttt gaa aac ctc aaa gat aac cag gtc att caa agg agc<br>Phe Lys Leu Phe Glu Asn Leu Lys Asp Asn Gln Val Ile Gln Arg Ser<br>            245                       250                   255 | | 768 |
| atg gat atc atc aag caa gac atg ttt cag aag ttc ttg aat ggc agc<br>Met Asp Ile Ile Lys Gln Asp Met Phe Gln Lys Phe Leu Asn Gly Ser<br>260                       265                       270 | | 816 |
| tct gag aaa ctg gag gac ttc aaa aag ctg att caa att ccg gtg gat<br>Ser Glu Lys Leu Glu Asp Phe Lys Lys Leu Ile Gln Ile Pro Val Asp<br>            275                       280                   285 | | 864 |
| gat ctg cag atc cag cgc aaa gcc ata aat gaa ctc atc aaa gtg atg<br>Asp Leu Gln Ile Gln Arg Lys Ala Ile Asn Glu Leu Ile Lys Val Met<br>290                       295                       300 | | 912 |
| aat gac ctg tca cca aaa tct aac ctc aga aag cgg aag aga agt cag<br>Asn Asp Leu Ser Pro Lys Ser Asn Leu Arg Lys Arg Lys Arg Ser Gln<br>305                     310                       315                   320 | | 960 |
| aat ctc ttt cga ggc cgg aga gca tca acg taa<br>Asn Leu Phe Arg Gly Arg Arg Ala Ser Thr<br>            325                       330 | | 993 |

<210> SEQ ID NO 111
<211> LENGTH: 330
<212> TYPE: PRT
<213> ORGANISM: Bos taurus

<400> SEQUENCE: 111

Met Gly Val Lys Val Leu Phe Ala Leu Ile Cys Ile Ala Val Ala Glu
1                   5                       10                     15

Ala Lys Pro Thr Glu Asn Asn Glu Asp Phe Asn Ile Val Ala Val Ala
                   20                       25                     30

Ser Asn Phe Ala Thr Thr Asp Leu Asp Ala Asp Arg Gly Lys Leu Pro
           35                       40                     45

Gly Lys Lys Leu Pro Leu Glu Val Leu Lys Glu Met Glu Ala Asn Ala
50                       55                       60

Arg Lys Ala Gly Cys Thr Arg Gly Cys Leu Ile Cys Leu Ser His Ile
65                    70                       75                   80

Lys Cys Thr Pro Lys Met Lys Lys Trp Leu Pro Gly Arg Cys His Thr
                   85                       90                     95

Tyr Glu Gly Asp Lys Glu Ser Ala Gln Gly Ile Gly Glu Ala Ile
                100                     105                    110

Val Asp Ile Pro Glu Ile Pro Gly Phe Lys Asp Leu Glu Pro Met Glu
           115                     120                    125

Gln Phe Ile Ala Gln Val Asp Leu Cys Val Asp Cys Thr Thr Gly Cys
130                       135                       140

Leu Lys Gly Leu Ala Asn Val Gln Cys Ser Asp Leu Leu Lys Lys Trp
145                     150                     155                   160

Leu Pro Gln Arg Cys Ala Thr Phe Ala Ser Lys Ile Gln Gly Gln Val
                165                     170                    175

Asp Lys Ile Lys Gly Ala Gly Gly Asp Gly Pro Gln Gly Gln Phe Phe
           180                     185                    190

```
Arg Glu Ile Glu Asn Leu Lys Glu Tyr Phe Asn Ala Ser Ser Pro Asp
        195                 200                 205

Val Ala Lys Gly Gly Pro Leu Phe Ser Glu Ile Leu Lys Asn Trp Lys
210                 215                 220

Asp Glu Ser Asp Lys Lys Ile Ile Gln Ser Gln Ile Val Ser Phe Tyr
225                 230                 235                 240

Phe Lys Leu Phe Glu Asn Leu Lys Asp Asn Gln Val Ile Gln Arg Ser
            245                 250                 255

Met Asp Ile Ile Lys Gln Asp Met Phe Gln Lys Phe Leu Asn Gly Ser
                260                 265                 270

Ser Glu Lys Leu Glu Asp Phe Lys Lys Leu Ile Gln Ile Pro Val Asp
            275                 280                 285

Asp Leu Gln Ile Gln Arg Lys Ala Ile Asn Glu Leu Ile Lys Val Met
        290                 295                 300

Asn Asp Leu Ser Pro Lys Ser Asn Leu Arg Arg Lys Arg Ser Gln
305                 310                 315                 320

Asn Leu Phe Arg Gly Arg Arg Ala Ser Thr
            325                 330

<210> SEQ ID NO 112
<211> LENGTH: 1092
<212> TYPE: DNA
<213> ORGANISM: Bos taurus
<220> FEATURE:
<221> NAME/KEY: CDS
<222> LOCATION: (1)..(1092)
<223> OTHER INFORMATION: SGlucON Lambda bovine

<400> SEQUENCE: 112
```

| | | | | | | | | | | | | | | | | |
|---|---|---|---|---|---|---|---|---|---|---|---|---|---|---|---|---|
| atg | gga | gtc | aaa | gtt | ctg | ttt | gcc | ctg | atc | tgc | atc | gct | gtg | gcc | gag | 48 |
| Met | Gly | Val | Lys | Val | Leu | Phe | Ala | Leu | Ile | Cys | Ile | Ala | Val | Ala | Glu | |
| 1 | | | | 5 | | | | | 10 | | | | | 15 | | |
| gcc | aag | ccc | acc | gag | aac | aac | gaa | gac | ttc | aac | atc | gtg | gcc | gtg | gcc | 96 |
| Ala | Lys | Pro | Thr | Glu | Asn | Asn | Glu | Asp | Phe | Asn | Ile | Val | Ala | Val | Ala | |
| | | | 20 | | | | | 25 | | | | | 30 | | | |
| agc | aac | ttt | gcg | acc | acg | gat | ctc | gat | gct | gac | cga | ggg | aag | ttg | ccc | 144 |
| Ser | Asn | Phe | Ala | Thr | Thr | Asp | Leu | Asp | Ala | Asp | Arg | Gly | Lys | Leu | Pro | |
| | | 35 | | | | | 40 | | | | | 45 | | | | |
| ggc | aag | aag | ctg | ccg | ctg | gag | gtg | ctc | aaa | gag | atg | gaa | gcc | aat | gcc | 192 |
| Gly | Lys | Lys | Leu | Pro | Leu | Glu | Val | Leu | Lys | Glu | Met | Glu | Ala | Asn | Ala | |
| 50 | | | | | 55 | | | | | 60 | | | | | | |
| cgg | aaa | gct | ggc | tgc | acc | agg | ggc | tgt | ctg | atc | tgc | ctg | tcc | cac | atc | 240 |
| Arg | Lys | Ala | Gly | Cys | Thr | Arg | Gly | Cys | Leu | Ile | Cys | Leu | Ser | His | Ile | |
| 65 | | | | | 70 | | | | | 75 | | | | | 80 | |
| aag | tgc | acg | ccc | aag | atg | aag | aag | tgg | ctc | cca | gga | cgc | tgc | cac | acc | 288 |
| Lys | Cys | Thr | Pro | Lys | Met | Lys | Lys | Trp | Leu | Pro | Gly | Arg | Cys | His | Thr | |
| | | | | 85 | | | | | 90 | | | | | 95 | | |
| tac | gaa | ggc | gac | aaa | gag | tcc | gca | cag | ggc | ggc | ata | ggc | gag | gcg | atc | 336 |
| Tyr | Glu | Gly | Asp | Lys | Glu | Ser | Ala | Gln | Gly | Gly | Ile | Gly | Glu | Ala | Ile | |
| | | | 100 | | | | | 105 | | | | | 110 | | | |
| gtc | gat | att | cct | gag | att | cct | ggg | ttc | aag | gac | ttg | gag | cca | atg | gag | 384 |
| Val | Asp | Ile | Pro | Glu | Ile | Pro | Gly | Phe | Lys | Asp | Leu | Glu | Pro | Met | Glu | |
| | | | 115 | | | | | 120 | | | | | 125 | | | |
| cag | ttc | atc | gca | cag | gtc | gat | ctg | tgt | gtg | gac | tgc | aca | act | ggc | tgc | 432 |
| Gln | Phe | Ile | Ala | Gln | Val | Asp | Leu | Cys | Val | Asp | Cys | Thr | Thr | Gly | Cys | |
| | | 130 | | | | | 135 | | | | | 140 | | | | |
| ctc | aaa | ggg | ctt | gcc | aac | gtg | cag | tgt | tct | gac | ctg | ctc | aag | aag | tgg | 480 |
| Leu | Lys | Gly | Leu | Ala | Asn | Val | Gln | Cys | Ser | Asp | Leu | Leu | Lys | Lys | Trp | |
| 145 | | | | | 150 | | | | | 155 | | | | | 160 | |

```
ctg ccg caa cgc tgt gcg acc ttt gcc agc aag atc cag ggc cag gtg         528
Leu Pro Gln Arg Cys Ala Thr Phe Ala Ser Lys Ile Gln Gly Gln Val
            165                 170                 175 gac aag atc aag ggg gcc ggt ggt gac ggg ccc agg aca gga gca gtt         576
Asp Lys Ile Lys Gly Ala Gly Gly Asp Gly Pro Arg Thr Gly Ala Val
            180                 185                 190 cct gtg ccc tct gcc ccc agg gcc ctc cca cct gcc agg ggc tgc cac         624
Pro Val Pro Ser Ala Pro Arg Ala Leu Pro Pro Ala Arg Gly Cys His
            195                 200                 205 gtg gcc cag ttc aag tct ctg tcc cct caa gag ctg cag gcc ttc aag         672
Val Ala Gln Phe Lys Ser Leu Ser Pro Gln Glu Leu Gln Ala Phe Lys
            210                 215                 220 acg gcc agg gat gcc ttt gaa gac tcg ttc ttg cca aag gac tgg gac         720
Thr Ala Arg Asp Ala Phe Glu Asp Ser Phe Leu Pro Lys Asp Trp Asp
225                 230                 235                 240 tgc agc acc cac ctt ttc ccc agg acc cgg gac ctg aag cac ctg cag         768
Cys Ser Thr His Leu Phe Pro Arg Thr Arg Asp Leu Lys His Leu Gln
                245                 250                 255 gtg tgg gag cgc cct gtg gct ctg gag gca gag ctg gcc ctg aca ctg         816
Val Trp Glu Arg Pro Val Ala Leu Glu Ala Glu Leu Ala Leu Thr Leu
            260                 265                 270 acg gtc ctg gag gcc atg gct aac tca tcc ctg ggc cac agc ctg gag         864
Thr Val Leu Glu Ala Met Ala Asn Ser Ser Leu Gly His Ser Leu Glu
            275                 280                 285 cag ccc ctt ctc acg ctg cag aac atc cac tcc aag ctc cag gcc tgt         912
Gln Pro Leu Leu Thr Leu Gln Asn Ile His Ser Lys Leu Gln Ala Cys
            290                 295                 300 gtc cca gct cag ccc aca gca agc tcc agg ccc cgg ggc cgc ctc cac         960
Val Pro Ala Gln Pro Thr Ala Ser Ser Arg Pro Arg Gly Arg Leu His
305                 310                 315                 320 cac tgg ctg cac cgc ctc cag gag gcc cgg aag gag tcc cag gac tgc        1008
His Trp Leu His Arg Leu Gln Glu Ala Arg Lys Glu Ser Gln Asp Cys
                325                 330                 335 ctc gaa gcc tct gtg atg ttc aac ctc ctc cgc ctc ctc acc cgg gac        1056
Leu Glu Ala Ser Val Met Phe Asn Leu Leu Arg Leu Leu Thr Arg Asp
            340                 345                 350 ctg aaa tgt gtt gcc agc gga gac cag tgt gtc tga                        1092
Leu Lys Cys Val Ala Ser Gly Asp Gln Cys Val
            355                 360

<210> SEQ ID NO 113
<211> LENGTH: 363
<212> TYPE: PRT
<213> ORGANISM: Bos taurus

<400> SEQUENCE: 113

Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
        35                  40                  45

Gly Lys Lys Leu Pro Leu Glu Val Leu Lys Glu Met Glu Ala Asn Ala
    50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Trp Leu Pro Gly Arg Cys His Thr
                85                  90                  95
```

-continued

```
Tyr Glu Gly Asp Lys Glu Ser Ala Gln Gly Gly Ile Gly Glu Ala Ile
            100                 105                 110

Val Asp Ile Pro Glu Ile Pro Gly Phe Lys Asp Leu Glu Pro Met Glu
        115                 120                 125

Gln Phe Ile Ala Gln Val Asp Leu Cys Val Asp Cys Thr Thr Gly Cys
        130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp Gly Pro Arg Thr Gly Ala Val
            180                 185                 190

Pro Val Pro Ser Ala Pro Arg Ala Leu Pro Pro Ala Arg Gly Cys His
        195                 200                 205

Val Ala Gln Phe Lys Ser Leu Ser Pro Gln Glu Leu Gln Ala Phe Lys
    210                 215                 220

Thr Ala Arg Asp Ala Phe Glu Asp Ser Phe Leu Pro Lys Asp Trp Asp
225                 230                 235                 240

Cys Ser Thr His Leu Phe Pro Arg Thr Arg Asp Leu Lys His Leu Gln
                245                 250                 255

Val Trp Glu Arg Pro Val Ala Leu Glu Ala Glu Leu Ala Leu Thr Leu
            260                 265                 270

Thr Val Leu Glu Ala Met Ala Asn Ser Ser Leu Gly His Ser Leu Glu
        275                 280                 285

Gln Pro Leu Leu Thr Leu Gln Asn Ile His Ser Lys Leu Gln Ala Cys
        290                 295                 300

Val Pro Ala Gln Pro Thr Ala Ser Ser Arg Pro Arg Gly Arg Leu His
305                 310                 315                 320

His Trp Leu His Arg Leu Gln Glu Ala Arg Lys Glu Ser Gln Asp Cys
                325                 330                 335

Leu Glu Ala Ser Val Met Phe Asn Leu Leu Arg Leu Leu Thr Arg Asp
            340                 345                 350

Leu Lys Cys Val Ala Ser Gly Asp Gln Cys Val
        355                 360
```